US010851099B2

(12) United States Patent
Blaszczyk et al.

(10) Patent No.: US 10,851,099 B2
(45) Date of Patent: Dec. 1, 2020

(54) DIPEPTIDE PIPERIDINE DERIVATIVES

(71) Applicant: OncoArendi Therapeutics S.A., Warsaw (PL)

(72) Inventors: Roman Blaszczyk, Lodz (PL); Anna Gzik, Wartkowice (PL); Bartlomiej Borek, Lodz (PL); Marek Dziegielewski, Lodz (PL); Karol Jedrzejczak, Lodz (PL); Julita Nowicka, Wola Grzymkowa (PL); Jacek Chrzanowski, Lodz (PL); Joanna Brzezinska, Lodz (PL); Adam Golebiowski, Madison, CT (US); Jacek Olczak, Lodz (PL); Marcin Mikolaj Grzybowski, Lask (PL); Jolanta Peczkowicz-Szyszka, Warsaw (PL)

(73) Assignee: OncoArendi Therapeutics S.A., Warsaw (PL)

( * ) Notice: Subject to any disclaimer, the term of this patent is extended or adjusted under 35 U.S.C. 154(b) by 0 days.

(21) Appl. No.: 16/369,982

(22) Filed: Mar. 29, 2019

(65) Prior Publication Data

US 2019/0300525 A1 Oct. 3, 2019

Related U.S. Application Data

(60) Provisional application No. 62/649,752, filed on Mar. 29, 2018.

(51) Int. Cl.
| | |
|---|---|
| C07F 5/02 | (2006.01) |
| A61K 31/454 | (2006.01) |
| C07D 471/04 | (2006.01) |
| A61P 11/16 | (2006.01) |
| A61P 9/00 | (2006.01) |
| A61P 17/02 | (2006.01) |
| A61P 37/00 | (2006.01) |
| A61P 35/00 | (2006.01) |
| C07K 5/02 | (2006.01) |
| C07D 211/60 | (2006.01) |
| A61K 45/06 | (2006.01) |

(52) U.S. Cl.
CPC ............. *C07D 471/04* (2013.01); *A61P 9/00* (2018.01); *A61P 11/16* (2018.01); *A61P 17/02* (2018.01); *A61P 35/00* (2018.01); *A61P 37/00* (2018.01); *C07D 211/60* (2013.01); *C07F 5/025* (2013.01); *C07K 5/0202* (2013.01); *C07K 5/0215* (2013.01); *A61K 45/06* (2013.01)

(58) Field of Classification Search
CPC ........ C07F 5/02; A61K 31/454; A61K 31/445
USPC ............................ 546/13; 514/329, 326, 320
See application file for complete search history.

(56) References Cited

U.S. PATENT DOCUMENTS

| | | |
|---|---|---|
| 10,065,974 B2 | 9/2018 | Sjogren et al. |
| 2010/0056480 A1 | 3/2010 | Meurs et al. |
| 2012/0083469 A1 | 4/2012 | Van Zandt et al. |
| 2016/0194340 A1 | 7/2016 | Christianson et al. |
| 2017/0000808 A1 | 1/2017 | Van Zandt et al. |
| 2018/0161349 A1 | 6/2018 | Makkouk et al. |
| 2018/0362459 A1 | 12/2018 | Van Zandt et al. |

FOREIGN PATENT DOCUMENTS

| | | |
|---|---|---|
| WO | 2010085797 | 7/2010 |
| WO | 2011133653 | 10/2011 |
| WO | 2012058065 | 5/2012 |
| WO | 2012091757 | 7/2012 |
| WO | 2013059437 | 4/2013 |
| WO | 2013158262 | 10/2013 |
| WO | 2016108707 | 7/2016 |
| WO | 2016153078 A1 | 9/2016 |
| WO | 2016210106 | 12/2016 |
| WO | 2016210106 A1 | 12/2016 |
| WO | 2017075363 | 5/2017 |
| WO | 2017191130 | 11/2017 |
| WO | 2018119440 | 6/2018 |
| WO | 2018236828 A2 | 12/2018 |
| WO | 2019145453 A1 | 8/2019 |
| WO | 2019159120 A1 | 8/2019 |
| WO | 2019177873 A1 | 9/2019 |

OTHER PUBLICATIONS

Golebiowski, Adam et al. "2-Substituted-2-amino-6-boronohexanoic acids as arginase inhibitors" Biorganic & Medicinal Chemistry Letters 23 (2013), pp. 2027-2030.
Golebiowski, Adam et al. "Synthesis of quaternary α-amino acid-based arginase inhibitors via the Ugi reaction" Biorganic & Medicinal Chemistry Letters 23 (2013), pp. 4837-4841.
Kabalka, George W. et al. "Synthesis of a series of boronated unnatural cyclic amino acids as potential boron neutron capture therapy agents" Applied Organometallic Chemistry (2008) vol. 22, pp. 516-522.
Steggerda, Susanne M. et al. "Inhibition of arginase by CB-1158 blocks myeloid cell-mediated immune suppression in the tumor microenvironment" Journal of ImmunoTherapy of Cancer (2017) vol. 5(101), pp. 1-18.
Rouzaut, Ana et al. "Co-expression of inducible nitric oxide synthase and arginases in different human monocyte subsets. Apoptosis regulated by endogenous NO" Biochimica et Biophysica Acta (1999) vol. 1451, pp. 319-333.
Hannemann, Nicole et al. "Transcription factor Fra-1 targets arginase-1 to enhance macrophage-mediated inflammation in arthritis" Journal of Clinical Investigation (2019) vol. 129(7), pp. 2669-2684.
Rahman, Saifur et al. "Low-density granulocytes activate T cells and demonstrate a non-suppressive role in systemic lupus erythematosus" Ann Rheum Dis (2019) vol. 78, pp. 957-966.

(Continued)

*Primary Examiner* — Charanjit Aulakh
(74) *Attorney, Agent, or Firm* — McDonnell Boehnen Hulbert & Berghoff LLP

(57) ABSTRACT

The disclosure relates to pharmaceutical compositions, to methods of preparing such compositions, and to methods for using such compositions for treating or preventing a disease or condition associated with arginase activity.

22 Claims, 6 Drawing Sheets

(56) References Cited

OTHER PUBLICATIONS

Liu, Yu-feng et al. "Expansion and activation of monocytic-myeloid-derived suppressor cell via STAT3/ arginase-I signaling in patients with ankylosing spondylitis" Arthritis Research & Therapy (2018) vol. 20:168, 13 pages.
Abeyakirthi, S. et al. "Arginase is overactive in psoriatic skin" British Journal of Dermatology (2010), vol. 163, pp. 193-196.
Chandrasekharan, Unnikrishnan et al. "Evelevated levels of plasma symmetric dimethylarginine and increased arginase activity as potential indicators of cardiovascular comorbidity in rheumatoid arthritis" Arthritis Research & Therapy (2018) vol. 20(123), pp. 1-12.
Choudry, Miriam et al. "Deficient Arginase II Expression without Alteration in Arginase I Expression Attenuated Experimental Autoimmune Encephalomyelitis in Mice" Immunology (2018) vol. 55, pp. 85-98.
Bagi, Zsolt et al. "Selective up-regulation of arginase-1 in coronary arteries of diabetic patients" Frontiers in Immunology (2013) vol. 4(293), pp. 1-6.
Xu, Lingyun et al., "Arginase and autoimmune inflammation in the central nervous system", Immunology (2003) vol. 110, pp. 141-148.
Hill, Anita et al. "Effect of eculizumab on haemolysis-associated nitric oxide depletion, dyspnoea, and measures of pulmonary hypertension in patients with paroxysmal nocturnal haemoglobinuria" British Journal of Hematology (2010) vol. 149, pp. 414-425.
Li, Yan et al. "Myeloid-Derived Suppressor Cells as a Potential Therapy for Experimental Autoimmune Myasthenia Gravis" Journal of Immunology (2014); http://www.jimmunol.org/content/early/2014/07/23/jimmun ol.1400857, pp. 1-8.
Ljubisavljevic, Srdjan et al. "Modulation of nitric oxide synthase by arginase and methylated arginines during the acute phase of experimental multiple sclerosis" Journal of the Neurological Sciences 318 (2012), pp. 106-111.
Hernandez, Luis et al. "Effect of Arginase-1 Inhibition on the Incidence of Autoimmune Diabetes in NOD Mice" Curr Res Diabetes Obes J. (2018) vol. 5(3), pp. 1-13.
Dufait, Ines, et al. "Ex vivo generation of myeloid-derived suppressor cells that model the tumor immunosuppressive environment in colorectal cancer" Oncotarget, Advance Publications (2015), pp. 1-14.
Mondanelli, Giada et al. "A Relay Pathway between Arginine and Tryptophan Metabolism Confers Immunosuppressive Properties on Dendritic Cells" Immunity (2017)vol. 46, pp. 233-244.
Bronte, Vincenzo et al. "IL-4-Induced Arginase 1 Suppresses Alloreactive T Cells in Tumor-Bearing Mice" The Journal of Immunology (2003) vol. 170, pp. 270-278.
Bronte, Vincenzo et al. "Boosting antitumor responses of T lymphocytes infiltrating human prostate cancers" The Journal of Experimental Medicine (2005) vol. 201(8), pp. 1257-1268.
Searafini, Paolo et al. "Phosphodiesterase-5 inhibition augments endogenous antitumor immunity by reducing myeloid-derived suppressor cell function" The Journal of Experimental Medicine (2006) vol. 203(12), pp. 2691-2702.
Zea, Arnold et al. "Arginase-Producing Myeloid Suppressor Cells in Renal Cell Carcinoma Patients: A Mechanism of Tumor Evasion" Cancer Research (2005) vol. 65(8), pp. 3044-3048.
Norian, Lyse A. et al., "Tumor-Infiltrating Regulatory Dendritic Cells Inhibit CD8+T Cell Function via L-Arginine Metabolism" Cancer Research (2009) vol. 69(7), pp. 3086-3094.
Rodriguez, Paulo et al. "Arginase I Production in the Tumor Microenvironment by Mature Myeloid Cells Inhibits T-Cell Receptor Expression and Antigen-Specific T-Cell Responses" Cancer Research (2004) vol. 64, pp. 5839-5849.
Vasquez-Dunddel, David et al. "STAT3 regulates arginase-1 in myeloid-derived suppressor cells from cancer patients" The Journal of Clinical Investigation (2013) vol. 123(4), pp. 1580-1589.
You, Jia et al. "The Oncogenic Role of ARG1 in progression and Metasis of Hepatocellular Carcinoma" BioMed Research International (2018) Article ID2109865, 10 pages.
Arlauckas, Sean et al. "Arg1 expression defines immunosuppressive subsets of tumor-associated macrophages" Theranostics (2018) vol. 8(21), pp. 5842-5854.
Saligan, Leorey N. et al., "Altered Cd8+ T lymphoctye Response Triggered by Arginase 1: Implication for Fatigue Intensification during Localized Radiation Therapy in Prostate Cancer Patients" Neuropsychiatry (2018) vol. 8(4), pp. 1249-1262.
Dunand-Sauthier, Isabelle et al. "Repression of arginase-2 expression in dendritic cells by microRNA-155 is critical for promoting T cell proliferation" The Journal of Immunology (2014) vol. 139(4), pp. 1690-1700.
Mussai, Francis et al. "Neuroblastoma Arginase Activity Creates an Immunosuppressive Microenvironment That Impairs Autologous and Engineered Immunity" Cancer Research (2015) vol. 75(15), pp. 3043-3053.
Secondini, Chiara et al. "Arginase inhibition suppresses lung metastasis in the 4T1 breast cancer model independently of the immunomodulatory and anti-metastatic effects of VEGFR-2 blockade" Oncoimmunology (2017) vol. 6(6), e1316437 (14 pages).
Wallmann, Tatjana et al. "Microglia Induce PDGFRB Expression in Glioma Cells to Enhance Their Migratory Capacity" iScience (2018) vol. 9, pp. 71-83.
Ng, King Pan et al. "The arginase inhibitor Nω-hydroxy-nor-arginine (nor-NOHA) induces apoptosis in leukemic cells specifically under hypoxic conditions but CRISPR/Cas9 excludes arginase 2 (ARG2) as the functional target" PLOS One (2018), pp. 1-19.
Setty, Bhuvana A. et al. "Hypoxic Proliferation of Osteosarcoma Cells Depends on Arginase II" Cell Physiol Biochem (2016) vol. 39, pp. 802-813.
Geiger, Roger et al. "L-Arginine Modulates T Cell Metabolism and Enhances Survival and Anti-tumor Activity" Cell (2016) vol. 167, pp. 829-842.
Brittenden, J. et al. "Dietary supplementation with L-arginine in patients with breast cancer (> 4 cm) receiving multimodality treatment: report of a feasibility study" Cancer (1994) vol. 69, pp. 918-921.
Zhang, Cuihua et al. "Upregulation of Vascular Arginase in Hypertension Decreases Nitric Oxide-Mediated Dilation of Coronary Arterioles" Hypertension (2004) vol. 44, pp. 935-943.
Crittenden, Marka R. et al. "Expression of Arginase I in Myeloid Cells Limits Control of Residual Disease after Radiation Therapy of Tumors in Mice" Radiation Research (2014) vol. 182, pp. 182-190.
Zaytouni, Tamara et al. "Critical role for arginase 2 in obesity-associated pancreatic cancer" Nature Communication (2017) vol. 8(242), pp. 1-12.
Rodriguez, Paulo C. et al. "Regulation of T Cell Receptor CD3ς Chain Expression by L-Arginine" The Journal of Biological Chemistry (2002) vol. 277(24), pp. 21123-21129.
Sharda, Daniel R. et al. "Regulation of Macrophage Arginase Expression and Tumor Growth by the Ron Receptor Tyrosine Kinase" The Journal of Immunology (2011) vol. 187, pp. 1-13.
Ino, Yoshinori et al. "Arginase II Expressed in Cancer-Associated Fibroblasts Indicates Tissue Hypoxia and Predicts Poor Outcome in Patients with Pancreatic Cancer" PLOS One (2013) vol. 8(2), p. e55146, 14 pages.
Wim, Leonard et al. "Myeloid-derived suppressor cells reveal radioprotective properties through arginase-induced L-arginine depletion" Radiotherapy and Oncology (2016) http://dx.doi.org/10.1016/j.radonc.2016.01.014., pp. 1-9.
Miret, Juan J. et al. "Suppression of Myeloid Cell Arginase Activity leads to Therapeutic Response in a NSCLC Mouse Model by Activating Anti-Tumor Immunity" Journal for ImmunoTherapy of Caner (2019) vol. 7(32), pp. 1-12.
Czystowska-Kuzmicz, Malgorzata et al. "Small extracellular vesicles containing arginase-1 suppress T-cell responses and promote tumor growth in ovarian carcinoma" Nature Communications (2019) vol. 10(3000), pp. 1-16.
Singh, Rajan et al. "Arginase Activity in Human Breast Cancer Cell Lines: Nω-Hydroxy-L-arginine Selectively Inhibits Cell Proliferation and Induces Apoptosis in MDA-MB-468 Cells1" Cancer Research (2000) vol. 60, pp. 3305-3312.

(56) References Cited

OTHER PUBLICATIONS

Secondini, Chiara et al. "Arginase inhibition suppresses lung metastasis in the 4T1 breast cancer model independently of the immunomodulatory and anti-metastatic effects of VEGFR-2 blockade" Oncoimmunology (2017) DOI: 10.1080/2162402X.2017. 1316437, pp. 1-38.
Rigamonti, Nicolo et al. "Modulators of Arginine Metabolism Do Not Impact on Peripheral T-Cell Tolerance and Disease Progression in a Model of Spontaneous Prostate Cancer" Clinical Cancer Research (2011) vol. 17(5), pp. 1012-1023.
Sippel, Trisha R. et al. "Neutrophil Degranulation and Immunosuppression in Patients with GBM: Restoration of Cellular Immune Function by Targeting Arginase I" Clinical Cancer Research (2011) vol. 17(22), pp. 6992-7002.
Ahammad, Ishtiaque "Protein-Protein Interaction Network Analysis and Identification of Key Players in nor-NOHA and NOHA Mediated Pathways for Treatment of Cancer through Arginase Inhibition: Insights from Systems Biology" Preprints 2018, 2018030213 (doi: 10.20944/preprints201803.0213.v1).
Mussai, Francis et al. "Acute myeloid leukemia creates an arginase-dependent immunosuppressive microenvironment" Blood (2013) vol. 122(5), pp. 749-758.
Xu, Weiling et al. "Increased arginase II and decreased NO synthesis in endothelial cells of patients with pulmonary arterial hypertension" The FASEB Journal express article 10.1096/fj.04-2317fje. Published online Sep. 13, 2004, pp. 1-23.
Ogino, Keiki et al. "Anti-inflammatory Effect of Arginase Inhibitor and Corticosteroid on Airway Allergic Reactions in a Dermatophogoides farinae-induced NC/Nga Mouse Model" Inflammation (2013) vol. 36(1), pp. 141-151.
Zimmermann, Nives et al. "Dissection of experimental asthma with DNA microarray analysis identifies arginase in asthma pathogenesis" The Journal of Clinical Investigation (2003) vol. 111(12), pp. 1863-1874.
Maarsingh, Harm et al. "Arginase Inhibition Protects against Allergen-induced Airway Obstruction, Hyperresponsiveness, and Inflammation" American Journal of Respiratory and Critical Care Medicine (2008) vol. 178, pp. 565-573.
Meurs, Herman et al. "Increased arginase activity underlies allergen-induced deficiency of cNOS-derived nitric oxide and airway hyper-responsiveness" British Journal of Pharmacology (2002) vol. 136, pp. 391-398.
North, Michelle L. et al. "Arginase in Asthma—Recent Developments in Animal and Human Studies" The Open Nitric Oxide Journal (2010) vol. 2, pp. 20-36.
Ckless, Karina et al. "Inhibition of Arginase Activity Enhances Inflammation in Mice with Allergic Airway Disease, in Association with Increases in Protein S-Nitrosylation and Tyrosine Nitration1" The Journal of Immunology (2008) vol. 181, pp. 4255-4264.
Pera, T. et al. "Arginase Inhibition Prevents Inflammation and Remodeling in a Guinea Pig Model of Chronic Obstructive Pulmonary Disease" The Journal of Pharmacology and Experimental Therapeutics (2014) vol. 349, pp. 229-238.
Jaecklin, Thomas et al. "Lung arginase expression and activity is increased in cystic fibrosis mouse models" J Appl Physiol (2014) vol. 117, pp. 284-288.
Mehl, Anne et al. "Effect of Arginase Inhibition on Pulmonary L-Arginine Metabolism in Murine Pseudomonas Pneumonia" PLOS One (2014) vol. 9(3): e90232. doi:10.1371/journal.pone.0090232.
Arikan-Ayyildiz, Z. et al. "Beneficial effects of arginase inhibition and inhaled L-arginine administration on airway histology in a murine model of chronic asthma" Allergol Immunopathol Madr (2013), pp. 1-8; http://dx.doi.org/10.1016/j.aller.2013.01.001.
Salam, Muhammad T. et al. "Roles of arginase variants, atopy, and ozone in childhood asthma" J Allergy Clin Immunol (2009) vol. 123, pp. 596-602.
Henno, Priscilla et al. "Is arginase a potential drug target in tobacco-induced pulmonary endothelial dysfunction?" Respiratory Research (2015) vol. 16:46, 8 pages.
Kavalukas, Sandra L. et al. "Arginase inhibition promotes wound healing in mice" Surgery (2012) vol. 151, pp. 287-295.
The Written Opinion of the International Searching Authority for PCT/US2019/21247 dated Aug. 1, 2019, pp. 1-5.
Yang, Jiangning et al. "Red Blood Cells in Type 2 Diabetes Impair Cardiac Post-Ischemic Recovery Through an Arginase-Dependent Modulation of Nitric Oxide Synthase and Reactive Oxygen Species" JACC: Basic to Translational Science (2018) vol. 3(4), pp. 450-463.
Cowburn, Andrew S. et al. "HIF2α-arginase axis is essential for the development of pulmonary hypertension" PNAS (2016) vol. 113(31), pp. 8801-8806.
Grasemann, Hartmut et al. "Arginase inhibition prevents bleomycin-induced pulmonary hypertension, vascular remodeling, and collagen deposition in neonatal rat lungs" Am J Physiol Lung Cell Mol Physiol (2015) vol. 308, pp. L503-L-510.
Zhang, Yiming et al. "Hepatic arginase 2 (Arg2) is sufficient to convey the therapeutic metabolic effects of fasting" Nature Communications (2019) vol. 10(1587), pp. 1-16.
Lacchini, Riccardo et al. "Relationship between Arginase 1 and Arginase 2 levels and genetic polymorphisms with erectile dysfunction" Nitric Oxide 51 (2015), pp. 36-42.
Koo, Bon-Hyeock et al. "Arginase II inhibition prevents interleukin-8 production through regulation of p38 MAPK phosphorylation activated by loss of mitochondrial membrane potential in nLDL-stimulated hAoSMCs" Experimental & Molecular Medicine (2018) vol. 50, pp. 1-11.
Kudryavtsev, K.V. et al."Pharmacological Efficacy of an Inhibitor of Arginase-2 KUD975 with L-Name-Induced Endothelial Dysfunction" Pharmacology and Clinical Pharmacology (2017) vol. 3(1), pp. 10-17.
Elagin, Vladislav et al. "Correction of morphofunctional disorders with asialoerythropoietin and selective inhibitor of arginase II KUD975 in cases of ischemic kidney damage in the experiment" Research Results in Pharrmacology (2018) vol. 4(4), pp. 29-40.
Korokin, Mikhail V. et al. "The compounds of phenolic nature—new opportunities for pharmacological correction of endothelial dysfunction." International Journal of Advanced Biotechnology and Research (2016) vol. 7(3), pp. 1115-1118.
Ming, Xiu-Fen et al. "Arginase II Promotes Macrophage Inflammatory Responses Through Mitochondrial Reactive Oxygen Species, Contributing to Insulin Resistance and Atherogenesis" Journal of the American Heart Association (2012), pp. 1-18.
El-Bassossy, Hany M. et al. "Arginase inhibition alleviates hypertension in the metabolic syndrome" British Journal of Pharmacology (2013) vol. 169, pp. 639-703.
Ryoo, Sungwoo et al. "Endothelial Arginase II—A Novel Target for the Treatment of Atherosclerosis" Circulation Research (2008) vol. 102, pp. 923-932.
Bagnost, Teddy et al. "Cardiovascular effects of arginase inhibition in spontaneously hypertensive rats with fully developed hypertension" Cardiovascular Research (2010) vol. 87, pp. 569-577.
Pernow, John et al. "Arginase as a potential target in the treatment of cardiovascular disease: reversal of arginine steal?" Cardiovascular Research (2013) vol. 98, pp. 334-343.
Pillai, Samyuktha Muralidharan et al. "Kidney Mass Reduction Leads to L-Arginine Metabolism-Dependent Blood Pressure Increase in Mice" Journal of the American Heart Association (2018) vol. 7, pp. 1-15.
Jung, Christian et al. "Arginase Inhibition Reverses Monocrotaline-Induced Pulmonary Hypertension" International Journal of Molecular Sciences (2017) vol. 18(1609), 13 pages.
Schlüter, Klaus-Dieter et al. "Arginase induction and activation during ischemia and reperfusion and functional consequences for the heart" Frontiers in Physiology (2015) vol. 6, Article 65, pp. 1-8.
Morris, Claudia R. et al. "Role of Arginase in Sickle Cell Lung Disease and Hemolytic Anemias" The Open Nitric Oxide Journal (2010) vol. 2, pp. 41-54.
Segal, Robert et al. "Chronic Oral Administration of the Arginase Inhibitor 2(S)-amino-6-boronohexanoic Acid (ABH) Improves Erectile Function in Aged Rats" Journal of Andrology (2012) vol. 33(6), pp. 1169-1175.

(56) References Cited

OTHER PUBLICATIONS

Tratsiakovich, Yahor et al. "Arginase as a target for treatment of myocardial ischemia-reperfusion injury" European Journal of Pharmacology 720 (2013), pp. 121-123.
Iyamu, Efemwonkiekie W. et al. "Modulation of erythrocyte arginase activity in sickle cell disease patients during hydroxyurea therapy" British Journal of Haematology (2005) vol. 131, pp. 389-394.
Koo, Bon-Hyeock et al. "Arginase II Contributes to the Ca2+/CaMKII/eNOS Axis by Regulating Ca2+ Concentration Between the Cytosol and Mitochondria in a p32-Dependent Manner" Journal of the American Heart Association (2018) DOI: 10.1161/JAHA.118.009579, 27 pages.
Van Zandt, Michael C. et al. "Discovery of (R)-2-Amino-6-borono-2-(2-(piperidin-1-yl)ethyl)hexanoic Acid and Congeners as Highly Potent Inhibitors of Human Arginases I and II for Treatment of Myocardial Reperfusion Injury" Journal of Medicinal Chemistry (2013) vol. 56, pp. 2568-2580.
Morris, Claudis R. et al. "Dysregulated Arginine Metabolism, Hemolysis-Associated Pulmonary Hypertension, and Mortality in Sickle Cell Disease" JAMA (2005) vol. 294(1), pp. 81-90.
Gonon, Adrian T. et al. "Local Arginase Inhibition during Early Reperfusion Mediates Cardioprotection via Increased Nitric Oxide Production" PLoS ONE (2012), vol. 7(7): e42038. doi:10.1371/journal.pone.0042038.
Pokrovskii, M.V. et al. "Study of Endothelial Protective Activity of Phenol-Derived Thrombin and Arginase-2 Inhibitors KUD-259 and KUD-974" Bulletin of Experimental Biology and Medicine (2017) vol. 163(4), pp. 436-438.
Mahdi, Ali et al. "Arginase inhibition improves endothelial function in an age-dependent manner in healthy elderly humans" downloaded by Tulane University from www.liebertpub.com at Dec. 20, 2018.(DOI: 10.1089/rej.2018.2135).
Morris, Claudis R. et al. "Dysregulated Arginine Metabolism, Hemolysis-Associated Pulmonary Hypertension, and Mortality in Sickle Cell Disease" JAMA Author Manuscript (2005), pp. 1-22.
Steppan, Jochen et al. "Arginase Inhibition Reverses Endothelial Dysfunction, Pulmonary Hypertension and Vascular Stiffness in Transgenic Sickle Cell Mice" Anesth Analg. Author manuscript (2017), 16 pages.
Peyton, Kelly J. et al. "Arginase Inhibition Prevents the Development of Hypertension and Improves Insulin Resistance in Obese Rats" Amino Acids. Author manuscript (2019), pp. 1-16.
Olivon, Vania C. et al. "Arginase inhibition prevents the low shear stress-induced development of vulnerable atherosclerotic plaques in ApoE −/− mice" Atheroslerosis 227 (2013) pp. 236-243.
Yang, Jiangning et al. "Arginase regulates red blood cell nitric oxide synthase and export of cardioprotective nitric oxide bioactivity" PNAS (2013) vol. 110(37) pp. 15049-15054.
Kovamees, Oskar et al. "Effect of Arginase Inhibition on Ischemia-Reperfusion Injury in Patients with Coronary Artery Disease with and without Diabetes Mellitus" PLOS One (2014) vol. 9(7), e103260.
Fouda, Abdelrahman Y. et al. "Arginase 1 promotes retinal neurovascular protection from ischemia through suppression of macrophage inflammatory responses" Cell Death & Disease (2018) vol. 9:1001, 15 pages.
Sandqvist, Anna et al. "Plasma l-arginine levels distinguish pulmonary arterial hypertension from left ventricular systolic dysfunction" Heart Vessels (2018) vol. 33, pp. 255-263.
Telen, Marilyn J. et al. "Therapeutic strategies for sickle cell disease: towards a multi-agent approach" Nature Reviews Drug Discovery (2019) vol. 18, pp. 139-158.
Telem, D. et al. "The Evaluation of Arginase Activity During Acute Vasoocclusive Sickle Cell Crisis" Annals of Emergency Medicine (2004) vol. 44(4) p. S56.
Grasemann, Hartmut et al. "Increased Arginase Activity in Cystic Fibrosis Airways" American Journal of Respiratory and Critical Care Medicine (2005) vol. 172, pp. 1523-1528.
Van Den Berg, Mariska PM et al. "Targeting arginase and nitric oxide metabolism in chronic airway diseases and their co-morbidities" Current Opinion in Pharmacology (2018) vol. 40, pp. 126-133.
Henno, Priscilla et al. "Is arginase a potential drug target in tobacco-induced pulmonary endothelial dysfunction?" Respiratory Research (2015) vol. 16:46, doi:10.1186/s12931-015-0196-4.
Morris, Claudia R. et al. "Decreased Arginine Bioavailability and Increased Serum Arginase Activity in Asthma" Am J Respir Crit Care Med (2004) vol. 170, pp. 148-153.
Maarsingh, Harm et al. "Arginase and pulmonary diseases" Naunyn-Schmiedberg's Arch Pharmacol (2008) vol. 378, pp. 171-184.
Maarsingh, H. et al. "Increased arginase activity contributes to airway remodelling in chronic allergic asthma" European Respiratory Journal (2011) vol. 38(2), pp. 318-328.
Arikan-Ayyildiz, Z. et al. "Beneficial effects of arginase inhibition and inhaled I-arginine administration on airway histology in a murine model of chronic asthma" Allergol Immunopathol Madr (2014) vol. 42(4), pp. 316-323.
Maarsingh, Harm et al. "Arginase attenuates inhibitory nonadrenergic noncholinergic nerve-induced nitric oxide generation and airway smooth muscle relaxation" Respiratory Research (2005) vol. 6(23) 6 pages.
North, Michelle L. et al. "Augmentation of arginase 1 expression by exposure to air pollution exacerbates the airways hyperresponsiveness in murine models of asthma" Respiratory Research (2011) vol. 12(19), 14 pages.
Aristoteles, Luciana RCRB et al. "Modulation of the oscillatory mechanics of lung tissue and the oxidative stress response induced by arginase inhibition in a chronic allergic inflammation model" BMC Pulmonary Medicine (2013) vol. 13:52, 13 pages.
North, Michelle L. et al. "Examining the role of arginase in air pollutioninduced exacerbation of asthma" Allergy, Asthma & Clinical Immunology (2010) vol. 6(Suppl 3):p. 5.
Ingersoll, Sarah A. et al. "Mature Cystic Fibrosis Airway Neutrophils Suppress T Cell Function: Evidence for a Role of Arginase 1 but Not Programmed Death-Ligand 1" The Journal of Immunology (2015) vol. 194, pp. 5520-5528.
North, Michelle L. et al. "Functionally important role for arginase 1 in the airway hyperresponsiveness of asthma" American Journal of Physiology Lung Cellular and Molecular Physiology (2009) vol. 296, pp. L911-L920.
Sterggerda, Susanne, et al, "Inhibition of arginase by CB-1158 blocks myeloid cell-mediated immune suppression in the tumor microenvironment", Journal for ImmunoTherapy of Cancer (2017) 5:101.
Crittenden, Marka et al, "Expression of Arginase I in Myeloid Cells Limits Control of Residual Disease after Radiation Therapy of Tumors in Mice," Radiation Research 182, 182-190 (2014).
Dufait, Ines, et al., "Ex vivo generation of myeloid-derived suppressor cells that model the tumor immunosuppressive environment in colorectal cancer", www.impactjournals.com/oncotarget/ Oncotarget, Advance Publications 2015.
Miret, Juan et al., "Suppression of Myeloid Cell Arginase Activity leads to Therapeutic Response in a NSCLC Mouse Model by Activating Anti-Tumor Immunity", Miret et al. Journal for ImmunoTherapy of Cancer (2019) 7:32 https://doi.org/10.1186/s40425-019-0504-5.
Rodriguez, Paulo C., "Arginase I Production in the Tumor Microenvironment by Mature Myeloid Cells Inhibits T-Cell Receptor Expression and Antigen-Specific T-Cell Responses", Cancer Research 64, 5839-5849, Aug. 15, 2004.
Rodriguez, Paulo C., "Regulation of T Cell Receptor CD3t Chain Expression by L-Arginine", The Journal of Biological Chemistry vol. 277, No. 24, Issue of Jun. 14, pp. 21123-21129, 2002.
Zaytouni, Tamara, et al., "Critical role for arginase 2 in obesity-associated pancreatic cancer", Nature Comm 8:242, 2017, 1-12.

DIPEPTIDE PIPERIDINE DERIVATIVES

CROSS-REFERENCE TO RELATED APPLICATION

This application claims priority to U.S. Provisional Application No. 62/649,752, filed Mar. 29, 2018, and to Polish Patent Application No. P.425077, filed Mar. 29, 2018, the disclosures of which are hereby incorporated by reference in their entirety.

BACKGROUND OF THE INVENTION

Field of the Invention

The disclosure relates to small molecule therapeutic inhibitors of arginase 1 and arginase 2.

Description of Related Art

Two arginase isozymes, arginase 1 and arginase 2 (denoted also as ARG1 and ARG2) exist in mammals. Both enzymes catalyze the same biochemical reaction (hydrolysis of L-arginine into L-ornithine and urea), but they differ in cellular expression level, regulation and subcellular localization. ARG1 is a cytosolic protein and ARG2 is mainly localized in mitochondria.

The arginases are implicated in various pathological states. These include, without limitation: asthma, pulmonary hypertension, hypertension, T cell dysfunction, erectile dysfunction, atherosclerosis, renal disease, ischemia reperfusion injury, neurodegenerative diseases, wound healing, inflammatory diseases, fibrotic diseases and cancer.

Arginase expression and L-arginine depletion is known as an important immune-suppressive pathway of the mammalian immune system. L-arginine deficiency down-regulates expression of T cell receptor (TCR) chain, a key signaling element of the TCR, thereby impairing T cell function. Depletion of L-arginine from the tumor microenvironment leads to an arrest in T cell cycle progression, inhibition of IFN-γ production, and blocking of signaling through the T cell receptor.

Arginases are mainly produced by myeloid-derived suppressor cells (MDSC) that are highly enriched in the tumor-bearing state. Induction of the arginase pathway is an important mechanism involved in the evasion of the anti-tumor immunity. High arginase activity has been observed in patients with various malignancies, both in blood and within tumor mass.

It was shown that T cell functions are restored and tumor growth is inhibited upon inhibition of arginase produced by tumor-associated MDSCs or tumor-infiltrating CD11b$^+$Gr-1$^-$ mature myeloid cells in various murine tumor models. Depletion of the myeloid suppressor cells re-establishes T cell activation regulated by TCR and costimulatory signals.

Arginase was shown to participate in the suppression of tumor-infiltrating lymphocytes in patients with prostate carcinoma, non-small cell lung carcinoma and multiple myeloma. Not only MDSC but also dendritic cells (DCs) have been shown to suppress CD8$^+$ T cells and antitumor immune responses through ARG1 production.

The pathological role of arginase was also revealed in sickle cell disease (SCD), which is an L-arginine deficiency syndrome. Since ARG1 is present in human erythrocytes, in SCD patients it is aberrantly released in active form into plasma resulting in the impaired metabolism of L-arginine. Moreover, arginase together with hemoglobin, both released during the intravascular hemolysis, cause an abnormally high NO consumption leading to the diminished NO bioavailability. Clinically, the hemolysis and altered L-arginine metabolism contribute to the development of various SCD-related complications, i.e.: endothelial dysfunction, vaso-occlusion, pulmonary hypertension, priapism, cutaneous leg ulceration, stroke, renal dysfunction, asthma, and—ultimately—early mortality. Hence, arginase inhibitors represent a group of very promising drug candidates for the treatment of SCD.

Given the role of arginase in various pathological states and their role in chronic inflammation and suppression of anti-tumor immunity, the present invention provides novel boron-containing compounds as inhibitors of arginase activity, as well as methodologies for using these compounds as therapeutics.

Numerous boron-containing arginase inhibitors are well-known from the literature. One of such inhibitors is 2(S)-amino-6-boronohexanoic acid, as described in WO 99/19295A1, published on Apr. 22, 1999 (incorporated by reference), and in WO 08/061612A1, published on May 29, 2008 (incorporated by reference). Besides, WO 11/133653, published on Oct. 27, 2011 (incorporated by reference), and WO 13/059437, published on Apr. 25, 2013 (incorporated by reference), describe a number of alphα-amino acid derivatives bearing a terminal B(OH)$_2$ group and a spacer, usually being a 1,3-cyclobutylene moiety. Mono- or polycyclic boron-containing amino acid compounds suitable as arginase inhibitors are described in WO 12/058065, published on May 3, 2012 (incorporated by reference). Other related patent application publications are WO 10/085797 of Jul. 29, 2010 (incorporated by reference), WO 13/158262 of Oct. 24, 2013 (incorporated by reference), and WO 12/091757 of Jun. 5, 2012 (incorporated by reference).

Significance of the substitution at the alpha center of 2-amino-6-boronohecanoic acid for the inhibitory potency of arginase 1 and arginase 2 inhibitors has been discussed.

There is a need to investigate the inhibition of arginases, and to discover treatments for conditions associated with elevated expression of arginases, such as asthma and allergic responses. In particular, there is a need to explore new molecular scaffolds that effectively inhibit arginases and, therefore, can act as therapeutic agents for the treatment of these conditions.

SUMMARY OF THE INVENTION

In one aspect, the invention provides compounds represented by Formula (I):

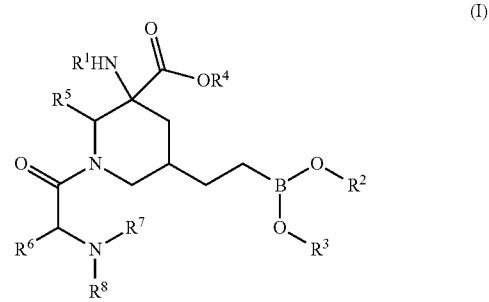

wherein:
R¹ is selected from the group consisting of H, straight-chain or branched ($C_1$-$C_6$)alkyl, HC(O)—, and ($C_1$-$C_6$) alkyl-C(O)—;
R² and R³ are each independently selected from hydrogen, straight-chain or branched ($C_1$-$C_6$)alkyl and ($C_1$-$C_6$) alkyl-C(O)—,
or R² and R³ taken together with the boron atom and oxygen atoms to which they are bound form a 4-, 5-, 6- or 7-membered ring that is fully saturated, or partially saturated,
or R² and R³ taken together with the boron atom and oxygen atoms to which they are bound form a diester of the boronic acid and polyalcohols selected from (but not limited to): pinanediol, mannitol, glycerol, xylitol, sorbitol, and erythritol,
or R² and R³ taken together with the boron atom and oxygen atoms to which they are bound form an anhydride or mixed ester-anhydride of the boronic acid and hydroxy acids or di-carboxylic acids selected from (but not limited to): iminodiacetic acid or N-methyliminodiacetic acid or oxalic acid or tartaric acid or citric acid or malic acid or malonic acid or mandelic acid or glycolic acid or lactic acid or 3-hydroxypropionic acid;
R⁴ is selected from the group consisting of H and straight-chain or branched ($C_1$-$C_6$)alkyl;
R⁵ is selected from the group consisting of H, F, methyl, ethyl, propyl, isopropyl, —$CH_2NH_2$, —$CH_2NHCH_3$, —$CH_2NHCH_2CH_3$, —$CH_2NHCH(CH_3)_2$, —$CH_2N(CH_3)_2$, —$CH_2N(CH_3)CH_2CH_3$, —$CH_2N(CH_2CH_3)_2$, —$CH_2N(CH_3)CH(CH_3)_2$, —$CH_2$— azetidinyl, —$CH_2$-pyrrolidinyl, and —$CH_2$-piperidinyl;
R⁶ is selected from the amino acid side chains of Gly, Ala, Val, Ser, Phe, Lys, Thr, Met, Tyr, His, Asp, Glu, Asn, Gln, Cys, Sec, Ile, Leu, Arg, Orn, Cit, Trp, 1-Me-Trp and Nva; and
R⁷ and R⁸ are each independently selected from hydrogen and methyl, or R⁷ is H and R⁶ and R⁸ together with the nitrogen atom carrying R⁸ form a pyrrolidine ring (proline side chain);
or a pharmaceutically acceptable salt thereof.

In another aspect, the invention provides compounds that are useful as intermediates in the preparation of compounds of formula I.

Also provided herein are pharmaceutical compositions, comprising (i) a therapeutically effective amount of at least one compound of the invention, or a pharmaceutically acceptable salt thereof; and (ii) a pharmaceutically acceptable carrier, including, but not limited to, bioavailability enhancers, penetration enhancers, biopolymers, PLGA-based nanoparticles, sugar-based nanoparticles, coating to avoid the deleterious effects of the stomach environment, either by protection of the compound of the invention or derivative thereof, or by release of the biologically active material beyond the stomach environment, such as in the intestine.

In another aspect, the invention provides a method for inhibiting arginase 1, arginase 2, or a combination thereof in a cell, comprising contacting the cell with at least one compound according to the invention, or a pharmaceutically acceptable salt thereof.

In another aspect, the invention provides a method for the treatment or prevention of a disease or condition associated with expression or activity of arginase 1, arginase 2, or a combination thereof in a subject, comprising administering to the subject a therapeutically effective amount of at least one compound according to the invention, or a pharmaceutically acceptable salt thereof.

In another aspect, the invention provides use of a compound according to the invention, or a pharmaceutically acceptable salt thereof in the manufacture of a medicament for the treatment or prevention of a disease or condition associated with expression or activity of arginase 1, arginase 2, or a combination thereof.

In another aspect, the invention provides a compound according to the invention, or a pharmaceutically acceptable salt thereof for the treatment or prevention of a disease or condition associated with expression or activity of arginase 1, arginase 2, or a combination thereof.

In another aspect, the invention provides use of a compound according to the invention, or a pharmaceutically acceptable salt thereof, for protecting an organ during transport.

In a further aspect, a process for manufacturing a compound of Formula I or a pharmaceutically acceptable salt thereof is provided.

DETAILED DESCRIPTION

Figure 1:
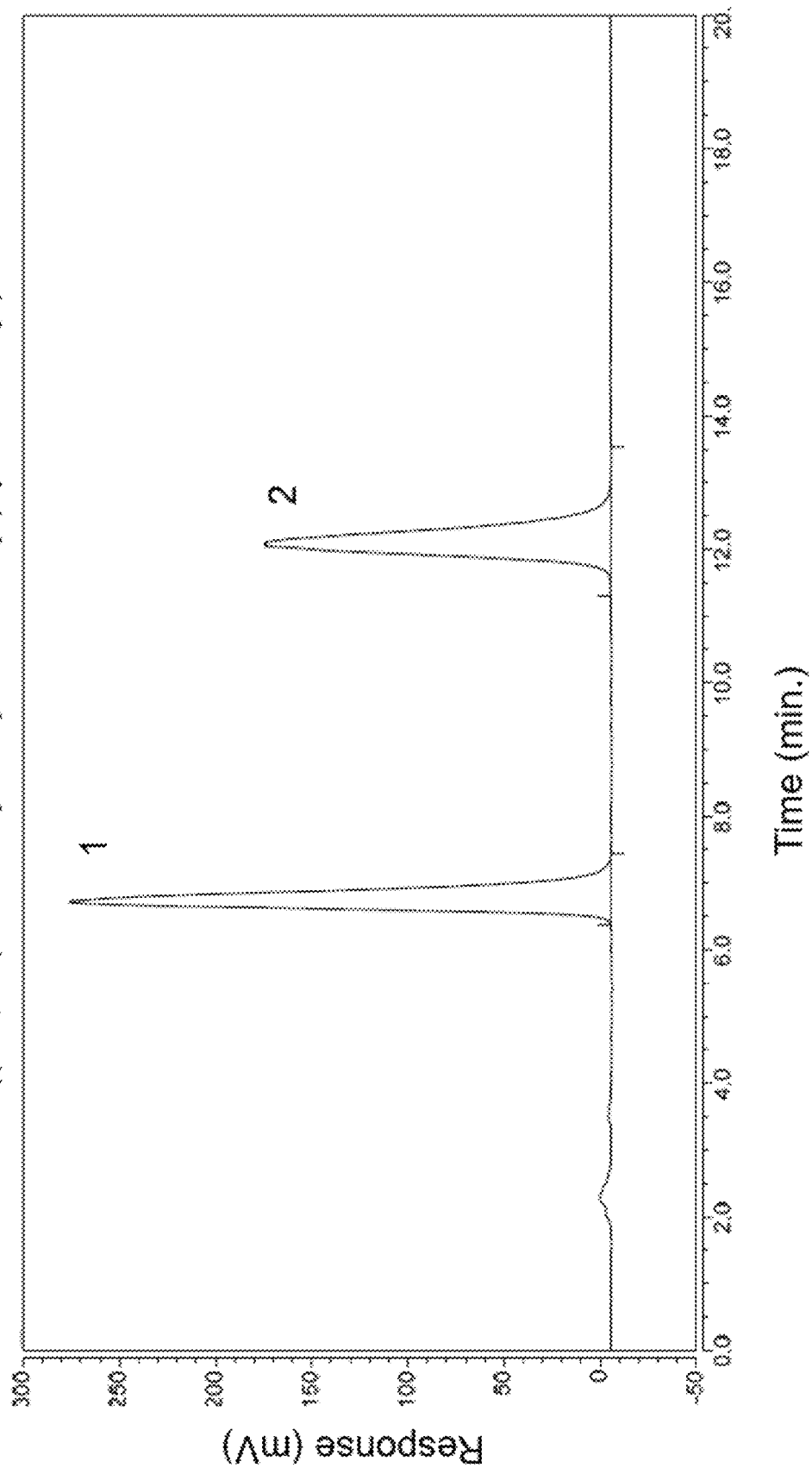
FIG. 1 is a chromatogram indicating certain compounds described herein. See Example 29; Table 3)

The present invention is based on a surprising finding that some small molecule arginase inhibitors possess very high activity accompanied by superior pharmacokinetics.

Definitions

The articles "a" and "an" are used herein to refer to one or to more than one (i.e., to at least one) of the grammatical object of the article. By way of example, "an element" means one element or more than one element.

The terms used herein may be preceded and/or followed by a single dash "—", or a double dash "=", to indicate the bond order of the bond between the named substituent and its parent moiety; a single dash indicates a single bond and a double dash indicates a double bond. In the absence of a single or double dash, it is understood that a single bond is formed between the substituent and its parent moiety; further, substituents are intended to be read "from left to right," unless a dash indicates otherwise. For example, ($C_1$-$C_6$)-alkoxycarbonyloxy and —OC(O)O($C_1$-$C_6$)alkyl indicate the same functionality; similarly arylalkyl and -alkylaryl indicate the same functionality.

The term "heteroatom" is art-recognized and refers to an atom of any element other than carbon or hydrogen. Illustrative heteroatoms include boron, nitrogen, oxygen, phosphorus, sulfur and selenium.

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, 10 or fewer, or preferably 1-6 carbons. Representative examples of alkyl include, but are not limited to, methyl, ethyl, n-propyl, isopropyl, n-butyl, sec-butyl, isobutyl, tert-butyl, n-pentyl, isopentyl, neopentyl, and n-hexyl.

The term "cycloalkyl" means mono- or bicyclic or bridged saturated or partially saturated carbocyclic rings, each having from 3 to 12 carbon atoms. Certain cycloalkyls have from 3-8, or from 3-6 carbon atoms in their ring structure. Certain cycloalkyls have from 5-12 carbon atoms in their ring structure, and may have 6-10 carbon atoms in the ring structure. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems include bridged monocyclic rings and fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted.

The term "heterocyclyl" as used herein refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 14, or 3 to 12 atoms including at least one heteroatom, such as nitrogen, oxygen, or sulfur. More preferred heterocycloalkyl groups have from 5-10 ring members where from 1-4 of the ring members are hetero atoms selected from the group consisting of 0, N, and S, the remaining ring atoms being C. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinicludinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocyclyl group is optionally substituted by one or more substituents as described below.

As used herein, the term "heterocyclylene" refers to a bivalent heterocyclyl (heterocycloalkyl) group, i.e., a cyclic alkylene group, having from 3-10 members and from 1-4 hetero atoms selected from S, O, and N. An example is piperidine-2,3-dicarboxylic acid, i.e., in that compound, the piperidine ring is a heterocyclyl group.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "cycloalkylalkyl" as used herein refers to an alkyl group substituted with one or more cycloalkyl groups.

The term "heterocycloalkylalkyl" as used herein refers to an alkyl group substituted with one or more heterocycloalkyl heterocyclyl) groups.

The term "alkenyl" as used herein means a straight-chain or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s).

The term "alkynyl" as used herein means a straight-chain or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

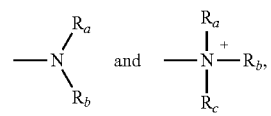

wherein $R_a$, $R_b$, and $R_c$ each independently represent a hydrogen, an alkyl, an alkenyl, —$(CH_2)_x$—$R_d$, or $R_a$ and $R_b$, taken together with the N atom to which they are attached complete a heterocycle having from 4 to 8 atoms in the ring structure; $R_d$ represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or —$(CH_2)_x$—$R_d$. In certain embodiments, the term "amino" refers to —$NH_2$.

The term "amido", as used herein, means —NHC(=O)—, wherein the amido group is bound to the parent molecular moiety through the nitrogen. Examples of amido include alkylamido such as $CH_3C$(=O)N(H)— and $CH_3CH_2C$(=O)N(H)—.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of art and as used herein refers to an acyl group substituted with one or more amino groups.

The term "azide" or "azido", as used herein, means an —$N_3$ group.

The term "carbonyl" as used herein refers to —C(=O)—.

The term "thiocarbonyl" as used herein refers to —C(=S)—.

The term "alkylthio" as used herein refers to alkyl-S—.

The term "carboxy", as used herein, means a —$CO_2H$ group.

The term "aryl" is a term of art and as used herein refers to includes monocyclic, bicyclic and polycyclic aromatic hydrocarbon groups, for example, benzene, naphthalene, anthracene, 1,2,3,4-tetrahydronaphthalene, indene, 2,3-dihydroindene, and pyrene. The aromatic ring may be substituted at one or more ring positions with one or more substituents, such as halogen, azide, alkyl, aralkyl, alkenyl, alkynyl, cycloalkyl, cycloalkylalkyl, (cycloalkyl)alkoxyl, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocyclyl, heterocyclylalkyl, aromatic or heteroaromatic moieties, aminoalkyl, haloalkyl, fluoroalkyl (such as trifluoromethyl), haloalkoxyl, cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. Representative examples of the polcyclic aryl ring systems include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-6-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl, or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted. In certain embodiments, the term "aryl" refers to a phenyl group.

The term "heteroaryl" is a term of art and as used herein refers to a monocyclic, bicyclic, and polycyclic aromatic group having 3 to 14, 5 to 14, or 3 to 12 total atoms including one or more heteroatoms such as nitrogen, oxygen, or sulfur in the ring structure. More preferred heteroaryl groups have from 5-10 ring members where from 1-4 of the ring members are hetero atoms selected from the group consisting of O, N, and S. Exemplary heteroaryl groups include, for example, azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. Any heteroaryl or bicyclic heteroaryl can be optionally substituted as detailed below.

The term "aralkyl", "arylalkyl", or "aryl($C_1$-$C_6$)alkyl" is a term of art and as used herein refers to an alkyl group, for example a $C_1$-$C_6$ alkyl group, substituted with an aryl group, wherein the moiety is appended to the parent molecule through the alkyl group.

The term "heteroaralkyl", "heteroarylalkyl", or "heteroaryl($C_1$-$C_6$)alkyl" is a term of art and as used herein refers to an alkyl group, for example a $C_1$-$C_6$ alkyl group, substituted with a heteroaryl group, appended to the parent molecular moiety through the alkyl group.

The term "alkoxy" or "alkoxyl" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein. Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2$=CH—$CH_2$—O—) and vinyloxy $CH_2$=CH—O—).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The terms "cyano" and "nitrile" are a term of art and as used herein refer to —CN.

The term "nitro", as used herein, means —$NO_2$.

The term "halo" is a term of art and as used herein refers to —F, —Cl, —Br, or —I.

The term "haloalkyl" as used herein refers to an alkyl group, as defined herein, wherein some or all of the hydrogens are replaced with halogen atoms. The term "haloalkoxyl" refers to an alkoxy group, as defined herein, wherein some or all of the hydrogens are replaced with halogen atoms. An exemplary haloalkyl group is trifluoromethyl.

The term "hydroxy" is a term of art and as used herein refers to —OH.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "silyl", as used herein, includes hydrocarbyl derivatives of the silyl ($H_3$Si—) group (i.e., (hydrocarbyl)$_3$Si—), wherein hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy", as used herein, means a silyl group, as defined herein, is appended to the parent molecule through an oxygen atom.

As used herein, the term "the amino acid side chains of Gly, Ala, Val, Ser, Phe, Lys, Thr, Met, Tyr, His, Asp, Glu, Asn, Gln, Cys, Sec, Ile, Leu, Arg, Orn, Cit, Trp, 1-Me-Trp and Nva" refers to the moiety $R_{aa}$ in the formula shown below

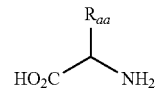

wherein $R_{aa}$ is hydrogen, methyl, sec-butyl, isobutyl, isopropyl, propyl, benzyl, 1H-indol-3-ylmethyl, 1-methyl-1H-indol-3-ylmethyl, 4-hydroxybenzyl, carboxymethyl, carboxyethyl, 3-guanidinopropyl, 1H-imidazol-4-ylmethyl, 4-aminobutyl, hydroxymethyl, 2-hydroxyethyl, thiomethyl, selenylomethyl, methylthioethyl, carbamoylmethyl, carbamoylethyl, 3-aminopropyl, or 3-(carbamoylamino)propyl. The amino acid corresponding to each side chain is listed in Table 1, below:

TABLE 1

| Side Chains | | |
| --- | --- | --- |
| $R_{aa}$ | Amino Acid | Abbrev. |
| hydrogen | Glycine | Gly |
| methyl | Alanine | Ala |
| sec-butyl | Isoleucine | Ile |
| isobutyl | Leucine | Leu |
| isopropyl | Valine | Val |
| propyl | Norvaline | Nva |
| benzyl | Phenylalanine | Phe |
| 1H-indol-3-ylmethyl | Tryptophan | Trp |
| 1-methyl-1H-indol-3-ylmethyl | 1-Methyltryptophan | 1-Me-Trp |

TABLE 1-continued

Side Chains

| $R_{aa}$ | Amino Acid | Abbrev. |
| --- | --- | --- |
| 4-hydroxybenzyl | Tyrosine | Tyr |
| carboxymethyl | Aspartic Acid | Asp |
| carboxyethyl | Glutamic Acid | Glu |
| 3-guanidinopropyl | Arginine | Arg |
| 1H-imidazol-4-ylmethyl | Histidine | His |
| 4-aminobutyl | Lysine | Lys |
| hydroxymethyl | Serine | Ser |
| 1-hydroxyethyl | Threonine | Thr |
| thiomethyl | Cysteine | Cys |
| selenylomethyl | Selenocysteine | Sec |
| methylthioethyl | Methionine | Met |
| carbamoylmethyl | Asparagine | Asn |
| carbamoylethyl | Glutamine | Gln |
| 3-aminopropyl | Ornithine | Orn |
| 3-(carbamoylamino)propyl | Citrulline | Cit |

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, halogen, azide, alkyl, aralkyl, alkenyl, alkynyl, cycloalkyl, cycloalkylalkyl, (cycloalkyl)alkoxy, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocyclyl, heterocyclylalkyl, aromatic or heteroaromatic moieties, aminoalkyl, haloalkyl, fluoroalkyl (such as trifluoromethyl), haloalkoxyl, cyano, or other substituents described above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

A "saturated" or "fully saturated" compound means that the referenced chemical structure does not contain any multiple carbon-carbon bonds. For example, a saturated cycloalkyl group as defined herein includes cyclohexyl, cyclopropyl, and the like.

An "unsaturated" or "partially saturated" compound means that the referenced chemical structure may contains on or more multiple carbon-carbon bonds, but is not aromatic. For example, an unsaturated cycloalkyl group as defined herein includes cyclohexenyl, cyclopentenyl, cyclohexadienyl, and the like.

For purposes of the invention, the chemical elements are identified in accordance with the Periodic Table of the Elements, CAS version, Handbook of Chemistry and Physics, 67th Ed., 1986-87, inside cover.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

The chemical structure of examples that are a mixture of diastereoisomers or a single diastereoisomer but with unknown relative configuration are drawn and named without defined stereochemical configuration.

In this document, compound structures that are depicted with particular stereochemistry and identified as being "racemic" (or "rac-") refer to an equimolar mixture of a pair of enantiomers as described at IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8. https://doi.org/10.1351/goldbook.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, pamoic (embonic), succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula (I). As another example, the salt may comprise less than one inorganic or organic acid molecule per molecule of base, such as two molecules of compound of Formula (I) per molecule of tartaric acid.

As used herein, a protic solvent is a solvent that has a hydrogen atom bound to an oxygen (as in a hydroxyl group) or a nitrogen (as in an amine group). In general terms, any solvent that contains labile $H^+$ is called a protic solvent. The molecules of such solvents readily donate protons ($H^+$) to reagents. In contrast, an aprotic solvent is a solvent that does not have a hydrogen atom bound to an oxygen (as in a hydroxyl group) or a nitrogen (as in an amine group), and it cannot donate hydrogen.

As used herein, a polar protic solvent is a protic solvent that will dissolve many salts. In general, these solvents have high dielectric constants and high polarity. Non-limiting examples of polar protic solvents include acetic acid, ammonia, ethanol, formic acid, isopropanol, methanol, n-butanol, nitromethane, n-propanol, t-butanol, and water.

As used herein, a polar aprotic solvent is a solvent that will dissolve many salts, but lacks an acidic hydrogen; these solvents generally have intermediate to high dielectric constants and polarity. Non-limiting examples of polar aprotic solvents include acetone, acetonitrile, dichloromethane (DCM), dimethyl sulfoxide (DMSO), ethyl acetate, hexamethylphosphoric triamide (HMPT), N,N-dimethylformamide (DMF), and tetrahydrofuran (THF).

As used herein, a nonpolar aprotic solvent is a solvent that will dissolve many salts, but lacks an acidic hydrogen; these solvents generally have low dielectric constants and polarity. Non-limiting examples of nonpolar aprotic solvents include benzene, chloroform, cyclohexane, diethyl ether, hexane, pentane, and toluene.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, the mode of administration, the bioavailability of the particular compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

"Modulating" or "modulate" refers to the treating, prevention, suppression, enhancement or induction of a function, condition or disorder.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, "subject" refers to a warm-blooded animal such as a mammal, preferably a human, or a human child, which is afflicted with, or has the potential to be afflicted with one or more diseases and disorders described herein.

"$EC_{50}$" refers to a dosage, concentration or amount of a particular test compound that elicits a dose-dependent response at 50% of maximal expression of a particular response that is induced, provoked or potentiated by the particular test compound.

"$IC_{50}$" refers to an amount, concentration or dosage of a particular test compound that achieves a 50% inhibition of a maximal response in an assay that measures such response.

Compounds of the Invention

In one aspect, the invention provides compounds represented by Formula (I):

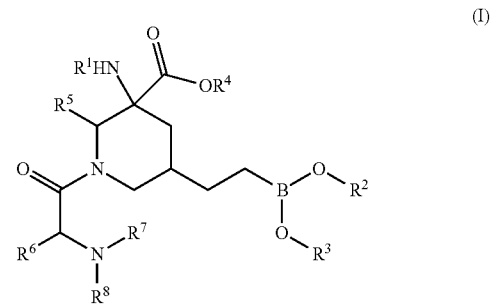

wherein:
  $R^1$ is selected from the group consisting of H, straight-chain or branched $(C_1-C_6)$alkyl, HC(O)—, and $(C_1-C_6)$alkyl-C(O)—;
  $R^2$ and $R^3$ are each independently selected from hydrogen, straight-chain or branched $(C_1-C_6)$alkyl and $(C_1-C_6)$alkyl-C(O)—,
  or $R^2$ and $R^3$ taken together with the boron atom and oxygen atoms to which they are bound form a 4-, 5-, 6- or 7-membered ring that is fully saturated, or partially saturated, or $R^2$ and $R^3$ taken together with the boron atom and oxygen atoms to which they are bound form a diester of the boronic acid and polyalcohols selected from (but not limited to): pinanediol, mannitol, glycerol, xylitol, sorbitol, and erythritol, or $R^2$ and $R^3$ taken together with the boron atom and oxygen atoms to which they are bound form an anhydride or mixed ester-anhydride of the boronic acid and hydroxy acids or di-carboxylic acids selected from (but not limited to): iminodiacetic acid or N-methyliminodiacetic acid or oxalic acid or tartaric acid or citric acid or malic acid or malonic acid or mandelic acid or glycolic acid or lactic acid or 3-hydroxypropionic acid;

$R^4$ is selected from the group consisting of H, straight-chain and branched $(C_1-C_6)$alkyl;

$R^5$ is selected from the group consisting of H, F, methyl, ethyl, propyl, isopropyl, —$CH_2NH_2$, —$CH_2NHCH_3$, —$CH_2NHCH_2CH_3$, —$CH_2NHCH(CH_3)_2$, —$CH_2N(CH_3)_2$, —$CH_2N(CH_3)CH_2CH_3$, —$CH_2N(CH_2CH_3)_2$, —$CH_2N(CH_3)CH(CH_3)_2$, —$CH_2$— azetidinyl, —$CH_2$-pyrrolidinyl, and —$CH_2$-piperidinyl;

$R^6$ is selected from the amino acid side chain of Gly, Ala, Val, Ser, Phe, Lys, Thr, Met, Tyr, His, Asp, Glu, Asn, Gln, Cys, Sec, Ile, Leu, Arg, Orn, Cit, Trp, 1-Me-Trp and Nva; and $R^7$ and $R^8$ are each independently selected from hydrogen and methyl, or $R^7$ is H and $R^6$ and $R^8$ together with the nitrogen atom carrying $R^8$ form a pyrrolidine ring (proline side chain);

or a pharmaceutically acceptable salt thereof.

Additionally, in certain embodiments as otherwise described herein, the invention provides a tautomer, stereoisomer, racemate, or solvate of a compound of Formula I as otherwise described herein. In certain embodiments as otherwise described herein, the invention provides an ester of a compound of Formula I as otherwise described herein.

The above-defined general Formula (I) covers certain compounds of the invention, which can be described in more detail as follows.

In certain embodiments, $R^1$ is H.
In certain embodiments, $R^2$ is H and $R^3$ is H.
In certain embodiments, $R^4$ is H.
In certain embodiments, $R^5$ is H.
In certain embodiments, $R^5$ is $CH_3$.
In certain embodiments, $R^5$ is —$CH_2NH_2$ or —$CH_2N(CH_3)_2$ or —$CH_2NHCH_3$ or _$CH_2N(CH_3)_2$ or —$CH_2N(CH_3)CH_2CH_3$ or —$CH_2$-pyrrolidinyl or —$CH_2$-azetidinyl or —$CH_2$— piperidinyl;

In certain embodiments, $R^6$ is selected from the amino acid side chain of Gly, Ala, Val, Ser, Phe, Lys, Thr, Met, Tyr, His, Asp, Glu, Asn, Gln, Cys, Sec, Ile, Leu, Arg, Orn, Cit, Trp, 1-Me-Trp and Nva.

In certain embodiments, $R^6$ is selected from the amino acid side chain of Gly, Ala, Val, Ser, Phe, Lys, Thr, Met, Tyr, His, Asp, Glu, Asn, Gln, Cys, Sec, Ile, Leu, Arg, Orn, Cit, Trp, and 1-Me-Trp.

In certain embodiments, $R^7$ is H and $R^6$ and $R^8$ together with the nitrogen atom carrying $R^8$ form a pyrrolidine ring (proline side chain).

In certain embodiments of Formula I, $R^5$ is hydrogen or methyl and $R^6$ is $C_1-C_4$ alkyl. In other embodiments, $R^5$ is hydrogen or methyl and $R^6$ is $C_1-C_2$ alkyl. In still other embodiments, $R^5$ is hydrogen or methyl and $R^6$ is methyl.

In certain embodiments of Formula I, $R^6$ is —$C_1-C_6$-alkyl-NH(CO)NH$_2$. In other embodiments, $R^6$ is —$C_1-C_4$-alkyl-NH(NH)NH$_2$. In still other embodiments, $R^6$ is —$C_2-C_4$-alkyl-NH(NH)NH$_2$. In still other embodiments, $R^6$ is —$C_3$-alkyl-NH(NH)NH$_2$.

In certain embodiments, the compounds of Formula (I) according to the invention have the structure of Formula (Ia):

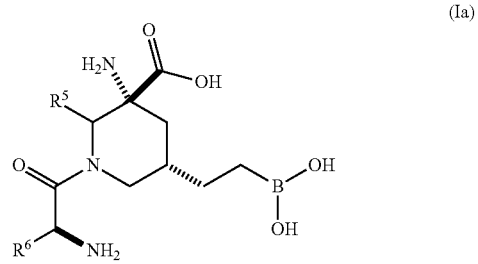

wherein:

$R^5$ is selected from the group consisting of H, —$CH_3$, —$CH_2NH_2$, —$CH_2NHCH_3$, —$CH_2N(CH_3)_2$, and —$CH_2$-pyrrolidinyl;

$R^6$ is selected from the amino acid side chain of Gly, Ala, Val, Ser, Phe, Lys, Thr, Met, Tyr, His, Asp, Glu, Asn, Gln, Cys, Sec, Ile, Leu, Arg, Orn, Cit, Trp, 1-Me-Trp and Nva;

or a pharmaceutically acceptable salt thereof.

In certain embodiments of Formula Ia, $R^5$ is hydrogen or methyl and $R^6$ is $C_1-C_4$ alkyl. In other embodiments, $R^5$ is hydrogen or methyl and $R^6$ is $C_1-C_2$ alkyl. In still other embodiments of Formula Ia, $R^5$ is hydrogen or methyl and $R^6$ is methyl.

In certain embodiments of Formula Ia, $R^5$ is hydrogen or methyl and $R^6$ is —$C_1-C_6$-alkyl-NH(NH)NH$_2$. In other embodiments of Formula Ia, $R^5$ is hydrogen or methyl and $R^6$ is —$C_1-C_4$-alkyl-NH(NH)NH$_2$. In still other embodiments, $R^5$ is hydrogen or methyl and $R^6$ is —$C_2-C_4$-alkyl-NH(NH)NH$_2$. In still other embodiments, $R^5$ is hydrogen or methyl and $R^6$ is —$C_3$-alkyl-NH(NH)NH$_2$.

In certain embodiments, the compounds of Formula (I) according to the invention have the structure of Formula (Ib):

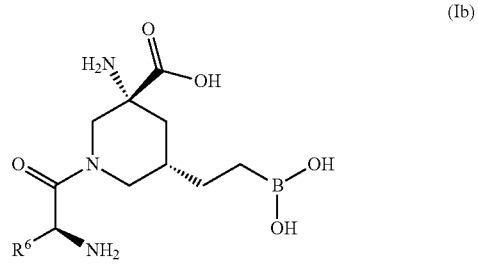

wherein:

$R^6$ is selected from the amino acid side chains of Gly, Ala, Val, Ser, Phe, Lys, Thr, Met, Tyr, His, Asp, Glu, Asn, Gln, Cys, Sec, Ile, Leu, Arg, Orn, Cit, Trp, 1-Me-Trp, and Nva or a pharmaceutically acceptable salt thereof.

In certain embodiments of Formula Ib, $R^6$ is $C_1$-$C_4$ alkyl. In other embodiments, $R^6$ is $C_1$-$C_2$ alkyl. In still other embodiments, $R^6$ is methyl.

In certain embodiments of Formula Ib, $R^6$ is —$C_1$-$C_6$-alkyl-NH(NH)NH$_2$. In other embodiments of Formula Ia, $R^6$ is —$C_1$-$C_4$-alkyl-NH(NH)NH$_2$. In still other embodiments, $R^6$ is —$C_2$-$C_4$-alkyl-NH(NH)NH$_2$. In still other embodiments, $R^6$ is —$C_3$-alkyl-NH(NH)NH$_2$.

Representative compounds of Formula (I) according to the invention are provided in Table 2, below:

TABLE 2

Representative Compounds

| Example No. | Compound Structure | Compound Name |
|---|---|---|
| 1 | 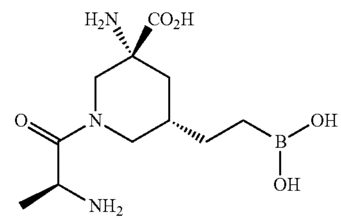 [SMILES: C[C@H](N)C(=O)N1C[C@@H](CCB(O)O)C[C@](N)(C(=O)O)C1] | (3R,5S)-1-(L-alanyl)-3-amino-5-(2-boronoethyl)piperidine-3-carboxylic acid |
| 2 | 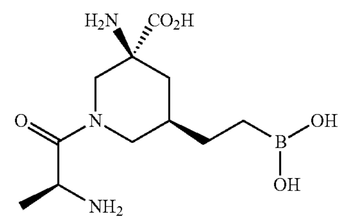 [SMILES: C[C@H](N)C(=O)N1C[C@H](CCB(O)O)C[C@@](N)(C(=O)O)C1] | (3S,5R)-1-(L-alanyl)-3-amino-5-(2-boronoethyl)piperidine-3-carboxylic acid |
| 3 | 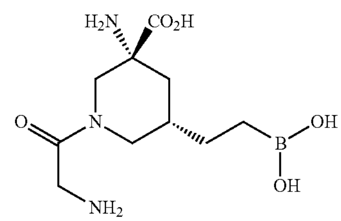 [SMILES: NCC(=O)N1C[C@@H](CCB(O)O)C[C@](N)(C(=O)O)C1] | (3R,5S)-3-amino-5-(2-boronoethyl)-1-glycylpiperidine-3-carboxylic acid |
| 4 | 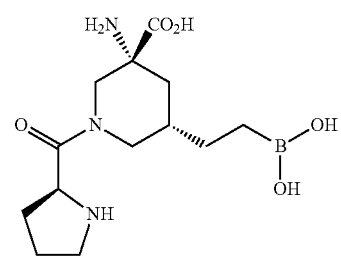 [SMILES: N[C@]1(C(=O)O)C[C@H](CCB(O)O)CN(C(=O)[C@@H]2CCCN2)C1] | (3R,5S)-1-(L-prolyl)-3-amino-5-(2-boronoethyl)piperidine-3-carboxylic acid |
| 5 | 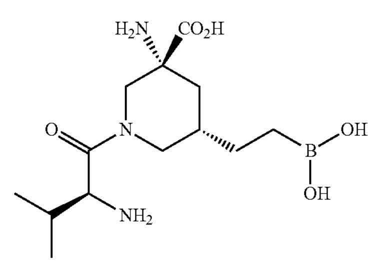 [SMILES: CC(C)[C@H](N)C(=O)N1C[C@@H](CCB(O)O)C[C@](N)(C(=O)O)C1] | (3R,5S)-1-(L-valyl)-3-amino-5-(2-boronoethyl)piperidine-3-carboxylic acid |
| 6 | 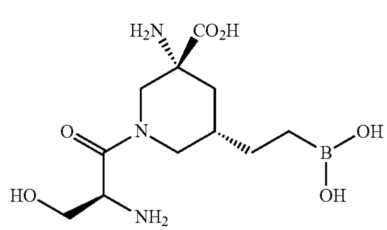 | (3R,5S)-1-(L-seryl)-3-amino-5-(2-boronoethyl)piperidine-3-carboxylic acid |

TABLE 2-continued

Representative Compounds

| Example No. | Compound Structure | Compound Name |
|---|---|---|
| 7 | 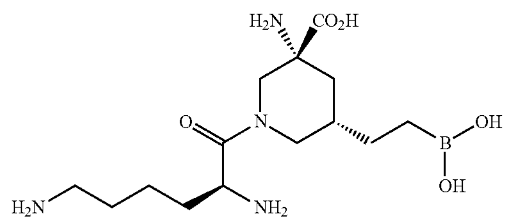 [SMILES: NCCCC[C@H](N)C(=O)N1C[C@@H](CCB(O)O)C[C@](N)(C(=O)O)C1] | (3R,5S)-1-(L-lysyl)-3-amino-5-(2-boronoethyl)piperidine-3-carboxylic acid |
| 8 | 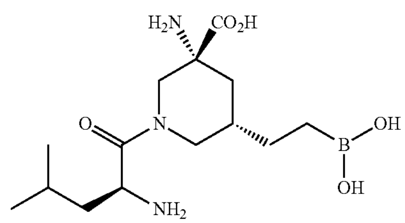 [SMILES: CC(C)C[C@H](N)C(=O)N1C[C@@H](CCB(O)O)C[C@](N)(C(=O)O)C1] | (3R,5S)-1-(L-leucyl)-3-amino-5-(2-boronoethyl)piperidine-3-carboxylic acid |
| 9 | 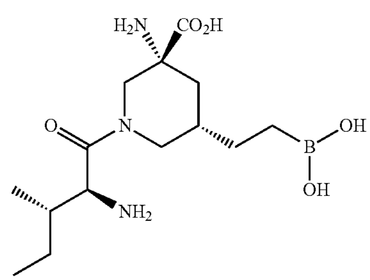 [SMILES: CC[C@H](C)[C@H](N)C(=O)N1C[C@@H](CCB(O)O)C[C@](N)(C(=O)O)C1] | (3R,5S)-1-(L-isoleucyl)-3-amino-5-(2-boronoethyl)piperidine-3-carboxylic acid |
| 10 | 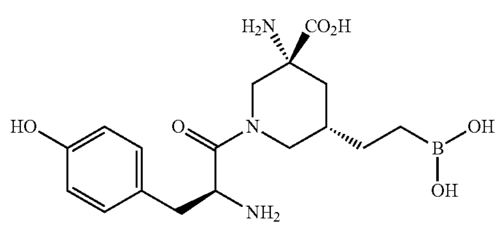 [SMILES: N[C@@H](Cc1ccc(O)cc1)C(=O)N1C[C@@H](CCB(O)O)C[C@](N)(C(=O)O)C1] | (3R,5S)-1-(L-tyrosyl)-3-amino-5-(2-boronoethyl)piperidine-3-carboxylic acid |
| 11 | 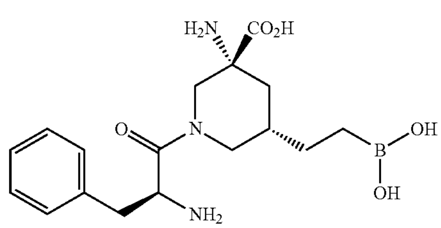 [SMILES: N[C@@H](Cc1ccccc1)C(=O)N1C[C@@H](CCB(O)O)C[C@](N)(C(=O)O)C1] | (3R,5S)-1-(L-phenylalanyl)-3-amino-5-(2-boronoethyl)piperidine-3-carboxylic acid |
| 12 | 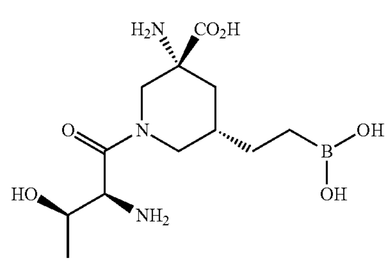 [SMILES: C[C@@H](O)[C@H](N)C(=O)N1C[C@@H](CCB(O)O)C[C@](N)(C(=O)O)C1] | (3R,5S)-1-(L-threonyl)-3-amino-5-(2-boronoethyl)piperidine-3-carboxylic acid |

TABLE 2-continued

Representative Compounds

| Example No. | Compound Structure | Compound Name |
|---|---|---|
| 13 | 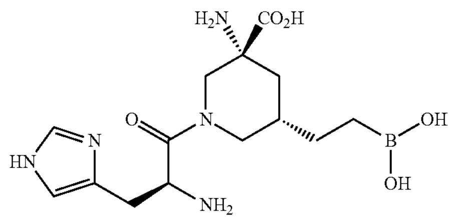 [SMILES: N[C@@H](Cc1c[nH]cn1)C(=O)N1C[C@@H](CCB(O)O)C[C@](N)(C(=O)O)C1] | (3R,5S)-1-(L-histidyl)-3-amino-5-(2-boronoethyl)piperidine-3-carboxylic acid |
| 14 | 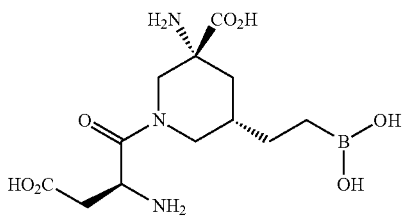 [SMILES: N[C@@H](CC(=O)O)C(=O)N1C[C@@H](CCB(O)O)C[C@](N)(C(=O)O)C1] | (3R,5S)-1-(L-aspartyl)-3-amino-5-(2-boronoethyl)piperidine-3-carboxylic acid |
| 15 | 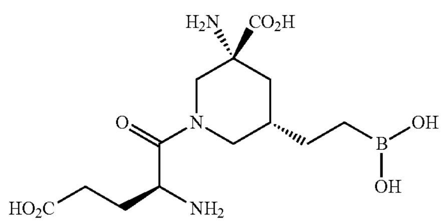 [SMILES: N[C@@H](CCC(=O)O)C(=O)N1C[C@@H](CCB(O)O)C[C@](N)(C(=O)O)C1] | (3R,5S)-1-(L-glutamyl)-3-amino-5-(2-boronoethyl)piperidine-3-carboxylic acid |
| 16 | 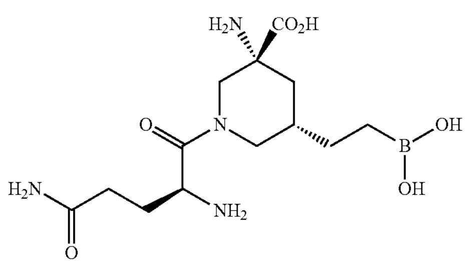 [SMILES: NC(=O)CC[C@H](N)C(=O)N1C[C@@H](CCB(O)O)C[C@](N)(C(=O)O)C1] | (3R,5S)-1-(L-glutaminyl)-3-amino-5-(2-boronoethyl)piperidine-3-carboxylic acid |
| 17 | 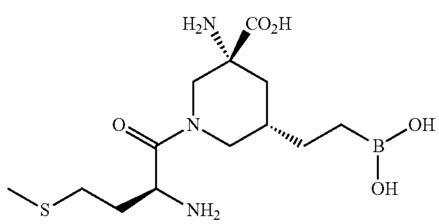 [SMILES: CSCC[C@H](N)C(=O)N1C[C@@H](CCB(O)O)C[C@](N)(C(=O)O)C1] | (3R,5S)-1-(L-methionyl)-3-amino-5-(2-boronoethyl)piperidine-3-carboxylic acid |
| 18 | 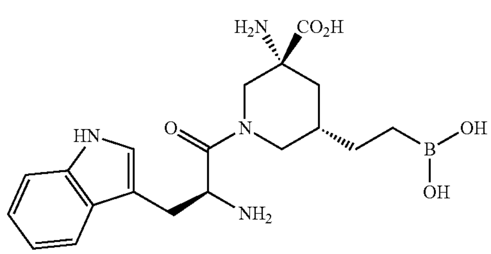 [SMILES: N[C@@H](Cc1c[nH]c2ccccc12)C(=O)N1C[C@@H](CCB(O)O)C[C@](N)(C(=O)O)C1] | (3R,5S)-1-(L-tryptophyl)-3-amino-5-(2-boronoethyl)piperidine-3-carboxylic acid |

TABLE 2-continued

Representative Compounds

| Example No. | Compound Structure | Compound Name |
|---|---|---|
| 19 | 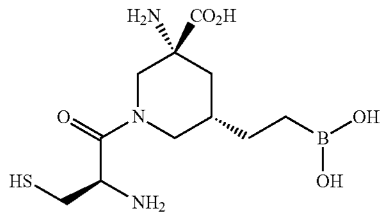 [SMILES: N[C@@H](CS)C(=O)N1C[C@@H](CCB(O)O)C[C@](N)(C(=O)O)C1] | (3R,5S)-1-(L-cysteinyl)-3-amino-5-(2-boronoethyl)piperidine-3-carboxylic acid |
| 20 | 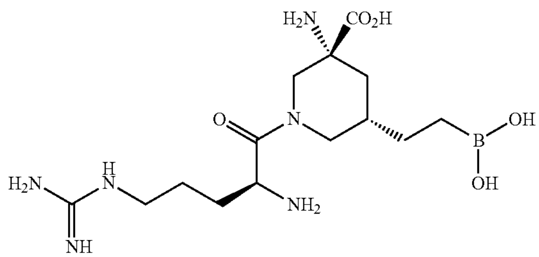 [SMILES: N=C(N)NCCC[C@H](N)C(=O)N1C[C@@H](CCB(O)O)C[C@](N)(C(=O)O)C1] | (3R,5S)-1-(L-arginyl)-3-amino-5-(2-boronoethyl)piperidine-3-carboxylic acid |
| 21 | 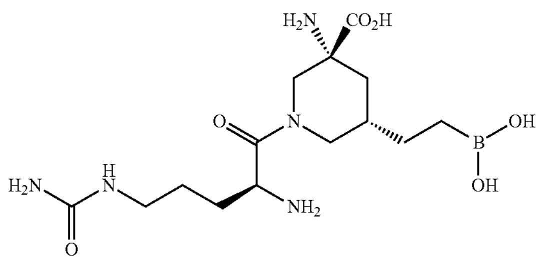 [SMILES: NC(=O)NCCC[C@H](N)C(=O)N1C[C@@H](CCB(O)O)C[C@](N)(C(=O)O)C1] | (3R,5S)-3-amino-1-((S)-2-amino-5-ureidopentanoyl)-5-(2-boronoethyl)piperidine-3-carboxylic acid |
| 22 | 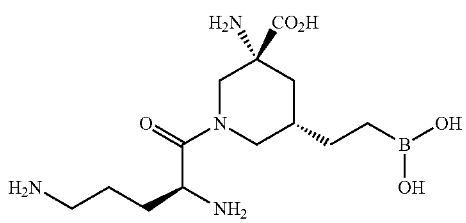 [SMILES: NCCC[C@H](N)C(=O)N1C[C@@H](CCB(O)O)C[C@](N)(C(=O)O)C1] | (3R,5S)-3-amino-5-(2-boronoethyl)-1-((S)-2,5-diaminopentanoyl)piperidine-3-carboxylic |
| 23 | 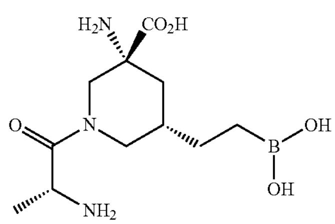 [SMILES: C[C@@H](N)C(=O)N1C[C@@H](CCB(O)O)C[C@](N)(C(=O)O)C1] | (3R,5S)-1-(D-alanyl)-3-amino-5-(2-boronoethyl)piperidine-3-carboxylic acid |
| 24 | 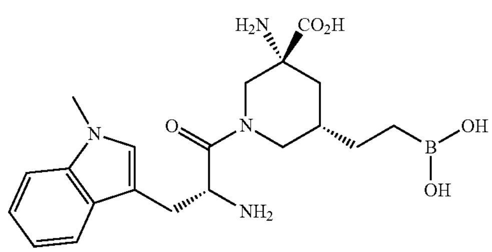 [SMILES: Cn1cc(C[C@@H](N)C(=O)N2C[C@@H](CCB(O)O)C[C@](N)(C(=O)O)C2)c2ccccc21] | (3R,5S)-3-amino-5-(2-boronoethyl)-1-(1-methyl-D-tryptophyl)piperidine-3-carboxylic acid |

TABLE 2-continued

Representative Compounds

| Example No. | Compound Name |
|---|---|
| 25 | (3R,5S)-3-amino-1-((S)-2-aminopentanoyl)-5-(2-boronoethyl)piperidine-3-carboxylic acid |
| 26 | (3R,5S)-1-(L-asparaginyl)-3-amino-5-(2-boronoethyl)piperidine-3-carboxylic acid |
| 27 | (3R,5S)-3-amino-5-(2-boronoethyl)-1-(methylglycyl)piperidine-3-carboxylic acid |
| 28 | (2-((3S,5R)-1-(L-alanyl)-5-amino-5-(methoxycarbonyl)piperidin-3-yl)ethyl)boronic acid |
| 29 | (3R,5S)-1-(L-arginyl)-3-amino-5-(2-(4-carboxy-4-(carboxymethyl)-6-oxo-1,3,2-dioxaborinan-2-yl)ethyl)piperidine-3-carboxylic acid |
| 30 | (2S,3R,5S)-1-(L-alanyl)-3-amino-5-(2-boronoethyl)-2-methylpiperidine-3-carboxylic acid |

TABLE 2-continued

Representative Compounds

| Example No. | Compound Structure | Compound Name |
|---|---|---|
| 31 | 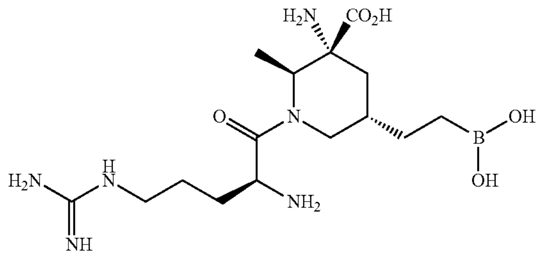 [SMILES: C[C@@H]1N(C(=O)[C@@H](N)CCCNC(=N)N)C[C@@H](CCB(O)O)C[C@]1(N)C(=O)O] | (2S,3R,5S)-1-(L-Arginyl)-3-amino-5-(2-boronoethyl)-2-methylpiperidine-3-carboxylic acid |
| 32 | 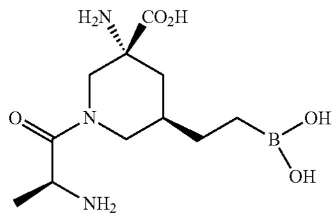 [SMILES: C[C@H](N)C(=O)N1C[C@H](CCB(O)O)C[C@](N)(C(=O)O)C1] | (3R,5R)-1-(L-alanyl)-3-amino-5-(2-boronoethyl)piperidine-3-carboxylic acid |
| 33 | 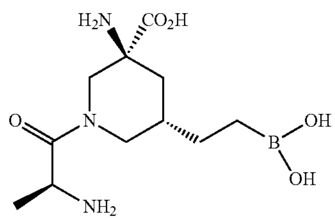 [SMILES: C[C@H](N)C(=O)N1C[C@@H](CCB(O)O)C[C@@](N)(C(=O)O)C1] | (3S,5S)-1-(L-alanyl)-3-amino-5-(2-boronoethyl)piperidine-3-carboxylic acid |

The above compounds can be obtained and used as a free acid or free base, or as a pharmaceutically acceptable salt thereof, or a stereoisomer, a tautomer, and/or a solvate thereof.

The invention also provides intermediates useful in preparing compounds of Formula I. Representative compounds of Formula I that may be prepared using the intermediates of this invention include compounds of Formula Ib:

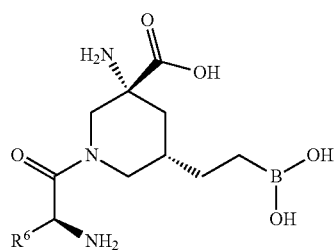

Ib

Intermediates of this invention include compounds of Formula II:

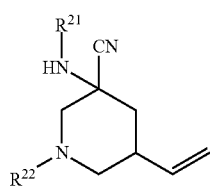

II wherein $R^{21}$ is hydrogen, $C_1$-$C_6$ alkyl, or $R^N$, wherein $R^N$ is a nitrogen protecting group; and $R^{22}$ is hydrogen, $C_1$-$C_6$ alkyl, or Pg, wherein Pg is a nitrogen protecting group which may be the same as or different than $R^N$.

Preferred Pg protecting groups within $R^{22}$ are benzyl, 4-methylbenzyl, 4-methoxybenzyl, 4-bromobenzyl, 4-nitrobenzyl, 3-methylbenzyl, 2-methylbenzyl, 3,4-dimethoxybenzyl, 2,4,6-trimethylbenzyl, benzhydryl, and trityl.

Preferred $R^N$ protecting groups are acetyl, benzyloxycarbonyl, and t-butoxycarbonyl.

Particular compounds of Formula II include those where $R^{21}$ is hydrogen. Other particular compounds of Formula II include those where $R^{21}$ is hydrogen and $R^{22}$ is benzyl.

Still other compounds of Formula II are those where $R^{22}$ is benzyl and $R^{21}$ is $C_1$-$C_6$ alkyl. Other compounds of Formula II are those where $R^{22}$ is benzyl and $R^{21}$ is $R^N$, preferably acetyl or benzyloxycarbonyl.

Other intermediates of this invention include compounds of Formula III:

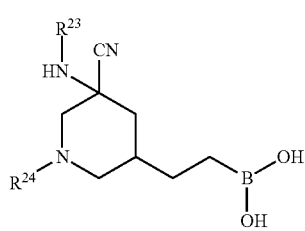

III wherein
R$^{23}$ is hydrogen, C$_1$-C$_6$ alkyl, or R$^N$, wherein R$^N$ is a nitrogen protecting group; and
R$^{24}$ is hydrogen, C$_1$-C$_6$ alkyl, or Pg, wherein Pg is a nitrogen protecting group which may be the same as or different than R$^N$.

Preferred R$^N$ protecting groups within R$^{23}$ are acetyl, benzyloxycarbonyl, and t-butoxycarbonyl.

Preferred Pg protecting groups within R$^{24}$ are benzyl, 4-methylbenzyl, 4-methoxybenzyl, 4-bromobenzyl, 4-nitrobenzyl, 3-methylbenzyl, 2-methylbenzyl, 3,4-dimethoxybenzyl, 2,4,6-trimethylbenzyl, benzhydryl, and trityl.

Particular compounds of Formula III include those where R$^{23}$ is hydrogen. Other particular compounds of Formula III include those where R$^{23}$ is hydrogen and R$^{24}$ is benzyl.

Still other compounds of Formula III are those where R$^{24}$ is benzyl and R$^{23}$ is C$_1$-C$_6$ alkyl. Other compounds of Formula III are those where R$^{24}$ is benzyl and R$^{23}$ is R$^N$, preferably acetyl or benzyloxycarbonyl.

Pharmaceutical Compositions of the Invention

Also provided herein are pharmaceutical compositions, comprising (i) a therapeutically effective amount of at least one compound of the invention, or a pharmaceutically acceptable salt thereof; and (ii) a pharmaceutically acceptable carrier, including, but not limited to, bioavailability enhancers, penetration enhancers, biopolymers, PLGA-based nanoparticles, sugar-based nanoparticles, coating to avoid the deleterious effects of the stomach environment, either by protection of the compound of the invention or derivative thereof, or by release of the biologically active material beyond the stomach environment, such as in the intestine.

The exact nature of the carrier, or, for example, excipient or diluent, will depend upon the desired use for the composition, and may be suitable or acceptable for veterinary use or suitable or acceptable for human use. The composition may optionally include one or more additional compounds, including one or more additional therapeutic agents.

Compounds of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents that may be administered with the compounds of the invention include steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, rituximab, p38 inhibitors, PDE4 inhibitors, and antihistamines, immunotherapeutic agents, including checkpoint inhibitors such as PD-1, PD-L1, CTLA-4, LAG-3, TIM-3, TIGIT, VISTA inhibitors, IDO/TDO inhibitors, adenosine A2A receptor antagonists, ectonucleotidase (CD73 and CD39) inhibitors, immunosuppressants, agents affecting interleukins, cytokines and chemokines, kinase inhibitors, chemotherapeutic agents including alkylating antineoplastic agents, antimetabolites, anti-microtubule agents, topoisomerase inhibitors, cytotoxic antibiotics or targeted therapies such as antibodies, antibodies drug conjugates, cell-based immunotherapies, nanoparticles, anti-cancer vaccines and radiotherapy.

In some embodiments, the one or more additional chemotherapeutic agents includes aminoglutethimide, amsacrine, anastrozole, asparaginase, AZD5363, Bacillus Calmette-Guerin vaccine (BCG), bicalutamide, bleomycin, bortezomib, buserelin, busulfan, camptothecin, capecitabine, carboplatin, carfilzomib, carmustine, chlorambucil, chloroquine, cisplatin, cladribine, clodronate, cobimetinib, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, erlotinib, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, nilutamide, nocodazole, octreotide, olaparib, oxaliplatin, paclitaxel, pamidronate, pazopanib, pentostatin, perifosine, plicamycin, pomalidomide, porfimer, procarbazine, raltitrexed, rituximab, rucaparib, selumetinib, sorafenib, streptozocin, sunitinib, suramin, talazoparib, tamoxifen, temozolomide, temsirolimus, teniposide, testosterone, thalidomide, thioguanine, thiotepa, titanocene dichloride, topotecan, trametinib, trastuzumab, tretinoin, veliparib, vinblastine, vincristine, vindesine, or vinorelbine. In some embodiments, the one or more additional chemotherapeutic agents includes abagovomab, adecatumumab, afutuzumab, anatumomab mafenatox, apolizumab, avelumab, blinatumomab, catumaxomab, durvalumab, epratuzumab, inotuzumab ozogamicin, intelumumab, ipilimumab, isatuximab, lambrolizumab, nivolumab, ocaratuzumab, olatatumab, pembrolizumab, pidilizumab, ticilimumab, samalizumab, tremelimumab, BMS-936559.

In some embodiments, the one or more additional immunotherapeutic agents includes AB122, AB154, AB680, AB928, BMS202, BMS-813160, BMS-986016, BMS-986205, BMS-986207, CA-170, CA-327, EOS200271, epacadostat, GDC-0919, LY3321367, 1-methyl-D-tryptophan, MGA012, MK-7684, OMP-313M32, PF-06840003, REGN2810, SHR-1210 or TSR-022.

In some embodiments, the one or more additional chemotherapeutic agents includes atezolizumab, avelumab, durvalumab, ipilimumab, nivolumab, pembrolizumab or pidilizumab.

In some embodiments, the one or more additional therapeutic agents includes hydroxyurea.

In other embodiments, the method further comprises administering one or more non-chemical methods of cancer treatment, such as radiation therapy, surgery, thermoablation, focused ultrasound therapy, cryotherapy, or a combination thereof.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.0001 milligrams/kg per day, 0.001 milligrams/kg per day, or 0.01 milligrams/kg per day to about 100 milligrams/kg per day or 1000 milligrams/kg per day. It is expected that oral doses in the range of 0.5 to 50 milligrams/kg, in one or several administrations per day, will yield the desired results. Dosage may be adjusted appropriately to achieve desired drug levels sufficient to achieve or maintain a desired therapeutic effect, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds. The compounds may be administered once per week, several times per week (e.g., every other day), once per day or multiple times per day, depending upon, among other things, the mode of administration, the specific indication being treated and the judgment of the prescribing physician.

In one embodiment, intravenous administration of a compound of the invention may typically be from 0.1 mg/kg/day to 100 mg/kg/day.

Determination of an effective dosage of a compound for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients.

Pharmaceutical compositions comprising the compound of the invention may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to oral, buccal, nasal, rectal, vaginal, ocular, topical, intravenous, intramuscular, intraperitoneal, subcutaneous, transdermal, direct injection (for example, into an abscess), mucosal, inhalation, and insufflation.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, lozenges, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragée cores. Suitable excipients are, in particular, binding agents, fillers, lubricants, disintegrants, and wetting agents. Suitable fillers include sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA, for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

For buccal administration, the compositions may take the form of tablets or lozenges formulated in conventional manner.

For topical administration, the compound may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (µm), most preferably 0.5 to 5 µm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as sterile suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, buffer, dextrose solution, before use. To this end, the active compound may be dried by any art-known technique, such as lyophilization, and reconstituted prior to use.

The compounds may also be formulated in rectal or vaginal compositions such as suppositories or retention enemas, e.g., containing conventional suppository bases such as cocoa butter or other glycerides.

For transmucosal administration, penetrants appropriate to the barrier to be permeated are used in the formulation. Such penetrants are known in the art.

For ocular administration, the compound(s) may be formulated as a solution, emulsion, suspension, etc. suitable for administration to the eye. A variety of vehicles suitable for administering compounds to the eye are known in the art.

In addition to the formulations described above, for prolonged delivery, the compounds may also be formulated as a depot preparation for administration by, for example, implantation or intramuscular injection. Such long acting formulations may be formulated with suitable polymeric or hydrophobic materials (for example as an emulsion in an acceptable oil) or ion exchange resins, or as sparingly soluble derivatives, for example, as a sparingly soluble salt. Alternatively, transdermal delivery systems manufactured as an adhesive disc or patch which slowly releases the compound for percutaneous absorption may be used. To this end, permeation enhancers may be used to facilitate transdermal penetration of the compound.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, Science 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulfuric, nitric, phosphoric, maleic, acetic, salicylic, p-toluenesulfonic, tartaric, citric, methane sulfonic, formic, malonic, succinic, naphthalene-2-sulfonic, and benzenesulfonic. Also, such salts can be prepared as alkaline metal or alkaline earth salts, such as sodium, potassium or calcium salts of the carboxylic acid group. Typically, such salts are more soluble in aqueous solutions than the corresponding free acids and bases, but salts having lower solubility than the corresponding free acids and bases may also be formed.

The compounds may alternatively be formulated in the pharmaceutical composition per se, or in the form of a hydrate, solvate, or N-oxide.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

Methods of the Invention

Another aspect of the invention is a method for treating asthma, comprising administering to a subject in need thereof a therapeutically effective amount of a compound of the invention, for example, a compound of Formula (I).

In another aspect, the invention provides a method for inhibiting arginase 1, arginase 2, or a combination thereof in a cell, comprising contacting the cell with at least one compound according to the invention, for example, a compound of Formula (I), or a pharmaceutically acceptable salt thereof.

In another aspect, the invention provides a method for the treatment or prevention of a disease or condition associated with expression or activity of arginase 1, arginase 2, or a combination thereof, comprising administering to a subject in need thereof a therapeutically effective amount of at least one compound according to the invention, for example, a compound of Formula (I), or a pharmaceutically acceptable salt thereof.

In certain embodiments, the disease or condition is selected from the group consisting of cardiovascular disorders, pulmonary disorders, autoimmune disorders, immune disorders, hemolytic disorders, gastrointestinal disorders, sexual disorders, infections, cancers, and wound healing disorders.

In certain embodiments, the disease or condition is cardiovascular disorder selected from the group consisting of systemic hypertension, pulmonary arterial hypertension (PAH), pulmonary arterial hypertension in high altitude, ischemia reperfusion (IR) injury, myocardial infarction and atherosclerosis.

In certain embodiments, the disease or condition is pulmonary arterial hypertension (PAH).

In certain embodiments, the disease or condition is myocardial infarction or atherosclerosis.

In certain embodiments, the disease or condition is a pulmonary disorder selected from the group consisting of chemically-induced lung fibrosis, idiopathic pulmonary fibrosis, cystic fibrosis, chronic obstructive pulmonary disease (COPD), and asthma.

In certain embodiments, the disease or condition is an autoimmune disorder selected from the group consisting of encephalomyelitis, multiple sclerosis, anti-phospholipid syndrome 1, autoimmune hemolytic anemia, chronic inflammatory demyelinating polyradiculoneuropathy, dermatitis herpetiformis, dermatomyositis, myasthenia gravis, pemphigus, rheumatoid arthritis, stiff-person syndrome, type 1 diabetes, ankylosing spondylitis, paroxysmal nocturnal hemoglobinuria (PNH), paroxysmal cold hemoglobinuria, severe idiopathic autoimmune hemolytic anemia, and Goodpasture's syndrome.

In certain embodiments, the disease or condition is an immune disorder selected from the group consisting of myeloid-derived suppressor cell (MDSC) mediated T-cell dysfunction, human immunodeficiency virus (HIV) infection, autoimmune encephalomyelitis, and ABO mismatch transfusion reaction.

In certain embodiments, the disease or condition is T-cell dysfunction mediated by myeloid-derived suppressor cells (MDSC).

In certain embodiments, the disease or condition is a hemolytic disorder selected from the group consisting of sickle-cell disease, thalassemias, hereditary spherocytosis, stomatocytosis, microangiopathic hemolytic anemias, pyruvate kinase deficiency, infection-induced anemia, cardiopulmonary bypass, mechanical heart valve-induced anemia, and chemical-induced anemia.

In certain embodiments, the disease or condition is sickle-cell disease.

In certain embodiments, the disease or condition is a gastrointestinal disorder selected from the group consisting of gastrointestinal motility disorders, gastric cancers, inflammatory bowel disease, Crohn's disease, ulcerative colitis, and gastric ulcers.

In certain embodiments, the disease or condition is a sexual disorder selected from the group consisting of Peyronie's disease and erectile dysfunction.

In certain embodiments, the disease or condition is ischemia reperfusion (IR) injury selected from the group consisting of liver IR, kidney IR, and myocardial IR.

In certain embodiments, the disease or condition is a cancer selected from the group consisting of oesophagic, gastric, colon, ovary, breast, pancreatic, head-and-neck, bladder, and lung cancers (including squamous and non-small cell lung carcinoma), renal cell carcinoma, prostate carcinoma, multiple myeloma, neuroblastoma, glioblastoma, astrocytoma, mesothelioma and melanoma, B cells, T cells and NK cells lymphomas, acute and chronic, myeloid and lymphoid leukemia.

In certain embodiments, the cancer is selected from the group consisting of gastric (including but not limited to gastric or gastroesophageal junction cancer), colorectal cancer, pancreatic cancer, liver cancer, breast cancer, lung cancers (including but not limited to non-small cell lung carcinoma), renal cell carcinoma, prostate carcinoma, multiple myeloma, acute and chronic leukemias, T cell, B cell and NK cell lymphomas, brain tumors (including but not limited to neuroblastoma, glioblastoma, astrocytoma), squamous-cell carcinomas of the head and neck, and melanoma.

In certain embodiments, the disease or condition is selected from the group consisting of renal disease inflammation, psoriasis, leishmaniosis, neurodegenerative diseases, wound healing, human immunodeficiency virus (HIV) infection, hepatitis B virus (HBV) infection, *Helicobacter pylori* infection, fibrotic disorders, arthritis, candidiasis, periodontal disease, keloids, adenotonsilar disease, African sleeping sickness and Chagas' disease.

In certain embodiments, the disease or condition is a wound healing disorder selected from the group consisting of infected and uninfected wound healing.

In certain embodiments, the subject is a mammal selected from the group consisting of human, dog, cat, horse, cow, pig, sheep, goat, ape and rodent.

In certain embodiments, the method of treatment further comprises administering to the patient a therapeutically effective amount of anti-viral agents, a chemotherapeutic agents (including alkylating antineoplastic agents, antimetabolites, anti-microtubule agents), immunosuppressants, radiation, an anti-tumor vaccines, an antiviral vaccines, cytokine therapy, tyrosine kinase inhibitors, immunotherapeutic agents, including checkpoint inhibitors such as PD-1, PD-L1 or CTLA-4 inhibitors and IDO/TDO inhibitors, adenosine A2A receptor antagonists, ectonucleotidase (CD73 and CD39) inhibitors, agent affecting interleukins, cytokines and chemokines, topoisomerase inhibitors, cytotoxic antibiotics or targeted therapies such as antibodies, antibody drug conjugates, cell-based immunotherapy, nanoparticles, radiotherapy prior to, simultaneously with, or after administration of the at least one compound according to the invention, for example, a compound of Formula (I), or a pharmaceutically acceptable salt thereof.

In certain embodiments, the method of treatment further comprises administering to the subject a therapeutically effective amount of anti-PD-1, anti-PD-L1 or anti-CTLA4 antibodies.

In some embodiments, the cancer is chronic lymphocytic leukemia, acute lymphoblastic leukemia, chronic myelogenous leukemia, acute myeloid leukemia, adrenocortical carcinoma, anal cancer, appendix cancer, atypical teratoid/rhabdoid tumor, basal cell carcinoma, bile duct cancer, bladder cancer, bone cancer, brain tumor, brain and spinal cord tumor, brain stem glioma, central nervous system atypical teratoid/rhabdoid tumor, central nervous system embryonal tumors, breast cancer, bronchial tumors, Burkitt lymphoma, carcinoid tumor, carcinoma of unknown primary origin, central nervous system cancer, cervical cancer, childhood cancers, chordoma, chronic myeloproliferative disorders, colon cancer, craniopharyngioma, cutaneous T-cell lymphoma, ductal carcinoma in situ, embryonal tumors, endometrial cancer, ependymoblastoma, ependymoma, esophageal cancer, esthesioneuroblastoma, Ewing sarcoma, extracranial germ cell tumor, extrahepatic bile duct cancer, eye cancer, fibrous histiocytoma of bone, gallbladder cancer, gastric cancer, gastrointestinal carcinoid tumor, gastrointestinal stromal tumors, germ cell tumor, extracranial germ cell tumor, extragonadal germ cell tumor, ovarian germ cell tumor, gestational trophoblastic tumor, glioma, hairy cell leukemia, head and neck cancer, heart cancer, hepatocellular cancer, histiocytosis, Langerhans cell cancer, Hodgkin's lymphoma, hypopharyngeal cancer, intraocular melanoma, islet cell tumors, Kaposi sarcoma, kidney cancer, Langerhans cell histiocytosis, laryngeal cancer, lip and oral cavity cancer, lobular carcinoma in situ, lymphoma, AIDS-related lymphoma, macroglobulinemia, male breast cancer, medulloblastoma, medulloepithelioma, Merkel cell carcinoma, malignant mesothelioma, metastatic squamous neck cancer, midline tract carcinoma involving NUT gene, mouth cancer, multiple endocrine neoplasia syndrome, plasma cell neoplasm, mycosis fungoides, myeloma, chronic myeloproliferative disorder, nasal cavity cancer, paranasal sinus cancer, nasopharyngeal cancer, non-Hodgkin's lymphoma, oral cancer, oral cavity cancer, lip cancer, oropharyngeal cancer, osteosarcoma, ovarian cancer, papillomatosis, paraganglioma, paranasal sinus cancer, nasal cavity cancer, parathyroid cancer, penile cancer, pharyngeal cancer, pheochromocytoma, pineal parenchymal tumors of intermediate differentiation, pineoblastoma, pituitary tumor, plasma cell neoplasm, pleuropulmonary blastoma, primary central nervous system lymphoma, rectal cancer, renal cell cancer, renal pelvis cancer, ureter cancer, transitional cell cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, squamous neck cancer with occult primary, stomach cancer, supratentorial primitive neuroectodermal tumors, testicular cancer, throat cancer, thymoma, thymic carcinoma, thyroid cancer, transitional cell cancer of the renal pelvis and ureter, gestational trophoblastic tumor, unknown primary, unusual cancer of childhood, urethral cancer, uterine cancer, uterine sarcoma, Waldenstroms macroglobulinemia, or Wilms' tumor.

Uses

In another aspect, the invention provides use of a compound according to the invention, for example, a compound of Formula (I), or a pharmaceutically acceptable salt thereof in the manufacture of a medicament for the treatment or prevention of a disease or condition associated with expression or activity of arginase 1, arginase 2, or a combination thereof.

In another aspect, the invention provides use of a compound according to the invention, for example, a compound of Formula (I), or a pharmaceutically acceptable salt thereof, for protecting an organ during transport.

Process for Manufacturing

The compounds of Formula I can be prepared by different ways with reactions known to a person skilled in the art.

The invention further relates to a first process for manufacturing of compounds of Formula Ib comprising steps illustrated below:

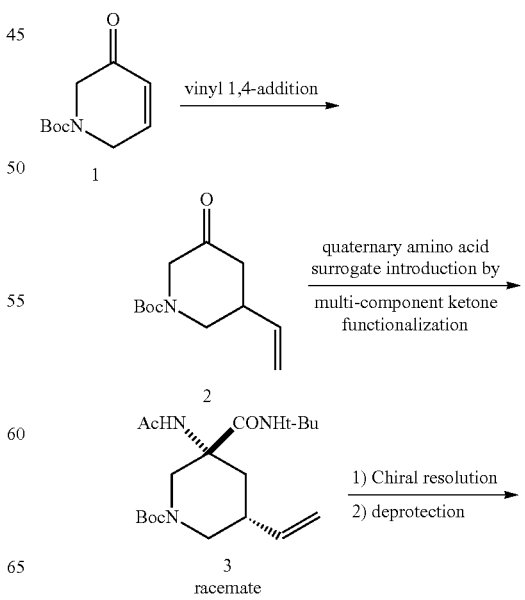

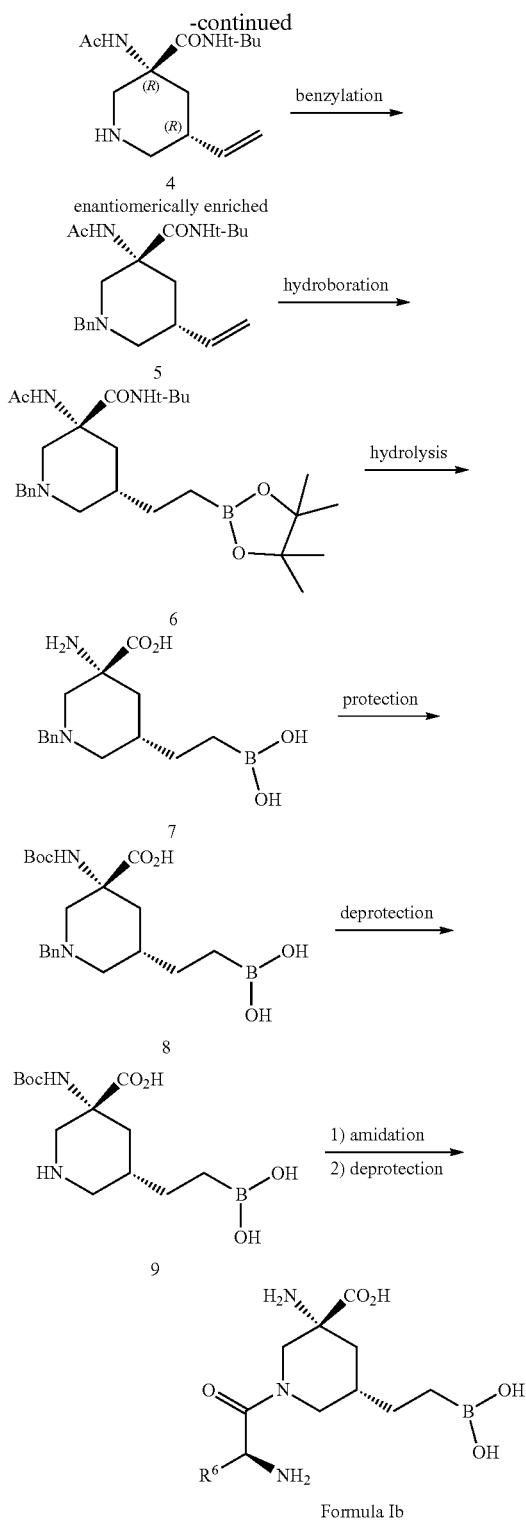

boronic acid esters, metal salts of vinyl trifluoroborate or vinyl alkoxysilanes. The addition may also be assisted with Lewis acids or transitional metals. Solvents can include any of those suitable for conjugated addition, such as but not limited to diethyl ether, tetrahydrofuran, 2-methyltetrahydrofuran, 1,4-dioxane. For the addition of borane and silane derivatives, methanol, ethanol, isopropanol or their combination can be also used as a solvent, with or without the addition of base like trialkylamines or metal hydroxides. Piperidone 2 can then be transformed to racemic amino acid derivative 3 in a multi-component reaction. Such multi-component reactions can include but are not limited to, the Ugi reaction, the Bucherer-Bergs reaction, the Strecker reaction, and variations thereof. Solvents can include any of those suitable for such reactions: methanol, ethanol, isopropanol, trifluoroethanol, water, acetonitrile, dichloromethane, tetrahydrofuran, and mixtures thereof, and can include additives such as triethylamine or ammonium hydroxide. Single racemic diastereoisomer with the relative configuration as in the structure of compound 3 can be obtained by chromatographic method on silica gel of the diastereoisomeric mixture or by crystallization from appropriate solvents. Such solvents include but are not limited to DCM, chloroform, hexane, pentane, cyclohexane, heptane, ethyl acetate, diisopropyl ether, diethyl ether, methyl tert-butyl ether. The racemic amino acid derivative 3 can then be resolved into single enantiomers using chromatographic methods with chiral stationary phase. Enantiomerically enriched amino acid derivative can then be deprotected under readily available conditions (e.g., removal of Boc with TFA or HCl) to afford enantiomerically enriched piperidine 4 as an appropriate salt. Piperidine 4 can be then benzylated using known methods readily apparent to those of skill in the art, such as with benzaldehyde under reductive amination conditions or by the use of benzyl halide in the presence of base. Hydroboration can be accomplished using known methods readily apparent to those of skill in the art, such as using pinacol borane or bis(pinacolato)diboron in the present of an appropriate catalyst that include but is not limited to iridium, rhodium, cobalt, iron, nickel, $BH_3$-THF $BH_3$-$Me_2S$ and can includes additives like NaOH, t-BuONa or sodium triethylborohydride. Hydrolysis of amide 6 to amino acid 7 can be accomplished using known methods readily apparent to those of skill in the art, such as heating with mineral acids (e.g. hydrochloric or hydrobromic acid). The protection of amino acid 7 can be accomplished using aqueous sodium bicarbonate, sodium carbonate or sodium hydroxide and di-tert-butyl dicarbonate ($Boc_2O$) in the appropriate solvent (e.g. water, acetone, acetonitrile, THF, 1,4-dioxane, isopropanol). Boc-amino acid 8 can be next deprotected under hydrogenolytic conditions readily apparent to those of skill in the art (e.g. $H_2$/Pd(OH)$_2$/MeOH). An amidation of 9 can be accomplished using known methods readily apparent to those of skill in the art. It can include but is not limited to the use of appropriate protected amino acid with activated carboxyl group (e.g. by using protected hydroxysuccinimide esters or mixed anhydrides). Solvents can include any of those suitable for peptide synthesis, such as but not limited to DMF, acetonitrile, THF, water, acetone, 1,4-dioxane, DCM with or without addition of tertiary amine (e.g. triethylamine). The activation of carboxyl group can be alternatively accomplished in situ using coupling reagent that include but is not limited to DCC, EDCI, TBTU, HOBt, HATU. Global deprotection can afford arginase inhibitor represented by formula Ib.

The invention further relates to an alternative process for manufacturing of compounds of Formula Ib:

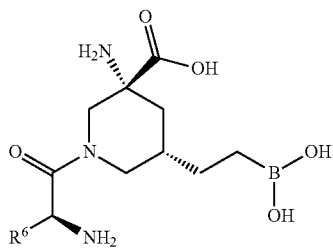

or precursors thereof, wherein:
R⁶ is selected from the amino acid side chain of Gly, Ala, Val, Ser, Phe, Lys, Thr, Met, Tyr, His, Asp, Glu, Asn, Gln, Cys, Sec, Ile, Leu, Arg, Orn, Cit, Trp; 1-Me-Trp and Nva;
or a pharmaceutically acceptable salt thereof;
comprising:
reducing an ester of the formula

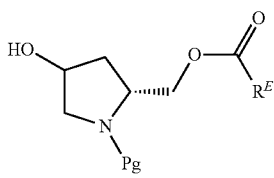

in which
$P_g$ is methyl substituted with 1, 2, or 3 phenyl groups, where each phenyl group is optionally substituted with 1, 2 or 3 groups independently selected from halogen, nitro, $C_1$-$C_6$ alkoxy, or $C_1$-$C_6$ alkyl;
$R^E$ is $C_1$-$C_6$ alkyl, $C_3$-$C_6$ cycloalkyl, $C_3$-$C_6$ cycloalkyl($C_1$-$C_6$)alkyl, or methyl substituted with 1, 2, or 3 phenyl groups, where each phenyl group is optionally substituted with 1, 2 or 3 groups independently selected from halogen, nitro, $C_1$-$C_6$ alkoxy, or $C_1$-$C_6$ alkyl
to yield a protected hydroxymethylpyrrolidine of the formula:

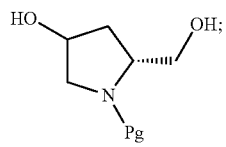

then
subjecting the protected hydroxymethylpyrrolidine to ring expansion conditions to produce a protected piperidine of the formula:

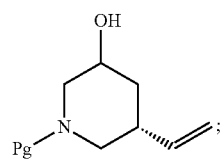

then
oxidizing the protected piperidine to form an enantiomerically enriched product comprising a ketone of the formula:

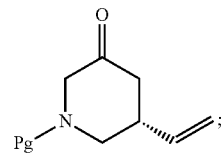

then
reacting the ketone with cyanide and an amine source to yield an α-cyanoamine of the formula:

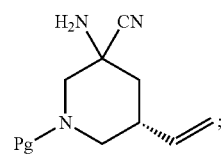

then
acylating the amino group of the α-cyanoamine to produce an acylated α-cyanoamine of the formula:

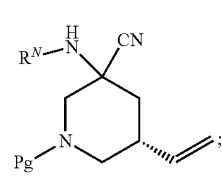

wherein $R^N$ is $C_2$-$C_6$ alkanoyl.

In certain such embodiments, the process further comprises subjecting the acylated α-cyanoamine to hydroboration conditions, and then deprotecting the resulting cyclic boronate ester to produce a boronic acid of the formula:

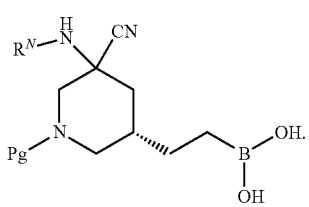

In certain such embodiments, the process further comprises hydrolyzing the acyl group to yield an α-amino acid with an unprotected amino group, and then protecting the amino group of the α-amino acid to generate a boronic acid of formula B-1:

(B-1)

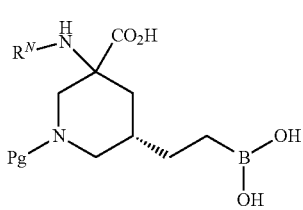

wherein $R^N$ is a nitrogen protecting group.

In certain such embodiments, the process further comprises reacting the compound of formula B-1 with a compound of the formula:

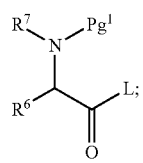

in which

L is a leaving group, such as N-hydroxysuccinimidyl or carboxylate or carbonate;

Pg$^1$ is a nitrogen protecting group;

R$^6$ represents a side chain of an amino acid selected from the group consisting of Gly, Ala, Val, Ser, Phe, Lys, Thr, Met, Tyr, His, Asp, Glu, Asn, Gln, Cys, Sec, Ile, Leu, Arg, Orn, Cit, Trp; 1-Me-Trp and Nva; and R$^7$ is hydrogen or methyl.

In certain embodiments of the process, desired stereoisomers can be obtained at any point using appropriate methods, for example, by fractional crystallization or chromatographic means well known in the art.

For example, in certain embodiments, the process for preparing a compound of formula Ib comprises the following steps:

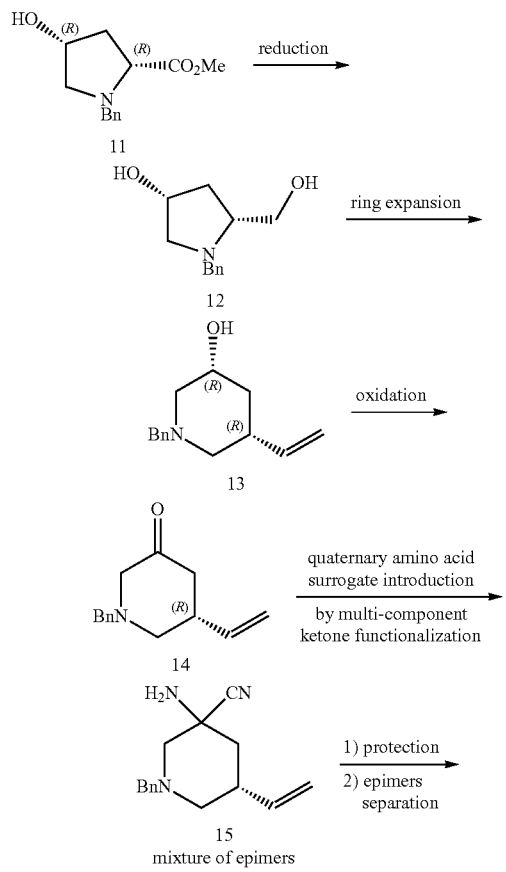

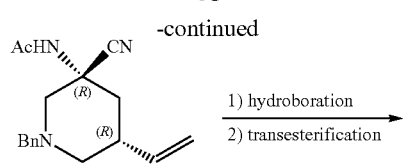

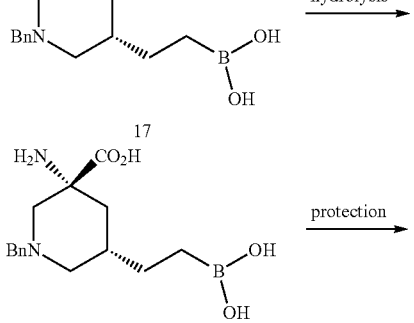

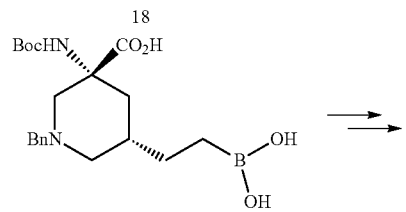

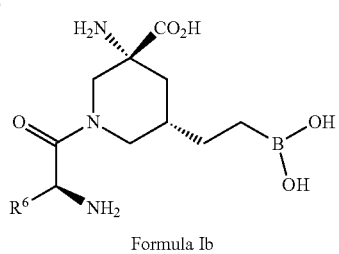

Formula Ib

Methyl (2R,4R)-1-benzyl-4-hydroxypyrrolidine-2-carboxylate 11 can be obtained commercially or prepared from cis-hydroxy-D-proline using literature methods. Reduction of ester 11 to alcohol 12 can be accomplished using known methods, for example, by using LiAlH$_4$, LiBH$_4$ or NaBH$_4$ in an appropriate solvent such as THF, diethyl ether or a mixture of THF and methanol. Pyrrolidine 12 can be then reacted to form to piperidine 13 via a ring expansion reaction according to the methods as otherwise described herein.

The ring expansion of enantiomerically and diastereoisomerically enriched protected (3R,5R)-5-(hydroxymethyl)pyrrolidin-3-ol A into enantiomerically and diastereoisomerically enriched protected (3R,5R)-5-vinylpiperidin-3-ol C is illustrated in the scheme below:

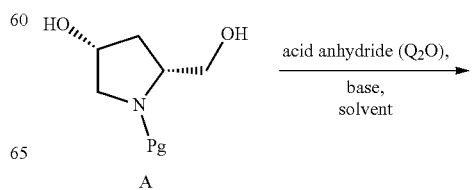

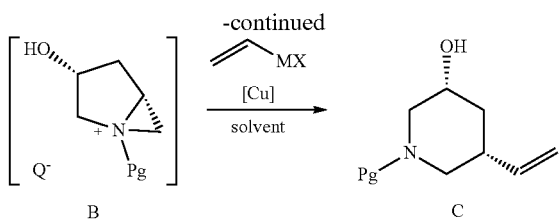

In this example, Pg is a protecting group including benzyl and its derivatives. The protecting group of A includes but is not limited to benzyl, 4-methylbenzyl, 4-methoxybenzyl, 4-bromobenzyl, 4-nitrobenzyl, 3-methylbenzyl, 2-methylbenzyl, 3,4-dimethoxybenzyl, 2,4,6-trimethylbenzyl, benzhydryl, trityl. Preferentially, the protecting group is benzyl. The formation of C take place via azabicyclo[3.1.0]hexan-1-ium salt B. A is treated with acid anhydride in the presence of the base in an appropriate solvent. The acid anhydride can include but is not limited to trifluoromethanesulfonic (triflic) anhydride, methanesulfonic anhydride, p-toluenesulfonic anhydride, trifluoroacetic anhydride. Preferentially, the acid anhydride is trifluoromethanesulfonic anhydride. The base can include but is not limited to N,N-diisoprophylethylamine (DIPEA), trimethylamine (TEA), DBU, DBN, DABCO, proton-sponge, Cs$_2$CO$_3$; preferentially the base is DIPEA. In some embodiment the formation of B can be accomplished without use of any external base. The solvent can include but is not limited to dichloromethane (DCM), tetrahydrofuran (THF), diethyl ether (Et$_2$O); preferentially the solvent is DCM. The reaction can be performed at a temperature within the range of −78° C. to room temperature; preferentially at −40° C. The same conditions can be used to synthesize protected (3S,5S)-5-vinylpiperidin-3-ol, starting from protected (3S,5S)-5-(hydroxymethyl) pyrrolidin-3-ol.

The formation of protected (3R,5R)-5-vinylpiperidin-3-ol C can be accomplished by aziridinium ring opening of azabicyclo[3.1.0]hexan-1-ium salt B, using a vinyl metal nucleophile such as a vinyl lithium reagent, a vinyl magnesium reagent, a vinyl zinc reagent, a vinyl copper reagent, or reagents including mixtures of these metals. Preferentially, the vinyl metal nucleophile is vinylmagnesium chloride (solution in THF). The ring opening reaction may also be assisted with copper salts [Cu] that include but are not limited to copper(I) chloride, copper(I) bromide, copper(I) iodide, copper(I) cyanide, copper(I) bromide dimethyl sulfide complex, and lithium tetrachlorocuprate; preferentially copper(I) chloride. The solvent can include but is not limited to THF, 2-Me-THF, and Et$_2$O. The reaction can be performed at a temperature within the range of −78° C. to room temperature; preferentially at −40° C.

The enantio- and diastereomerically enriched alcohol 13 can then be oxidized to enantiomerically enriched ketone 14 using known methods for secondary alcohols, such as but not limited to, Corey-Kim oxidation, Parikh-Doering oxidation, Swern oxidation, oxidation using hypervalent iodine, and the like.

Ketone 14 can then be transformed to diastereomerically enriched amino acid derivative 15 in a multi-component reaction. Such multi-component reactions can include but are not limited to, the Strecker reaction, the Ugi reaction, the Bucherer-Bergs reaction, and variations thereof. Solvents can include any of those suitable for such reactions: methanol, ethanol, isopropanol, trifluoroethanol, water, acetonitrile, dichloromethane, tetrahydrofuran, and mixtures thereof, and can include additives such as triethylamine or ammonium hydroxide. In the case of the Strecker reaction the cyanide source can be but is not limited to acetone cyanohydrine, sodium cyanide, and potassium cyanide. The ammonia source can be but is not limited to aqueous ammonia solution (NH$_4$OH), methanolic solution of ammonia, ammonium chloride, and ammonium acetate. Solvents can include any of those suitable for such reactions: methanol, ethanol, isopropanol, trifluoroethanol, water, acetonitrile, tetrahydrofuran, and mixtures thereof. The reaction can be performed at a temperature within the range of room temperature to 100° C.; preferentially at 60° C. In the case of the Strecker reaction the appropriate cyanoamine 15 can be formed as a mixture of epimers, (3R,5R)-3-amino-1-benzyl-5-vinylpiperidine-3-carbonitrile and (3S,5R)-3-amino-1-benzyl-5-vinylpiperidine-3-carbonitrile, present in the range from 1:1 to 10:1. The pure single epimer (3R,5R)-3-amino-1-benzyl-5-vinylpiperidine-3-carbonitrile can be obtained through chromatographic methods or by crystallization of the appropriate salt (e.g. oxalate) from a suitable solvent (e.g. ethanol). Preferentially the mixture of epimers can be used in subsequent steps without separation. The mixture of epimers 15 can then be protected under readily available conditions (e.g., acetylation with Ac$_2$O or AcCl in the presence of TEA) to afford a mixture of protected cyanoamines that can be then separated into the single enantiomerically and diastereomerically enriched protected cyanoamine 16 through chromatography (e.g. SiO$_2$ column chromatography) or crystallization of the appropriate salt (e.g. oxalate). Further steps can include hydroboration of cyanoamine 16 followed by pinacole removal by transesterification using phenylboronic acid to afford boronic acid 17, and can be accomplished using known methods. Subsequent hydrolysis and protection can be accomplished under readily available conditions (e.g., hydrolysis with aqueous hydrochloric acid, then Boc-protection using Boc$_2$O in alkaline aqueous media) to afford intermediate 8. Intermediate 8 can be subjected to steps as otherwise described herein to afford arginase inhibitors of formula Ib.

EXAMPLES

The present invention is further illustrated by the following examples, which in no way should be construed as limiting the scope of the claimed invention.

Methods of Preparation and Characterization

The compounds of the present disclosure may be prepared by use of known chemical reactions and procedures. Representative methods for synthesizing compounds of the disclosure are presented below. It is understood that the nature of the substituents required for the desired target compound often determines the method of synthesis. All variable groups of these methods are as described in the generic description if they are not specifically defined below.

Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978).

For the more specific guidance concerning the synthetic approach to boron bearing alpha-amino acids, the reader is referred to the international patent application publications WO 11/133653 (incorporated by reference), WO 13/059437 (incorporated by reference), WO 17/075363, WO 16/108707 and WO 17/191130.

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are in J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides;" Volume 3 (editors: E. Gross and J. Meienhofer), Academic Press, London and New York 1981, in "Methoden der organischen Chemie," Houben-Weyl, 4th edition, Vol. 15/1, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art. The disclosures of all articles and references mentioned in this application, including patents, are incorporated herein by reference in their entirety.

Starting materials can be obtained from commercial sources or prepared by literature methods.

All solvents, substrates and reagents that were commercially available were used without further purification. TLC analysis was performed using pre-coated glass plates (TLC silica gel 60 $F_{254}$) from Merck. Column chromatography was performed using high-purity grade silica gel (pore size 60 Å, 230-400 mesh particle size, 40-63 μm particle size) from Merck.

Preparative HPLC were performed on LC-20AP Shimadzu with ELSD-LTII detector equipped with Hypersil GOLD 21.2/250 mm, 5 μm C18 column.

$^1$H and $^{13}$C NMR spectra were recorded on Bruker AVANCE II PLUS (Ultra Shield) NMR spectrometer at 700 MHz.

All spectra were recorded in appropriate deuterated solvents (CDCl$_3$, DMSO-d$_6$, D$_2$O, CD$_3$OD, etc.) that were commercially available.

Resonances are given in parts per million relative to tetramethylsilane. Data are reported as follows: chemical shift, multiplicity (s=singlet, d=doublet, t=triplet, m=multiplet, bs=broad singlet), coupling constants (Hz) and integration.

ESI-MS spectra were obtained on a Shimadzu LC-20AD LPG separation module with a SPD-M20A UV detector and LCMS-2020 mass detector equipped with Kinetex 2.1/50 mm, 2.6 μm C18 column eluted with 0.5 mL/min flow of 10-90% gradient (over 5 min) of acetonitrile in water.

Abbreviations used are those conventional in the art or the following:

Ac=acetyl, aq=aqueous, Bn=benzyl, Boc=tert-butoxycarbonyl, t-Bu=tert-butyl, ° C.=degree Celsius, Cit=citrulline or citrullinyl, cod=1,5-cyclooctadiene, DCE=1,2-dichloroethane, DCM=dichloromethane, DMF=N,N-dimethylformamide, DMSO=dimethyl sulfoxide, dppe=1,2-bis(diphenylphosphino)ethane, ELSD=evaporative light scattering detector, EtOAc or AcOEt=ethyl acetate, EtOH=ethanol, ESI+MS=electrospray ionisation mass spectrometry (in the positive ion mode), ESI-MS=electrospray ionisation mass spectrometry (in the negative ion mode), g=gram, h=hour(s), HMPA=hexamethylphosphoramide, HPLC=high pressure liquid chromatography, K=kelvin, L=liter, LCMS=liquid chromatography and mass spectrometry, MeCN=acetonitrile, MeOH=methanol, min=minutes, mL=milliliter(s), M=molar, m/z=mass to charge ratio, NCS=N-chlorosuccinimide, nM=nanomolar, NMR=nuclear magnetic resonance, N=normal, Nva=norvaline or norvalinyl, Orn=ornithine or ornithinyl, OSu=N-oxysuccinimidyl, RT or rt=room temperature, TEA=triethyl amine, TFA=trifluoroacetic acid, THF=tetrahydrofuran, TMSCl=chlorotrimethylsilane.

Exemplary general synthetic methodologies for making compounds of Formula (I) are provided below.

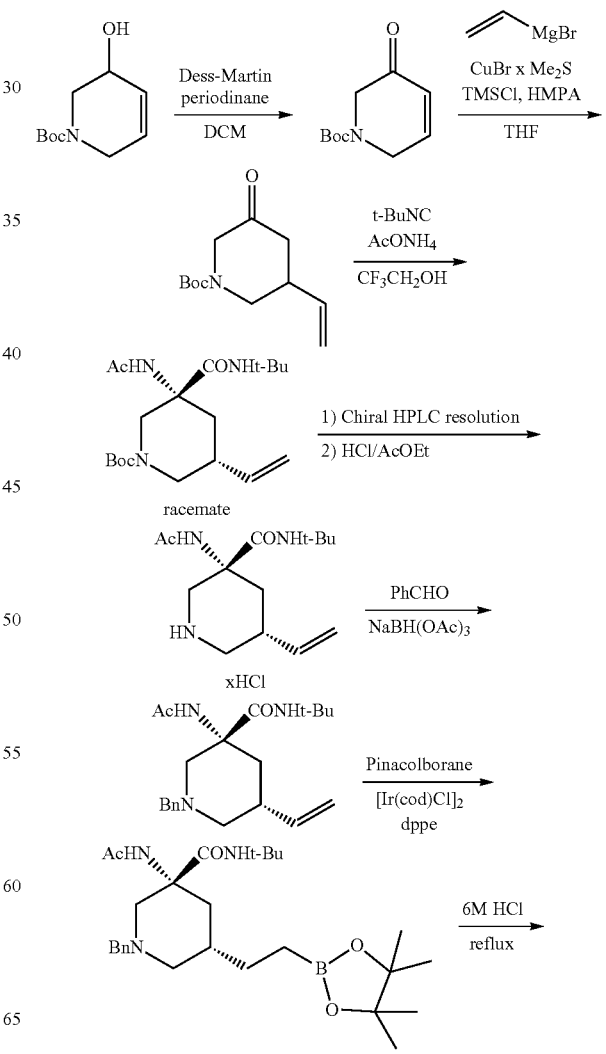

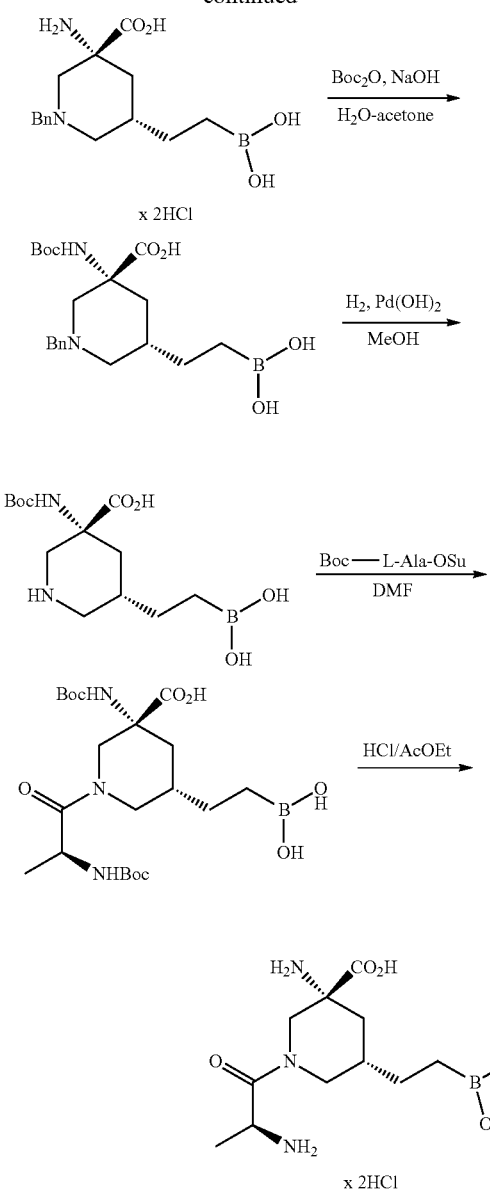

Example 1. (3R,5S)-1-(L-Alanyl)-3-amino-5-(2-boronoethyl)piperidine-3-carboxylic acid dihydrochloride

Step A. tert-Butyl 3-oxo-3,6-dihydropyridine-1(2I-O-carboxylate

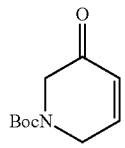

To a solution of tert-butyl 3-hydroxy-3,6-dihydropyridine-1(2H)-carboxylate (CAS: 224779-27-5, 10 g, 50.19 mmol) in DCM (200 mL) was added Dess-Martin periodinane (25.55 g, 60.2 mmol). After stirring for 1.5 h additional amount of Dess-Martin periodinane (2.50 g, 12.54 mmol) was added together with DCM (50 mL). The reaction mixture was stirred for additional 1.5 h; then 750 mL of hexane was added and stirring was continued for 10 min. The solid that precipitated was filtered off. The filtrate was concentrated and treated with a fresh portion of hexane (500 mL), filtered and concentrated in vacuo to give 10.01 g (100%) of tert-butyl 3-oxo-3,6-dihydropyridine-1(2H)-carboxylate as a pale orange solid. ESI+MS: m/z=142.20 (M−56+1)+. 1H NMR (700 MHz, 300 K, DMSO-d6) δ 7.22 (bs, 1H), 6.10 (dt, J=10.3, 2.3 Hz, 1H), 4.18 (bs, 1H), 4.01 (bs, 1H), 1.42 (s, 9H).

Step B. tert-Butyl 3-oxo-5-vinylpiperidine-1-carboxylate

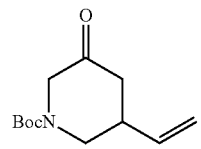

To a flask charged with CuBr×Me$_2$S complex (0.78 g, 3.8 mmol) and dry THF (125 mL) were added HMPA (17.60 mL, 101.40 mmol) and vinylmagnesium bromide 1M solution in THF (88.72 mL, 88.72 mmol) at −78° C. under Ar. The reaction mixture was stirred for 15 min followed by a solution of tert-butyl 3-oxo-3,6-dihydropyridine-1(2H)-carboxylate (5 g, 25.35 mmol) and chlorotrimethylsilane (16.08 mL, 126.75 mmol) in THF (75 mL) was added dropwise for over 30 min. The reaction mixture was stirred for 2 h at −78° C. and subsequently overnight at RT. After the reaction was completed, 60 mL of saturated aqueous NH$_4$Cl solution was added, and then the layers were separated. The organic layer was washed with NH$_4$Cl (3×30 mL). The aqueous layer was diluted with H$_2$O (100 mL) and washed with AcOEt (2×40 mL). The combined organic layers were washed with brine (20 mL), dried over MgSO$_4$ and concentrated in vacuo. The crude product was purified by silica gel column chromatography using hexane/EtOAc (1:0 to 1:4) as an eluent. The desired product was obtained as a colorless oil. Yield: 4.23 g (74%). ESI+MS: m/z=170.15 (M−56+1)+. 1H NMR (700 MHz, 300 K, chloroform-d) δ 5.77 (ddd, J=17.0, 10.5, 6.3 Hz, 1H), 5.15 5.10 (m, 2H), 4.09 (d, J=18.0 Hz, 1H), 4.05-3.72 (m, 2H), 3.21 (bs, 1H), 2.78-2.71 (m, 1H), 2.61 (dd, J=16.3, 4.7 Hz, 1H), 2.37 (dd, J=16.2, 10.0 Hz, 1H), 1.46 (s, 9H).

Step C. tert-Butyl (3R,5R)-3-acetamido-3-(tert-butylcarbamoyl)-5-vinylpiperidine-1-carboxylate (racemate)

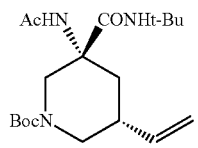

To the stirred solution of tert-butyl 3-oxo-5-vinylpiperidine-1-carboxylate (4.23 g, 21.45 mmol), and ammonium acetate (5.80 g, 77.25 mmol) in 2,2,2-trifluoroethanol (60 mL), tert-butyl isocyanide (3.10 mL, 27.41 mmol) was added dropwise and the resulting mixture was stirred at room temperature overnight. After the reaction was completed, the solvent was evaporated under reduced pressure and the residue was diluted with DCM (60 mL) and water (25 mL). The separated aqueous layer was washed with DCM (3×10 mL). The combined organic layers were washed with brine (20 mL), dried over MgSO$_4$, filtered and concentrated under reduced pressure to volume of 10-15 mL. The residue was treated with hexane (50 mL) and left for 24 h for crystallization. The precipitated solid was filtered and dried under vacuum to give 3.85 g (49% yield) of the desired product as a white crystalline solid (single racemic diastereoisomer). ESI+MS: m/z=368.25 (M+1)$^+$. $^1$H NMR (700 MHz, 300K, chloroform-d) δ 7.00 (bs, 1H), 5.96 (bs, 1H), 5.73 (ddd, J=17.1, 10.6, 6.1 Hz, 1H), 5.14 (dt, J=17.1, 1.2 Hz, 1H), 5.08 (dt, J=10.6, 1.2 Hz, 1H), 4.38 (d, J=14.2 Hz, 1H), 3.78 (dd, J=13.5, 2.4 Hz, 1H), 3.47 (d, J=13.9 Hz, 1H), 3.02 (dd, J=12.8, 8.8 Hz, 1H), 2.36 (bs, 1H), 2.27 (d, J=11.8 Hz, 1H), 1.96-1.89 (m, 4H), 1.48 (s, 9H), 1.33 (s, 9H).

Step D. tert-Butyl (3S,5S)-3-acetamido-3-(tert-butylcarbamoyl)-5-vinylpiperidine-1-carboxylate and tert-butyl (3R,5R)-3-acetamido-3-(tert-butylcarbamoyl)-5-vinylpiperidine-1-carboxylate

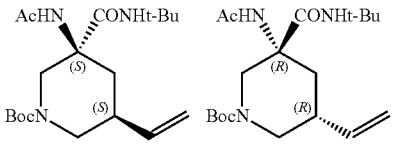

The racemic mixture of tert-butyl (3R,5R)-3-acetamido-3-(tert-butylcarbamoyl)-5-vinylpiperidine-1-carboxylate (1.9 g, 5.17 mmol) was separated for its enantiomers using a chiral preparative HPLC method (LumiSep Chiralcel AD column) with propan-2-ol and n-hexane (gradient: 5-30%) as an eluent and ELSD detection. Retention time of tert-butyl (3S,5S)-3-acetamido-3-(tert-butylcarbamoyl)-5-vinylpiperidine-1-carboxylate in preparative HPLC was in the range from 4.3 to 8.2 min. Retention time of tert-butyl (3R,5R)-3-acetamido-3-(tert-butylcarbamoyl)-5-vinylpiperidine-1-carboxylate in preparative HPLC was in the range from 9.7 to 14.7 min. The enantiomeric excess for both enantiomers was determined with the use of chiral analytical HPLC method with ELSD detection with RegisPack (5 μm, 4.6×250 mm) column using 10% propan-2-ol in n-hexane as eluent for 10 min. The first enantiomer tert-butyl (3S,5S)-3-acetamido-3-(tert-butylcarbamoyl)-5-vinylpiperidine-1-carboxylate (0.85 g, 45%, white solid) with the retention time of 5.21 min and the second desired enantiomer tert-butyl (3R,5R)-3-acetamido-3-(tert-butylcarbamoyl)-5-vinylpiperidine-1-carboxylate (0.82 g, 43%, white solid) at 7.57 min, each with enantiomeric excess of approximately 98% ee or higher.

Step E. (3R,5R)-3-Acetamido-N-(tert-butyl)-5-vinylpiperidine-3-carboxamide hydrochloride

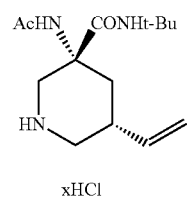

tert-Butyl (3R,5R)-3-acetamido-3-(tert-butylcarbamoyl)-5-vinylpiperidine-1-carboxylate (732 mg, 1.99 mmol) was treated with 4M HCl in EtOAc (15 mL). The reaction mixture was stirred for 1 h. The solvent was evaporated under reduced pressure to give 603 mg (100%) of the desired product as a white solid. ESI+MS: m/z=268.25 (M+1)$^+$. $^1$H NMR (700 MHz, 300K, chloroform-d) δ 10.44 (d, J=6.8 Hz, 1H), 8.52 (s, 1H), 8.17 (d, J=8.2 Hz, 1H), 7.35 (s, 1H), 5.66 (ddd, J=17.1, 10.4, 6.5 Hz, 1H), 5.17 (d, J=17.1, 1H), 5.15 (d, J=10.4 Hz, 1H), 4.17 (d, J=12.4 Hz, 1H), 3.37 (d, J=11.4 Hz, 1H), 2.93 (t, J=10.8 Hz, 1H), 2.86 (q, J=12.2 Hz, 1H), 2.59-2.49 (m, 2H), 2.10 (s, 3H), 1.95 (t, J=12.8 Hz, 1H), 1.33 (s, 9H).

Step F. (3R,5R)-3-Acetamido-1-benzyl-N-(tert-butyl)-5-vinylpiperidine-3-carboxamide

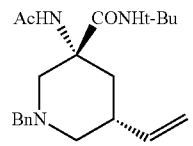

To the solution of (3R,5R)-3-acetamido-N-(tert-butyl)-5-vinylpiperidine-3-carboxamide hydrochloride (684 mg, 2.25 mmol) and benzaldehyde (274 μL, 2.70 mmol) in 1,2-dichloroethane (20 mL) was added NaBH(OAc)$_3$ (2384 mg, 11.25 mmol). The reaction mixture was stirred overnight at RT. In the next step the mixture was washed with 5% aqueous solution of NaHCO$_3$ (3×15 mL), and subsequent with 1M aqueous KHSO$_4$ (2×20 mL). The combined aqueous acidic layers were alkalized to pH 12 with 2M NaOH and washed with DCM (5×15 mL). The combined organic layers were washed with brine (20 mL), dried over MgSO$_4$, concentrated in vacuo to give 696 mg (87%) of the desired product as a white solid. ESI+MS: m/z=358.25 (M+1)$^+$. $^1$H NMR (700 MHz, 300K, acetonitrile-d$_3$ 500 μL+deuterium oxide 100 μL) δ 7.36-7.31 (m, 2H), 7.31-7.27 (m, 3H), 5.64 (ddd, J=17.3, 10.4, 6.6 Hz, 1H), 4.99 (dt, J=17.3, 1.3 Hz, 1H), 4.96 (dt, J=10.4, 1.1 Hz, 1H), 3.67 (d, J=11.7 Hz, 1H), 3.56 (d, J=12.3 Hz, 1H), 3.43 (d, J=12.9 Hz, 1H), 2.90-2.85

(m, 1H), 4.41-2.33 (m, 1H), 2.00 (d, J=11.3 Hz, 1H), 1.86-1.83 (m, 1H), 1.81 (s, 3H), 1.72 (t, J=11.4 Hz, 1H), 1.31-1.23 (m, 10H).

Step G. (3R,5S)-3-Acetamido-1-benzyl-N-(tert-butyl)-5-(2-(4,4,5,5-tetramethyl-1,3,2-dioxaborolan-2-yl)ethyl)piperidine-3-carboxamide

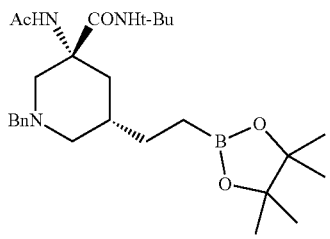

A round-bottom flask charged with bis(1,5-cyclooctadiene)diiridium (I) dichloride (40 mg, 0.06 mmol), 1,2-bis(diphenylphosphino)ethane (48 mg, 0.12 mmol) and dry DCM (10 mL) was flushed with argon (bubbling). Subsequently, the separately prepared solution of 4,4,5,5-tetramethyl-1,3,2-dioxaborolane (702 µL, 4.84 mmol) and (3R, 5R)-3-acetamido-1-benzyl-N-(tert-butyl)-5-vinylpiperidine-3-carboxamide (692 mg, 1.94 mmol) in DCM (19 mL) was added dropwise. The resulting mixture was then stirred at room temperature for 24 h. The solvent was removed under reduced pressure and the residue was subjected to flash chromatography on silica gel (using EtOAc-hexane, 1:10 to 1:0 as the eluent) to afford 639 mg (68%) of the desired product as a light yellow oil. ESI+MS: m/z=486.10 (M+1)$^+$. $^1$H NMR (700 MHz, 300K, chloroform-d) δ 9.11 (s, 1H), 7.37-7.33 (m, 2H), 7.32-7.26 (m, 3H), 6.71 (s, 1H), 3.54 (s, 2H), 3.13 (d, J=11.2 Hz, 1H), 2.99-2.93 (m, 2H), 2.00-1.97 (m, 1H), 1.96 (s, 3H), 1.81-1.76 (m, 2H), 1.76-1.71 (m, 1H), 1.39-1.26 (m, 11H), 1.24 (12H), 0.76 (ddd, J=16.1, 10.5, 6.3 Hz, 1H), 0.68 (ddd, J=16.1, 10.4, 6.2 Hz, 1H).

Step H. (3R,5S)-3-Amino-1-benzyl-5-(2-boronoethyl)piperidine-3-carboxylic acid dihydrochloride

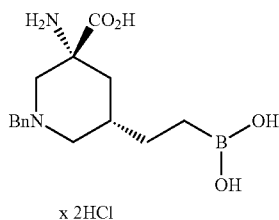 [SMILES: N[C@]1(C(=O)O)C[C@H](CCB(O)O)CN(Cc2ccccc2)C1]

A mixture of (3R,5S)-3-acetamido-1-benzyl-N-(tert-butyl)-5-(2-(4,4,5,5-tetramethyl-1,3,2-dioxaborolan-2-yl)ethyl)piperidine-3-carboxamide (0.63 g, 1.30 mmol) and 12M HCl$_{(ac)}$ (15 mL) was heated at 130° C. overnight. The reaction mixture was concentrated under reduced pressure to give 0.49 g (99%) of the corresponding product as a beige solid. ESI+MS: m/z=307.10 (M+1)$^+$. $^1$H NMR (700 MHz, 300 K, deuterium oxide) δ 7.61-7.56 (m, 5H), 4.66 (d, J=13.3 Hz, 1H), 4.34 (d, J=13.3 Hz, 1H), 3.76-3.69 (m, 1H), 3.66 (dt, J=12.0, 1.9 Hz, 1H), 3.08 (d, J=12.0 Hz, 1H), 2.87 (t, J=12.3 Hz, 1H), 2.37 (ddt, J=13.1, 3.6, 1.7 Hz, 1H), 2.17-2.09 (m, 1H), 1.58-1.40 (m, 3H), 0.91-0.76 (m, 2H).

Step I. (3R,5S)-1-Benzyl-5-(2-boronoethyl)-3-((tert-butoxycarbonyl)amino)piperidine-3-carboxylic acid

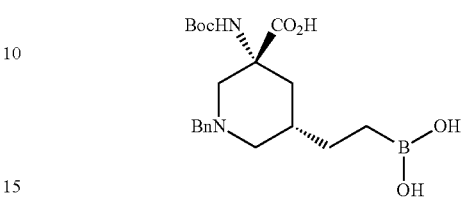

To a suspension of (3R,5S)-3-amino-1-benzyl-5-(2-boronoethyl)piperidine-3-carboxylic acid dihydrochloride (0.50 g, 1.32 mmol) in acetone (12 mL) was added 1M NaOH (8 mL, to pH~9) and di-tert-butyl dicarbonate (0.63 g, 2.90 mmol). The resulting mixture was stirred at room temperature overnight. An inorganic contaminations were precipitated using acetone (10 mL) and were filtered off. A filtrate was neutralized to pH~7 with 1M HCl (2 drops) and concentrated under reduced pressure. The residue was triturated with small amount of methanol to remove the rest of the inorganic salts. The crude product was obtain after filtration of methanolic solution and concentration to give 0.53 g of a pale yellow foam that was used to the next step without any further purification. ESI+MS: m/z=407.10 (M+1)$^+$; ESI-MS: m/z=405.15 (M−1)$^−$. $^1$H NMR (700 MHz, 300 K, deuterium oxide) δ 7.63-7.52 (m, 5H), 4.70-4.58 (m, 1H), 4.06 (d, J=13.1 Hz, 1H), 3.85-3.73 (m, 1H), 3.69 (d, J=11.9 Hz, 1H), 2.87-2.60 (m, 2H), 2.12-2.07 (m, 1H), 1.99-1.88 (m, 1H), 1.54-1.29 (m, 3H), 1.11 (s, 9H), 0.90-0.73 (m, 2H).

Step J. (3R,5S)-5-(2-Boronoethyl)-3-((tert-butoxycarbonyl)amino)piperidine-3-carboxylic acid

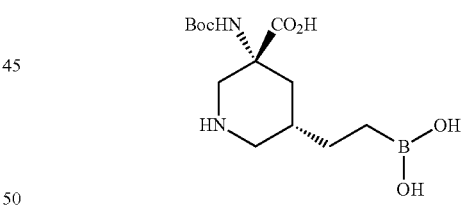

To a solution of (3R,5S)-1-benzyl-5-(2-boronoethyl)-3-((tert-butoxycarbonyl)amino)piperidine-3-carboxylic acid (0.27 g, 0.66 mmol), in MeOH (5 mL) under argon, 20% Pd(OH)$_2$/C (50 mg) was added. The mixture was degassed, charged with H$_2$, and stirred for 2 days at room temperature under hydrogen atmosphere (7 bar). The reaction mixture was filtered through a Celite pad, washed with MeOH (2×5 mL) and filtered. The filtrate was concentrated in vacuo. The residue was purified by preparative HPLC (5-60% of acetonitrile in water) to give the corresponding product (0.09 g, 43%, white solid). ESI+MS: m/z=317.00 (M+1)$^+$; ESI-MS: m/z=315.05 (M−1)$^−$. $^1$H NMR (700 MHz, 300 K, deuterium oxide) δ 4.01 (dt, J=12.1, 1.6 Hz, 1H), 3.45 (dd, J=12.3, 4.1 Hz, 1H), 2.79 (d, J=12.1 Hz, 1H), 2.64 (t, J=12.4 Hz, 1H), 2.12 (bs, 1H), 1.83 (bs, 1H), 1.49-1.34 (m, 12H), 0.88-0.76 (m, 2H).

Step K. (3R,5S)-5-(2-Boronoethyl)-1-((tert-butoxy-carbonyl)-L-alanyl)-3-((tert-butoxycarbonyl)amino)piperidine-3-carboxylic acid

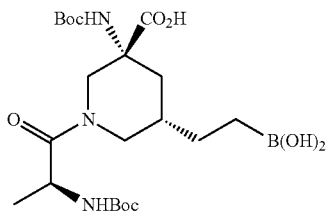 [SMILES: C[C@H](NC(=O)OC(C)(C)C)C(=O)N1C[C@@H](CCB(O)O)C[C@](NC(=O)OC(C)(C)C)(C(=O)O)C1]

To a stirred solution of (3R,5S)-5-(2-boronoethyl)-3-((tert-butoxycarbonyl)amino)piperidine-3-carboxylic acid (0.08 g, 0.25 mmol) in DMF (2 mL), Boc-L-Ala-OSu (0.13 g, 0.46 mmol) was added and the resulting mixture was stirred at room temperature overnight. DMF was evaporated under reduced pressure and the residue was purified by column chromatography on silica gel using DCM/MeOH (80:1 to 0:1) to afford 0.11 g (89%) of the corresponding product as a colorless film (5:2 mixture of rotamers in CD$_3$OD solution at room temperature based on NMR). ESI+MS: m/z=488.20 (M+1)$^+$; ESI-MS: m/z=486.25 (M−1)$^-$. $^1$H NMR (700 MHz, 300 K, methanol-d$_4$) δ 5.17-5.07 (m, 0.3H), 4.80-4.73 (m, 0.7H), 4.59-4.42 (m, 1H), 4.19 (bs, 0.7H), 4.03 (bs, 0.3H), 2.62-2.75 (m, 3H), 2.38 (d, J=12.8 Hz, 0.3H), 2.30 (d, J=12.9 Hz, 0.7H), 1.64 (s, 1H), 1.47 (dd, J=7.5, 4.9 Hz, 18H), 1.38-1.24 (m, 5H), 0.94-0.76 (m, 2H).

Step L. (3R,5S)-1-(L-Alanyl)-3-amino-5-(2-boronoethyl)piperidine-3-carboxylic acid dihydrochloride (3R,5S)-5-(2-Boronoethyl)-1-((tert-butoxycarbonyl)-L-alanyl)-3-((tert-butoxycarbonyl)amino)piperidine-3-carboxylic acid (0.10 g, 0.21 mmol) was treated with 4M HCl in EtOAc (4 mL) and the resulting mixture was stirred at room temperature for 1.5 h. Then the reaction mixture was concentrated under reduced pressure and the residue was purified by preparative HPLC (0.1-1% of acetonitrile in water) to give (after acidification with 2M HCl and subsequent lyophilization) 52 mg (67%) of the corresponding product as a white solid (4:1 mixture of rotamers in D$_2$O solution at room temperature based on NMR). ESI+MS: m/z=288.10 (M+1)$^+$; 270.00 (M−18+1)$^+$; ESI-MS: m/z=268.05 (M−18−1)$^-$. $^1$H NMR (700 MHz, 300 K, deuterium oxide) δ 4.95-4.92 (m, 1H), 4.56 (q, J=7.1 Hz, 1H), 3.88 (dd, J=13.1, 4.2 Hz, 1H), 3.01-2.91 (m, 2H), 2.54-2.47 (m, 1H), 2.15-2.06 (m, 0.8H), 2.01-1.95 (m, 0.2H), 1.62-1.48 (m, 5H), 1.48-1.35 (m, 1H), 0.92-0.81 (m, 2H).

(3R,5S)-1(L-alanyl)-3-amino-5-(2-boronoethyl)piperidine-3-carboxylic acid

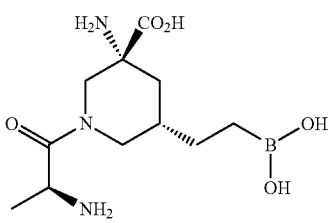 [SMILES: C[C@H](N)C(=O)N1C[C@@H](CCB(O)O)C[C@](N)(C(=O)O)C1]

(3R,5S)-1-(L-Alanyl)-3-amino-5-(2-boronoethyl)piperidine-3-carboxylic acid dihydrochloride can be converted to zwitterionic form using DOWEX® ion exchange resin. Thus (3R,5S)-1-(L-alanyl)-3-amino-5-(2-boronoethyl)piperidine-3-carboxylic acid dihydrochloride (680 mg) was subjected to flash chromatography on DOWEX® ion exchange resin 50WX8 hydrogen form; 50-100 mesh (eluent 0.1N ammonia in water) to give (after lyophilization) the corresponding (3R,5S)-1-(L-alanyl)-3-amino-5-(2-boronoethyl)piperidine-3-carboxylic acid (405 mg) as a white solid (5:2 mixture of rotamers in D$_2$O solution at 333 K based on NMR). ESI+MS: m/z=288.10 (M+1)$^+$; 270.05 (M−18+1)$^+$; ESI-MS: m/z=268.05 (M−18−1)$^-$. $^1$H NMR (700 MHz, 333 K, deuterium oxide) δ 5.02 (d, J=12.9 Hz, 0.7H), 4.65 (d, J=7.3 Hz, 1H), 4.51 (d, J=13.1 Hz, 0.3H), 4.40 (d, J=13.3 Hz, 0.3H), 4.07 (d, J=13.7 Hz, 0.7H), 3.45 (d, J=13.4 Hz, 0.3H), 3.10 (t, J=12.7 Hz, 0.7H), 3.00 (d, J=12.9 Hz, 0.7H), 2.86 (t, J=12.4 Hz, 0.3H), 2.61 (d, J=12.8 Hz, 1H), 2.23 (bs, 0.7H), 2.08 (bs, 0.3H), 1.78-1.61 (m, 5H), 1.59-1.48 (m, 1H), 1.1-1.06 (m, 2H).

Example 2. (3S,5R)-1-(L-Alanyl)-3-amino-5-(2-boronoethyl)piperidine-3-carboxylic acid dihydrochloride

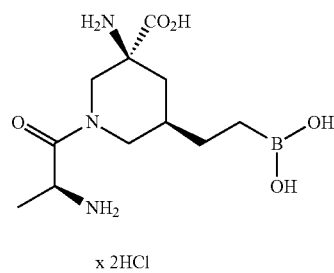 [SMILES: C[C@H](N)C(=O)N1C[C@H](CCB(O)O)C[C@@](N)(C(=O)O)C1]

Step A. (3S,5S)-3-Acetamido-N-(tert-butyl)-5-vinylpiperidine-3-carboxamide hydrochloride

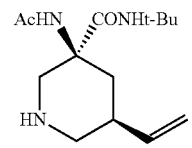

The title compound was obtained according to step (E) of Example 1, using tert-butyl (3S,5S)-3-acetamido-3-(tert-butylcarbamoyl)-5-vinylpiperidine-1-carboxylate (0.99 g, 2.68 mmol) and 4M HCl in EtOAc (30 mL). The reaction mixture was concentrated under reduced pressure to give a corresponding product (0.66 g, 80%, pale yellow foam). ESI+MS: m/z=268.25 (M+1)$^+$. $^1$H NMR (700 MHz, 300 K, chloroform-d) δ 10.33 (bs, 1H), 8.52 (s, 1H), 8.17 (bs, 1H), 7.27 (s, 1H), 5.66 (ddd, J=17.1, 10.5, 6.5 Hz, 1H), 5.21-5.00 (m, 2H), 4.20 (d, J=12.1 Hz, 1H), 3.38 (d, J=12.5 Hz, 1H), 2.94-2.81 (m, 2H), 2.57-2.48 (m, 2H), 2.10 (s, 3H), 2.00-1.90 (m, 1H), 1.33 (s, 9H).

Step B. (3S,5S)-3-Acetamido-1-benzyl-N-(tert-butyl)-5-vinylpiperidine-3-carboxamide

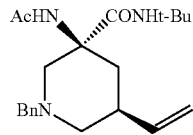

The title compound was obtained according to step (F) of Example 1, using (3S,5S)-3-acetamido-N-(tert-butyl)-5-vinylpiperidine-3-carboxamide hydrochloride (0.64 g, 2.11 mmol), benzaldehyde (0.26 mL, 2.53 mmol), sodium triacetoxyborohydride (2.23 g, 10.53 mmol) and DCE (21.5 mL). The desired product was obtained as a white solid (0.75 g, 99%). ESI+MS: m/z=358.25 (M+1)$^+$; 380.25 (M+23)$^+$; ESI-MS: m/z=356.15 (M−1)$^−$. $^1$H NMR (700 MHz, 300 K, chloroform-d) δ 9.04 (s, 1H), 7.42-7.29 (m, 5H), 6.70 (s, 1H), 5.63 (ddd, J=17.2, 10.4, 6.6 Hz, 1H), 5.30 (s, 2H), 5.05-4.96 (m, 2H), 3.59-3.49 (m, 2H), 3.16 (d, J=11.5 Hz, 1H), 3.00-2.89 (m, 2H), 2.55-2.41 (m, 1H), 2.23 (t, J=12.9 Hz, 1H), 1.95 (s, 3H), 1.35 (s, 9H).

Step C. (3S,5R)-3-Acetamido-1-benzyl-N-(tert-butyl)-5-(2-(4,4,5,5-tetramethyl-1,3,2-dioxaborolan-2-yl)ethyl)piperidine-3-carboxamide

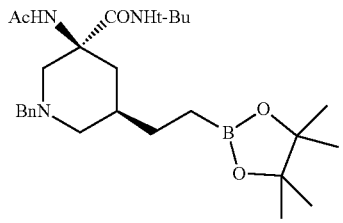

The title compound was obtained according to step (G) of Example 1, using (3S,5S)-3-acetamido-1-benzyl-N-(tert-butyl)-5-vinylpiperidine-3-carboxamide (0.73 g, 2.04 mmol), dppe (49 mg, 0.12 mmol), bis(1,5-cyclooctadiene)diiridium(I) dichloride (41 mg, 0.06 mmol), 4,4,5,5-tetramethyl-1,3,2-dioxaborolane (0.74 mL, 5.10 mmol) and DCM (40 mL). The crude product was purified by column chromatography on silica gel (hexane:EtOAc, 5:1 to 1:3) to give 0.57 g (58%) of the corresponding product as a white solid. ESI+MS: m/z=486.35 (M+1)$^+$; 508.40 (M+23)$^+$. $^1$H NMR (700 MHz, 300 K, chloroform-d) δ 9.08 (s, 1H), 7.32-7.26 (m, 5H), 6.69 (s, 1H), 3.51 (s, 2H), 3.10 (d, J=11.4 Hz, 1H), 2.97-2.87 (m, 2H), 1.93 (s, 3H), 1.80-1.68 (m, 3H), 1.36-1.34 (m, 1H), 1.33 (s, 9H), 1.27 (s, 2H), 1.21 (s, 12H), 0.76-0.63 (m, 2H).

Step D. (3S,5R)-3-Amino-1-benzyl-5-(2-boronoethyl)piperidine-3-carboxylic acid dihydrochloride

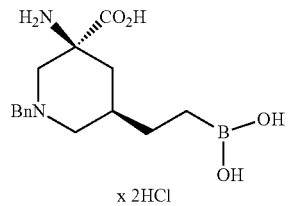 [SMILES: N[C@@]1(C(=O)O)C[C@@H](CCB(O)O)CN(Cc2ccccc2)C1]

The title compound was obtained according to step (H) of Example 1, using (3S,5R)-3-acetamido-1-benzyl-N-(tert-butyl)-5-(2-(4,4,5,5-tetramethyl-1,3,2-dioxaborolan-2-yl)ethyl)piperidine-3-carboxamide (0.56 g, 1.14 mmol) and 12M HCl$_{(aq)}$(25 mL). The reaction mixture was concentrated under reduced pressure to afford the corresponding product (0.43 g, 99%, beige solid). ESI+MS: m/z=307.25 (M+1)$^+$. $^1$H NMR (700 MHz, 300 K, deuterium oxide) δ 7.61-7.56 (m, 5H), 4.66 (d, J=13.3 Hz, 1H), 4.34 (d, J=13.3 Hz, 1H), 3.76-3.69 (m, 1H), 3.66 (dt, J=12.0, 1.9 Hz, 1H), 3.08 (d, J=12.0 Hz, 1H), 2.87 (t, J=12.3 Hz, 1H), 2.37 (ddt, J=13.1, 3.6, 1.7 Hz, 1H), 2.17-2.09 (m, 1H), 1.58-1.40 (m, 3H), 0.91-0.76 (m, 2H).

Step E. (3S,5R)-1-Benzyl-5-(2-boronoethyl)-3-((tert-butoxycarbonyl)amino)piperidine-3-carboxylic acid

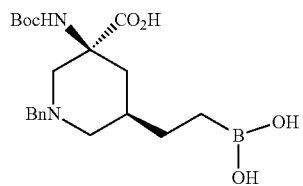 [SMILES: CC(C)(C)OC(=O)N[C@@]1(C(=O)O)C[C@@H](CCB(O)O)CN(Cc2ccccc2)C1]

The title compound was obtained according to step (I) of Example 1, using (3S,5R)-3-amino-1-benzyl-5-(2-boronoethyl)piperidine-3-carboxylic acid dihydrochloride (0.43 g, 1.13 mmol), di-tert-butyl dicarbonate (0.62 g, 2.84 mmol), 1M NaOH$_{(aq)}$ (4 mL) and acetone (10 mL). The desired product was obtained as a white solid (0.45 g, 99%). ESI+MS: m/z=407.25 (M+1)$^+$; ESI-MS: m/z=405.10 (M−1)$^−$. $^1$H NMR (700 MHz, 300 K, deuterium oxide) δ 7.57 (s, 5H), 4.66 (d, J=13.1 Hz, 1H), 4.06 (d, J=13.1 Hz, 1H), 3.78 (d, J=11.8 Hz, 1H), 3.69 (d, J=11.9 Hz, 1H), 2.85-2.61 (m, 2H), 2.11 (d, J=13.0 Hz, 1H), 1.99-1.88 (m, 1H), 1.52-1.41 (m, 3H), 1.11 (s, 9H), 0.88-0.75 (m, (s, 2H).

Step F. (3S,5R)-5-(2-Boronoethyl)-3-((tert-butoxycarbonyl)amino)piperidine-3-carboxylic acid

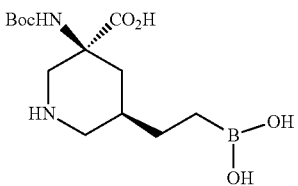 [SMILES: CC(C)(C)OC(=O)N[C@]1(C(=O)O)CNC[C@H](CCB(O)O)C1]

The title compound was obtained according to step (J) of Example 1, using (3S,5R)-1-benzyl-5-(2-boronoethyl)-3-((tert-butoxycarbonyl)amino)piperidine-3-carboxylic acid (0.24 g, 0.59 mmol), 20% Pd(OH)$_2$/C (50 mg) and MeOH (5 mL). The desired product was obtained as a grey solid (0.18 g, 99%). ESI+MS: m/z=317.20 (M+1)$^+$; ESI-MS: m/z=315.10 (M−1)$^−$. $^1$H NMR (700 MHz, 300 K, methanol-d$_4$) δ 4.56 (s, 1H), 3.89 (d, J=11.7 Hz, 1H), 3.38-3.36 (m, 1H), 2.94-2.85 (m, 1H), 2.50 (t, J=12.3 Hz, 1H), 2.08-2.00 (m, 1H), 1.97-1.88 (m, 1H), 1.43 (s, 9H), 1.40-1.28 (m, 2H), 0.85-0.73 (m, 2H).

Step G. (3S,5R)-5-(2-Boronoethyl)-1-((tert-butoxy-carbonyl)-L-alanyl)-3-((tert-butoxycarbonyl)amino)piperidine-3-carboxylic acid

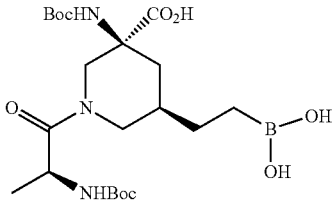 [SMILES: C[C@H](NC(=O)OC(C)(C)C)C(=O)N1C[C@H](CCB(O)O)C[C@@](NC(=O)OC(C)(C)C)(C(=O)O)C1]

The title compound was obtained according to step (K) of Example 1, using (3S,5R)-5-(2-boronoethyl)-3-((tert-butoxycarbonyl)amino)piperidine-3-carboxylic acid (0.17 g, 0.54 mmol), Boc-L-Ala-OSu (0.20 g, 0.70 mmol), and DMF (4.5 mL). The reaction mixture was stirred overnight at room temperature. DMF was evaporated and the residue was purified by column chromatography on silica gel using DCM/MeOH (20:1 to 0:1) to give 0.20 g (76%) of the desired product as a white solid (3:2 mixture of rotamers in CD$_3$OD at room temperature based on NMR). ESI+MS: m/z=488.20 (M+1)$^+$; ESI-MS: m/z=486.20 (M−1)$^−$. $^1$H NMR (700 MHz, 300 K, methanol-d$_4$) δ 5.14-5.05 (m, 0.6H), 5.04-4.97 (m, 0.4H), 4.67-4.55 (m, 1.4H), 4.53-4.46 (m, 0.6H), 3.06-2.94 (m, 0.4H), 2.76-2.60 (m, 2.6H), 2.42-2.14 (m, 2H), 1.54-1.43 (m, 18H), 1.42-1.23 (m, 5H), 0.91-0.81 (m, 2H).

Step H. (3S,5R)-1-(L-Alanyl)-3-amino-5-(2-boronoethyl)piperidine-3-carboxylic acid dihydrochloride The title compound was obtained according to step (L) of Example 1, using (3S,5R)-5-(2-boronoethyl)-1-((tert-butoxycarbonyl)-L-alanyl)-3-((tert-butoxycarbonyl)amino)piperidine-3-carboxylic acid (0.20 g, 0.41 mmol) and 4M HCl in EtOAc (6 mL). The crude product was purified by preparative HPLC (0.1-1% of acetonitrile in water) to give (after acidification with 2M HCl and subsequent lyophilization) 47 mg (32%) of the corresponding product as a white solid (5:2 mixture of rotamers in D$_2$O solution at room temperature, based on NMR). ESI+MS: m/z=288.00 (M+1)$^+$. $^1$H NMR (700 MHz, 300 K, deuterium oxide) δ 4.93 (dt, J=13.3, 1.9 Hz, 0.7H), 4.63 (dt, J=14.1, 7.1 Hz, 1H), 4.54-4.49 (m, 0.3H), 4.27 (dt, J=13.7, 1.9 Hz, 0.3H), 3.96-3.91 (m, 0.7H), 3.43 (d, J=13.7 Hz, 0.3H), 2.98 (d, J=13.4 Hz, 0.7H), 2.91 (dd, J=14.1, 12.1 Hz, 0.7H), 2.53-2.44 (m, 1H), 2.42 (dd, J=13.3, 12.0 Hz, 0.3H), 2.12 (ddt, J=14.6, 11.7, 4.9 Hz, 0.7H), 1.77 (ddt, J=11.9, 8.8, 3.9 Hz, 0.3H), 1.62-1.34 (m, 6H), 0.91-0.84 (m, 2H).

Example 3. (3R,5S)-3-Amino-5-(2-boronoethyl)-1-glycylpiperidine-3-carboxylic acid dihydrochloride

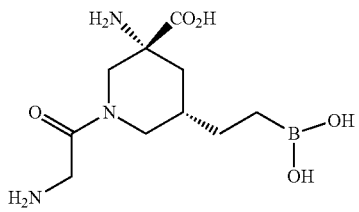

x 2HCl

Step A. (3R,5S)-5-(2-Boronoethyl)-3-((tert-butoxycarbonyl)amino)-1-((tert-butoxycarbonyl)glycyl)piperidine-3-carboxylic acid

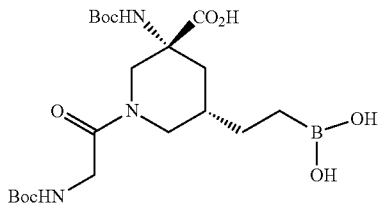 [SMILES: CC(C)(C)OC(=O)NCC(=O)N1C[C@@H](CCB(O)O)C[C@](NC(=O)OC(C)(C)C)(C(=O)O)C1]

The title compound was obtained according to step (K) of Example 1, using (3R,5S)-5-(2-boronoethyl)-3-((tert-butoxycarbonyl)amino)piperidine-3-carboxylic acid (0.10 g, 0.33 mmol), Boc-Gly-OSu (0.12 g, 0.42 mmol) and DMF (2.5 mL). The crude product was purified by column chromatography on silica gel using DCM/MeOH (80:1 to 0:1) to give 130 mg (84%) of the corresponding product as a white solid (4:1 mixture of rotamers in CD$_3$OD solution at room temperature, based on NMR). ESI+MS: m/z=474.15 (M+1)$^+$; ESI-MS: m/z=472.15 (M−1)$^−$. $^1$H NMR (700 MHz, 300 K, methanol-d$_4$) δ 4.70-4.62 (m, 0.7H), 4.58-4.51 (m, 1.3H), 3.93-3.80 (m, 1H), 3.70-3.60 (m, 1H), 2.96-2.87 (m, 0.7H), 2.64-2.54 (m, 0.3H), 2.41-2.33 (m, 0.3H), 2.32-2.25 (m, 0.7H), 2.24-2.11 (m, 0.7H), 1.58-1.43 (m, 18H), 1.42-1.18 (m, 4H), 0.88-0.80 (m, 2H).

Step B. (3R,5S)-3-Amino-5-(2-boronoethyl)-1-glycylpiperidine-3-carboxylic acid dihydrochloride The title compound was obtained according to step (L) of Example 1, using (3R,5S)-5-(2-boronoethyl)-3-((tert-butoxycarbonyl)amino)-1-((tert-butoxycarbonyl)glycyl)piperidine-3-carboxylic acid (0.12 g, 0.26 mmol) and 4M HCl in EtOAc (5 mL). The crude product was purified by preparative HPLC (0.1-1% of acetonitrile in water) to give (after acidification with 2M HCl and subsequent lyophilization) 36 mg (34%) of the corresponding product as a white foam (5:2 mixture of rotamers in D$_2$O solution at room temperature, based on NMR). ESI+MS: m/z=274.00 (M+1)$^+$; ESI-MS: m/z=272.05 (M−1)$^−$. $^1$H NMR (700 MHz, 300 K, deuterium oxide) δ 4.92-4.84 (m, 0.7H), 4.55-4.49 (m, 0.3H), 4.22-4.17 (m, 0.3H), 4.16-4.01 (m, 2H), 3.82-3.75 (m, 0.7H), 3.39 (d, J=14.0 Hz, 0.3H), 3.06 (d, J=13.5 Hz, 0.7H), 2.87 (t, J=12.6 Hz, 0.7H), 2.50 (dd, J=13.4, 4.6 Hz, 1H), 2.43 (t, J=12.6 Hz, 0.3H), 2.10-2.02 (m, 0.7H), 1.77-1.69 (m, 0.3H), 1.61-1.53 (m, 1H), 1.50-1.44 (m, 1H), 1.43-1.37 (m, 1H), 0.87-0.80 (m, 2H).

Example 4. (3R,5S)-1-(L-Prolyl)-3-amino-5-(2-boronoethyl)piperidine-3-carboxylic acid dihydrochloride

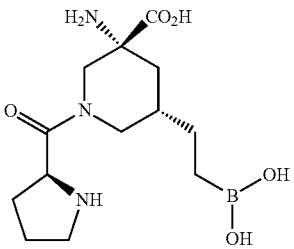

x 2HCl

Step A. (3R,5S)-5-(2-Boronoethyl)-1-((tert-butoxy-carbonyl)-L-prolyl)-3-((tert-butoxycarbonyl)amino) piperidine-3-carboxylic acid

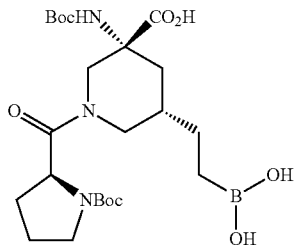

The title compound was obtained according to step (K) of Example 1, using (3R,5S)-5-(2-boronoethyl)-3-((tert-butoxycarbonyl)amino)piperidine-3-carboxylic acid (0.10 g, 0.33 mmol), Boc-L-Pro-OSu (0.18 g, 0.59 mmol) and DMF (2.5 mL). The reaction mixture was stirred for 2 days at 50° C. DMF was evaporated under reduced pressure and the residue was purified by column chromatography on silica gel using DCM/MeOH (80:1 to 0:1) to afford 86 mg (51%) of the desired product as a white solid (4:1 mixture of rotamers in $CD_3OD$ solution at room temperature, based on NMR). ESI+MS: m/z=514.00 (M+1)$^+$; 414.15 (M-Boc+1)$^+$. $^1$H NMR (700 MHz, 300 K, methanol-$d_4$) δ 4.78-4.66 (m, 1.2H), 4.65-4.46 (m, 0.8H), 4.40-4.30 (m, 0.8H), 3.97-3.89 (m, 0.2), 3.69-3.61 (m, 0.2), 3.60-3.41 (m, 2.8H), 2.79-2.62 (m, 1H), 2.58-2.49 (m, 0.4H), 2.44-2.23 (m, 2.6H), 2.19-2.09 (m, 1H), 2.09-1.83 (m, 2.2H), 1.76-1.65 (m, 0.8H), 1.59-1.42 (m, 18H), 1.42-1.19 (m, 2H), 0.92-0.76 (m, 2H).

Step B. (3R,5S)-1-(L-Prolyl)-3-amino-5-(2-borono-ethyl)piperidine-3-carboxylic acid dihydrochloride The title compound was obtained according to step (L) of Example 1, using (3R,5S)-5-(2-boronoethyl)-1-((tert-butoxycarbonyl)-L-prolyl)-3-((tert-butoxycarbonyl)amino)piperidine-3-carboxylic acid (0.08 g, 0.16 mmol) and 4M HCl in EtOAc (5 mL). The crude product was purified by preparative HPLC (0.1-1% of acetonitrile in water) to give (after acidification with 2M HCl and subsequent lyophilization) 33 mg (54%) of the corresponding product as a white foam (4:1 mixture of rotamers in $D_2O$ solution at 333 K, based on NMR). ESI+MS: m/z=314.00 (M+1)$^+$; ESI-MS: m/z=294.05 (M-18-1)$^-$. $^1$H NMR (700 MHz, 333 K, deuterium oxide) δ 5.24 (d, J=13.3 Hz, 0.8H), 5.09 (t, J=7.9 Hz, 0.8H), 5.01 (t, J=8.3 Hz, 0.2H), 4.59 (d, J=13.9 Hz, 0.2H), 4.24-4.15 (m, 0.8H), 3.90-3.83 (m, 1H), 3.82-3.75 (m, 1.2H), 3.37 (d, J=13.3 Hz, 1H), 3.28 (t, J=12.8 Hz, 0.8H), 3.00-2.86 (m, 1H), 2.88-2.81 (m, 1.2H), 2.54-2.31 (m, 4H), 1.95-1.80 (m, 2H), 1.80-1.71 (m, 1H), 1.25-1.12 (m, 2H).

Example 5. (3R,5S)-1-(L-Valyl)-3-amino-5-(2-boronoethyl)piperidine-3-carboxylic acid dihydrochloride

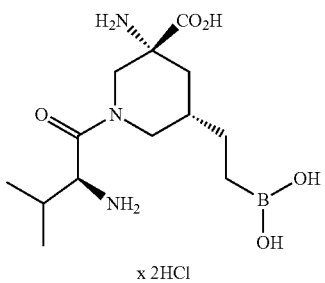 [SMILES: CC(C)[C@H](N)C(=O)N1C[C@@H](CCB(O)O)C[C@](N)(C(=O)O)C1]

Step A. (3R,5S)-5-(2-Boronoethyl)-1-((tert-butoxy-carbonyl)-L-valyl)-3-((tert-butoxycarbonyl)amino) piperidine-3-carboxylic acid

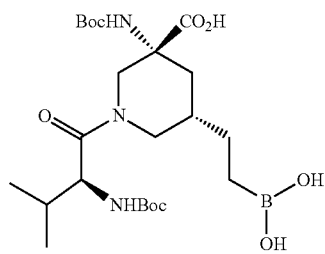

The title compound was obtained according to step (K) of Example 1, using (3R,5S)-5-(2-boronoethyl)-3-((tert-butoxycarbonyl)amino)piperidine-3-carboxylic acid (97 mg, 0.31 mmol), Boc-L-Val-OSu (0.13 g, 0.40 mmol) and DMF (2 mL). The crude product was purified by column chromatography on silica gel using DCM/MeOH (80:1 to 0:1) to give 38 mg (24%) of the corresponding product as a white solid (3:2 mixture of rotamers in $CD_3OD$ solution at room temperature, based on NMR). ESI+MS: m/z=516.20 (M+1)$^+$; ESI-MS: m/z=514.20 (M-1)$^-$. $^1$H NMR (700 MHz, 300 K, methanol-$d_4$) δ 5.05-5.02 (m, 0.4H), 4.46-4.41 (m, 0.4H), 4.24-4.18 (m, 0.6H), 4.05-3.89 (m, 0.6H), 3.60-3.55 (m, 1H), 2.84-2.73 (m, 2H), 2.45-2.36 (m, 0.6H), 2.35-2.31 (m, 0.4H), 2.22-2.17 (m, 0.6H), 2.15-2.04 (m, 0.4H), 1.89-1.82 (m, 0.4H), 1.81-1.72 (m, 0.6H), 1.63-1.55 (m, 1H), 1.53-1.45 (m, 18H), 1.41-1.29 (m, 2H), 1.04-0.91 (m, 6H), 0.92-0.71 (m, 2H).

Step B. (3R,5S)-1-(L-Valyl)-3-amino-5-(2-boronoethyl)piperidine-3-carboxylic acid dihydrochloride The title compound was obtained according to step (L) of Example 1, using (3R,5S)-5-(2-boronoethyl)-1-((tert-butoxycarbonyl)-L-valyl)-3-((tert-butoxycarbonyl)amino)piperidine-3-carboxylic acid (17 mg, 0.03 mmol) and 4M HCl in EtOAc (2 mL). The crude product was purified by preparative HPLC (0.1-1% of acetonitrile in water) to give (after acidification with 2M HCl and subsequent lyophilization) 7.5 mg (59%) of the corresponding product as a white foam (9:1 mixture of rotamers in $D_2O$ solution at room temperature). ESI+MS: m/z=316.10 (M+1)$^+$; ESI-MS: m/z=296.05 (M-18-1)$^-$. $^1$H NMR (700 MHz, 300 K, deuterium oxide) δ 4.98-4.93 (m, 0.9H), 4.45 (d, J=4.9 Hz, 0.9H), 4.38 (d, J=4.0 Hz, 0.1H), 4.34 (dd, J=13.1, 4.2 Hz, 0.1H), 4.29-4.22 (m, 0.1H), 3.94 (dd, J=13.7, 4.3 Hz, 0.9H), 3.49 (d, J=13.8 Hz, 0.1H), 3.03-2.86 (m, 1.8H), 2.67-2.63 (m, 0.1H), 2.47 (d, J=12.6 Hz, 1H), 2.43-2.38 (m, 0.1H), 2.37-2.28 (m, 0.9H), 2.18-2.10 (m, 0.9H), 2.09-2.01 (d, J=12.8 Hz, 0.1H), 1.55-1.45 (m, 2H), 1.43-1.37 (m, 1H), 1.12 (d, J=7.0 Hz, 3H), 1.01 (d, J=6.9 Hz, 2.7H), 0.97 (d, J=6.9 Hz, 0.3H), 0.93-0.80 (m, 2H).

67

Example 6. (3R,5S)-1-(L-Seryl)-3-amino-5-(2-boronoethyl)piperidine-3-carboxylic acid dihydrochloride

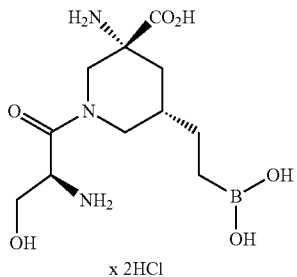 [SMILES: N[C@@H](CO)C(=O)N1C[C@@H](CCB(O)O)C[C@](N)(C(=O)O)C1]

x 2HCl

Step A. (3R,5S)-1-(O-Benzyl-N-(tert-butoxycarbonyl)-L-seryl)-5-(2-boronoethyl)-3-((tert-butoxycarbonyl)amino)piperidine-3-carboxylic acid

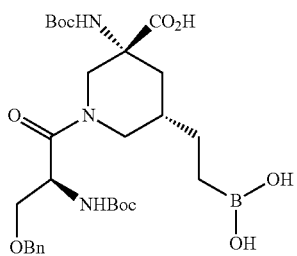

The title compound was obtained according to step (K) of Example 1, using (3R,5S)-5-(2-boronoethyl)-3-((tert-butoxycarbonyl)amino)piperidine-3-carboxylic acid (96 mg, 0.30 mmol), Boc-L-Ser(Bzl)-OSu (0.16 g, 0.40 mmol) and DMF (2 mL). The crude product was purified by column chromatography on silica gel using DCM/MeOH (80:1 to 0:1) to give 75 mg (42%) of the corresponding product as a white solid (3:2 mixture of rotamers in CD$_3$OD solution at room temperature, based on NMR). ESI+MS: m/z=594.25 (M+1)$^+$; ESI-MS: m/z=592.15 (M−1)$^−$. $^1$H NMR (700 MHz, 300 K, methanol-d$_4$) δ 7.41-7.23 (m, 5H), 5.13-5.00 (m, 1H), 4.65-4.59 (m, 1H), 4.59-4.51 (m, 1H), 4.03-3.87 (m, 1H), 3.81-3.76 (m, 1H), 3.77-3.70 (m, 1H), 3.69-3.63 (m, 1H), 2.67-2.60 (m, 1H), 2.44-2.36 (m, 0.6H), 2.29-2.24 (m, 0.4H), 1.70-1.60 (m, 2H), 1.47 (d, J=2.5 Hz, 18H), 1.43-1.24 (m, 3H), 0.93-0.70 (m, 2H).

Step B. (3R,5S)-3-Amino-1-(O-benzyl-L-seryl)-5-(2-boronoethyl)piperidine-3-carboxylic acid dihydrochloride

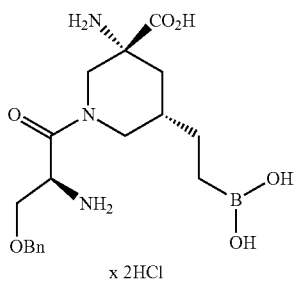 [SMILES: N[C@@H](COCc1ccccc1)C(=O)N1C[C@@H](CCB(O)O)C[C@](N)(C(=O)O)C1]

x 2HCl

68

The title compound was obtained according to step (L) of Example 1, using (3R,5S)-1-(O-benzyl-N-(tert-butoxycarbonyl)-L-seryl)-5-(2-boronoethyl)-3-((tert-butoxycarbonyl)amino)piperidine-3-carboxylic acid (39 mg, 0.07 mmol) and 4M HCl in EtOAc (2 mL). The crude product was obtained as a white foam (30 mg, 99%; 4:1 mixture of rotamers in CD$_3$OD solution at 333 K, based on NMR). ESI+MS: m/z=394.05 (M+1)$^+$; ESI-MS: m/z=374.00 (M−18−1)$^−$. $^1$H NMR (700 MHz, 300 K, methanol-d$_4$) δ 7.47-7.31 (m, 5H), 5.02 (d, J=13.1 Hz, 0.8H), 4.73-4.62 (m, 2.2H), 3.90-3.85 (m, 1H), 3.79-3.67 (m, 2H), 2.87 (d, J=12.9 Hz, 1H), 2.69-2.55 (m, 1H), 2.51-2.38 (m, 2H), 2.21-2.17 (m, 1H), 1.56-1.27 (m, 3H), 0.94-0.80 (m, 2H).

Step C. (3R,5S)-1-(L-Seryl)-3-amino-5-(2-boronoethyl)piperidine-3-carboxylic acid dihydrochloride (3R,5S)-3-Amino-1-(O-benzyl-L-seryl)-5-(2-boronoethyl)piperidine-3-carboxylic acid dihydrochloride (30 mg, 0.06 mmol) was dissolved in 2 mL of MeOH and flushed with argon. Next, 5 mg of Pd/C (wet, 10%) was added and the resulting mixture was stirred under hydrogen atmosphere (balloon) overnight. In the next step, the reaction mixture was filtered through the pad of Celite and concentrated. The crude product was purified by preparative HPLC (0.1-1% of acetonitrile in water) to give (after acidification with 2M HCl and subsequent lyophilization) 12.4 mg (51%) of the corresponding product as a yellow foam (4:1 mixture of rotamers in D$_2$O solution at room temperature, based on NMR). ESI+MS: m/z=304.00 (M+1)$^+$; ESI-MS: m/z=283.95 (M−18−1)$^−$. $^1$H NMR (700 MHz, 300 K, deuterium oxide) δ 4.99-4.92 (m, 0.8H), 4.68 (dd, J=5.7, 3.9 Hz, 0.8H), 4.58 (dd, J=6.7, 3.8 Hz, 0.2H), 4.47-4.41 (m, 0.2H), 4.03 (dd, J=12.6, 3.8 Hz, 1H), 3.94 (dd, J=12.7, 5.6 Hz, 1.8H), 3.88 (dd, J=12.6, 6.9 Hz, 0.2H), 3.48 (d, J=13.7 Hz, 0.1H), 2.99-2.94 (m, 1.8H), 2.78-2.74 (m, 0.1H), 2.58-2.47 (m, 1H), 2.21-2.06 (m, 0.8H), 1.99-1.90 (m, 0.2H), 1.59-1.46 (m, 2H), 1.46-1.36 (m, 1H), 0.92-0.80 (m, 2H).

Example 7. (3R,5S)-1-(L-Lysyl)-3-amino-5-(2-boronoethyl)piperidine-3-carboxylic acid trihydrochloride

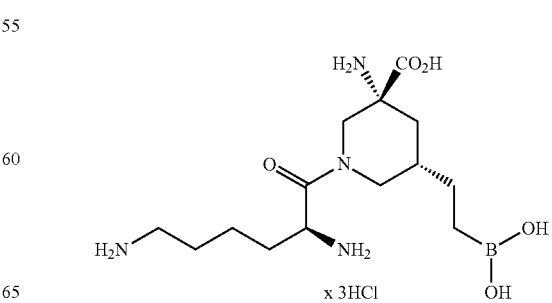

x 3HCl

Step A. (3R,5S)-1-(N²,N⁶-bis(tert-Butoxycarbonyl)-L-lysyl)-5-(2-boronoethyl)-3-((tert-butoxycarbonyl)amino)piperidine-3-carboxylic acid

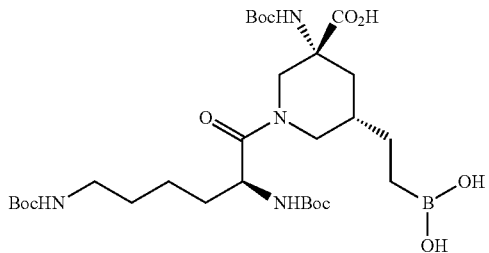 [SMILES: CC(C)(C)OC(=O)NCCCC[C@H](NC(=O)OC(C)(C)C)C(=O)N1C[C@@H](CCB(O)O)C[C@](NC(=O)OC(C)(C)C)(C(=O)O)C1]

The title compound was obtained according to step (K) of Example 1, using (3R,5S)-5-(2-boronoethyl)-3-((tert-butoxycarbonyl)amino)piperidine-3-carboxylic acid (97 mg, 0.31 mmol), Boc-L-Lys(Boc)-OSu (0.18 g, 0.40 mmol) and DMF (2 mL). The crude product was purified by column chromatography on silica gel using DCM/MeOH (80:1 to 3:1) to give 79.6 mg (40%) of the corresponding product as a white solid (3:2 mixture of rotamers in CD$_3$OD solution at room temperature, based on NMR). ESI+MS: m/z=645.30 (M+1)⁺; ESI-MS: m/z=643.25 (M−1)⁻. ¹H NMR (700 MHz, 300 K, methanol-d$_4$) δ 5.23-5.11 (m, 0.6H), 4.70-4.60 (m, 0.4H), 4.43-4.30 (m, 0.6H), 4.05-3.94 (m, 1H), 3.71-3.57 (m, 0.4H), 3.11-3.04 (m, 3H), 2.87-2.76 (m, 0.4H), 2.63-2.53 (m, 0.6H), 2.43-2.37 (m, 0.6H), 2.33-2.25 (m, 0.4H), 1.94-1.86 (m, 0.4H), 1.85-1.78 (m, 0.6H), 1.71-1.62 (m, 1H), 1.50-1.44 (m, 29H), 1.43-1.26 (m, 6H), 0.95-0.76 (m, 2H).

Step B. (3R,5S)-1-(L-Lysyl)-3-amino-5-(2-boronoethyl)piperidine-3-carboxylic acid trihydrochloride The title compound was obtained according to step (L) of Example 1, using (3R,5S)-1-(N²,N⁶-bis(tert-butoxycarbonyl)-L-lysyl)-5-(2-boronoethyl)-3-((tert-butoxycarbonyl)amino)piperidine-3-carboxylic acid (40 mg, 0.06 mmol) and 4M HCl in EtOAc (5 mL). The crude product was purified by preparative HPLC (0.1-1% of acetonitrile in water) to give (after acidification with 2M HCl and subsequent lyophilization) 16.2 mg, (58%) of the corresponding product as a white foam (9:1 mixture of rotamers in D$_2$O at room temperature, based on NMR). ESI+MS: m/z=345.10 (M+1)⁺; ESI-MS: m/z=325.05 (M−18−1)⁻. ¹H NMR (700 MHz, 300 K, deuterium oxide) δ 4.89 (d, J=13.3, 0.9H), 4.53 (dd, J=7.2, 4.9 Hz, 0.9H), 4.46 (dd, J=7.3, 4.1 Hz, 0.1H), 4.38 (dd, J=13.3, 4.3 Hz, 0.1H), 4.24 (d, J=13.7 Hz, 0.1H), 3.81 (dd, J=13.8, 4.4 Hz, 0.9H), 3.40 (d, J=13.7 Hz, 0.1H), 3.00-2.84 (m, 3.8H), 2.47-2.40 (m, 1.1H), 2.08-1.98 (m, 0.9H), 1.89-1.80 (m, 2.1H), 1.69-1.62 (m, 2H), 1.51-1.38 (m, 4H), 1.37-1.29 (m, 1H), 0.85-0.71 (m, 2H).

Example 8. (3R,5S)-1-(L-Leucyl)-3-amino-5-(2-boronoethyl)piperidine-3-carboxylic acid dihydrochloride

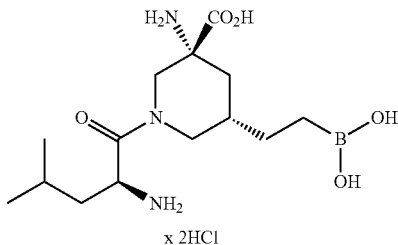 [SMILES: CC(C)C[C@H](N)C(=O)N1C[C@@H](CCB(O)O)C[C@](N)(C(=O)O)C1]

x 2HCl

Step A. (3R,5S)-5-(2-Boronoethyl)-1-((tert-butoxycarbonyl)-L-leucyl)-3-((tert-butoxycarbonyl)amino)piperidine-3-carboxylic acid

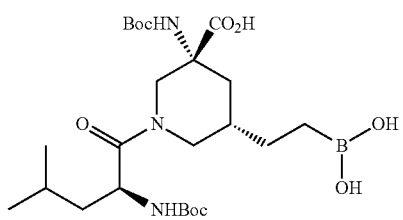 [SMILES: CC(C)C[C@H](NC(=O)OC(C)(C)C)C(=O)N1C[C@@H](CCB(O)O)C[C@](NC(=O)OC(C)(C)C)(C(=O)O)C1]

The title compound was obtained according to step (K) of Example 1, using (3R,5S)-5-(2-boronoethyl)-3-((tert-butoxycarbonyl)amino)piperidine-3-carboxylic acid (97 mg, 0.31 mmol), Boc-L-Leu-OSu (111 mg, 0.34 mmol) and DMF (1 mL). The crude reaction mixture was purified by preparative HPLC to give a desired product as a white solid. Yield: 23 mg (14%). ESI+MS: m/z=530.25 (M+1)⁺.

Step B. (3R,5S)-1-(L-Leucyl)-3-amino-5-(2-boronoethyl)piperidine-3-carboxylic acid dihydrochloride (3R,5S)-5-(2-Boronoethyl)-1-((tert-butoxycarbonyl)-L-leucyl)-3-((tert-butoxycarbonyl)amino)piperidine-3-carboxylic acid (23 mg, 43.44 µmol) was treated with a solution of 50% 2,2,2-trifluoroacetic acid in dichloromethane (5 mL) and stirred for 30 min. Next, the solvent was evaporated and a crude product was purified by preparative HPLC. The concentrated fractions contained a corresponding product were evaporated from 0.5 M HCl$_{(aq)}$ two times and freeze dried from water to give a desired product as a colorless solid (as 9:1 mixture of rotamers in D$_2$O at room temperature, based on NMR). Yield: 10.6 mg (61%). ESI+MS: m/z=330.05 (M+1)⁺. ¹H NMR (700 MHz, 300K, deuterium oxide) δ 4.88 (d, J=13.3 Hz, 0.9H), 4.5 (dd, J=9.4, 3.6 Hz, 0.9H), 4.44-4.33 (m, 0.2H), 4.18 (d, J=13.6 Hz, 0.1H), 3.83-3.67 (m, 1H), 3.41 (d, J=13.8 Hz, 0.1H), 2.90 (d, J=13.3, 0.9H), 2.90 (t, J=5.3 Hz, 1H), 2.50-2.37 (m, 1H), 2.17-1.90 (m, 1H), 1.84-1.58 (m, 3H), 1.55-1.29 (m, 3H), 1.06-0.89 (m, 6H), 0.86-0.72 (m, 2H).

Example 9. (3R,5S)-1-(L-Isoleucyl)-3-amino-5-(2-boronoethyl)piperidine-3-carboxylic acid dihydrochloride

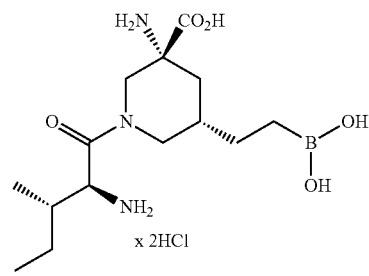 [SMILES: CC[C@H](C)[C@H](N)C(=O)N1C[C@@H](CCB(O)O)C[C@](N)(C(=O)O)C1]

x 2HCl

Step A. (3R,5S)-5-(2-Boronoethyl)-1-((tert-butoxycarbonyl)-L-isoleucyl)-3-((tert-butoxycarbonyl)amino)piperidine-3-carboxylic acid

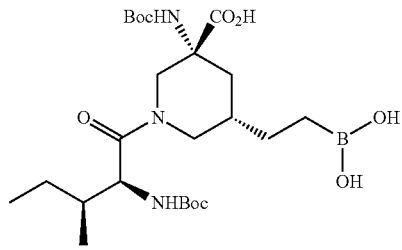 [SMILES: CC[C@H](C)[C@H](NC(=O)OC(C)(C)C)C(=O)N1C[C@@H](CCB(O)O)C[C@](NC(=O)OC(C)(C)C)(C(=O)O)C1]

The title compound was obtained according to step (K) of Example 1, using (3R,5S)-5-(2-boronoethyl)-3-((tert-butoxycarbonyl)amino)piperidine-3-carboxylic acid (97 mg, 0.31 mmol), Boc-L-Ile-OSu (111 mg, 0.34 mmol) and DMF (1 mL). The crude reaction mixture was purified by preparative HPLC to give a desired product as a white solid. Yield: 22 mg (13%). ESI+MS: m/z=530.25 (M+1)$^+$.

Step B. (3R,5S)-1-(L-Isoleucyl)-3-amino-5-(2-boronoethyl)piperidine-3-carboxylic acid dihydrochloride (3R,5S)-5-(2-Boronoethyl)-1-((tert-butoxycarbonyl)-L-isoleucyl)-3-((tert-butoxycarbonyl)amino)piperidine-3-carboxylic acid (22 mg, 41.55 μmol) was treated with a solution of 50% 2,2,2-trifluoroacetic acid in dichloromethane (5 mL) and stirred for 30 min. Next, solvent was evaporated and the crude product was purified by preparative HPLC. The concentrated fractions contained a corresponding product were evaporated from 0.5 M HCl$_{(aq)}$ two times and freeze dried from water to give 9 mg (62%) of a desired product as a colorless solid (as a 9:1 mixture of rotamers in D$_2$O solution at 300K, based on NMR). ESI+MS: m/z=330.05 (M+1)$^+$. $^1$H NMR (700 MHz, 300K, deuterium oxide) δ 4.92 (d, J=13.1 Hz, 1H), 4.44 (d, J=4.2 Hz, 0.9H), 4.34 (d, J=3.9 Hz, 0.1H), 4.23 (d, J=13.3 Hz, 0.9H), 3.95-3.80 (m, 0.9H), 3.46 (d, J=14.7 Hz, 0.1H), 3.05 (d, J=12.3 Hz, 0.1H), 2.93 (d, J=13.1 Hz, 0.9H), 2.92 (t, J=12.9 Hz, 0.9H), 2.58 (t, J=12.8 Hz, 0.1H), 2.50-2.37 (m, 1H), 2.19-1.88 (m, 2H), 1.56-1.27 (m, 4H), 1.26-1.08 (m, 1H), 1.04 (d, J=6.5 Hz, 3H), 0.94-0.69 (m, 5H).

Example 10. (3R,5S)-1-(L-Tyrosyl)-3-amino-5-(2-boronoethyl)piperidine-3-carboxylic acid dihydrochloride

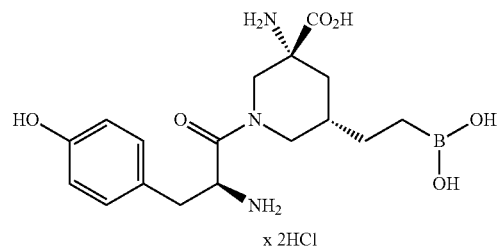 [SMILES: N[C@@H](Cc1ccc(O)cc1)C(=O)N1C[C@@H](CCB(O)O)C[C@](N)(C(=O)O)C1]

Step A. (3R,5S)-5-(2-Boronoethyl)-1-((tert-butoxycarbonyl)-L-tyrosyl)-3-((tert-butoxycarbonyl)amino)piperidine-3-carboxylic acid

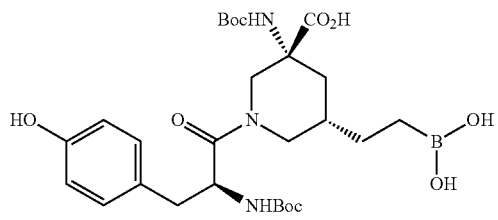 [SMILES: CC(C)(C)OC(=O)N[C@@H](Cc1ccc(O)cc1)C(=O)N1C[C@@H](CCB(O)O)C[C@](NC(=O)OC(C)(C)C)(C(=O)O)C1]

The title compound was obtained according to step (K) of Example 1, using (3R,5S)-5-(2-boronoethyl)-3-((tert-butoxycarbonyl)amino)piperidine-3-carboxylic acid (97 mg, 0.31 mmol), Boc-L-Tyr-OSu (127 mg, 0.34 mmol) and DMF (1 mL). The crude reaction mixture was purified by preparative HPLC to give a desired product as a colorless solid. Yield: 26 mg (15%). ESI+MS: m/z=580.25 (M+1)$^+$.

Step B. (3R,5S)-1-(L-Tyrosyl)-3-amino-5-(2-boronoethyl)piperidine-3-carboxylic acid dihydrochloride (3R,5S)-5-(2-Boronoethyl)-1-((tert-butoxycarbonyl)-L-tyrosyl)-3-((tert-butoxycarbonyl)amino)piperidine-3-carboxylic acid (26 mg, 44.87 μmol) was treated with a solution of 50% 2,2,2-trifluoroacetic acid in dichloromethane (5 mL) and stirred for 30 min. Next, solvent was evaporated and the product was purified by preparative HPLC. The concentrated fractions contained a corresponding product were evaporated from 0.5 M HCl$_{(aq)}$ two times and freeze dried from water to give a desired product as a colorless solid. Yield: 19.9 mg (73%). ESI+MS: m/z=380.05 (M+1)$^+$. $^1$H NMR (700 MHz, 300K, deuterium oxide) δ 7.19-7.07 (m, 2H), 6.92-6.83 (m, 2H), 4.93-4.76 (m, 2H), 4.71 (dd, J=8.4, 6.2 Hz, 1H), 3.52 (d, J=9.7 Hz, 0.9H), 3.44 (d, J=9.7 Hz, 0.1H), 3.17 (dd, J=13.9, 6.4 Hz, 1H), 3.02 (dd, J=13.8, 8.4 Hz, 1H), 2.72 (d, J=13.2 Hz, 0.9H), 2.63 (d, J=11.6 Hz, 0.1H), 2.45 (d, J=12.7 Hz, 0.1H), 2.35 (d, J=13.4 Hz, 0.9H), 2.06-1.82 (m, 2H), 1.47-1.15 (m, 3H), 0.88-0.75 (m, 0.2H), 0.75-0.61 (m, 1.8).

Example 11. (3R,5S)-1-(L-Phenylalanyl)-3-amino-5-(2-boronoethyl)piperidine-3-carboxylic acid dihydrochloride

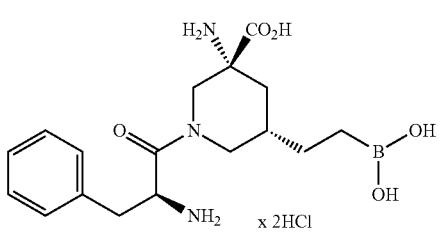 [SMILES: N[C@@H](Cc1ccccc1)C(=O)N1C[C@@H](CCB(O)O)C[C@](N)(C(=O)O)C1]

Step A. (3R,5S)-5-(2-Boronoethyl)-1-((tert-butoxy-carbonyl)-L-phenylalanyl)-3-((tert-butoxycarbonyl)amino)piperidine-3-carboxylic acid

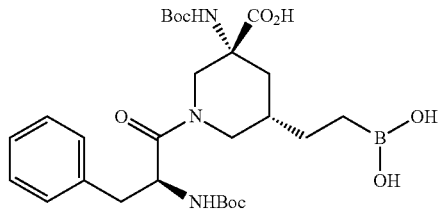 [SMILES: CC(C)(C)OC(=O)N[C@@H](Cc1ccccc1)C(=O)N1C[C@@H](CCB(O)O)C[C@](NC(=O)OC(C)(C)C)(C(=O)O)C1]

The title compound was obtained according to step (K) of Example 1, using (3R,5S)-5-(2-boronoethyl)-3-((tert-butoxycarbonyl)amino)piperidine-3-carboxylic acid (0.12 g, 0.37 mmol), Boc-L-Phe-OSu (0.17 g, 0.48 mmol) and DMF (2 mL). The crude product was purified by column chromatography on silica gel using DCM/MeOH (80:1 to 0:1) to give 103 mg (49%) of the corresponding product as a white solid (5:2 mixture of rotamers in CD$_3$OD solution at room temperature, based on NMR). ESI+MS: m/z=564.25 (M+1)$^+$; ESI-MS: m/z=562.15 (M−1)$^-$. $^1$H NMR (250 MHz, 300 K, Methanol-d$_4$) δ 7.33-7.11 (m, 5H), 5.16-5.00 (m, 0.7H), 4.64-6.52 (m, 1H), 4.48-4.4 (m, 0.3H), 3.90-3.73 (m, 1H), 3.06-2.77 (m, 2H), 2.55-2.17 (m, 2H), 1.69-1.54 (m, 1H), 1.51-1.10 (m, 22H), 0.92-0.65 (m, 2H).

Step B. (3R,5S)-1-(L-Phenylalanyl)-3-amino-5-(2-boronoethyl)piperidine-3-carboxylic acid dihydrochloride The title compound was obtained according to step (L) of Example 1, using (3R,5S)-5-(2-boronoethyl)-1-((tert-butoxycarbonyl)-L-phenylalanyl)-3-((tert-butoxycarbonyl)amino) piperidine-3-carboxylic acid (55 mg, 0.01 mmol) and 4M HCl in EtOAc (4 mL). The crude product was purified by preparative HPLC (0.1-1% of acetonitrile) to give (after acidification with 2M HCl and subsequent lyophilization) 15 mg (35%) of the corresponding product as a white solid. ESI+MS: m/z=364.05 (M+1)$^+$; ESI-MS: m/z=344.05 (M−18−1)$^-$. $^1$H NMR (250 MHz, 333 K, Deuterium Oxide) δ 7.85-7.66 (m, 3H), 7.66-7.53 (m, 2H), 5.18 (d, J=13.2 Hz, 1H), 5.13-4.99 (m, 1H), 3.86-3.78 (m, 1H), 3.63-3.40 (m, 2H), 3.07 (d, J=13.2 Hz, 1H), 2.74-2.62 (m, 1H), 2.34-2.13 (m, 2H), 1.78-1.47 (m, 3H), 1.11-0.96 (m, 2H).

Example 12. (3R,5S)-1-(L-Threonyl)-3-amino-5-(2-boronoethyl)piperidine-3-carboxylic acid dihydrochloride

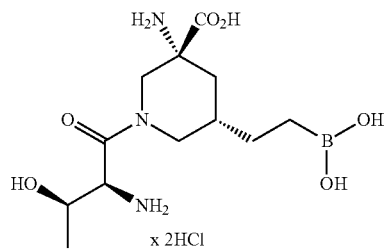 [SMILES: C[C@@H](O)[C@H](N)C(=O)N1C[C@@H](CCB(O)O)C[C@](N)(C(=O)O)C1]

Step A. (3R,5S)-5-(2-Boronoethyl)-1-((tert-butoxy-carbonyl)-L-threonyl)-3-((tert-butoxy carbonyl)amino)piperidine-3-carboxylic acid

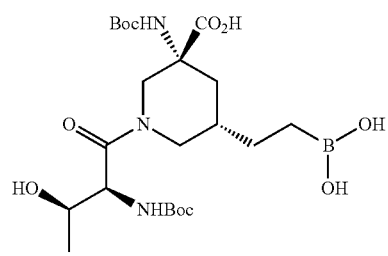 [SMILES: C[C@@H](O)[C@H](NC(=O)OC(C)(C)C)C(=O)N1C[C@@H](CCB(O)O)C[C@](NC(=O)OC(C)(C)C)(C(=O)O)C1]

The title compound was obtained according to step (K) of Example 1, using (3R,5S)-5-(2-boronoethyl)-3-((tert-butoxycarbonyl)amino)piperidine-3-carboxylic acid (87 mg, 0.28 mmol), Boc-L-Thr-OSu (113 mg, 0.36 mmol) and DMF (2 mL). The crude product was purified by column chromatography on silica gel using DCM/MeOH (20:1 to 0:1) to give 117 mg (71%) of the corresponding product as a white solid (7:3 mixture of rotamers in CD$_3$OD solution at room temperature, based on NMR). ESI+MS: m/z=518.15 (M+1)$^+$; ESI-MS: m/z=515.95 (M−1)$^-$. $^1$H NMR (700 MHz, 300K, Methanol-d$_4$) δ 5.30-5.18 (m, 0.7H), 4.76-4.63 (m, 0.3H), 4.63-4.55 (m, 0.3H), 4.46-4.39 (m, 0.3H), 4.36-4.16 (m, 2.4H), 4.06-3.93 (m, 4H), 2.58-2.49 (m, 1H), 2.47-2.36 (m, 0.7H), 2.30 (d, J=13.7 Hz, 0.3H), 1.43-1.25 (m, 3H), 1.22 (s, 9H), 1.21 (s, 9H), 1.02-0.68 (m, 3H).

Step B. (3R,5S)-1-(L-Threonyl)-3-amino-5-(2-boronoethyl)piperidine-3-carboxylic acid dihydrochloride The title compound was obtained according to step (L) of Example 1, using (3R,5S)-5-(2-boronoethyl)-1-((tert-butoxycarbonyl)-L-threonyl)-3-((tert-butoxycarbonyl)amino) piperidine-3-carboxylic acid (115 mg, 0.22 mmol) and 4M HCl in EtOAc (8 mL). The crude product was purified by preparative HPLC (0.1-1% of acetonitrile in water) to give (after acidification with 2M HCl and subsequent lyophilization) 15.4 mg, (17%) of the corresponding product as a white solid (9:1 mixture of rotamers in D$_2$O at room temperature, based on NMR). ESI+MS: m/z=317.80 (M+1)$^+$; ESI-MS: m/z=315.90 (M−1)$^-$. $^1$H NMR (700 MHz, 300K, Deuterium Oxide) δ 4.94 (dt, J=13.0, 1.9 Hz, 0.9H), 4.55 (d, J=4.7 Hz, 0.9H), 4.45 (d, J=3.5 Hz, 0.1H), 4.41 (dd, J=6.6, 3.5 Hz, 0.1H), 4.34 (dd, J=6.6, 4.7 Hz, 0.1H), 4.27 (qd, J=6.5, 4.6 Hz, 0.9H), 3.99 (dd, J=13.7, 4.4 Hz, 0.9H), 3.79-3.70 (m, 0.1H), 3.50 (d, J=13.7 Hz, 0.1H), 3.04-2.89 (m, 1.9H), 2.72-2.63 (m, 0.1H), 2.52-2.40 (m, 0.9H), 2.30-2.08 (m, 0.9H), 2.06-1.98 (m, 0.1H), 1.55-1.30 (m, 6H), 0.98-0.78 (m, 2H).

Example 13. (3R,5S)-1-(L-Histidyl)-3-amino-5-(2-boronoethyl)piperidine-3-carboxylic acid trihydrochloride

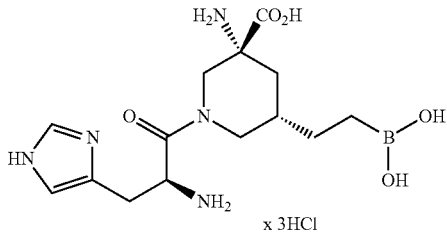 [SMILES: N[C@@H](Cc1c[nH]cn1)C(=O)N1C[C@@H](CCB(O)O)C[C@](N)(C(=O)O)C1]

Step A. (3R,5S)-1-N$^\alpha$,N$^T$-bis(tert-Butoxycarbonyl)-L-histidyl)-5-(2-boronoethyl)-3-((tert-butoxycarbonyl)amino)piperidine-3-carboxylic acid

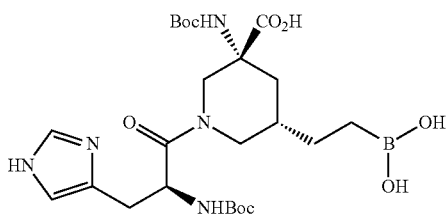 [SMILES: CC(C)(C)OC(=O)N[C@@H](Cc1c[nH]cn1)C(=O)N1C[C@@H](CCB(O)O)C[C@](NC(=O)OC(C)(C)C)(C(=O)O)C1]

The title compound was obtained according to step (K) of Example 1, using (3R,5S)-5-(2-boronoethyl)-3-((tert-butoxycarbonyl)amino)piperidine-3-carboxylic acid (0.12 g, 0.34 mmol), Boc-L-His-(1-Boc)-OSu (0.22 g, 0.49 mmol) and DMF (2 mL). The crude product was purified by column chromatography on silica gel using DCM/MeOH (80:1 to 0:1) to give 38 mg (16%) of the corresponding product as a white solid. ESI+MS: m/z=654.25 (M+1)$^+$; ESI-MS: m/z=652.25 (M−1)$^−$. $^1$H NMR (250 MHz, 300 K, Methanol-d$_4$) δ 8.19-8.01 (m, 1H), 7.32-7.24 (m, 1H), 5.25-5.01 (m, 1H), 4.65-4.50 (m, 1H), 3.98-3.81 (m, 1H), 3.74-3.53 (m, 1H), 3.15-2.71 (m, 3H), 2.55-2.40 (m, 2H), 1.61 (s, 9H), 1.50-1.21 (m, 20H), 1.18-1.12 (m, 1H), 0.91-0.65 (m, 2H).

Step B. (3R,5S)-1-(L-Histidyl)-3-amino-5-(2-boronoethyl)piperidine-3-carboxylic acid trihydrochloride The title compound was obtained according to step (L) of Example 1, using (3R,5S)-1-(N$^\alpha$,N$^T$-bis(tert-butoxycarbonyl)-L-histidyl)-5-(2-boronoethyl)-3-((tert-butoxycarbonyl)amino)piperidine-3-carboxylic acid (35 mg, 0.05 mmol) and 4M HCl in EtOAc (5 mL). The crude product was purified by preparative HPLC (0.1-1% of acetonitrile) to give (after acidification with 2M HCl and subsequent lyophilization) 15 mg, (61%) of the corresponding product as a white solid (4:1 mixture of rotamers in D$_2$O solution at room temperature, based on NMR). ESI+MS: m/z=354.05 (M+1)$^+$; ESI-MS: m/z=352.05 (M−1)$^−$. $^1$H NMR (250 MHz, 300 K, Deuterium Oxide) δ 8.64 (d, J=1.4 Hz, 0.8H), 8.61 (d, J=1.4 Hz, 0.2H), 7.38 (d, J=1.4 Hz, 0.8H), 7.35 (d, J=1.4 Hz, 0.2H), 4.86-4.73 (m, 2H), 4.33-4.21 (m, 0.2H), 3.82-3.66 (m, 0.8H), 3.40-3.22 (m, 2.2H), 2.83 (d, J=13.2 Hz, 0.8H), 2.72-2.52 (m, 0.8H), 2.42-2.32 (m, J=12.7 Hz, 1.2H), 2.10-1.90 (m, 0.8H), 1.75-1.88 (m, 0.2H), 1.46-1.16 (m, 3H), 0.80-0.60 (m, 3H).

Example 14. (3R,5S)-1-(L-Aspartyl)-3-amino-5-(2-boronoethyl)piperidine-3-carboxylic acid dihydrochloride

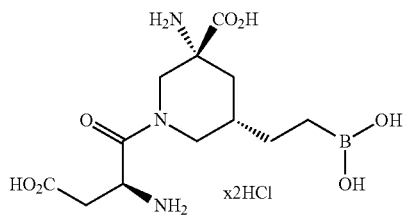 [SMILES: N[C@@H](CC(=O)O)C(=O)N1C[C@@H](CCB(O)O)C[C@](N)(C(=O)O)C1]

Step A. (3R,5S)-1-((S)-4-(Benzyloxy)-2-((tert-butoxycarbonyl)amino)-4-oxobutanoyl)-5-(2-boronoethyl)-3-((tert-butoxycarbonyl)amino)piperidine-3-carboxylic acid

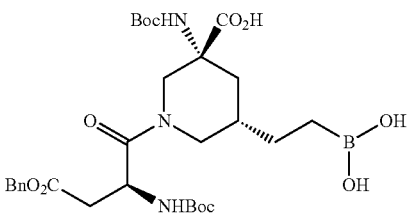

The title compound was obtained according to step (K) of Example 1, using (3R,5S)-5-(2-boronoethyl)-3-((tert-butoxycarbonyl)amino)piperidine-3-carboxylic acid (0.103 g, 0.326 mmol), Boc-L-Asp(OBzl)-OSu (0.178 g, 0.423 mmol) and DMF (5 mL). The crude product was purified by column chromatography on silica gel using CHCl$_3$/MeOH (100:1 to 10:1) to give 0.1206 mg (59.6%) of the corresponding product as a white solid. ESI+MS: m/z=622.15 (M+1)$^+$. $^1$H NMR (700 MHz, 300 K, DMSO-d$_6$) δ 7.56-7.24 (m, 4H), 7.12-6.20 (m, 3H), 5.08 (d, J=8.3 Hz, 2H), 4.83 (m, 1H), 4.45-4.17 (m, 1H), 4.07 (s, 1H), 3.65 (s, 0.3H), 3.01-2.76 (m, 1H), 2.66-2.54 (m, 1H), 2.29-2.05 (m, 1H), 2.04-1.60 (m, 2H), 1.37 (d, J=18.9 Hz, 18H), 1.27-1.17 (m, 2H), 0.69-0.41 (m, 2H).

Step B. (3R,5S)-3-amino-1-((S)-2-amino-4-(benzyloxy)-4-oxobutanoyl)-5-(2-boronoethyl)piperidine-3-carboxylic acid dihydrochloride

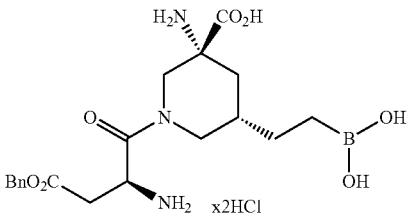

The title compound was obtained in the same manner like in Example 1, step L, using (3R,5S)-1-((S)-4-(benzyloxy)-2-((tert-butoxycarbonyl)amino)-4-oxobutanoyl)-5-(2-boronoethyl)-3-((tert-butoxycarbonyl)amino)piperidine-3-carboxylic acid (0.101 g, 0.163 mmol) and 4M HCl in EtOAc (3 mL). The crude product (80 mg, 100%) was used in the next step without any further purification ESI+MS: m/z=421.95 (M+1)$^+$; ESI-MS: m/z=401.85 (M−18)$^-$.

Step C. (3R,5S)-1-(L-Aspartyl)-3-amino-5-(2-boronoethyl)piperidine-3-carboxylic acid dihydrochloride (3R,5S)-3-amino-1-((S)-2-amino-4-(benzyloxy)-4-oxobutanoyl)-5-(2-boronoethyl)piperidine-3-carboxylic acid dihydrochloride (0.080 g, 0.163 mmol) was dissolved in MeOH (5 mL). The reaction mixture was degassed and refilled with argon. Pd/C (10 mg) was added and the mixture was degassed and refilled with H$_2$. The reaction mixture was stirred overnight at room temperature, under hydrogen atmosphere (balloon), filtered through a pad of Celite, washed with MeOH (2×5 mL) and concentrated. The crude product was purified by preparative HPLC (0.1-1% of acetonitrile in water) to give (after acidification with 2M HCl and subsequent lyophilization) 21.3 mg (31.3%) of the corresponding product as a white solid (3:1 mixture of rotamers in D$_2$O solution at room temperature, based on NMR). ESI+MS: m/z=331.85 (M+1)$^+$; ESI-MS: m/z=329.85 (M−1)$^-$. $^1$H NMR (700 MHz, Deuterium Oxide) δ 5.00-4.84 (m, 2H), 4.59-4.40 (m, 0.3H), 4.32 (t, J=5.5 Hz, 0.6H), 3.89 (d, J=18.1 Hz, 1H), 3.80 (d, J=13.1 Hz, 0.6H), 3.56 (dd, J=12.6, 4.0 Hz, 0.6H), 3.45 (d, J=13.4 Hz, 0.2H), 3.33-3.16 (m, 1H), 3.18-3.11 (m, 1H), 3.08 (dd, J=17.9, 3.7 Hz, 1H), 3.01-2.86 (m, 3H), 2.79-2.59 (m, 1H), 2.57-2.26 (m, 0.6H), 2.21-2.01 (m, 1H), 1.89-1.80 (m, 0.2H), 1.65-1.24 (m, 5H), 0.86 (ddtt, J=30.0, 19.8, 9.4, 5.1 Hz, 3H).

Example 15. (3R,5S)-1-(L-Glutamyl)-3-amino-5-(2-boronoethyl)piperidine-3-carboxylic acid dihydrochloride

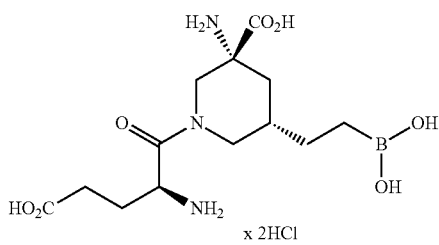 [SMILES: N[C@@H](CCC(=O)O)C(=O)N1C[C@@H](CCB(O)O)C[C@](N)(C(=O)O)C1]

x 2HCl

Step A. (3R,5S)-5-(2-Boronoethyl)-1-((tert-butoxycarbonyl)-L-glutamyl)-3-((tert-butoxycarbonyl)amino)piperidine-3-carboxylic acid

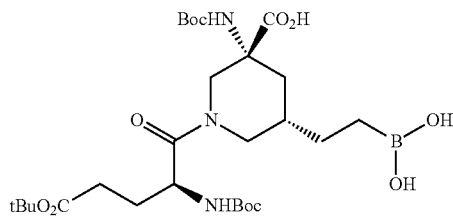 [SMILES: CC(C)(C)OC(=O)CC[C@H](NC(=O)OC(C)(C)C)C(=O)N1C[C@@H](CCB(O)O)C[C@](NC(=O)OC(C)(C)C)(C(=O)O)C1]

The title compound was obtained according to step (K) of Example 1, using (3R,5S)-5-(2-boronoethyl)-3-((tert-butoxycarbonyl)amino)piperidine-3-carboxylic acid (0.1 g, 0.32 mmol), Boc-L-Glu(Ot-Bu)-OSu (0.16 g, 0.41 mmol) and DMF (2 mL). The crude product was purified by column chromatography on silica gel using DCM/MeOH (80:1 to 6:1) to give 143 mg (75%) of the corresponding product as a pale yellow solid (5:2 mixture of rotamers in CD$_3$OD solution at room temperature, based on NMR). ESI+MS: m/z=602.10 (M+1)$^+$; ESI-MS: m/z=600.15 (M−1)$^-$. $^1$H NMR (700 MHz, Methanol-d$_4$) δ 4.74-4.68 (m, 0.7H), 4.62-4.47 (m, 1.3H), 4.08-3.97 (m, 1H), 2.84-2.58 (m, 2H), 2.42-2.21 (m, 3H), 2.06-2.00 (m, 0.7H), 1.91-1.78 (m, 1.3H), 1.72-1.51 (m, 2H), 1.51-1.40 (m, 27H), 1.39-1.26 (m, 2H), 0.87-0.77 (m, 2H).

Step B. (3R,5S)-1-(L-Glutamyl)-3-amino-5-(2-boronoethyl)piperidine-3-carboxylic acid dihydrochloride The title compound was obtained according to step (L) of Example 1, using (3R,5S)-5-(2-boronoethyl)-1-((tert-butoxycarbonyl)-L-glutamyl)-3-((tert-butoxycarbonyl)amino)piperidine-3-carboxylic acid (75 mg, 0.12 mmol) and 4M HCl in EtOAc (5 mL). The crude product was purified by preparative HPLC (0.1-1% of acetonitrile) to give (after acidification with 2M HCl and subsequent lyophilization) 36 mg (68%) of the corresponding product as a white solid (9:1 mixture of rotamers in D$_2$O solution at room temperature, based on NMR). ESI+MS: m/z=345.90 (M+1)$^+$; ESI-MS: m/z=343.85 (M−1)$^-$. $^1$H NMR (700 MHz, Deuterium Oxide) δ 4.84 (dt, J=13.3, 2.0 Hz, 0.9H), 4.59 (dd, J=7.7, 4.3 Hz, 0.9H), 4.53 (dd, J=7.7, 4.3 Hz, 0.1H), 4.36 (dd, J=13.3, 4.3 Hz, 0.1H), 4.30 (dt, J=13.3, 2.0 Hz, 0.1H), 3.92 (dd, J=13.5, 4.3 Hz, 0.9H), 3.41 (d, J=13.7 Hz, 0.1H), 2.94-2.81 (m, 1.8H), 2.57-2.53 (t, J=7.0 Hz, 2H), 2.52-2.43 (m, 0.1H), 2.44-2.37 (m, 1H), 2.31-2.21 (m, 0.1H), 2.23-2.13 (m, 0.9H), 2.10 (dq, J=14.6, 6.9 Hz, 1H), 2.06-1.97 (m, 1H), 1.93-1.82 (m, 0.1H), 1.51-1.40 (m, 2H), 1.38-1.31 (m, 1H), 0.84-0.74 (m, 2H).

Example 16. (3R,5S)-1-(L-Glutaminyl)-3-amino-5-(2-boronoethyl)piperidine-3-carboxylic acid dihydrochloride

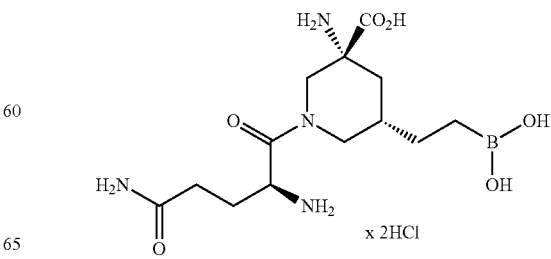

x 2HCl

Step A. (3R,5S)-5-(2-Boronoethyl)-1-((tert-butoxycarbonyl)-L-glutaminyl)-3-((tert-butoxycarbonyl)amino)piperidine-3-carboxylic acid

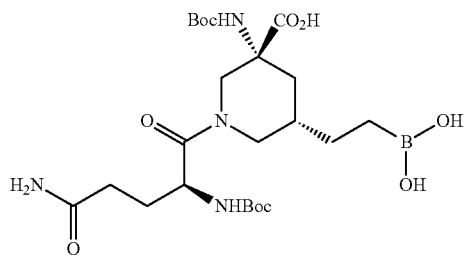 [SMILES: CC(C)(C)OC(=O)N[C@@H](CCC(N)=O)C(=O)N1C[C@@H](CCB(O)O)C[C@](NC(=O)OC(C)(C)C)(C(=O)O)C1]

The title compound was obtained according to step (K) of Example 1, using (3R,5S)-5-(2-boronoethyl)-3-((tert-butoxycarbonyl)amino)piperidine-3-carboxylic acid (0.10 g, 0.32 mmol), Boc-L-Gln-OSu (0.28 g, 0.92 mmol) and DMF (2 mL). The reaction mixture was heated to 50° C. and stirred for 2 days (10% of product, the progress of reaction was controlled on LCMS). After this time to reaction mixture was added N,N-diisopropylethylamine (0.17 mL, 0.99 mmol) and reaction continued for 1 day at 50° C. Then to reaction mixture was added O-(benzotriazol-1-yl)-N,N,N',N'-tetramethyluronium tetrafluoroborate (0.10 g, 0.32 mmol) and stirring was continued for 3 days at 50° C. The crude product was purified by column chromatography on silica gel using DCM/MeOH (80:1 to 0:1) to give 33 mg (19%) of the corresponding product as a colorless film. ESI+MS: m/z=545.05 (M+1)$^+$; ESI-MS: m/z=543.05 (M−1)$^−$. $^1$H NMR (250 MHz, 300 K, Methanol-d$_4$) δ 4.58-4.55 (m, 1H), 4.06-4.00 (m, 2H), 2.40-2.23 (m, 4H), 2.13-2.05 (m, 2H), 1.96-1.92 (m, 2H), 1.48-1.44 (m, 18H), 1.40-1.38 (m, 1H), 1.37-1.33 (m, 2H), 0.85-0.80 (m, 2H).

Step B. (3R,5S)-1-(L-Glutaminyl)-3-amino-5-(2-boronoethyl)piperidine-3-carboxylic acid dihydrochloride The title compound was obtained according to step (L) of Example 1, (3R,5S)-5-(2-boronoethyl)-1-((tert-butoxycarbonyl)-L-glutaminyl)-3-((tert-butoxycarbonyl)amino) piperidine-3-carboxylic acid (33 mg, 0.06 mmol) and 3M HCl in EtOAc (2.5 mL). The crude product was purified by preparative HPLC (0.1-1% of acetonitrile in water) to give (after acidification with 2M HCl and subsequent lyophilization) 3.7 mg (15%) of the corresponding product as a colorless film (9:1 mixture of rotamers in D$_2$O solution at room temperature, based on NMR). ESI+MS: m/z=344.09 (M+1)$^+$; ESI-MS: m/z=342.85 (M−1)$^−$. $^1$H NMR (700 MHz, Deuterium Oxide) δ 4.84 (d, J=13.2 Hz, 0.9H), 4.59-4.53 (m, 0.9H), 4.55-4.46 (m, 0.1H), 4.27 (d, J=13.2 Hz, 0.1H), 3.88 (dd, J=13.7, 4.2 Hz, 0.9H), 3.40 (dd, J=13.6, 4.2 Hz, 0.1H), 2.97-2.78 (m, 1.8H), 2.63-2.52 (m, 0.2H), 2.51-2.33 (m, 3H), 2.25-2.07 (m, 2H), 2.07-1.99 (m, 0.9) 1.93-1.86 (m, 0.1H), 1.49-1.30 (m, 3H), 0.84-0.73 (m, 2H).

Example 17. (3R,5S)-1-(L-Methionyl)-3-amino-5-(2-boronoethyl)piperidine-3-carboxylic acid dihydrochloride

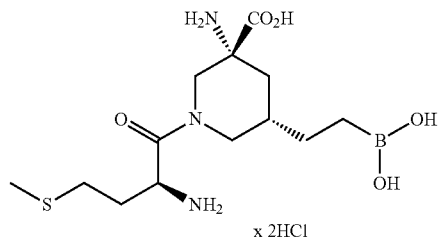 [SMILES: CSCC[C@H](N)C(=O)N1C[C@@H](CCB(O)O)C[C@](N)(C(=O)O)C1]

Step A. (3R,5S)-5-(2-Boronoethyl)-1-((tert-butoxycarbonyl)-L-methionyl)-3-((tert-butoxycarbonyl)amino)piperidine-3-carboxylic acid

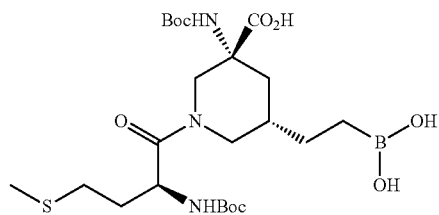 [SMILES: CSCC[C@H](NC(=O)OC(C)(C)C)C(=O)N1C[C@@H](CCB(O)O)C[C@](NC(=O)OC(C)(C)C)(C(=O)O)C1]

The title compound was obtained according to step (K) of Example 1, using (3R,5S)-5-(2-boronoethyl)-3-((tert-butoxycarbonyl)amino)piperidine-3-carboxylic acid (0.1 g, 0.32 mmol), Boc-L-Met-OSu (0.14 g, 0.41 mmol) and DMF (2 mL). The crude product was purified by column chromatography on silica gel using DCM/MeOH (80:1 to 0:1) to give 93 mg (54%) of the corresponding product as a white solid (5:2 mixture of rotamers in CD$_3$OD solution at room temperature, based on NMR). ESI+MS: m/z=548.10 (M+1)$^+$; ESI-MS: m/z=546.10 (M−1)$^−$. $^1$H NMR (700 MHz, 300 K, Methanol-d$_4$) δ 5.12-5.03 (m, 0.7H), 4.62-4.52 (m, 0.7H), 4.33-4.25 (m, 0.3H), 4.09-4.03 (m, 0.3H), 4.01-3.97 (m, 1H), 2.82-2.73 (m, 1H), 2.59-2.48 (m, 2H), 2.44-2.33 (m, 0.7H), 2.27-2.19 (m, 0.3H), 2.15-2.07 (m, 3H), 1.94-1.83 (m, 0.7H), 1.72-1.63 (m, 0.3H), 1.52-1.41 (m, 20H), 1.39-1.27 (m, 4H), 0.88-0.75 (m, 2H).

Step B. (3R,5S)-1-(L-Methionyl)-3-amino-5-(2-boronoethyl)piperidine-3-carboxylic acid dihydrochloride The title compound was obtained according to step (L) of Example 1, using (3R,5S)-5-(2-boronoethyl)-1-((tert-butoxycarbonyl)-L-methionyl)-3-((tert-butoxycarbonyl)amino) piperidine-3-carboxylic acid (89 mg, 0.16 mmol) and 4M HCl in EtOAc (8 mL). The crude product was purified by preparative HPLC (0.1-1% of acetonitrile in water) to give (after acidification with 2M HCl and subsequent lyophilization) 16 mg (23%) of the corresponding product as a white solid (9:1 mixture of rotamers in D$_2$O solution at room temperature, based on NMR). ESI+MS: m/z=347.75 (M+1)$^+$; ESI-MS: m/z=327.95 (M−18−1)$^−$. $^1$H NMR (700 MHz, 300 K, Deuterium Oxide) δ 4.88 (dt, J=13.3, 2.0 Hz, 0.9H), 4.65 (dd, J=8.1, 4.0 Hz, 0.9H), 4.55

(dd, J=8.1, 4.0 Hz, 0.1H), 4.37 (dd, J=13.1, 4.3 Hz, 0.1H), 4.26 (dt, J=13.3, 2.0 Hz, 0.1H), 4.16 (dd, J=6.9, 5.9 Hz, 0.1H), 3.91 (dd, J=13.4, 4.3 Hz, 0.9H), 3.44 (d, J=13.8 Hz, 0.1H), 2.95-2.84 (m, 1.8H), 2.68-2.55 (m, 2.2H), 2.50-2.42 (m, 1.2H), 2.30-2.21 (m, 0.1H), 2.21-2.01 (m, 5.4H), 1.89-1.83 (m, 0.1H), 1.52-1.32 (m, 3H), 0.86-0.73 (m, 2H).

Example 18. (3R,5S)-1-(L-Tryptophyl)-3-amino-5-(2-boronoethyl)piperidine-3-carboxylic acid dihydrochloride

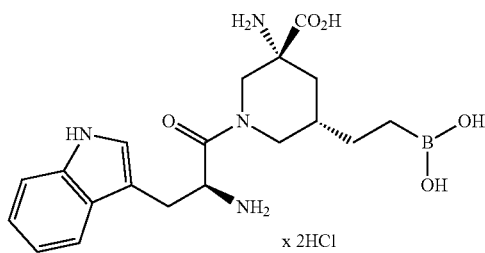 [SMILES: N[C@@H](Cc1c[nH]c2ccccc12)C(=O)N1C[C@@H](CCB(O)O)C[C@](N)(C(=O)O)C1]

x 2HCl

Step A. (3R,5S)-5-(2-Boronoethyl)-1-((tert-butoxycarbonyl)-L-tryptophyl)-3-((tert-butoxycarbonyl)amino)piperidine-3-carboxylic acid

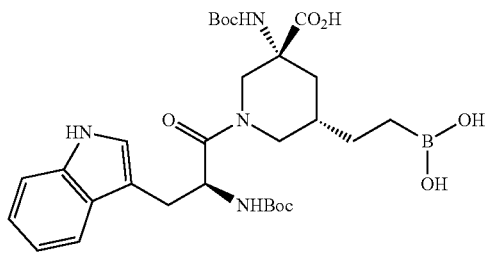 [SMILES: CC(C)(C)OC(=O)N[C@@H](Cc1c[nH]c2ccccc12)C(=O)N1C[C@@H](CCB(O)O)C[C@](NC(=O)OC(C)(C)C)(C(=O)O)C1]

The title compound was obtained according to step (K) of Example 1, using (3R,5S)-5-(2-boronoethyl)-3-((tert-butoxycarbonyl)amino)piperidine-3-carboxylic acid (0.116 g, 0.37 mmol), Boc-L-Trp-OSu (0.192 g, 0.48 mmol) and DMF (2 mL). The crude product was purified by column chromatography on silica gel using CHCl$_3$/MeOH (50:1 to 5:1) to give 0.140 mg (63%) of the corresponding product as a white solid. ESI+MS: m/z=603.20 (M+1)$^+$. $^1$H NMR (700 MHz, 300 K, Methanol-d$_4$) δ 7.60 (dd, J=15.1, 7.9 Hz, 1H), 7.30 (dd, J=29.2, 8.1 Hz, 1H), 7.26-6.57 (m, 3H), 5.24-4.91 (m, 1H), 3.77-3.64 (m, 1H), 3.57-3.39 (m, 1H), 3.26-2.99 (m, 2H), 2.62-2.44 (m, 1H), 2.31-1.96 (m, 2H), 1.73-1.51 (m, 1H), 1.49-1.30 (m, 20H), 1.33-1.26 (m, 1H), 0.85-0.48 (m, 2H).

Step B. (3R,5S)-1-(L-Tryptophyl)-3-amino-5-(2-boronoethyl)piperidine-3-carboxylic acid dihydrochloride The title compound was obtained according to step (L) of Example 1, using ((3R,5S)-5-(2-boronoethyl)-1-((tert-butoxycarbonyl)-L-tryptophyl)-3-((tert-butoxycarbonyl)amino)piperidine-3-carboxylic acid (0.101 g, 0.167 mmol) and 4M HCl in EtOAc (4 mL). The crude product was purified by preparative HPLC (0.1-1% of acetonitrile) to give (after acidification with 2M HCl and subsequent lyophilization) 37 mg (47%) of the corresponding product as a white solid (9:1 mixture of rotamers in D$_2$O solution at room temperature, based on NMR). ESI+MS: m/z=403.00 (M+1)$^+$; $^1$H NMR (700 MHz, 300 K, Deuterium Oxide) δ 7.64 (d, J=8.0 Hz, 0.1H), 7.58 (d, J=8.9 Hz, 2H), 7.35 (s, 1H), 7.34-7.28 (m, 1H), 7.26-7.19 (m, 1H), 4.72-4.75 (m, 1H), 3.79 (dd, J=13.3, 3.7 Hz, 0.1H), 3.56-3.40 (m, 1H), 3.41-3.14 (m, 2H), 2.90-2.73 (m, 0.1H), 2.46 (d, J=13.0 Hz, 1H), 2.38 (dd, J=13.7, 3.0 Hz, 0.1H), 2.26-2.12 (m, 1H), 1.87 (dq, J=12.0, 6.8 Hz, 1H), 1.80-1.70 (m, 0.1H), 1.62-1.45 (m, 1H), 1.44-1.31 (m, 0.1H), 1.24-1.07 (m, 2H), 1.06-0.94 (m, 1H), 0.88-0.77 (m, 0.1H), 0.56 (ddd, J=16.3, 11.0, 5.7 Hz, 1H), 0.41 (ddd, J=15.8, 11.2, 5.7 Hz, 1H).

Example 19. (3R,5S)-1-(L-Cysteinyl)-3-amino-5-(2-boronoethyl)piperidine-3-carboxylic acid dihydrochloride

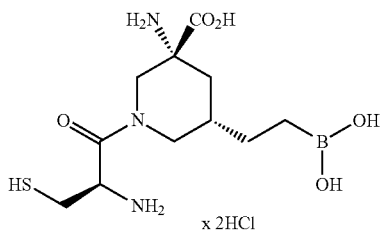 [SMILES: N[C@@H](CS)C(=O)N1C[C@@H](CCB(O)O)C[C@](N)(C(=O)O)C1]

x 2HCl

Step A. (3R,5S)-5-(2-Boronoethyl)-1-(N-(tert-butoxycarbonyl)-S-trityl-L-cysteinyl)-3-((tert-butoxycarbonyl)amino)piperidine-3-carboxylic acid

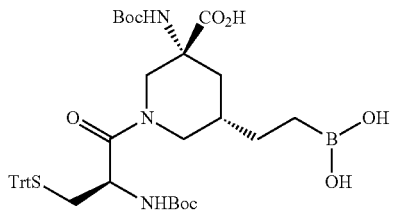

The title compound was obtained according to step (K) of Example 1, using (3R,5S)-5-(2-boronoethyl)-3-((tert-butoxycarbonyl)amino)piperidine-3-carboxylic acid (0.11 g, 0.35 mmol), Boc-L-Cys(Trt)-OSu (195 mg, 0.35 mmol), TEA (53 µL, 0.38 mmol) and acetonitrile (1.5 mL; instead of DMF). Next day, acetonitrile was evaporated. The residue was diluted with EtOAc (50 mL) and washed with 1M KHSO$_4$ (10 mL), H$_2$O (20 mL), brine (20 mL), dried over Na$_2$SO$_4$ and concentrated to give a crude product. A crude product was triturated with hexane (2 mL) to give 211 mg (79%) of the corresponding product as an off-white solid. ESI+MS: m/z=762.4 (M+1)$^+$; ESI-MS: m/z=760.15 (M−1)$^−$.

Step B. (3R,5S)-1-(L-Cysteinyl)-3-amino-5-(2-boronoethyl)piperidine-3-carboxylic acid dihydrochloride The title compound was obtained according to step (L) of Example 1, using (3R,5S)-5-(2-boronoethyl)-1-(N-(tert-butoxycarbonyl)-S-trityl-L-cysteinyl)-3-((tert-butoxycarbonyl)amino)piperidine-3-carboxylic acid (0.143 g, 0.188 mmol) and 4M HCl in dioxane (4 mL). Stirred for 5 days. The crude product was purified by preparative HPLC (0.1-1% of acetonitrile in water) to give (after acidification with 2M HCl and subsequent lyophilization) 20 mg (27%) of the corresponding product as a white solid (5:1 mixture of rotamers in $D_2O$ solution at room temperature, based on NMR). ESI+MS: m/z=319.85 (M+1)$^+$; $^1$H NMR (700 MHz, 300 K, Deuterium Oxide) δ 4.88 (ddt, J=13.2, 9.1, 2.0 Hz, 0.83H), 4.74 (dd, J=6.3, 4.7 Hz, 0.83H), 4.69-4.66 (m, 0.83H), 4.47-4.38 (m, 0.17H), 4.33-4.24 (m, 0.17H), 3.87 (ddd, J=45.8, 14.0, 4.2 Hz, 0.83H), 3.42 (dd, J=13.9, 12.2 Hz, 0.17H), 3.10-2.82 (m, 3.2H), 2.48-2.42 (m, 1H), 2.42-2.36 (m, 0.17H), 2.07-1.96 (m, 0.83H), 1.58-1.28 (m, 3H), 0.85-0.70 (m, 2H).

Example 20. (3R,5S)-1-(L-Arginyl)-3-amino-5-(2-boronoethyl)piperidine-3-carboxylic acid trihydrochloride

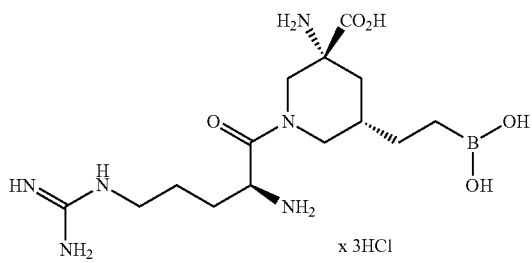 [SMILES: N=C(N)NCCC[C@H](N)C(=O)N1C[C@@H](CCB(O)O)C[C@](N)(C(=O)O)C1]

Step A. (3R,5S)-1-(N$^ω$,N$^{ω'}$-bis((Benzyloxy)carbonyl)-N$^2$-(tert-butoxycarbonyl)-L-arginyl)-5-(2-boronoethyl)-3-((tert-butoxycarbonyl)amino)piperidine-3-carboxylic acid

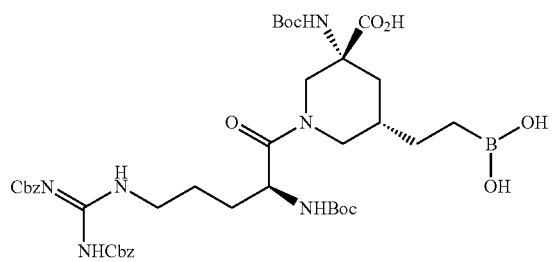

The title compound was obtained according to step (K) of Example 1, using (3R,5S)-5-(2-boronoethyl)-3-((tert-butoxycarbonyl)amino)piperidine-3-carboxylic acid (0.35 g, 1.11 mmol), Boc-L-Arg(Cbz)$_2$-OSu (0.17 g, 0.48 mmol) and DMF (7 mL). The crude product was purified by column chromatography on silica gel using DCM/MeOH (80:1 to 0:1) to give 505 mg (54%) of the corresponding product as a white foam (3:2 mixture of rotamers in CD$_3$OD solution at room temperature, based on NMR). ESI+MS: m/z=841.05 (M+1)$^+$; ESI-MS: m/z=839.25 (M−1)$^-$. $^1$H NMR (700 MHz, 300 K, Methanol-d$_4$) δ 7.49-7.25 (m, 10H), 5.31-5.24 (m, 2H), 5.16-5.09 (m, 2H), 5.05-4.95 (m, 0.4H), 4.67-4.56 (m, 0.4H), 4.49-4.37 (m, 0.6H), 4.10-3.82 (m, 2.6H), 2.58-2.45 (m, 1H), 2.36-2.20 (m, 1H), 1.78-1.55 (m, 5H), 1.48-1.29 (m, 22H), 1.27-1.21 (m, 1H), 0.88-0.66 (m, 2H).

Step B. (3R,5S)-1-(L-Arginyl)-3-amino-5-(2-boronoethyl)piperidine-3-carboxylic acid trihydrochloride To a solution of (3R,5S)-1-(N$^ω$,N$^{ω'}$-bis((benzyloxy)carbonyl)-N$^2$-(tert-butoxycarbonyl)-L-arginyl)-5-(2-boronoethyl)-3-((tert-butoxycarbonyl)amino)piperidine-3-carboxylic acid (0.78 g, 0.57 mmol) in MeOH (7 mL) under argon 10% Pd/C (50 mg) was added. The mixture was degassed, charged with H$_2$, and stirred overnight at room temperature under hydrogen atmosphere. The reaction mixture was filtered through a pad of Celite, washed with MeOH (3×2 mL) and then the filtrate was concentrated in vacuo to give 300 mg (92%) of the corresponding product as a white solid. ESI+MS: m/z=573.30 (M+1)$^+$; ESI-MS: m/z=571.30 (M−1)$^-$. The crude product was used to the next step without further purification. The title compound was obtained according to step (L) of Example 1, using (3R,5S)-5-(2-boronoethyl)-1-((tert-butoxycarbonyl)-L-arginyl)-3-((tert-butoxycarbonyl)amino)piperidine-3-carboxylic acid (300 mg, 0.52 mmol) and 4M HCl in EtOAc (10 mL). The crude product was purified by preparative HPLC (0.1-1% of acetonitrile in water) to give (after acidification with 2M HCl and subsequent lyophilization) 162 mg (65%) of the corresponding product as a white foam (9:1 mixture of rotamers in D$_2$O solution at room temperature, based on NMR). ESI+MS: m/z=372.90 (M+1)$^+$; ESI-MS: m/z=370.90 (M−1)$^-$. $^1$H NMR (700 MHz, 300 K, Deuterium Oxide) δ 4.89 (dt, J=13.2, 2.0 Hz, 0.9H), 4.55 (dd, J=7.2, 4.8 Hz, 0.9H), 4.49 (dd, J=6.8, 4.1 Hz, 0.1H), 4.40 (dd, J=13.2, 4.3 Hz, 0.1H), 4.22 (dt, J=13.2, 2.0 Hz, 0.1H), 3.81 (dd, J=13.4, 4.3 Hz, 0.9H), 3.38 (d, J=13.7 Hz, 0.1H), 3.21-3.16 (m, 2H), 2.99-2.70 (m, 1.7H), 2.49-2.39 (m, 1.2H), 2.09-1.98 (m, 0.9H), 1.94-1.84 (m, 2.1H), 1.71-1.53 (m, 2H), 1.51-1.29 (m, 3H), 0.85-0.70 (m, 2H).

Example 21. (3R,5S)-3-Amino-1-((S)-2-amino-5-ureidopentanoyl)-5-(2-boronoethyl) piperidine-3-carboxylic acid dihydrochloride

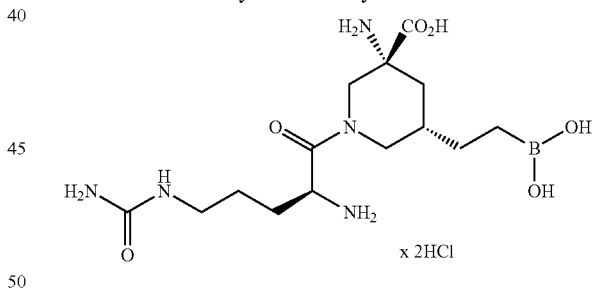

Step A. (3R,5S)-5-(2-Boronoethyl)-3-((tert-butoxycarbonyl)amino)-1-((S)-2-((tert-butoxy carbonyl)amino)-5-ureidopentanoyl)piperidine-3-carboxylic acid

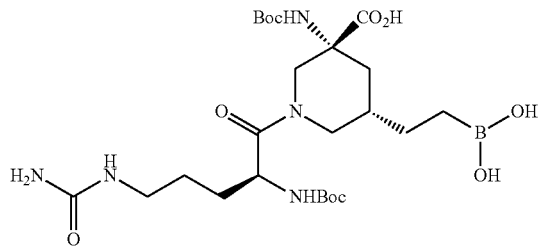 [SMILES: CC(C)(C)OC(=O)N[C@@H](CCCNC(N)=O)C(=O)N1C[C@@H](CCB(O)O)C[C@](NC(=O)OC(C)(C)C)(C(=O)O)C1]

To a solution of Boc-L-Cit-OH (87 mg, 0.32 mmol) in DCM/DMF (2 mL/0.3 mL) were added DIPEA (110 µL, 0.632 mmol) and CDI (53 mg, 0.33 mmol). The mixture was stirred for 30 min. and then (3R,5S)-5-(2-boronoethyl)-3-((tert-butoxycarbonyl)amino)piperidine-3-carboxylic acid (100 mg, 0.32) was added. The resulting mixture was stirred at room temperature for 48 h. The solvents were evaporated and the crude product was purified by column chromatography on silica gel using DCM/MeOH (80:1 to 0:1) to give 105 mg (56%) of the corresponding product as a white solid (3:2 mixture of rotamers in CD₃OD solution at room temperature, based on NMR). ESI+MS: m/z=574.15 (M+1)⁺; ESI-MS: m/z=572.10 (M−1)⁻. ¹H NMR (700 MHz, 300K, Methanol-d₄) δ 5.16 (d, J=14.3 Hz, 0.4H), 4.76-4.69 (m, 0.6H), 4.57-4.48 (m, 0.6H), 4.43-4.34 (m, 0.4H), 4.32-4.24 (m, 0.4H), 4.02-3.91 (m, 0.6H), 3.20-2.99 (m, 3H), 2.68 (t, J=12.1 Hz, 0.4H), 2.53-2.40 (m, 0.4H), 2.33 (dd, J=42.0, 13.1 Hz, 1.2H), 1.84-1.73 (m, 1H), 1.63 (dt, J=14.7, 7.6 Hz, 2H), 1.57-1.47 (m, 3H), 1.44 (s, 9H), 1.43 (s, 9H), 1.36-1.23 (m, 2H), 0.90-0.71 (m, 2H).

Step B. (3R,5S)-3-Amino-1-((S)-2-amino-5-ureidopentanoyl)-5-(2-boronoethyl)piperidine-3-carboxylic acid dihydrochloride The title compound was obtained according to step (L) of Example 1, using (3R,5S)-5-(2-boronoethyl)-3-((tert-butoxycarbonyl)amino)-1-((S)-2-((tert-butoxycarbonyl)amino)-5-ureidopentanoyl)piperidine-3-carboxylic acid (100 mg, 0.17 mmol) and 4M HCl in EtOAc (8 mL). The crude product was purified by preparative HPLC (0.1-1% of acetonitrile in water) to give (after acidification with 2M HCl and subsequent lyophilization) 28.9 mg, (37%) of the corresponding product as a white solid (4:1 mixture of rotamers in D₂O at room temperature, based on NMR). ESI+MS: m/z=373.90 (M+1)⁺; ESI-MS: m/z=371.90 (M−1)⁻. ¹H NMR (700 MHz, 300K, Deuterium Oxide) δ 4.93-4.85 (m, 0.8H), 4.57 (dd, J=7.4, 4.9 Hz, 0.8H), 4.51 (dd, J=8.1, 3.7 Hz, 0.2H), 4.37 (d, J=13.5 Hz, 0.2H), 4.21 (d, J=13.5 Hz, 0.2H), 3.87 (dd, J=13.6, 4.4 Hz, 0.8H), 3.43 (d, J=13.5 Hz, 0.2H), 3.18 (q, J=7.0 Hz, 2H), 2.93 (t, J=13.0 Hz, 1.8H), 2.67-2.54 (m, 0.2H), 2.47-2.39 (m, 1H), 2.19-2.13 (m, 0.8H), 2.09-1.98 (m, 0.2H), 1.92 (tt, J=16.8, 7.0 Hz, 1.8H), 1.67-1.59 (m, 2H), 1.57-1.37 (m, 3H), 0.96-0.75 (m, 2H).

Example 22. (3R,5S)-3-Amino-5-(2-boronoethyl)-1-((S)-2,5-diaminopentanoyl)piperidine-3-carboxylic acid trihydrochloride

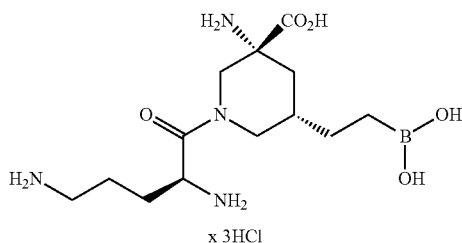 [SMILES: NCCC[C@H](N)C(=O)N1C[C@@H](CCB(O)O)C[C@](N)(C(=O)O)C1]

Step A. (3R,5S)-1-((S)-5-(((Benzyloxy)carbonyl)amino)-2-((tert-butoxycarbonyl)amino) pentanoyl)-5-(2-boronoethyl)-3-((tert-butoxycarbonyl)amino) piperidine-3-carboxylic acid

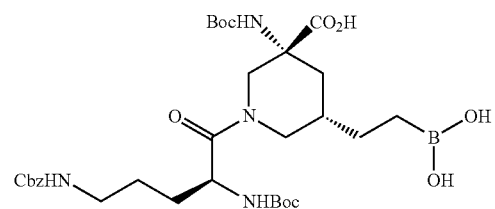 [SMILES: CC(C)(C)OC(=O)N[C@@H](CCCNC(=O)OCc1ccccc1)C(=O)N1C[C@@H](CCB(O)O)C[C@](NC(=O)OC(C)(C)C)(C(=O)O)C1]

The title compound was obtained according to step (K) of Example 1, using (3R,5S)-5-(2-boronoethyl)-3-((tert-butoxycarbonyl)amino)piperidine-3-carboxylic acid (100 mg, 0.32 mmol), Boc-L-Orn(Cbz)-OSu (190 mg, 0.41 mmol) and DMF (2 mL). The crude product was purified by column chromatography on silica gel using DCM/MeOH (50:1 to 2:1) to give 95 mg (45%) of the corresponding product as a colorless glass. ESI+MS: m/z=665.25 (M+1)⁺; ESI-MS: m/z=663.25 (M−1)⁻.

Step B. (3R,5S)-3-Amino-1-((S)-2-amino-5-(((benzyloxy)carbonyl)amino)pentanoyl)-5-(2-boronoethyl)piperidine-3-carboxylic acid dihydrochloride

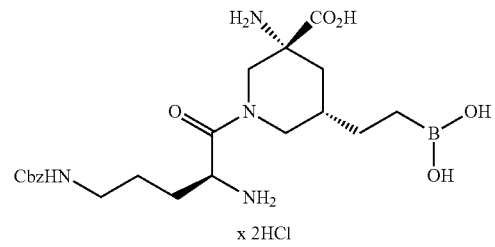 [SMILES: N[C@@H](CCCNC(=O)OCc1ccccc1)C(=O)N1C[C@@H](CCB(O)O)C[C@](N)(C(=O)O)C1]

The title compound was obtained according to step (L) of Example 1, using (3R,5S)-1-((S)-5-(((benzyloxy)carbonyl)amino)-2-((tert-butoxycarbonyl)amino)pentanoyl)-5-(2-boronoethyl)-3-((tert-butoxycarbonyl)amino)piperidine-3-carboxylic acid (95 mg, 0.14 mmol) and 4M HCl in EtOAc (6 mL). The desired product was obtained as a white solid (95 mg, 45%). ESI+MS: m/z=464.95 (M+1)⁺; ESI-MS: m/z=462.95 (M−1)⁻. ¹H NMR (700 MHz, 300K, Deuterium Oxide) δ 7.59-7.34 (m, 5H), 5.16 (s, 2H), 4.55-4.44 (m, 1H), 3.87-3.73 (m, 1H), 3.34-3.12 (m, 2H), 2.96-2.67 (m, 3H), 2.59-2.31 (m, 1H), 2.04-1.80 (m, 2H), 1.69-1.55 (m, 2H), 1.51-1.29 (m, 4H), 0.92-0.69 (m, 2H).

Step C. (3R,5S)-3-Amino-5-(2-boronoethyl)-1-((S)-2,5-diaminopentanoyl)piperidine-3-carboxylic acid trihydrochloride (3R,5S)-3-Amino-1-((S)-2-amino-5-(((benzyloxy)carbonyl)amino)pentanoyl)-5-(2-boronoethyl) piperidine-3-carboxylic acid dihydrochloride (76 mg, 0.14 mmol) was dissolved in 4 mL of MeOH and flushed with argon. Next, 3 mg of 10% Pd/C (wet) was added and the resulting mixture was stirred under hydrogen atmosphere (balloon) overnight. In the next step, the reaction mixture was filtered through the pad of Celite and the filtrate was concentrated. The crude product was purified by preparative HPLC (0.1-1% of acetonitrile in water) to give (after acidification with 2M HCl and subsequent lyophilization) 23.8 mg (34%) of the corresponding product as a white solid (7:3 mixture of rotamers in $D_2O$ solution at room temperature, based on NMR). ESI+MS: m/z=330.85 (M+1)$^+$; ESI-MS: m/z=328.85 (M−1)$^−$. $^1$H NMR (700 MHz, 300K, Deuterium Oxide) δ 4.92 (dt, J=13.0, 1.8 Hz, 0.7H), 4.64 (dd, J=6.9, 5.2 Hz, 0.7H), 4.60 (t, J=5.5 Hz, 0.3H), 4.50 (dd, J=13.0, 4.3 Hz, 0.3H), 4.26 (d, J=13.5 Hz, 0.3H), 3.89 (dd, J=13.6, 4.1 Hz, 0.7H), 3.40 (d, J=13.5 Hz, 0.3H), 3.15-3.04 (m, 2.7H), 2.99-2.87 (m, 1H), 2.54-2.42 (m, 1H), 2.23-2.12 (m, 0.7H), 2.10-1.94 (m, 2.3H), 1.89-1.77 (m, 1.7H), 1.77-1.69 (m, 0.3H), 1.56-1.30 (m, 3H), 0.99-0.74 (m, 2H).

Example 23. (3R,5S)-1-(D-Alanyl)-3-amino-5-(2-boronoethyl)piperidine-3-carboxylic acid dihydrochloride

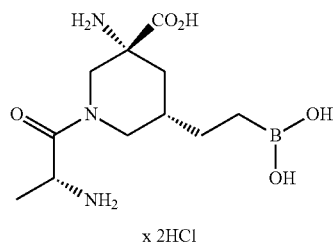 [SMILES: C[C@@H](N)C(=O)N1C[C@@H](CCB(O)O)C[C@](N)(C(=O)O)C1]

x 2HCl

Step A. (3R,5S)-5-(2-Boronoethyl)-1-((tert-butoxycarbonyl)-D-alanyl)-3-((tert-butoxycarbonyl)amino)piperidine-3-carboxylic acid

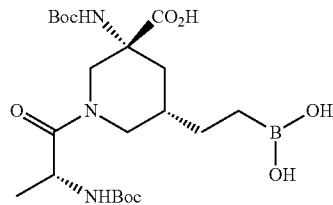 [SMILES: C[C@@H](NC(=O)OC(C)(C)C)C(=O)N1C[C@@H](CCB(O)O)C[C@](NC(=O)OC(C)(C)C)(C(=O)O)C1]

The title compound was obtained according to step (K) of Example 1, using (3R,5S)-5-(2-boronoethyl)-3-((tert-butoxycarbonyl)amino)piperidine-3-carboxylic acid (0.1 g, 0.32 mmol), Boc-D-Ala-OSu (0.13 g, 0.41 mmol) and DMF (2 mL). The crude product was purified by column chromatography on silica gel using DCM/MeOH (80:1 to 0:1) to give 80 mg (52%) of the corresponding product as a colorless film (5:2 mixture of rotamers in $CD_3OD$ solution at room temperature, based on NMR). ESI+MS: m/z=488.05 (M+1)$^+$; ESI-MS: m/z=486.05 (M−1)$^−$. $^1$H NMR (700 MHz, 300 K, Methanol-d$_4$) δ 5.05 (m, 0.7H), 4.97 (m, 0.3H), 4.63-4.41 (m, 2.7H), 3.99-3.90 (m, 0.3H), 3.73-3.59 (m, 1H), 3.04-2.92 (m, 1H), 2.41-2.15 (m, 2H), 1.57-1.36 (m, 18H), 1.22-1.35 (m, 5H), 0.95-0.74 (m, 2H).

Step B. (3R,5S)-1-(D-Alanyl)-3-amino-5-(2-boronoethyl)piperidine-3-carboxylic acid dihydrochloride The title compound was obtained according to step (L) of Example 1, using (3R,5S)-5-(2-boronoethyl)-1-((tert-butoxycarbonyl)-D-alanyl)-3-((tert-butoxycarbonyl)amino)piperidine-3-carboxylic acid (70 mg, 0.13 mmol) and 4M HCl in EtOAc (5 mL). The crude product was purified by preparative HPLC (0.1-1% of acetonitrile in water) to give (after acidification with 2M HCl and subsequent lyophilization) 39 mg, (73%) of the corresponding product as a white solid (4:1 mixture of rotamers in $D_2O$ solution at room temperature, based on NMR). ESI+MS: m/z=287.85 (M+1)$^+$; ESI-MS: m/z=267.85 (M−18−1)$^−$. $^1$H NMR (700 MHz, 300 K, Deuterium Oxide) δ 4.87 (dt, J=13.3, 2.0 Hz, 0.8H), 4.54 (q, J=7.1 Hz, 1H), 4.46-4.40 (m, 0.2H), 4.23 (dt, J=13.3, 2.0 Hz, 0.2H), 3.87-3.81 (m, 0.8H), 3.40 (d, J=13.9 Hz, 0.2H), 2.92 (d, J=13.4 Hz, 0.8H), 2.84 (dd, J=14.1, 12.1 Hz, 0.8H), 2.48-2.40 (m, 1H), 2.35 (dd, J=14.1, 12.1 Hz, 0.2H), 2.04-1.97 (m, 0.8H), 1.68-1.58 (m, 0.2H), 1.56-1.48 (m, 1H), 1.46-1.29 (m, 5H), 0.83-0.72 (m, 2H).

Example 24. (3R,5S)-3-amino-5-(2-boronoethyl)-1-(1-methyl-D-tryptophyl)piperidine-3-carboxylic acid dihydrochloride

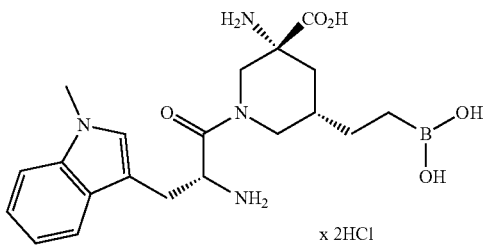 [SMILES: Cn1cc(C[C@@H](N)C(=O)N2C[C@@H](CCB(O)O)C[C@](N)(C(=O)O)C2)c2ccccc21]

x 2HCl

Step A. (3R,5S)-5-(2-Boronoethyl)-1-(N$^α$-(tert-butoxycarbonyl)-1-methyl-D-tryptophyl)-3-((tert-butoxycarbonyl)amino)piperidine-3-carboxylic acid

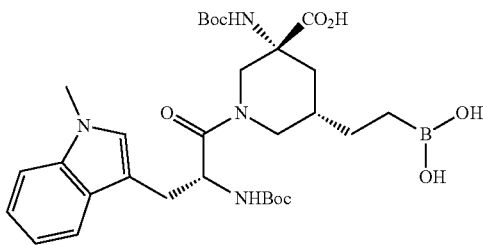 [SMILES: Cn1cc(C[C@@H](NC(=O)OC(C)(C)C)C(=O)N2C[C@@H](CCB(O)O)C[C@](NC(=O)OC(C)(C)C)(C(=O)O)C2)c2ccccc21]

The title compound was obtained according to step (K) of Example 1, using (3R,5S)-5-(2-boronoethyl)-3-((tert-butoxycarbonyl)amino)piperidine-3-carboxylic acid (0.1 g, 0.32 mmol), 1-Me-Boc-D-Trp-OSu (0.17 g, 0.41 mmol) and DMF (2 mL). Stirred at room temperature for 24 h and then at 70° C. for 2 days. The crude product was purified by column chromatography on silica gel using DCM/MeOH (50:1 to 15:1) to give 100 mg (51%) of the corresponding product as an off-white solid. ESI+MS: m/z=617.15 (M+1)$^+$.

Step B. (3R,5S)-3-Amino-5-(2-boronoethyl)-1-(1-methyl-D-tryptophyhl)piperidine-3-carboxylic acid dihydrochloride The title compound was obtained according to step (L) of Example 1, using (3R,5S)-5-(2-boronoethyl)-1-(N$^α$-(tert-butoxycarbonyl)-1-methyl-D-tryptophyl)-3-((tert-butoxycarbonyl)amino)piperidine-3-carboxylic acid (100 mg, 0.16 mmol) and 4M HCl in EtOAc (5 mL). The crude product was purified by preparative HPLC (0.1-5% of acetonitrile in water) to give (after acidification with 2M HCl and subsequent lyophilization) 70 mg, (89%) of the corresponding product as a white solid (3.3:1 mixture of rotamers in D$_2$O solution at room temperature, based on NMR). ESI+MS: m/z=417.00 (M+1)$^+$. $^1$H NMR (700 MHz, 300 K, Deuterium Oxide) δ 7.68 (d, J=7.9 Hz, 1H), 7.49-7.45 (m, 0.6H), 7.44 (d, J=8.0 Hz, 1H), 7.30-7.24 (m, 1.3H), 7.23-7.18 (m, 1.3H), 7.16 (t, J=7.5 Hz, 0.3H), 7.02 (s, 1H), 4.97-4.89 (m, 2H), 4.76 (dd, J=9.2, 5.2 Hz, 0.3H), 4.31-4.26 (m, 0.3H), 3.80 (d, J=14.2 Hz, 0.3H), 3.76 (s, 1H), 3.72 (s, 3H), 3.40 (dd, J=14.6, 5.2 Hz, 0.3H), 3.35 (dd, J=14.4, 4.6 Hz, 1H), 3.27-3.23 (m, 0.3H), 3.21 (dd, J=14.4, 11.0 Hz, 1H), 3.07 (dd, J=13.3, 4.0 Hz, 1H), 2.73 (d, J=13.3 Hz, 1H), 2.40 (t, J=12.4 Hz, 1H), 2.30-2.23 (m, 1.3H), 2.12 (d, J=13.9 Hz, 0.3H), 1.84 (t, J=12.6 Hz, 0.3H), 1.57-1.49 (m, 0.3H), 1.30-1.16 (m, 1H), 1.09 (t, J=12.8 Hz, 1H), 0.70 (t, J=8.2 Hz, 0.6H), 0.56-0.44 (m, 2H), 0.04 (ddd, J=15.9, 11.9, 3.9 Hz, 1H), −0.02−−0.12 (m, 1H), −0.21 (tt, J=12.5, 4.0 Hz, 1H).

Example 25. (3R,5S)-3-Amino-1-((S)-2-aminopentanoyl)-5-(2-boronoethyl)piperidine-3-carboxylic acid dihydrochloride

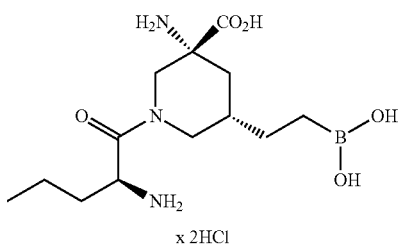 [SMILES: CCC[C@H](N)C(=O)N1C[C@@H](CCB(O)O)C[C@](N)(C(=O)O)C1]

Step A. (3R,5S)-5-(2-Boronoethyl)-3-((tert-butoxycarbonyl)amino)-1-((S)-2-((tert-butoxycarbonyl)amino)pentanoyl)piperidine-3-carboxylic acid

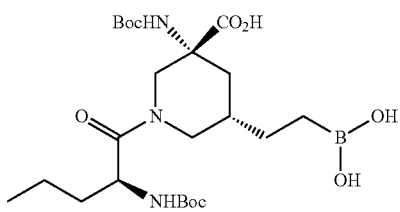 [SMILES: CCC[C@H](NC(=O)OC(C)(C)C)C(=O)N1C[C@@H](CCB(O)O)C[C@](NC(=O)OC(C)(C)C)(C(=O)O)C1]

The title compound was obtained according to step (K) of Example 1, using (3R,5S)-5-(2-boronoethyl)-3-((tert-butoxycarbonyl)amino)piperidine-3-carboxylic acid (0.1 g, 0.32 mmol), Boc-L-Nva-OSu (0.13 g, 0.41 mmol) and DMF (2 mL). The crude product was purified by column chromatography on silica gel using DCM/MeOH (80:1 to 0:1) to give 64 mg (39%) of the corresponding product as a white solid (5:2 mixture of rotamers in CD$_3$OD solution at room temperature, based on NMR). ESI+MS: m/z=516.05 (M+1)$^+$; ESI-MS: m/z=514.10 (M−1)$^−$. $^1$H NMR (700 MHz, 300 K, Methanol-d$_4$) δ 5.13-5.02 (m, 0.7H), 4.67-4.56 (m, 0.7H), 4.55-4.50 (m, 0.3H), 4.43-4.35 (m, 1H), 4.23-4.13 (m, 0.3H), 3.97-3.89 (m, 1H), 2.79-2.59 (m, 2H), 2.41-2.34 (m, 0.7H), 2.31-2.25 (m, 0.3H), 1.81-1.67 (m, 1H), 1.60-1.53 (m, 2H), 1.49-1.40 (m, 18H), 1.40-1.25 (m, 4H), 0.96 (t, J=7.4 Hz, 3H), 0.91-0.71 (m, 2H).

Step B. (3R,5S)-3-Amino-1-((S)-2-aminopentanoyl)-5-(2-boronoethyl)piperidine-3-carboxylic acid dihydrochloride The title compound was obtained according to step (L) of Example 1, (3R,5S)-5-(2-boronoethyl)-3-((tert-butoxycarbonyl)amino)-1-((S)-2-((tert-butoxycarbonyl)amino)pentanoyl) piperidine-3-carboxylic acid (58 mg, 0.11 mmol) and 4M HCl in EtOAc (7 mL). The crude product was purified by preparative HPLC (0.1-1% of acetonitrile in water) to give (after acidification with 2M HCl and subsequent lyophilization) 21 mg (49%) of the corresponding product as a white solid (9:1 mixture of rotamers in D$_2$O solution at room temperature, based on NMR). ESI+MS: m/z=315.85 (M+1)$^+$; 297.75 (M−18+1)$^+$; ESI-MS: m/z=295.85 (M−18−1)$^−$. $^1$H NMR (700 MHz, 300 K, Deuterium Oxide) δ 4.88 (d, J=13.2 Hz, 0.9H), 4.48 (dd, J=7.7, 4.7 Hz, 0.9H), 4.40 (dd, J=7.9, 3.9 Hz, 0.1H), 4.36 (dd, J=13.3, 4.4 Hz, 0.1H), 4.22 (d, J=13.8 Hz, 0.1H), 3.81 (dd, J=13.6, 4.4 Hz, 0.9H), 3.41 (d, J=13.8 Hz, 0.1H), 2.94-2.85 (m, 1.8H), 2.46-2.40 (m, 1.1H), 2.10-1.97 (m, 0.9H), 1.96-1.85 (m, 0.1H), 1.85-1.69 (m, 2H), 1.49-1.29 (m, 5H), 0.90 (t, J=7.3 Hz, 3H), 0.84-0.72 (m, 2H).

Example 26. (3R,5S)-1-(L-Asparaginyl)-3-amino-5-(2-boronoethyl)piperidine-3-carboxylic acid dihydrochloride

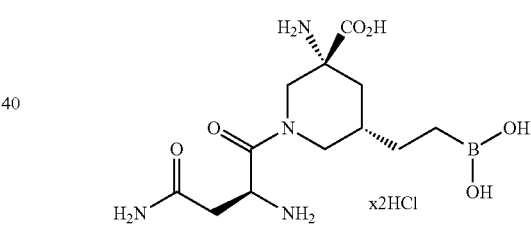

Step A. (3R,5S)-5-(2-Boronoethyl)-1-((tert-butoxycarbonyl)-L-asparaginyl)-3-((tert-butoxycarbonyl)amino)piperidine-3-carboxylic acid

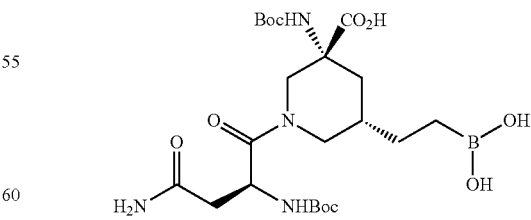

The title compound was obtained according to step (K) of Example 1, using (3R,5S)-5-(2-boronoethyl)-3-((tert-butoxycarbonyl)amino)piperidine-3-carboxylic acid (0.114 g, 0.36 mmol), Boc-L-Asn-OSu (0.154 g, 0.47 mmol) and DMF (2 mL). The crude product was purified by column chromatography on silica gel using CHCl$_3$/MeOH (10:1 to 3:1) to give 60 mg (31%) of the corresponding product as a white solid. ESI+MS: m/z=531.15 (M+1)$^+$; ESI-MS: m/z=529.05 (M−1)$^−$. $^1$H NMR (700 MHz, 300 K, Methanol-d$_4$) δ 5.40-5.18 (m, 1H), 4.63-4.48 (m, 1H), 4.29 (bs, 1H), 3.35 (bs, 1H), 2.94-2.81 (m, 1H), 2.81-2.61 (m, 2H), 2.58-2.32 (m, 1H), 2.25-2.13 (m, 1H), 1.64-1.22 (m, 22H), 0.85-0.70 (m, 1H).

Step B. (3R,5S)-1-(L-Asparaginyl)-3-amino-5-(2-boronoethyl)piperidine-3-carboxylic acid dihydrochloride The title compound was obtained according to step (L) of Example 1, using (3R,5S)-5-(2-boronoethyl)-1-((tert-butoxycarbonyl)-L-asparaginyl)-3-((tert-butoxycarbonyl)amino) piperidine-3-carboxylic acid (60 mg, 0.11 mmol) and 4M HCl in EtOAc (3 mL). The crude product was purified by preparative HPLC (0.1-1% of acetonitrile in water) to give (after acidification with 2M HCl and subsequent lyophilization) 7 mg (16%) of the corresponding product as a white solid (5:2 mixture of rotamers in D$_2$O solution at room temperature, based on NMR). ESI+MS: m/z=330.85 (M+1)$^+$; ESI-MS: m/z=328.85 (M−1)$^−$.

$^1$H NMR (700 MHz, 300 K, Deuterium Oxide) δ 4.94 (d, J=13.3 Hz, 1H), 4.88 (dd, J=8.9, 4.1 Hz, 1H), 4.48 (d, J=9.6 Hz, 0.2H), 4.42-4.26 (m, 0.2H), 3.90 (dd, J=13.6, 4.2 Hz, 1H), 3.46 (d, J=13.6 Hz, 0.2H), 3.26-2.90 (m, 3H), 2.86 (dd, J=16.9, 8.9 Hz, 1H), 2.53 (t, J=13.4 Hz, 1H), 2.24-2.08 (m, 1H), 1.90-1.85 (m, 0.2H), 1.62-1.47 (m, 2H), 1.43 (tdd, J=13.6, 11.0, 7.5 Hz, 1H), 0.87 (ttd, J=15.6, 9.8, 5.2 Hz, 2H).

Example 27. (3R,5S)-3-Amino-5-(2-boronoethyl)-1-(methylglycyl)piperidine-3-carboxylic acid dihydrochloride

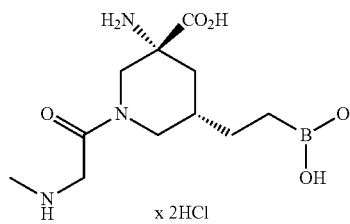

Step A. (3R,5S)-5-(2-Boronoethyl)-1-(N-(tert-butoxycarbonyl)-N-methylglycyl)-3-((tert-butoxycarbonyl)amino)piperidine-3-carboxylic acid

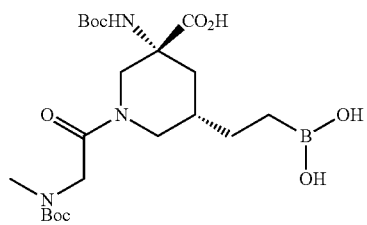 [SMILES: CN(CC(=O)N1C[C@@H](CCB(O)O)C[C@](NC(=O)OC(C)(C)C)(C(=O)O)C1)C(=O)OC(C)(C)C]

The title compound was obtained according to step (K) of Example 1, using (3R,5S)-5-(2-boronoethyl)-3-((tert-butoxycarbonyl)amino)piperidine-3-carboxylic acid (0.10 g, 0.32 mmol), Boc-Sar-OSu (91 mg, 0.32 mmol), TEA (49 μL, 0.35 mmol) and DMF (2 mL). Next day, DMF was evaporated. The residue was diluted with EtOAc (30 mL) and washed with 1M KHSO$_4$ (1×20 mL), H$_2$O (1×20 mL), brine (1×20 mL), dried over MgSO$_4$ and concentrated to give 119 mg (77%) of the corresponding product as a yellowish solid. ESI+MS: m/z=488.05 (M+1)$^+$; ESI-MS: m/z=485.95 (M−1)$^−$. $^1$H NMR (700 MHz, 300 K, Methanol-d$_4$) δ 4.65-4.48 (m, 2H), 4.43-4.34 (m, 1H), 4.32-4.25 (m, 1H), 2.92-2.83 (m, 4H), 2.30-2.22 (m, 1H), 1.51-1.43 (m, 19H), 1.40-1.28 (m, 4H), 0.89-0.78 (m, 2H).

Step B. (3R,5S)-3-Amino-5-(2-boronoethyl)-1-(methylglycyl)piperidine-3-carboxylic acid dihydrochloride The title compound was obtained according to step (L) of Example 1, using (3R,5S)-5-(2-boronoethyl)-1-(N-(tert-butoxycarbonyl)-N-methylglycyl)-3-((tert-butoxycarbonyl)amino)piperidine-3-carboxylic acid (110 mg, 0.23 mmol) and 3.6 M HCl in EtOAc (5 mL). The crude product was purified by preparative HPLC (0.1-1% of acetonitrile in water) to give (after acidification with 2M HCl and subsequent lyophilization) 40 mg (49%) of the corresponding product as a white foam (3:2 mixture of rotamers in D$_2$O solution at room temperature, based on NMR). ESI+MS: m/z=287.85 (M+1)$^+$; ESI-MS: m/z=267.90 (M−18−1)$^−$. $^1$H NMR (700 MHz, 300 K, Deuterium Oxide) δ 4.79-4.76 (m, 0.6H), 4.48-4.39 (m, 0.4H), 4.20-4.00 (m, 2.4H), 3.68 (dd, J=13.8, 4.2 Hz, 0.6H), 3.26 (d, J=13.8 Hz, 0.4H), 2.95 (d, J=13.3 Hz, 0.6H), 2.83-2.66 (m, 3.6H), 2.42-2.29 (m, 1.4H), 2.05-1.98 (m, 0.6H), 1.73-1.66 (m, 0.4H), 1.48-1.24 (m, 3H), 0.82-0.73 (m, 2H).

Example 28. (2-((3S,5R)-1-(L-Alanyl)-5-amino-5-(methoxycarbonyl)piperidin-3-yl)ethyl) boronic acid dihydrochloride

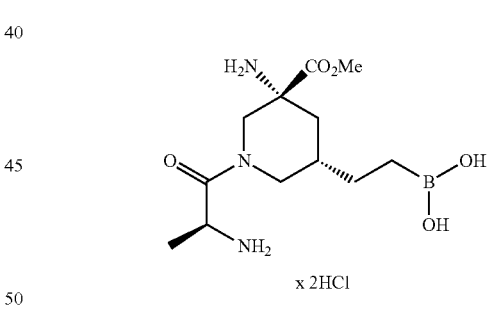

To a solution of (3R,5S)-1-(L-alanyl)-3-amino-5-(2-boronoethyl)piperidine-3-carboxylic acid dihydrochloride (82 mg, 0.23 mmol) in toluene (1 mL) and methanol (0.4 mL) was added trimethylsilyldiazomethane 2M solution in Et$_2$O (173 μL, 0.34 mmol). The mixture was stirred at room temperature overnight. The solvents were evaporated. The crude product was purified by preparative HPLC (0.1-10% of acetonitrile in water) to give (after acidification with 2M HCl and subsequent lyophilization) 6.4 mg (8%) of the corresponding product as a white solid (9:1 mixture of rotamers in D$_2$O solution at room temperature, based on NMR). ESI+MS: m/z=301.90 (M+1)$^+$. $^1$H NMR (700 MHz, 300K, Deuterium Oxide) δ 4.95 (dt, J=13.3, 2.0 Hz, 0.9H), 4.59 (q, J=7.1 Hz, 0.9H), 4.54 (q, J=7.0 Hz, 0.1H), 4.48 (d, J=13.7 Hz, 0.1H), 4.33 (d, J=13.7 Hz, 0.1H), 3.92-3.85 (m, 3.9H), 3.46 (d, J=13.8 Hz, 0.1H), 3.07-2.89 (m, 1.9H), 2.53

(dd, J=28.5, 13.1 Hz, 1H), 2.02 (dt, J=11.4, 5.2 Hz, 0.9H), 1.87-1.74 (m, 0.1H), 1.63-1.48 (m, 5H), 1.43 (ddt, J=13.6, 9.8, 6.7 Hz, 1H), 0.97-0.78 (m, 2H).

Example 29. (3R,5S)-1-(L-Arginyl)-3-amino-5-(2-(4-carboxy-4-(carboxymethyl)-6-oxo-1,3,2-dioxaborinan-2-yl)ethyl)piperidine-3-carboxylic acid trihydrochloride

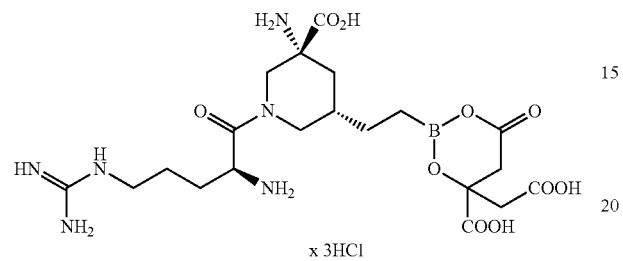

To a solution of (3R,5S)-1-(L-arginyl)-3-amino-5-(2-boronoethyl)piperidine-3-carboxylic acid trihydrochloride (20 mg, 0.04 mmol) in methanol (1 mL), citric acid was added (9 mg, 0.04 mmol) and resulting mixture was stirred at room temperature for 2 h. Reaction was concentrated to dryness to give 26 mg (98%) of corresponding product as a white solid. $^1$H NMR (700 MHz, 300 K, DMSO-$d_6$) δ 9.03-8.78 (m, 3H), 8.41-8.17 (m, 3H), 8.02-7.79 (m, 1H), 7.57-6.86 (m, 3H), 4.90-4.82 (m, 1H), 4.66-4.50 (m, 1H), 4.31-4.19 (m, 1H), 3.93-3.86 (m, 1H), 3.60-3.53 (m, 2H), 3.20-3.06 (m, 2H), 2.99-2.87 (m, 1H), 2.88-2.72 (m, 1H), 2.69-2.56 (m, 2H), 2.56-2.53 (m, 1H), 2.43-2.15 (m, 3H), 1.95-1.63 (m, 3H), 1.62-1.39 (m, 3H), 1.35-1.04 (m, 2H), 0.41-0.14 (m, 2H).

The intermediate for the preparation of Examples 1-29 can be alternatively obtained as described below.

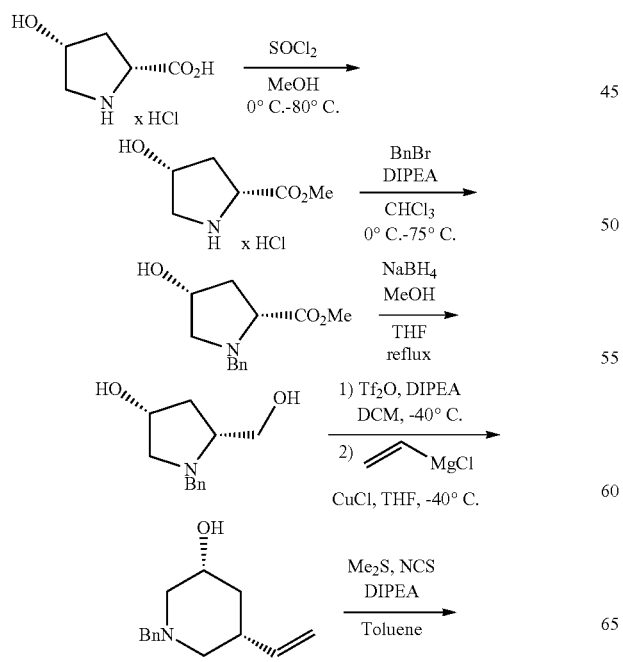

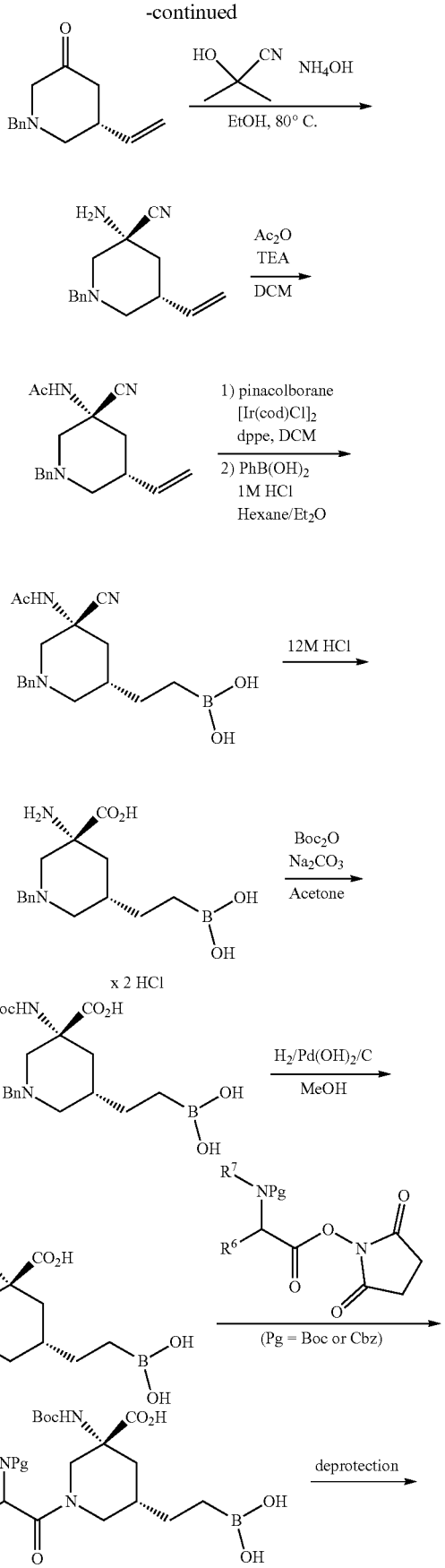

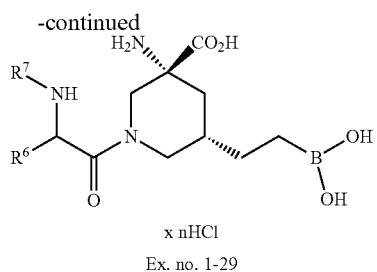

Ex. no. 1-29

Step A. Methyl (2R,4R)-4-hydroxypyrrolidine-2-carboxylate hydrochloride

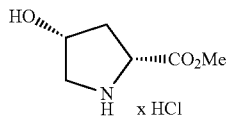

cis-4-Hydroxy-D-proline hydrochloride (200 g, 1.19 mol) was dissolved in MeOH (2 L) in four-neck flask (equipped with mechanical stirrer, reflux condenser, dropping funnel and septum) and was cooled to 0° C. Thionyl chloride (95.8 mL, 1.31 mol) was added dropwise to the reaction mixture for 1.5 h (maintain a temperature 0° C.). The reaction mixture was warmed to room temperature for 1 h and heated to reflux for 1 h. The reaction mixture was cooled to room temperature (overnight), transferred to round-bottom-flask and concentrated. The gel-like residue was evaporated with CHCl$_3$ (3×1 L) and dried under high vacuum for 1 h at 50° C. (water bath). The residue was crumbled with spatula, suspended in Et$_2$O (1 L) and placed in ultrasound bath for 40 minutes (2×20 minutes). The white solid was filtered, washed with Et$_2$O (2×0.5 L) and dried under high vacuum for 4 h at 50° C. (water bath) to give 234.6 g of the crude product that was used in the next step without further purification. ESI+MS m/z=146 (M+1)$^+$; $^1$H NMR (700 MHz, D$_2$O) δ 4.75 (d, J=3.1 Hz, 1H), 4.74 (d, J=3.0 Hz, 1H), 4.70 (qt, J=4.2, 1.6 Hz, 2H), 3.92 (s, 7H), 3.57-3.50 (m, 5H), 2.59 (ddd, J=14.4, 10.1, 4.2 Hz, 3H), 2.51-2.47 (m, 2H).

Step B. Methyl (2R,4R)-1-benzyl-4-hydroxpyrrolidine-2-carboxylate

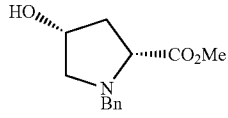 [SMILES: COC(=O)[C@H]1C[C@@H](O)CN1Cc1ccccc1]

Methyl (2R,4R)-4-hydroxypyrrolidine-2-carboxylate hydrochloride (1.19 mol) was suspended in CHCl$_3$ (2 L) in four-neck flask equipped with mechanical stirrer, reflux condenser, dropping funnel and septum and was cooled to 0° C. DIPEA (520 mL, 2.98 mol) was added dropwise at 0° C. and the reaction mixture was warmed to room temperature. Benzyl bromide (141.7 mL, 1.19 mol) was added dropwise for 1 h. The reaction mixture was heated to reflux (75° C., oil bath temp.) for 1 h and cooled to room temperature (water bath with crushed ice). Water (1 L) was added to the reaction mixture and layers were separated. Organic layer was washed with water (1×1 L), 1M NaOH (1×1 L), brine (1×1 L), dried over MgSO4, filtered and concentrated under reduced pressure to give 233.4 g (83%, after 2 steps) of the desired as a pale orange oil. ESI+MS m/z=235.95 (M+1)$^+$; $^1$H NMR (700 MHz, CDCl$_3$) δ 7.32-7.23 (m, 4H), 4.24 (m, 1H), 3.86 (d, J=13.1 Hz, 1H), 3.71 (d, J=13.1 Hz, 1H), 3.63 (s, 1H), 3.34 (dd, J=10.1, 3.8 Hz, 1H), 3.11 (d, J=10.7 Hz, 1H), 3.01 (dt, J=9.9, 1.6 Hz, 1H), 2.63 (dd, J=10.1, 3.8 Hz, 1H), 2.37 (ddd, J=14.2, 10.0, 5.7 Hz, 1H), 1.95 (m, 1H).

Step C. (3R,5R)-1-Benzyl-5-(hydroxymethyl)pyrrolidin-3-ol

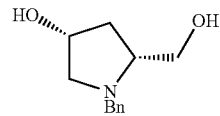

To a solution of methyl (2R,4R)-1-benzyl-4-hydroxypyrrolidine-2-carboxylate obtained as above (90 g, 0.38 mol) in dry THF (0.9 L) was slowly added NaBH$_4$ (44 g, 1.16 mol) at room temperature. The reaction mixture was heated to reflux and methanol (180 mL) was added dropwise over 1.5 h with effervescence being observed. The reaction mixture was cooled to room temperature and quenched with 1M NaOH (240 mL, dropped over 15 min). Inorganic contaminations were precipitated. The layers were separated and the white solid was dissolved in water (250 ml) and washed with Et$_2$O (3×200 mL). The combined organic layers were dried over MgSO$_4$, filtered and concentrated to give 75.3 g (95%) of (3R,5R)-1-benzyl-5-(hydroxymethyl)pyrrolidin-3-ol as a colorless oil that solidified in the fridge. ESI+MS: m/z=207.95 (M+1)$^+$; $^1$H NMR (700 MHz, Chloroform-d) δ 7.35-7.28 (m, 4H), 7.26-7.22 (m, 1H), 4.19 (t, J=4.9 Hz, 1H), 3.93 (d, J=13.2 Hz, 1H), 3.60-3.54 (m, 1H), 3.50 (d, J=13.2 Hz, 1H), 3.40 (d, J=11.0 Hz, 1H), 3.01 (dd, J=10.3, 2.1 Hz, 1H), 2.90-2.83 (m, 1H), 2.77 (bs, 2H), 2.46 (dd, J=10.2, 3.8 Hz, 1H), 2.35 (ddd, J=14.3, 10.3, 5.9 Hz, 1H), 1.82-1.75 (m, 1H).

Step D. (3R,5R)-1-benzyl-5-vinylpiperidin-3-ol

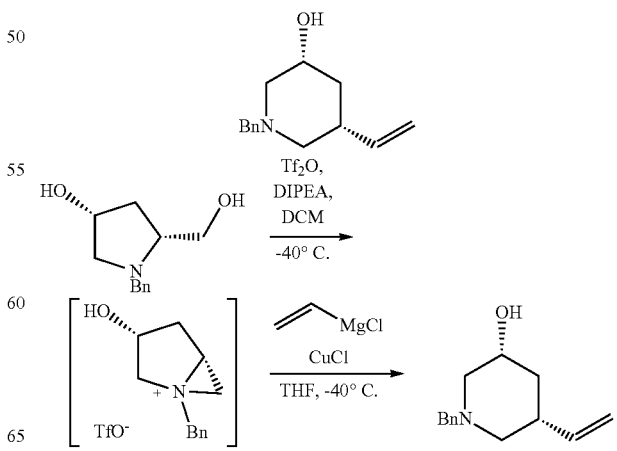

Preparation of salt: (3R,5R)-1-benzyl-3-hydroxy-1-azabicyclo[3.1.0]hexan-1-ium trifluoromethanesulfonate To a solution of (3R,5R)-1-benzyl(5-hydroxymethyl)-pirrolidin-3-ol (96.55 g, 0.466 mol) and DIPEA (162 mL, 0.932 mol) in dry DCM (450 mL) was added dropwise triflic anhydride (86 mL, 0.512 mol) for over 40 min, under Ar. The temperature of the reaction was maintained from −30° C. to −10° C. After the addition was completed the reaction mixture was stirred at −25° C. for 20 min to achieved ca. 95% of conversion. TLC: CHCl$_3$/MeOH (9:1)+MVP. (Total consumption of substrate observed on LC-MS with ELSD).
Ring Expansion:

To a suspension of CuCl (6.92 g, 0.07 mol) in dry THF (250 mL) was added dropwise vinylmagnesium chloride 1.7 M in THF (1100 mL, 1.86 mol) for over 60 min, under Ar. The temperature of the reaction mixture was maintained from −40° C. to −25° C. To this mixture was transferred the cold solution of freshly prepared (as above) (3R,5R)-1-benzyl-3-hydroxy-1-azabicyclo[3.1.0]hexan-1-ium trifluoromethanesulfonate via cannula for over 50 min, under Ar. The temperature of the reaction was maintained from −35° C. to −10° C. The resulting mixture was stirred at −30° C. for 60 min. Then the reaction mixture was quenched by the addition of 1M NaOH$_{aq}$ (1300 mL) and 4M NaOH$_{aq}$ (300 mL). The organic solvents were evaporated under reduced pressure (at 30° C., water bath). The aqueous residue was treated with Et$_2$O (ca. 500 mL). The suspension that was formed was filtered through a Celite. The solid was washed with Et$_2$O (ca. 1000 mL). The filtrate (organic and aqueous layer) was separated. The aqueous layer was washed with Et$_2$O (1×300 mL). The combined organic layers were dried over MgSO$_4$, filtered and concentrated under reduced pressure to give 108 g of the crude product as an orange oil. The crude product was treated with 4M HCl in dioxane (180 mL), then ca. 50 mL of dioxane was evaporated under reduced pressure. The solid was filtered off and washed with acetone (ca. 120 mL) and dried under vacuum to give 45 g (38%) of (3R,5R)-1-benzyl-5-vinylpiperidin-3-ol hydrochloride as a beige solid. To a suspension of hydrochloride salt in H$_2$O (200 mL) was added 4M NaOH$_{aq}$ (to pH 12) and the mixture was washed with DCM (2×400 mL). The combined organic layers were dried over MgSO$_4$, filtered and concentrated under reduced pressure to give 38.2 g (38%) of (3R,5R)-1-benzyl-5-vinylpiperidin-3-ol as a yellow oil that solidified in the fridge. The crude compound can be alternatively purified by flash chromatography on silica gel using hexane/AcOEt (8:1 to 1:1) as an eluent to afford pure (3R,5R)-1-benzyl-5-vinylpiperidin-3-ol in 50% yield. ESI+MS: m/z=217.95 (M+1)$^+$; $^1$H NMR (700 MHz, Chloroform-d) δ 7.36-7.31 (m, 4H), 7.29-7.29 (m, 1H), 5.75 (ddd, J=17.1, 10.5, 6.5 Hz, 1H), 5.15-4.95 (m, 2H), 3.84 (tt, J=9.6, 4.1 Hz, 1H), 3.62 (d, J=13.1 Hz, 1H), 3.54 (d, J=13.1 Hz, 1H), 3.07-2.99 (m, 1H), 2.83 (ddt, J=11.1, 3.6, 1.5 Hz, 1H), 2.39 (dtdt, J=7.9, 6.5, 5.2, 3.8 Hz, 1H), 2.10 (dtd, J=12.2, 4.0, 1.9 Hz, 1H), 1.87-1.76 (m, 2H), 1.14 (q, J=11.6 Hz, 1H).

Step E. (R)-1-benzyl-5-vinylpiperidin-3-one

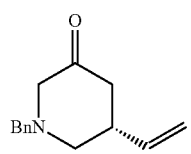

N-chlorosuccinimide (NCS) (44.7 g, 0.335 mol) was suspended in dry toluene (0.5 L) and it was cooled to 0° C. A solution of dimethyl sulfide (41 mL, 0.558 mol) in toluene (0.5 L) was added dropwise to the reaction mixture and it was stirred for 30 minutes at 0° C. Next, the mixture was cooled to −20° C. and a solution of (3R,5R)-1-benzyl-5-vinylpiperidin-3-ol (48.5 g, 0.223 mol) in toluene (0.5 L) was added dropwise to the reaction mixture and it was stirred for 2 h at −20° C. A solution of DIPEA (117 mL, 0.67 mol) in toluene (0.2 L) was added dropwise and the reaction mixture was warmed slowly (over ca. 1 h) to room temperature. The progress of the reaction was performed using UPLC/MS [ESI+MS m/z=233.95 (M+18)$^+$] and TLC (Hex: EtOAc 1:5). After full consumption of the substrate, the reaction mixture was cooled to 0° C. Saturated NaHCO$_3$ (2 L) and Et$_2$O (0.5 L) were added and it was stirred for 10 minutes. Layers were separated and water phase was extracted with Et$_2$O (3×0.5 L). Combined organic layers were washed with brine (1 L), dried over MgSO$_4$, filtered and concentrated. The crude product was used to the next step without any further purification. ESI+MS m/z=233.95 (M+18)$^+$. $^1$H NMR (700 MHz, 300 K, Chloroform-d) δ 7.37-7.26 (m, 5H), 5.76 (ddd, J=17.2, 10.6, 6.7 Hz, 1H), 5.10-5.03 (m, 2H), 3.66-3.56 (m, 2H), 3.19 (dt, J=14.4, 1.6 Hz, 1H), 2.95 (ddt, J=11.5, 3.3, 1.5 Hz, 1H), 2.80 (d, J=14.4 Hz, 1H), 2.78-2.71 (m, 1H), 2.53 (dd, J=15.4, 5.1 Hz, 1H), 2.29 (dd, J=11.5, 9.6 Hz, 1H), 2.20 (ddd, J=15.4, 11.0, 0.9 Hz, 1H).

Step F. (3R,5R)-3-amino-1-benzyl-5-vinylpiperidine-3-carbonitrile

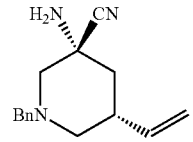

To the solution of (R)-1-benzyl-5-vinylpiperidin-3-one (0.223 mol) in aqueous ethanol (96%, 300 mL) was added acetone cyanohydrine (25 mL, 0.268 mol) followed by aqueous ammonia (25%, 300 mL) was added. The mixture was stirred at 60° C. (oil bath temperature) under autoclave conditions for 3 days. After cooling of the reaction mixture to room temperature ethanol was evaporated under reduced pressure. The biphasic mixture was obtained. The layers were separated. The aqueous layer was washed with diethyl ether (3×150 mL) and DCM (50 mL). The combined organic layers were washed with brine (50 mL), dried over Na$_2$SO$_4$ and concentrated under reduced pressure to give 54.6 g of the crude product as a pale brown oil. The crude product as a mixture of diastereoisomers 6.5:1 (based on $^1$H NMR) was used to the next steps without any further purification. ESI+MS: m/z=242.00 (M+1)$^+$.

Step G. N-((3R,5R)-1-Benzyl-3-cyano-5-vinylpiperidin-3-yl)acetamide

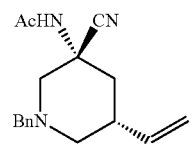 [SMILES: C=C[C@@H]1CN(Cc2ccccc2)C[C@](C#N)(NC(C)=O)C1]

To a solution of (3R,5R)-3-amino-1-benzyl-5-vinylpiperidine-3-carbonitrile obtained above (54.6 g, 0.22 mol) in DCM (800 mL) were added TEA (78 mL, 0.56 mol) and acetic anhydride (23 mL, 0.24 mol). The mixture was stirred at room temperature for 3 h. After this time TEA (12 mL, 0.09 mol) and acetic anhydride (4 mL, 0.04 mol) were added. The resulting mixture was stirred at room temperature overnight. The mixture was diluted with DCM (100 mL) and washed with 5% NaHCO$_3$ (2×300 mL). The aqueous layer was extracted with DCM (200 mL). The combined organic layers were washed with brine (200 mL), dried over MgSO$_4$ and concentrated in vacuo. The crude product was purified by column chromatography on silica gel using CH$_3$Cl/acetone (1:0 to 100:1) to give 35.0 g (55%, after 3 steps) of the corresponding product as a pale yellow foam (single major diastereoisomer with enantiomeric excess ee>99.9%). ESI+MS: m/z=284.05 (M+1)$^+$; ESI-MS: m/z=282.00 (M−1)$^−$. $^1$H NMR (700 MHz, 300K, Chloroform-d) δ 7.36-7.31 (m, 4H), 7.28-7.24 (m, 1H), 5.66 (ddd, J=17.2, 10.5, 6.5 Hz, 1H), 5.55 (s, 1H), 5.13-4.91 (m, 2H), 3.68-3.56 (m, 3H), 2.90 (d, J=11.2 Hz, 1H), 2.80-2.71 (m, 1H), 2.49 (d, J=12.8 Hz, 1H), 2.08 (d, J=11.1 Hz, 1H), 1.98 (s, 3H), 1.97-1.90 (m, 1H), 1.51-1.41 (m, 1H).

Figure 2:
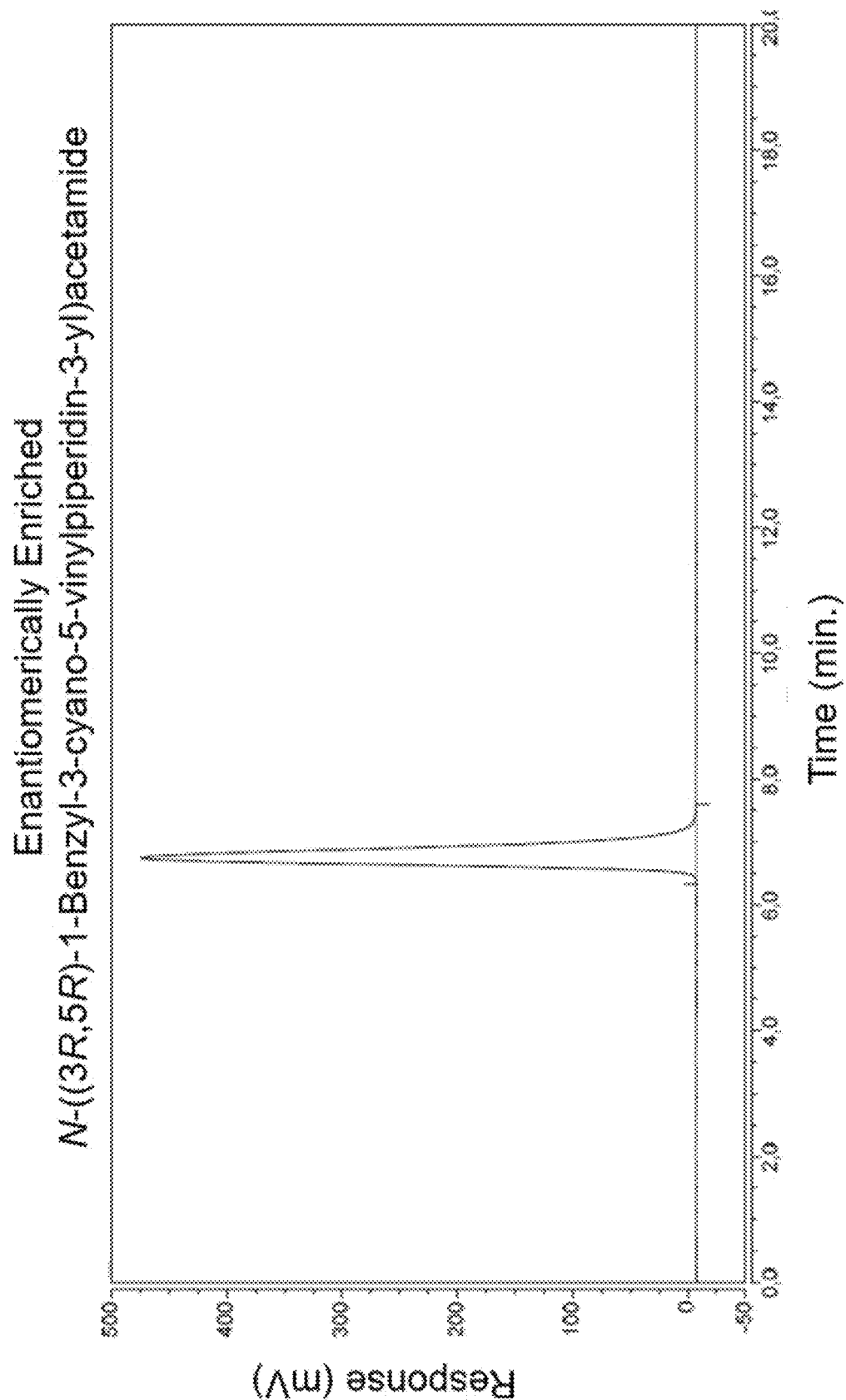
FIG. 2 is a chromatogram indicating certain compounds described herein. See Example 29; Table 4)
Figure 3:
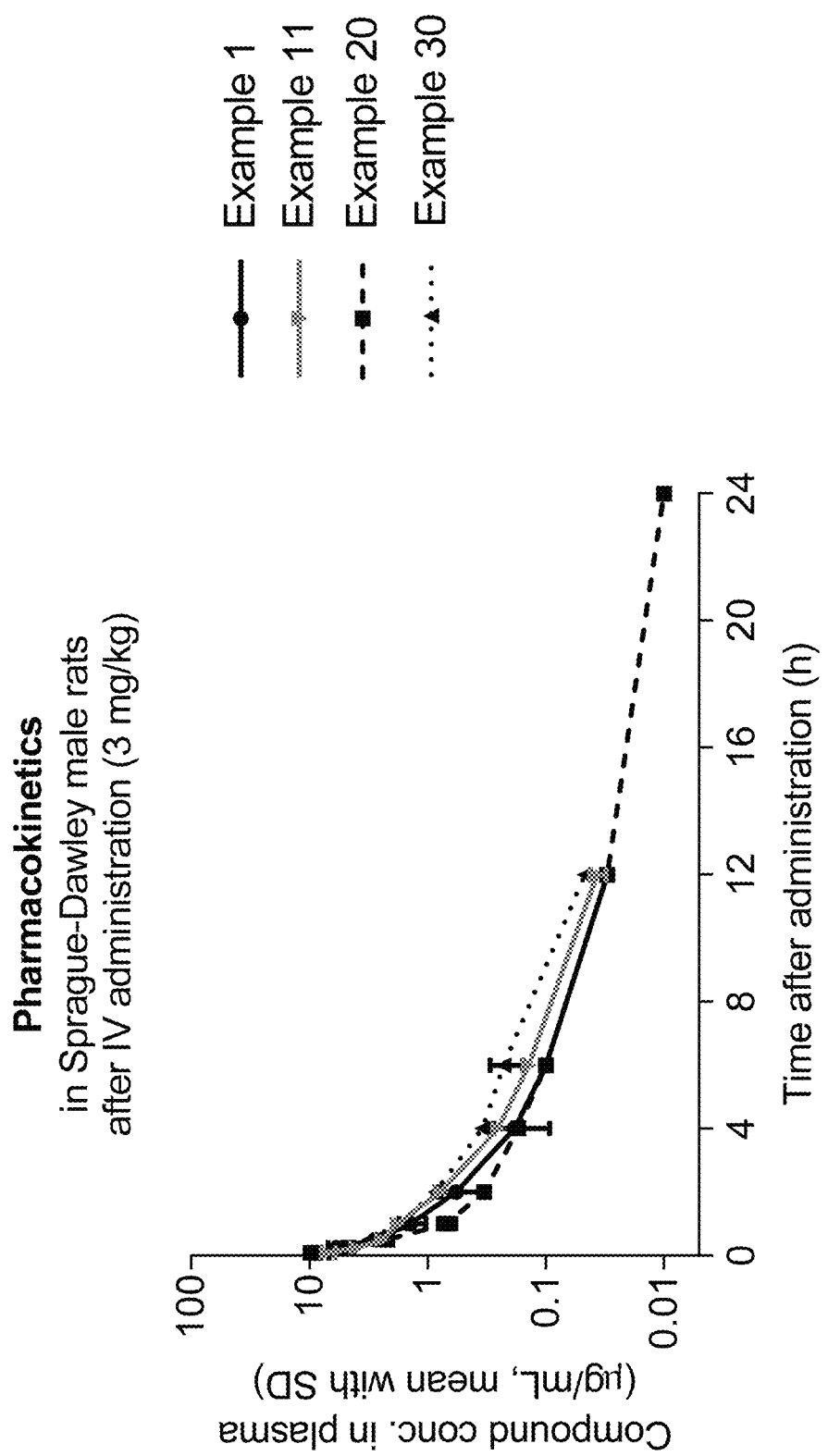
FIG. 3 is a plot showing the pharmacokinetic results (IV administration) of certain compounds described herein. See Example 34.
Figure 4:
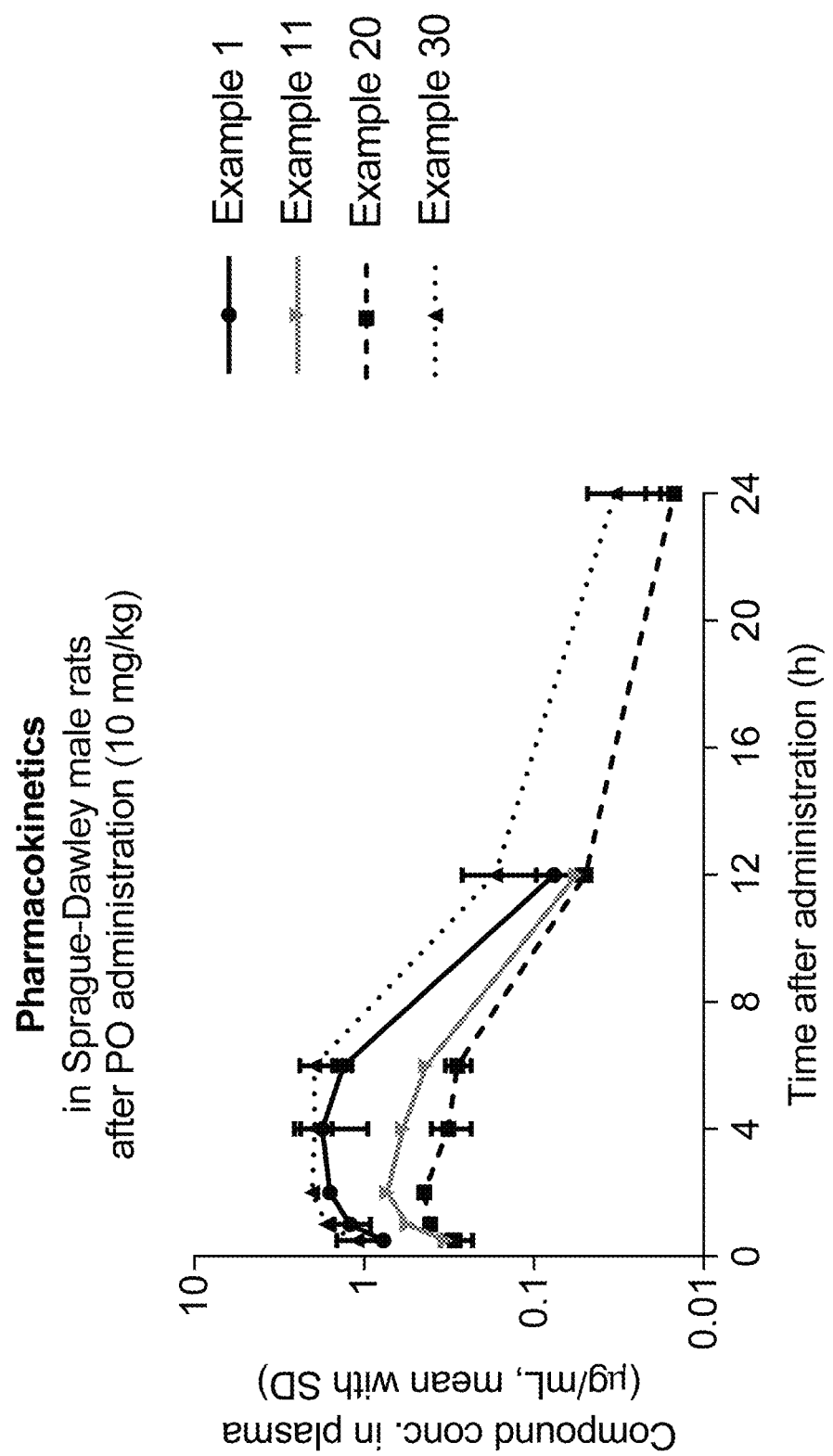
FIG. 4 is a plot showing the pharmacokinetic results (PO administration) of certain compounds described herein. See Example 34.
Figure 5:
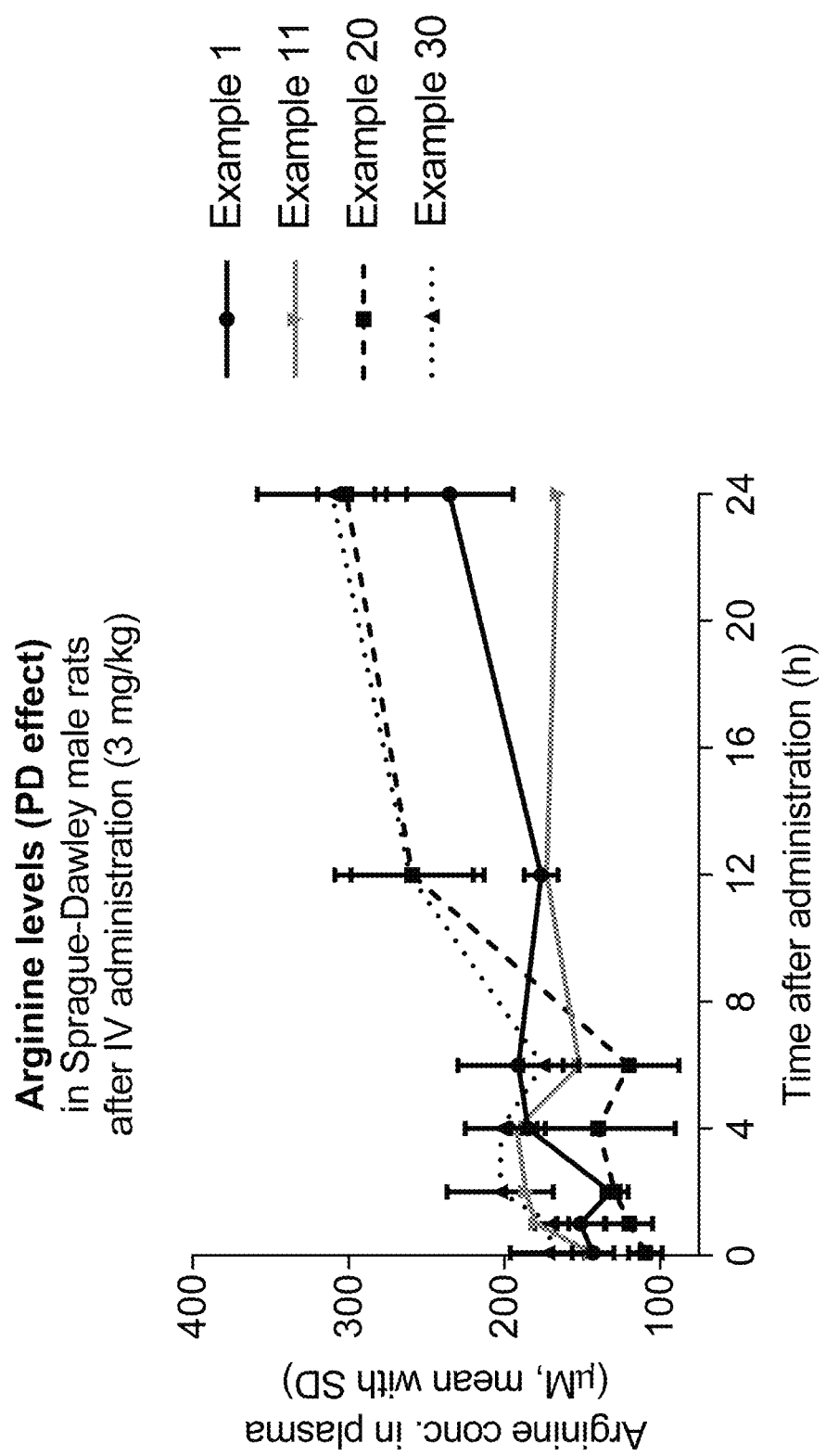
FIG. 5 is a plot showing the pharmacodynamic results (IV administration) of certain compounds described herein. See Example 34.
Figure 6:
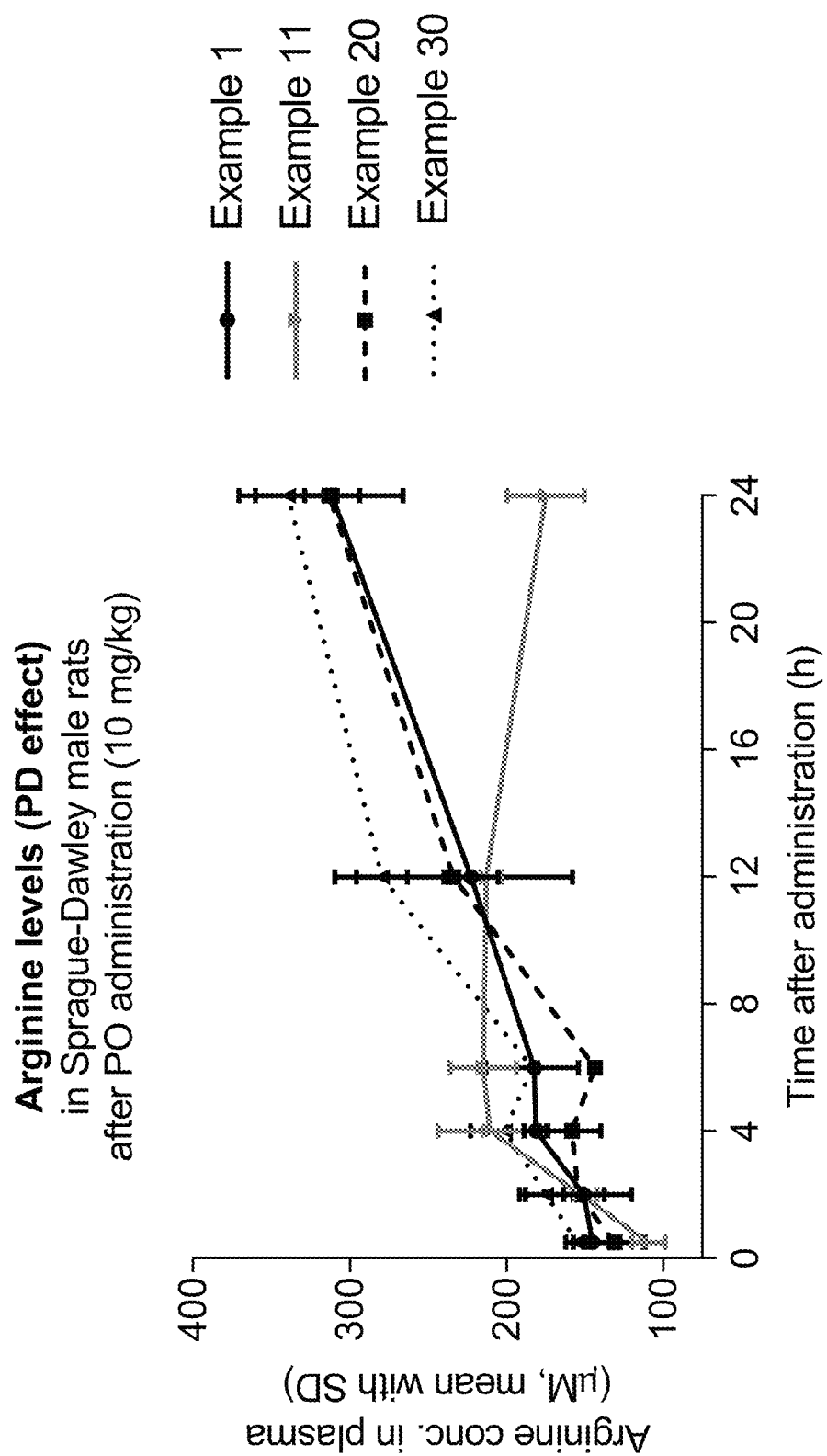
FIG. 6 is a plot showing the pharmacodynamic results (PO administration) of certain compounds described herein. See Example 34.

Ee>99.9%. Enantiomeric excess (ee) was measured using chiral HPLC: Column: Phenomenex Lux® 5 μm Cellulose 4 (150×4.6 mm); Elution system: from 5 to 10% (iPrOH:EtOH 4:1) in Hexane for 20 minutes; Flow rate: 1 mL/min; Detector: ELSD/UV (210 nm); Retention times: t$_{R1}$=6.72 min, t$_{R2}$=12.05 min. See FIGS. 1 and 2. Respective integration results are shown in Tables 3 and 4, below:

TABLE 3

Racemic N-((3R,5R)-1-Benzyl-3-cyano-5-vinylpiperidin-3-yl)acetamide

| Peak No. | Ret. Time (min.) | Area (mV * min.) | Height (mV) | Rel. Area (%) | Rel. Height (%) |
|---|---|---|---|---|---|
| 1 | 6.722 | 85.408 | 285.567 | 52.61 | 61.09 |
| 2 | 12.053 | 76.942 | 181.865 | 47.39 | 38.91 |

TABLE 4

Enantiomerically enriched N-((3R,5R)-1-Benzyl-3-cyano-5-vinylpiperidin-3-yl)acetamide

| Peak No. | Ret. Time (min.) | Area (mV * min.) | Height (mV) | Rel. Area (%) | Rel. Height (%) |
|---|---|---|---|---|---|
| 1 | 6.742 | 146.708 | 482.843 | 100.00 | 100.00 |

Step H. (2-((3S,5R)-5-acetamido-1-benzyl-5-cyanopiperidin-3-yl)ethyl)boronic acid

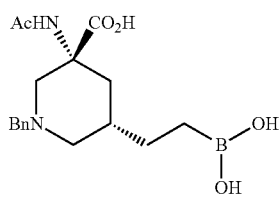

Bis(1,5-cyclooctadiene)diiridium (I) dichloride (1.05 g, 1.58 mmol) and 1,2-bis (diphenylphosphino)ethane (1.25 g, 3.15 mmol) were dissolved in DCM (195 mL) and stirred at room temperature for 15 min. Then N-((3R,5R)-1-benzyl-3-cyano-5-vinylpiperidin-3-yl)acetamide (29.8 g, 105 mmol) in DCM (120 mL) was added and the mixture was stirred at room temperature for 30 min. The mixture was cooled to 0° C. and 4,4,5,5-tetramethyl-1,3,2-dioxaborolane (21.2 mL, 147 mmol) was added over 15 min. The resulting mixture was stirred at room temperature for 48 h and then 4,4,5,5-tetramethyl-1,3,2-dioxaborolane (3.0 mL, 21 mmol) was added. The mixture was stirred for 4 h. The reaction was diluted with DCM (70 mL) and washed with 5% NaHCO$_3$ (200 mL) and brine (150 mL). The organic layer was dried over MgSO$_4$ and concentrated in vacuo to give 51.5 g of the corresponding product as an orange foam. ESI+MS: m/z=411.95 (M+1)$^+$. Crude N-(3R,5S)-1-benzyl-3-cyano-5-(2-(4,4,5,5-tetramethyl-1,3,2-dioxaborolan-2-yl)ethyl)piperidin-3-yl)acetamide (51.5 g, 105 mmol) was suspended in Et$_2$O (40 mL) and hexane (325 mL). 1M HCl (250 mL) and phenylboronic acid (13.44 g, 110 mmol) were added. The reaction mixture was stirred vigorously for 1 h (precipitate formed). The reaction mixture was filtered and the filtrate was transferred to separatory funnel. Layers were separated. The aqueous layer was washed with hexane (3×300 mL) and alkalized with 4M NaOH to pH≈12 (flask was cooled in ice-water bath). The aqueous layer contained an oily precipitation was washed with Et$_2$O (3×300 mL). After decantation the aqueous layer was washed again with Et$_2$O (2×150 mL). The oily residue was treated with a mixture of 1M NaOH (100 mL) and DCM (250 mL) and sonificated to obtain almost clear biphasic mixture. The layers were separated. The organic layer was washed with water (50 mL) and 1M NaOH (10 mL). The combined all aqueous layers were washed with Et$_2$O (3×200 mL), acidified with concentrate aqueous HCl to pH≈3 and subsequent carefully alkalized with solid NaHCO$_3$ to pH≈8. The aqueous layer was extracted with EtOAc (4×400 mL). The combined organic layers were dried over MgSO$_4$, filtered and concentrated to afford (2-((3S,5R)-5-acetamido-1-benzyl-5-cyanopiperidin-3-yl)ethyl)boronic acid as a white foam (29.17 g, 84%). ESI+MS: m/z=329.85 (M+1)$^+$. $^1$H NMR (700 MHz, 300 K, Methanol-d$_4$) δ 7.38-7.34 (m, 3H), 7.33-7.29 (m, 2H), 3.68-3.62 (m, 2H), 3.57 (d, J=13.5 Hz, 1H), 2.99-2.95 (m, 1H), 2.49 (dt, J=12.7, 1.8 Hz, 1H), 1.93 (s, 3H), 1.91-1.88 (m, 1H), 1.87 (d, J=11.0 Hz, 1H), 1.67 (t, J=11.0 Hz, 1H), 1.32 (dddd, J=20.8, 13.7, 9.7, 6.8 Hz, 2H), 1.11 (t, J=12.6 Hz, 1H), 0.83-0.73 (m, 2H).

Step I. (3R,5S)-3-Amino-1-benzyl-5-(2-boronoethyl)piperidine-3-carboxylic acid dihydrochloride

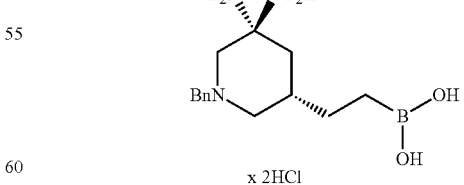

A mixture of (2-((3S,5R)-5-acetamido-1-benzyl-5-cyanopiperidin-3-yl)ethyl)boronic acid (28.43 g, 86.36 mmol) and 12M HCl (224 mL) was heated at 120° C. for 5 h. The reaction mixture was concentrated under reduced pressure. The residue was dissolved in H$_2$O (150 mL) and washed with Et$_2$O (2×100 mL). Next, aqueous layer was alkalized with NaHCO$_{3(s)}$ and washed with Et$_2$O (2×100 mL). The aqueous solution was used to the next step.

Step J. (3R,5S)-1-benzyl-5-(2-boronoethyl)-3-((tert-butoxycarbonyl)amino)piperidine-3-carboxylic acid

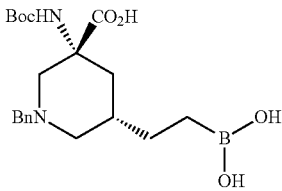 [SMILES: CC(C)(C)OC(=O)N[C@]1(C(=O)O)C[C@H](CCB(O)O)CN(Cc2ccccc2)C1]

To an alkaline solution of (3R,5S)-3-amino-1-benzyl-5-(2-boronoethyl)piperidine-3-carboxylic acid in H$_2$O was added solid Na$_2$CO$_3$ to pH=9, acetone (250 mL) and di-tert-butyl dicarbonate (50.89 g, 233 mmol). The resulting mixture was stirred at room temperature overnight. Inorganic contaminations were precipitated using acetone (500 mL) and filtered off. Solid was washed with acetone (5×50 mL). Acetone was evaporated under reduced pressure and solid that was precipitated was filtered off, washed with Et$_2$O (3×40 mL) and dried under high vacuum to give 24.04 g (69%) of the corresponding product as a white solid. The aqueous layer was washed with Et$_2$O (2×100 mL) followed by neutralized with 1M HCl (to pH=7) and concentrated under reduced pressure to a volume of 50 mL. The residue was left in the refrigerator overnight. The precipitated solid was filtered off, washed with Et$_2$O (2×100 mL) and dried under high vacuum to give 6.64 g (19%) of the corresponding product as a white solid. Total yield: 30.68 g (88%, after two steps). ESI+MS: m/z=407.10 (M+1)$^+$; ESI-MS: m/z=405.15 (M−1)$^−$. $^1$H NMR (700 MHz, 300 K, Deuterium Oxide) δ 7.63-7.52 (m, 5H), 4.70-4.58 (m, 1H), 4.06 (d, J=13.1 Hz, 1H), 3.85-3.73 (m, 1H), 3.69 (d, J=11.9 Hz, 1H), 2.87-2.60 (m, 2H), 2.12-2.07 (m, 1H), 1.99-1.88 (m, 1H), 1.54-1.29 (m, 9H), 1.11 (s, 3H), 0.90-0.73 (m, 2H).

Step K. (3R,5S)-5-(2-boronoethyl)-3-((tert-butoxycarbonyl)amino)piperidine-3-carboxylic acid

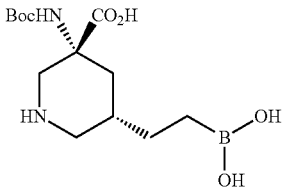 [SMILES: CC(C)(C)OC(=O)N[C@@]1(C(=O)O)CNC[C@@H](CCB(O)O)C1]

To a solution of (3R,5S)-1-benzyl-5-(2-boronoethyl)-3-((tert-butoxycarbonyl)amino)piperidine-3-carboxylic acid (30.68 g, 75.51 mmol) in MeOH (350 mL) was added 20% Pd(OH)$_2$/C (1 g), under argon. The mixture was stirred overnight under hydrogen atmosphere (from balloon). The reaction mixture was filtered through a pad of Celite that was next washed with MeOH (10×100 mL). The filtrate was concentrated in vacuo to give 22.66 g (95%) of the corresponding product as a white solid. ESI+MS: m/z=317.00 (M+1)$^+$; ESI-MS: m/z=315.05 (M−1)$^−$. $^1$H NMR (700 MHz, 300 K, Deuterium Oxide) δ 4.01 (dt, J=12.1, 1.6 Hz, 1H), 3.45 (dd, J=12.3, 4.1 Hz, 1H), 2.79 (d, J=12.1 Hz, 1H), 2.64 (t, J=12.4 Hz, 1H), 2.12 (bs, 1H), 1.83 (bs, 1H), 1.49-1.34 (m, 12H), 0.88-0.76 (m, 2H).

Example 30. (2S,3R,5S)-1-(L-alanyl)-3-amino-5-(2-boronoethyl)-2-methylpiperidine-3-carboxylic acid dihydrochloride

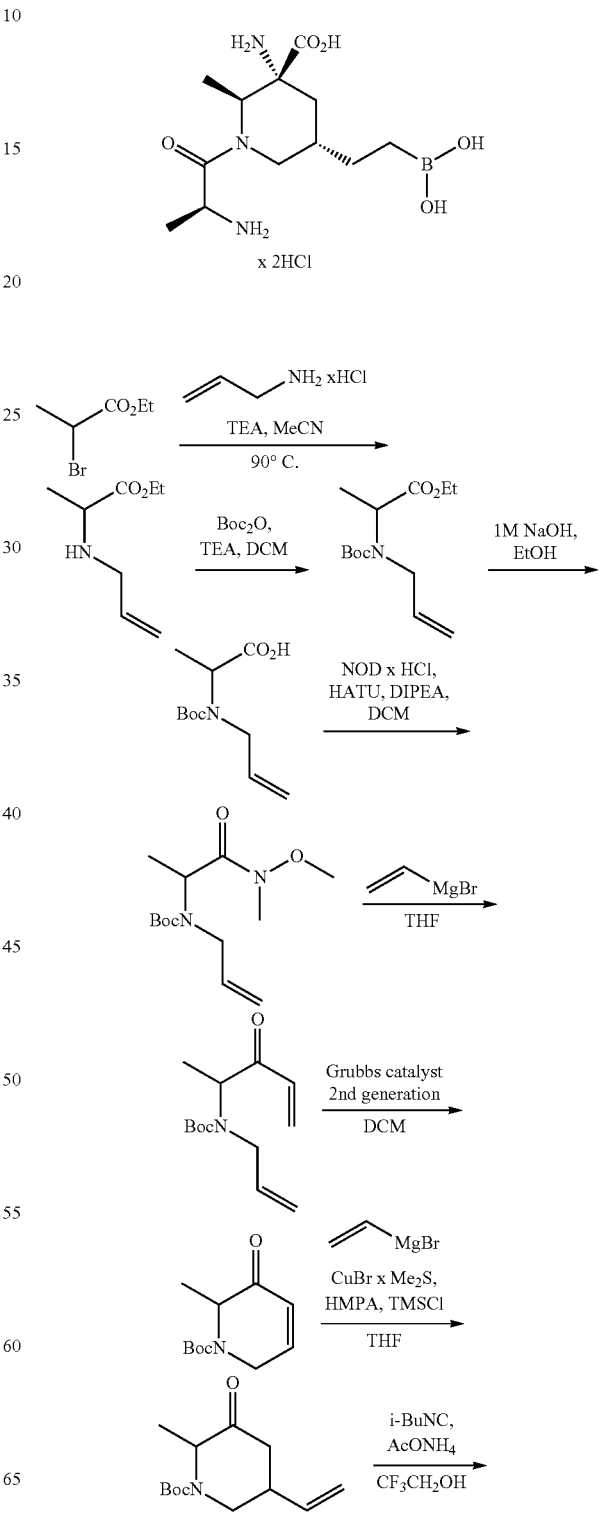

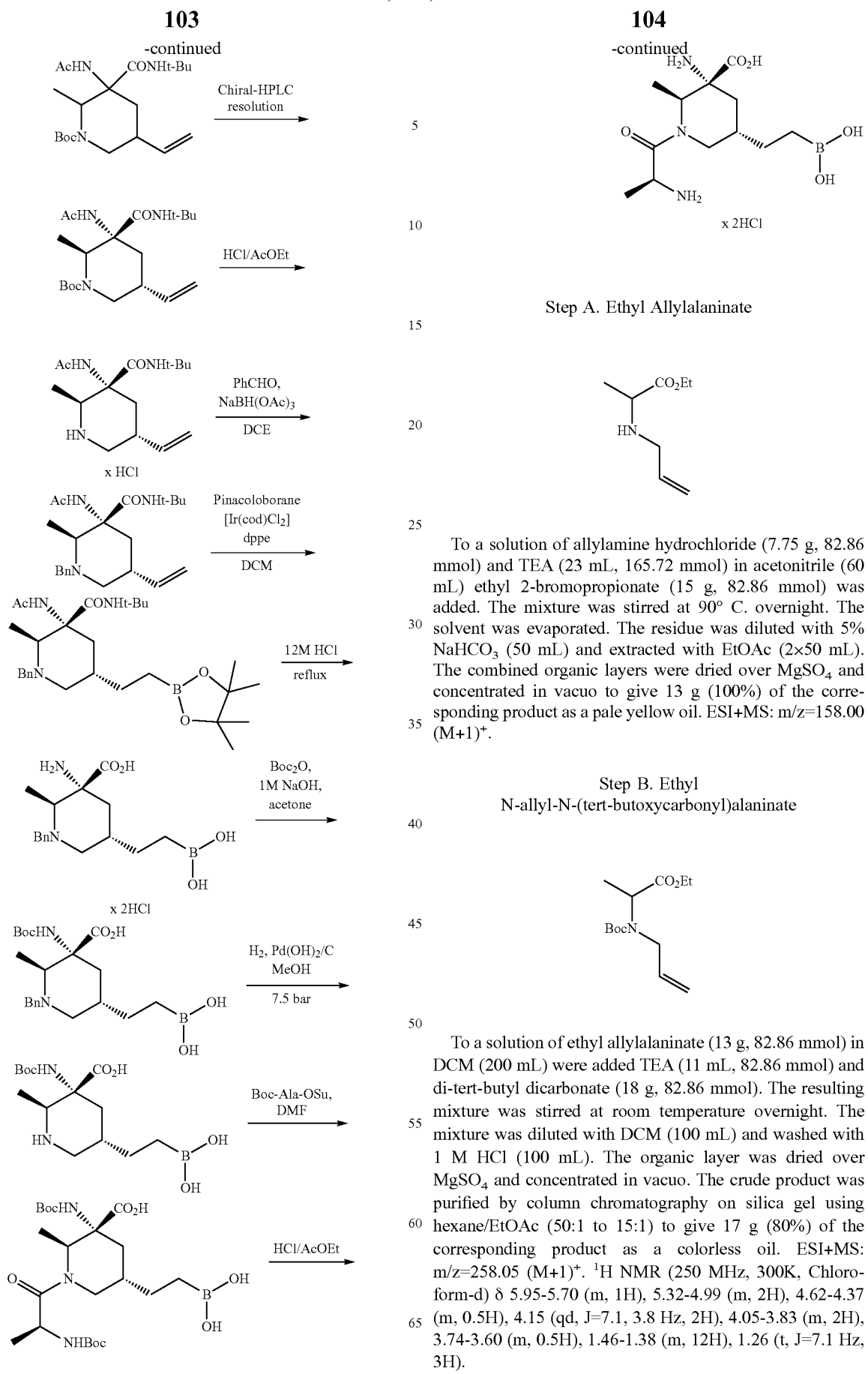

Step A. Ethyl Allylalaninate

To a solution of allylamine hydrochloride (7.75 g, 82.86 mmol) and TEA (23 mL, 165.72 mmol) in acetonitrile (60 mL) ethyl 2-bromopropionate (15 g, 82.86 mmol) was added. The mixture was stirred at 90° C. overnight. The solvent was evaporated. The residue was diluted with 5% $NaHCO_3$ (50 mL) and extracted with EtOAc (2×50 mL). The combined organic layers were dried over $MgSO_4$ and concentrated in vacuo to give 13 g (100%) of the corresponding product as a pale yellow oil. ESI+MS: m/z=158.00 $(M+1)^+$.

Step B. Ethyl N-allyl-N-(tert-butoxycarbonyl)alaninate

To a solution of ethyl allylalaninate (13 g, 82.86 mmol) in DCM (200 mL) were added TEA (11 mL, 82.86 mmol) and di-tert-butyl dicarbonate (18 g, 82.86 mmol). The resulting mixture was stirred at room temperature overnight. The mixture was diluted with DCM (100 mL) and washed with 1 M HCl (100 mL). The organic layer was dried over $MgSO_4$ and concentrated in vacuo. The crude product was purified by column chromatography on silica gel using hexane/EtOAc (50:1 to 15:1) to give 17 g (80%) of the corresponding product as a colorless oil. ESI+MS: m/z=258.05 $(M+1)^+$. $^1H$ NMR (250 MHz, 300K, Chloroform-d) δ 5.95-5.70 (m, 1H), 5.32-4.99 (m, 2H), 4.62-4.37 (m, 0.5H), 4.15 (qd, J=7.1, 3.8 Hz, 2H), 4.05-3.83 (m, 2H), 3.74-3.60 (m, 0.5H), 1.46-1.38 (m, 12H), 1.26 (t, J=7.1 Hz, 3H).

Step C. N-Allyl-N-(tert-butoxycarbonyl)alanine

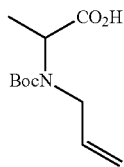

To a solution of ethyl N-allyl-N-(tert-butoxycarbonyl) alaninate (17 g, 66 mmol) in EtOH (132 mL) was added 1M NaOH (132 mL). The mixture was stirred at room temperature for 2.5 h. EtOH was evaporated. The aqueous layer was acidified by 2M HCl to pH=2 and extracted with $Et_2O$ (3×70 mL). The combined organic layers were dried over $MgSO_4$ and concentrated in vacuo to give 15 g (99%) of the corresponding product as a colorless oil. ESI+MS: m/z=251.95 $(M+23)^+$; ESI-MS: m/z=228.05 $(M-1)^-$. $^1H$ NMR (250 MHz, 300K, Chloroform-d) δ 5.84 (ddt, J=16.3, 10.6, 5.9 Hz, 1H), 5.29-4.91 (m, 2H), 4.59-4.37 (m, 0.5H), 4.16-3.84 (m, 2H), 3.88-3.64 (m, 0.5H), 1.48-1.39 (m, 12H).

Step D. tert-Butyl allyl(1-(methoxy(methyl)amino)-1-oxopropan-2-yl)carbamate

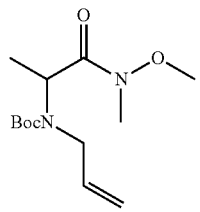 [SMILES: C=CCN(C(=O)OC(C)(C)C)C(C)C(=O)N(C)OC]

To a solution of N-allyl-N-(tert-butoxycarbonyl)alanine (15 g, 65 mmol) in DCM (150 mL) were added DIPEA (24 mL, 137 mmol), N,O-dimethylhydroxyamine (6.6 g, 68 mmol) and HATU (26 g, 68 mmol). The resulting mixture was stirred at room temperature overnight. The mixture was diluted with DCM (75 mL) and washed with 1M NaOH (75 mL), 1M HCl (75 mL) and brine (75 mL). The organic layer was dried over $MgSO_4$ and concentrated in vacuo. The crude product was purified by column chromatography on silica gel using hexane/EtOAc (20:1 to 4:1) to give 17.8 g (100%) of the corresponding product as a colorless oil. ESI+MS: m/z=273.05 $(M+1)^+$. $^1H$ NMR (250 MHz, 300K, Chloroform-d) δ 5.81 (ddd, J=21.4, 10.0, 5.0 Hz, 1H), 5.30-4.71 (m, 3H), 3.92-3.77 (m, 2H), 3.74 (s, 3H), 3.15 (s, 3H), 1.44 (s, 9H), 1.31 (d, J=7.2 Hz, 3H).

Step E. tert-Butyl allyl(3-oxopent-4-en-2-yl)carbamate

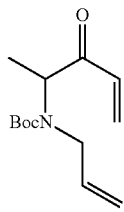 [SMILES: C=CCN(C(=O)OC(C)(C)C)C(C)C(=O)C=C]

To a solution of tert-butyl allyl(1-(methoxy(methyl)amino)-1-oxopropan-2-yl)carbamate (10 g, 36.7 mmol) in dry THF (50 mL) at −78° C. under Ar was added vinyl magnesium bromide 1M solution in THF (147 mL, 147 mmol) dropwise. The mixture was allowed to warm to −20° C. over 2 h. Then the reaction mixture was poured onto 3M HCl (chilled) (100 mL) and extracted with $Et_2O$ (2×100 mL). The combined organic layers were dried over $MgSO_4$ and concentrated in vacuo to give 8.8 g (100%) of the corresponding product as a pale yellow oil. ESI+MS: m/z=262.10 $(M+23)^+$. $^1H$ NMR (250 MHz, Chloroform-d) δ 6.71-6.44 (m, 1H), 6.35 (dd, J=17.3, 1.9 Hz, 1H), 5.99-5.56 (m, 2H), 5.32-4.69 (m, 3H), 4.19-3.49 (m, 2H), 1.58-1.20 (m, 12H).

Step F. tert-Butyl 2-methyl-3-oxo-3,6-dihydropyridine-1(2H)-carboxylate

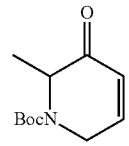

To a solution of tert-butyl allyl(3-oxopent-4-en-2-yl)carbamate (8.8 g, 36.7 mmol) in DCM (1200 mL) was added Grubbs catalyst $2^{nd}$ generation (1.56 g, 1.84 mmol). The mixture was stirred at room temperature overnight. The solvent was evaporated. The crude product was purified by column chromatography on silica gel using hexane/EtOAc (60:1 to 8:1) to give 5.16 g (66%) of the corresponding product as an orange oil. ESI+MS: m/z=235.10 $(M+23)^+$. $^1H$ NMR (700 MHz, 300K, Chloroform-d) δ 6.98 (s, 1H), 6.09 (dddd, J=10.3, 2.7, 1.9, 0.5 Hz, 1H), 4.77-4.56 (m, 2H), 3.82 (d, J=21.2 Hz, 1H), 1.48 (s, 9H), 1.26 (d, J=7.2 Hz, 3H).

Step G. tert-Butyl 2-methyl-3-oxo-5-vinylpiperidine-1-carboxylate

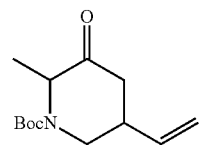 [SMILES: C=CC1CC(=O)C(C)N(C(=O)OC(C)(C)C)C1]

To a flask charged with $CuBr×Me_2S$ complex (0.75 g, 3.66 mmol) and dry THF (100 mL) were added HMPA (17 mL, 97.6 mmol) and vinylmagnesium bromide 1M solution in THF (85 mL, 85.4 mmol) at −78° C. under Ar. The reaction mixture was stirred for 15 min followed by a solution of tert-butyl 2-methyl-3-oxo-3,6-dihydropyridine-1 (2H)-carboxylate (5.16 g, 24.4 mmol) and chlorotrimethylsilane (15.4 mL, 122 mmol) in THF (65 mL) was added dropwise for over 30 min. The reaction mixture was stirred for 2 h at −78° C. and subsequently overnight at room temperature. After the reaction was completed, 80 mL of saturated aqueous $NH_4Cl$ solution was added, and then the layers were separated. The organic layer was washed with $NH_4Cl$ (3×30 mL). The aqueous layer was diluted with $H_2O$ (100 mL) and washed with $Et_2O$ (2×40 mL). The combined organic layers were dried over $MgSO_4$ and concentrated in vacuo. The crude product was purified by column chromatography on silica gel using hexane/EtOAc (100:1 to 15:1) to give 4.34 g (74%) of the corresponding product as a orange oil (7:3 mixture of diasteroisomers in CDCl$_3$ solution at room temperature, based on NMR). ESI+MS: m/z=183.90 (M−56+1)$^+$. $^1$H NMR (700 MHz, 300K, Chloroform-d) δ 5.85-5.77 (m, 0.7H), 5.77-5.69 (m, 0.3H), 5.16-5.05 (m, 2H), 4.54 (bs, 0.7H), 4.28 (bs, 0.3H), 3.88 (d, J=13.5 Hz, 1H), 3.35 (dd, J=13.5, 4.6 Hz, 0.7H), 2.87-2.76 (m, 1H), 2.68 (dddd, J=13.2, 11.6, 6.5, 3.3 Hz, 0.3H), 2.63-2.53 (m, 1H), 2.48 (ddt, J=16.0, 7.2, 1.0 Hz, 0.7H), 2.34 (dd, J=16.0, 11.8 Hz, 0.3H), 1.47 (s, 3H), 1.46 (s, 6H), 1.31 (d, J=7.2 Hz, 2H), 1.29 (d, J=7.2 Hz, 1H).

Step H. tert-Butyl (2S,3R,5R)-3-acetamido-3-(tert-butylcarbamoyl)-2-methyl-5-vinylpiperidine-1-carboxylate

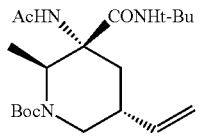

To a solution of tert-butyl 2-methyl-3-oxo-5-vinylpiperidine-1-carboxylate (3.3 g, 13.8 mmol), and ammonium acetate (4.25 g, 55.2 mmol) in 2,2,2-trifluoroethanol (44 mL), tert-butyl isocyanide (3 mL, 27.6 mmol) was added dropwise and the resulting mixture was stirred at room temperature overnight. After the reaction was completed, the solvent was evaporated under reduced pressure and the residue was diluted with EtOAc (60 mL) and water (25 mL). The separated aqueous layer was washed with EtOAc (3×20 mL). The combined organic layers were dried over MgSO$_4$, filtered and concentrated in vacuo. The crude product was purified by column chromatography on silica gel using hexane/EtOAc (50:1 to 1:3) to give 3 g (mixture of diasteroisomers 7:3). The mixture of diasteroisomers was crystallized from EtOAc to give 1.34 g as white solid (one single diasteroisomer). The racemic mixture was separated for its enantiomer using a chiral preparative HPLC method (Lux® 5 μm Cellulose-4 (21.2×250 mm)) with propan-2-ol and n-hexane (gradient: 8-30%) as an eluent and ELSD detection. Retention time of tert-butyl (2S,3R,5R)-3-acetamido-3-(tert-butylcarbamoyl)-2-methyl-5-vinylpiperidine-1-carboxylate in preparative HPLC was in the range from 3.1 to 5.5 min. Retention time of tert-butyl (2R,3S,5S)-3-acetamido-3-(tert-butylcarbamoyl)-2-methyl-5-vinylpiperidine-1-carboxylate in preparative HPLC was in the range from 7.7 to 10.5 min. The enantiomeric excess for both enantiomers was determined with the use of chiral analytical HPLC method with ELSD detection with Lux® 5 μm Cellulose-4 (4.6×150 mm) column using 10% propan-2-ol in n-hexane as eluent for 10 min. The first desired enantiomer tert-butyl (2S,3R,5R)-3-acetamido-3-(tert-butylcarbamoyl)-2-methyl-5-vinylpiperidine-1-carboxylate (0.64 g, 12%, white solid) with the retention time of 3.6 min and the second undesired enantiomer tert-butyl (2R,3S,5S)-3-acetamido-3-(tert-butylcarbamoyl)-2-methyl-5 vinylpiperidine-1-carboxylate (0.61 g, 12%, white solid) at 8.7 min, each with enantiomeric excess of approximately 98% ee or higher.

ESI+MS: m/z=382.00 (M+1)$^+$; ESI-MS: m/z=380.00 (M−1)$^−$. $^1$H NMR (700 MHz, 300K, Chloroform-d) δ 7.11 (bs, 1H), 5.67 (ddd, J=17.4, 10.6, 6.0 Hz, 1H), 5.53 (bs, 1H), 5.35 (bs, 1H), 5.14-5.02 (m, 2H), 4.13-3.84 (m, 1H), 2.68-2.56 (m, 1H), 2.40-2.18 (m, 2H), 1.94 (s, 3H), 1.48 (s, 9H), 1.33 (s, 9H), 1.28-1.24 (m, 1H), 1.11 (d, J=6.8 Hz, 3H).

Step I. (2S,3R,5R)-3-Acetamido-N-(tert-butyl)-2-methyl-5-vinylpiperidine-3-carboxamide hydrochloride

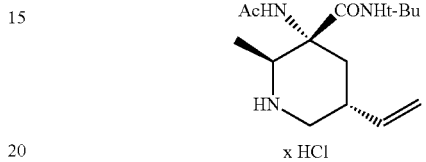

The title compound was obtained according to step (E) of Example 1, using tert-butyl (2S,3R,5R)-3-acetamido-3-(tert-butylcarbamoyl)-2-methyl-5-vinylpiperidine-1-carboxylate (0.59 g, 1.54 mmol) and 4M HCl in EtOAc (20 mL). The desired product was obtained as a white solid (0.49 g, 100%). ESI+MS: m/z=281.95 (M+1)$^+$; ESI-MS: m/z=280.00 (M−1)$^−$. $^1$H NMR (700 MHz, Chloroform-d) δ 10.45 (bs, 1H), 8.75 (bs, 1H), 8.52 (s, 1H), 6.88 (s, 1H), 5.65 (ddd, J=17.1, 10.5, 6.5 Hz, 1H), 5.24-5.11 (m, 2H), 4.74 (d, J=8.3 Hz, 1H), 3.17 (d, J=12.7 Hz, 1H), 2.82 (q, J=12.4 Hz, 1H), 2.58-2.49 (m, 1H), 2.15 (d, J=12.7 Hz, 1H), 2.10 (s, 3H), 2.10-2.02 (m, 3H), 1.37 (d, J=7.1 Hz, 3H), 1.34 (s, 9H).

Step J. (2S,3R,5R)-3-Acetamido-1-benzyl-N-(tert-butyl)-2-methyl-5-vinylpiperidine-3-carboxamide

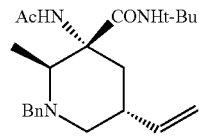

The title compound was obtained according to step (F) of Example 1, using (2S,3R,5R)-3-acetamido-N-(tert-butyl)-2-methyl-5-vinylpiperidine-3-carboxamide hydrochloride (0.49 g, 1.54 mmol), benzaldehyde (187 μL, 1.85 mmol), sodium triacetoxyborohydride (1.63 g, 7.70 mmol) and DCE (16 mL). The desired product was obtained as a white foam (395 mg, 68%). ESI+MS: m/z=372.15 (M+1)$^+$; ESI-MS: m/z=370.05 (M−1)$^−$. $^1$H NMR (700 MHz, 300K, Chloroform-d) δ 8.67 (s, 1H), 7.39-7.27 (m, 5H), 5.60 (ddd, J=17.1, 10.7, 6.3 Hz, 1H), 5.40 (s, 1H), 5.02-4.88 (m, 2H), 4.24 (br s, 1H), 3.76 (d, J=13.2 Hz, 1H), 3.48 (d, J=13.2 Hz, 1H), 2.62 (dd, J=11.7, 4.6 Hz, 1H), 2.44 (dq, J=11.8, 5.8 Hz, 1H), 2.15 (t, J=11.0 Hz, 1H), 1.98 (s, 3H), 1.87 (dd, J=12.5, 4.2 Hz, 1H), 1.45-1.39 (m, 1H), 1.35 (s, 9H), 1.05 (d, J=6.6 Hz, 3H).

Step K. (2S,3R,5S)-3-Acetamido-1-benzyl-N-(tert-butyl)-2-methyl-5-(2-(4,4,5,5-tetramethyl-1,3,2-dioxaborolan-2-yl)ethyl)piperidine-3-carboxamide

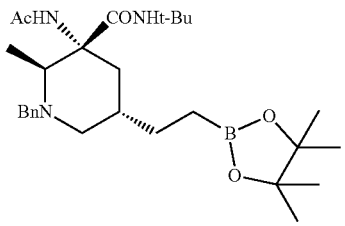

The title compound was obtained according to step (G) of Example 1, using (2S,3R,5R)-3-acetamido-1-benzyl-N-(tert-butyl)-2-methyl-5-vinylpiperidine-3-carboxamide (395 mg, 1.06 mmol), dppe (25 mg, 0.064 mmol), bis(1,5-cyclooctadiene)diiridium(I) dichloride (21 mg, 0.032 mmol), 4,4,5,5-tetramethyl-1,3,2-dioxaborolane (230 µL, 1.59 mmol) and DCM (20 mL). The crude product was purified by column chromatography on silica gel (hexane:EtOAc, 2:1 to 0:1) to give 488 mg (92%) of the corresponding product as a white foam. ESI+MS: m/z=500.15 (M+1)$^+$. $^1$H NMR (700 MHz, 300K, Chloroform-d) δ 8.80 (s, 1H), 7.33-7.27 (m, 5H), 5.34 (s, 1H), 4.24 (q, J=6.6 Hz, 1H), 3.75 (d, J=13.3 Hz, 1H), 3.43 (d, J=13.2 Hz, 1H), 2.63 (dd, J=11.6, 4.5 Hz, 1H), 1.97 (s, 3H), 1.97-1.88 (m, 1H), 1.83 (dd, J=12.4, 4.0 Hz, 1H), 1.66 (dq, J=12.8, 6.7 Hz, 1H), 1.32 (s, 12H), 1.28-1.22 (m, 2H), 1.19 (s, 9H), 1.18-1.09 (m, 1H), 1.01 (d, J=6.7 Hz, 3H), 0.72-0.65 (m, 1H), 0.61 (ddd, J=16.1, 9.7, 6.8 Hz, 1H).

Step L. (2S,3R,5S)-3-Amino-1-benzyl-5-(2-boronoethyl)-2-methylpiperidine-3-carboxylic acid dihydrochloride

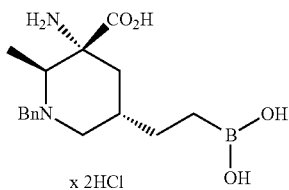 [SMILES: C[C@@H]1N(Cc2ccccc2)C[C@@H](CCB(O)O)C[C@]1(N)C(=O)O]

The title compound was obtained according to step (H) of Example 1, using (2S,3R,5S)-3-acetamido-1-benzyl-N-(tert-butyl)-2-methyl-5-(2-(4,4,5,5-tetramethyl-1,3,2-dioxaborolan-2-yl)ethyl)piperidine-3-carboxamide (440 mg, 0.88 mmol) and 12M HCl$_{(aq)}$ (8 mL). The desired product was obtained as a pale yellow foam (346 mg, 100%). ESI+MS: m/z=320.80 (M+1)$^+$; ESI-MS: m/z=318.95 (M-1)$^-$. $^1$H NMR (700 MHz, 300K, Deuterium Oxide) δ 7.58 (s, 5H), 4.53 (d, J=13.4 Hz, 1H), 4.41 (d, J=13.4 Hz, 1H), 3.86 (q, J=7.0 Hz, 1H), 3.41 (dd, J=12.8, 4.7 Hz, 1H), 3.03 (t, J=12.7 Hz, 1H), 2.18 (dd, J=13.5, 4.5 Hz, 1H), 2.07 (tt, J=11.3, 5.6 Hz, 1H), 1.78 (t, J=13.2 Hz, 1H), 1.55-1.41 (m, 5H), 0.87-0.70 (m, 2H).

Step M. (2S,3R,5S)-1-Benzyl-5-(2-boronoethyl)-3-((tert-butoxycarbonyl)amino)-2-methylpiperidine-3-carboxylic acid

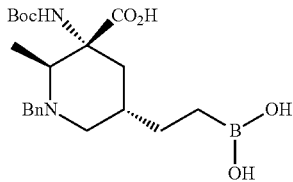 [SMILES: C[C@@H]1N(Cc2ccccc2)C[C@@H](CCB(O)O)C[C@]1(NC(=O)OC(C)(C)C)C(=O)O]

The title compound was obtained according to step (I) of Example 1, using (2S,3R,5S)-3-Amino-1-benzyl-5-(2-boronoethyl)-2-methylpiperidine-3-carboxylic acid dihydrochloride (340 mg, 0.86 mmol), di-tert-butyl dicarbonate (560 mg, 2.57 mmol), 1M NaOH$_{(aq)}$ (4 mL) and acetone (10 mL). The desired product was obtained as a white solid (360 mg, 99%). ESI+MS: m/z=420.95 (M+1)$^+$; ESI-MS: m/z=419.00 (M-1)$^-$. $^1$H NMR (700 MHz, Methanol-d$_4$) δ 7.55-7.46 (m, 5H), 4.48-4.41 (m, 1H), 4.35-4.27 (m, 1H), 4.17 (d, J=13.4 Hz, 1H), 3.87-3.75 (m, 1H), 3.36-3.28 (m, 1H), 2.98-2.80 (m, 1H), 1.89-1.78 (m, 1H), 1.48-1.30 (m, 2H), 1.27-1.21 (m, 4H), 1.03 (s, 9H), 0.81-0.67 (m, 2H).

Step N. (2S,3R,5S)-5-(2-boronoethyl)-3-((tert-butoxycarbonyl)amino)-2-methylpiperidine-3-carboxylic acid

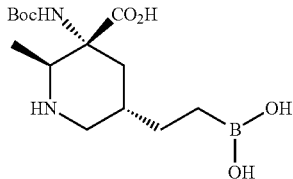 [SMILES: C[C@@H]1NC[C@@H](CCB(O)O)C[C@]1(NC(=O)OC(C)(C)C)C(=O)O]

The title compound was obtained according to step (J) of Example 1, using (2S,3R,5S)-1-benzyl-5-(2-boronoethyl)-3-((tert-butoxycarbonyl)amino)-2-methylpiperidine-3-carboxylic acid (360 g, 0.86 mmol), 20% Pd(OH)$_2$/C (30 mg) and MeOH (6 mL). The desired product was obtained as a white solid (282 mg, 100%). ESI+MS: m/z=330.85 (M+1)$^+$; ESI-MS: m/z=328.80 (M-1)$^-$. $^1$H NMR (700 MHz, 300K, Deuterium Oxide) δ 4.36 (p, J=8.5, 7.9 Hz, 1H), 4.10-4.02 (m, 1H), 3.24 (d, J=12.8 Hz, 1H), 2.81 (t, J=10.9 Hz, 1H), 1.95 (t, J=12.3 Hz, 1H), 1.83-1.72 (m, 1H), 1.55-1.49 (m, 1H), 1.44-1.39 (m, 1H), 1.31 (d, J=6.8 Hz, 3H), 1.22 (s, 9H), 0.91-0.73 (m, 2H).

Step O. (2S,3R,5S)-5-(2-Boronoethyl)-1-((tert-butoxycarbonyl)-L-alanyl)-3-((tert-butoxycarbonyl)amino)-2-methylpiperidine-3-carboxylic acid

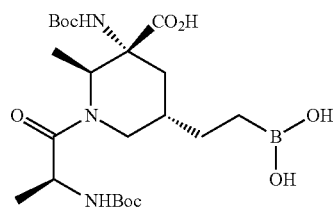 [SMILES: C[C@H](NC(=O)OC(C)(C)C)C(=O)N1C[C@@H](CCB(O)O)C[C@](NC(=O)OC(C)(C)C)(C(=O)O)[C@@H]1C]

The title compound was obtained according to step (K) of Example 1, using (2S,3R,5S)-5-(2-boronoethyl)-3-((tert-butoxycarbonyl)amino)-2-methylpiperidine-3-carboxylic acid (183 mg, 0.55 mmol), Boc-L-Ala-OSu (206 g, 0.72 mmol), and DMF (2.5 mL). The crude was purified by column chromatography on silica gel using CHCl$_3$/MeOH (80:1 to 2:1) to give 181 mg (65%) of the corresponding product as a white solid. ESI+MS: m/z=501.95 (M+1)$^+$; ESI-MS: m/z=500.00 (M−1)$^−$. $^1$H NMR (700 MHz, Methanol-d$_4$) δ 5.61 (q, J=7.5 Hz, 1H), 5.14-5.02 (m, 1H), 4.46-4.37 (m, 1H), 3.71-3.65 (m, 1H), 2.74 (t, J=11.7 Hz, 1H), 2.29-2.21 (m, 1H), 2.18-2.12 (m, 1H), 2.06 (d, J=10.1 Hz, 1H), 1.44 (s, 9H), 1.43 (s, 9H), 1.41-1.25 (m, 1H), 1.22 (d, J=6.9 Hz, 3H), 1.07 (d, J=7.1 Hz, 3H), 0.83-0.74 (m, 2H).

Step P. (2S,3R,5S)-1-(L-alanyl)-3-amino-5-(2-boronoethyl)-2-methylpiperidine-3-carboxylic acid dihydrochloride The title compound was obtained according to step (L) of Example 1, using (2S,3R,5S)-5-(2-boronoethyl)-1-((tert-butoxycarbonyl)-L-alanyl)-3-((tert-butoxycarbonyl) amino)-2-methylpiperidine-3-carboxylic acid (88 mg, 0.18 mmol) and 4M HCl in EtOAc (6 mL). The crude product was purified by preparative HPLC (0.1-1% of acetonitrile in water) to give (after acidification with 2M HCl and subsequent lyophilization) 35.3 mg (54%) of the corresponding product as a white solid (9:1 mixture of rotamers in D$_2$O solution at room temperature, based on NMR). ESI+MS: m/z=301.85 (M+1)$^+$. $^1$H NMR (700 MHz, Deuterium Oxide) δ 5.12 (q, J=7.1 Hz, 0.9H), 4.44 (q, J=7.0 Hz, 0.9H), 4.39 (dq, J=14.1, 7.0 Hz, 0.1H), 4.33 (dd, J=13.8, 4.7 Hz, 0.1H), 3.58 (dd, J=14.0, 4.6 Hz, 1H), 2.97 (dd, J=14.1, 12.2 Hz, 0.9H), 2.55-2.45 (m, 0.1H), 2.23-2.13 (m, 1H), 1.96 (dt, J=11.8, 5.5 Hz, 0.9H), 1.91-1.84 (m, 0.1H), 1.56 (t, J=12.7 Hz, 1H), 1.52-1.40 (m, 4H), 1.38-1.31 (m, 1H), 1.23 (d, J=7.1 Hz, 3H), 0.85-0.72 (m, 2H).

Example 31. (2S,3R,5S)-1-(L-Arginyl)-3-amino-5-(2-boronoethyl)-2-methylpiperidine-3-carboxylic acid trihydrochloride

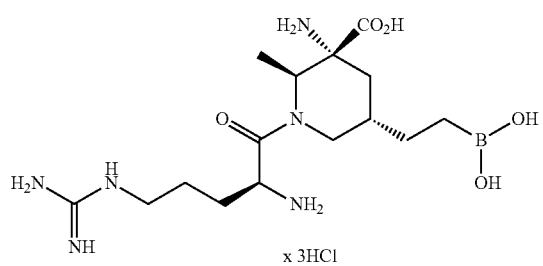 [SMILES: C[C@@H]1N(C(=O)[C@@H](N)CCCNC(=N)N)C[C@@H](CCB(O)O)C[C@]1(N)C(=O)O]

Step A. (2S,3R,5S)-1-(N$^ω$,N$^{ω'}$-Bis((benzyloxy)carbonyl)-N2-(tert-butoxycarbonyl)-L-arginyl)-5-(2-boronoethyl)-3-((tert-butoxycarbonyl)amino)-2-methylpiperidine-3-carboxylic acid

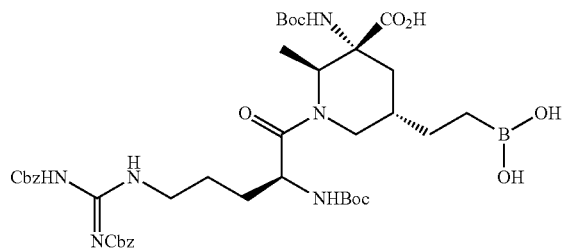

The title compound was obtained according to step (K) of Example 1, using (2S,3R,5S)-5-(2-boronoethyl)-3-((tert-butoxycarbonyl)amino)-2-methylpiperidine-3-carboxylic acid (100 mg, 0.30 mmol), Boc-L-Arg(Cbz)2-OSu (252 mg, 0.39 mmol) and DMF (2 mL). The crude product was purified by column chromatography on silica gel using CHCl$_3$/MeOH (80:1 to 6:1) to give 75 mg (27%) of the corresponding product as a white solid. ESI+MS: m/z=855.15 (M+1)$^+$; ESI-MS: m/z=853.20 (M−1)$^−$. $^1$H NMR (700 MHz, 300K, Methanol-d$_4$) δ 7.50-7.19 (m, 10H), 5.35-5.18 (m, 2H), 5.15-5.03 (m, 2H), 4.46-4.35 (m, 1H), 4.13-3.86 (m, 2H), 3.66-3.54 (m, 1H), 1.84-1.55 (m, 5H), 1.51-1.37 (m, 19H), 1.36-1.25 (m, 5H), 1.22-1.15 (m, 2H), 1.02-0.97 (m, 1H), 0.96-0.85 (m, 2H).

Step B. (2S,3R,5S)-3-Amino-1-((E)-N$^ω$,N$^{ω'}$-bis((benzyloxy)carbonyl)-L-arginyl)-5-(2-boronoethyl)-2-methylpiperidine-3-carboxylic acid dihydrochloride

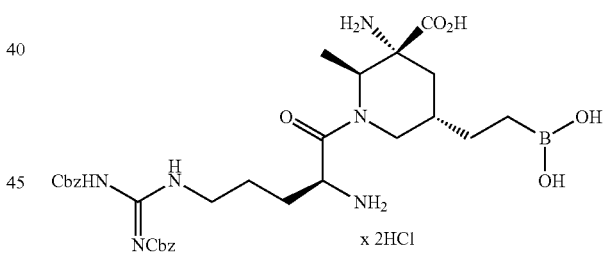

The title compound was obtained according to step (L) of Example 1, using (2S,3R,5S)-1-(N$^ω$,N$^{ω'}$-bis((benzyloxy)carbonyl)-N2-(tert-butoxycarbonyl)-L-arginyl)-5-(2-boronoethyl)-3-((tert-butoxycarbonyl)amino)-2-methylpiperidine-3-carboxylic acid (75 mg, 0.09 mmol) and 4M HCl in EtOAc (5 mL). The desired product was obtained as a pale yellow foam (63 mg, 100%). ESI+MS: m/z=655.25 (M+1)$^+$. $^1$H NMR (700 MHz, 300K, Methanol-d$_4$) δ 7.53-7.25 (m, 10H), 5.41-5.11 (m, 5H), 4.11 (dq, J=14.5, 7.2 Hz, 1H), 3.96-3.85 (m, 2H), 3.66-3.55 (m, 1H), 2.28 (dd, J=13.0, 4.8 Hz, 1H), 1.92-1.82 (m, 2H), 1.82-1.72 (m, 2H), 1.59-1.14 (m, 7H), 0.97-0.72 (m, 3H).

Step C. (2S,3R,5S)-1-(L-arginyl)-3-amino-5-(2-boronoethyl)-2-methylpiperidine-3-carboxylic acid trihydrochloride (2S,3R,5S)-3-amino-1-((E)-N$^ω$,N$^{ω'}$-bis((benzyloxy)carbonyl)-L-arginyl)-5-(2-boronoethyl)-2-methylpiperidine-3- carboxylic acid dihydrochloride (63 mg, 0.09 mmol) was dissolved in 2 mL of MeOH and flushed with argon. Next, 3 mg of Pd/C (wet, 10%) was added and the resulting mixture was stirred under hydrogen atmosphere (balloon) overnight. In the next step, the reaction mixture was filtered through the pad of Celite and concentrated. The crude product was purified by preparative HPLC (0.1-1% of acetonitrile in water) to give (after acidification with 2M HCl and subsequent lyophilization) 13.6 mg (32%) of the corresponding product as a white solid (9:1 mixture of rotamers in D$_2$O solution at room temperature, based on NMR). ESI+MS: m/z=387.00 (M+1)$^+$; ESI-MS: m/z=384.90 (M−1)$^−$. $^1$H NMR (700 MHz, 300K, Deuterium Oxide) δ 5.28 (q, J=7.1 Hz, 0.9H), 4.63 (t, J=6.0 Hz, 0.9H), 4.55 (t, J=5.1 Hz, 0.1H), 4.51 (dd, J=6.7, 5.3 Hz, 0.1H), 4.42 (dd, J=13.8, 4.7 Hz, 0.1H), 3.70 (dd, J=14.0, 4.6 Hz, 0.9H), 3.38-3.18 (m, 2H), 3.08 (dd, J=13.9, 11.8 Hz, 0.9H), 2.67-2.55 (m, 0.1H), 2.34 (d, J=13.6 Hz, 1H), 2.17-1.85 (m, 3H), 1.82-1.60 (m, 3.1H), 1.54 (ddt, J=13.0, 10.3, 6.4 Hz, 0.9H), 1.49-1.40 (m, 1H), 1.35 (dd, J=7.2, 1.2 Hz, 3H), 0.97-0.74 (m, 2H).

Example 32. (3R,5R)-1-(L-Alanyl)-3-amino-5-(2-boronoethyl)piperidine-3-carboxylic acid dihydrochloride

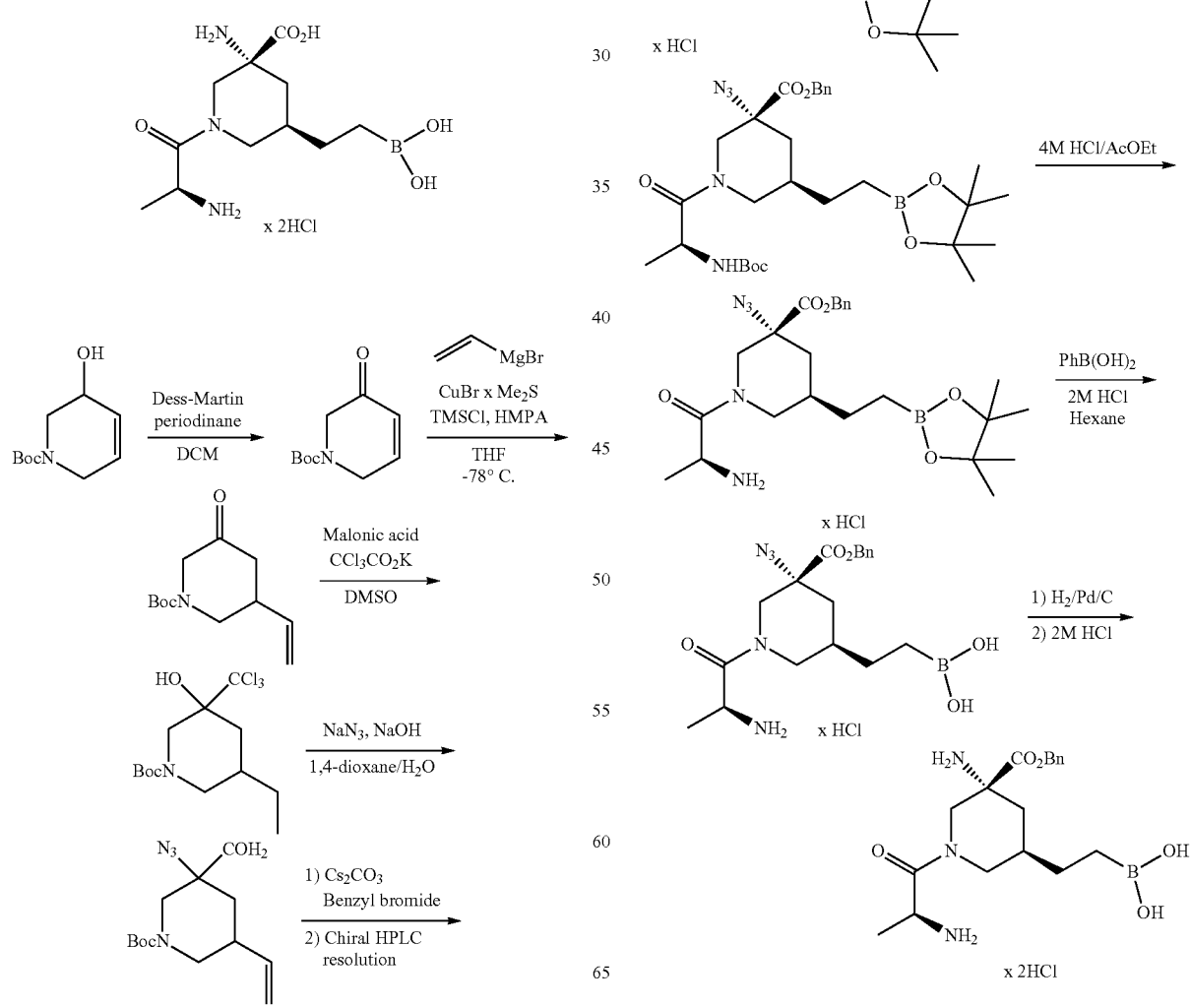

Step A. tert-Butyl 3-oxo-3,6-dihydropyridine-1(21-O-carboxylate

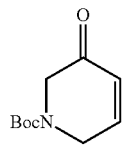

To a solution of tert-butyl 3-hydroxy-3,6-dihydropyridine-1(21-O-carboxylate (10 g, 50.19 mmol) in DCM (200 mL) was added Dess-Martin periodinane (25.55 g, 60.2 mmol). After stirring for 1.5 h additional amount of Dess-Martin periodinane (2.50 g, 12.54 mmol) was added together with DCM (50 mL). The reaction mixture was stirred for additional 1.5 h; then 750 mL of hexane was added and stirring was continued for 10 min. The solid that precipitated was filtered off. The filtrate was concentrated and treated with a fresh portion of hexane (500 mL), filtered and concentrated in vacuo to give 10.01 g (100%) of tert-butyl 3-oxo-3,6-dihydropyridine-1(2H)-carboxylate as a pale orange solid. ESI+MS: m/z=142.20 (M−56+1)$^+$. $^1$H NMR (700 MHz, 300 K, DMSO-d$_6$) δ 7.22 (bs, 1H), 6.10 (dt, J=10.3, 2.3 Hz, 1H), 4.18 (bs, 1H), 4.01 (bs, 1H), 1.42 (s, 9H).

Step B. tert-Butyl 3-oxo-5-vinylpiperidine-1-carboxylate

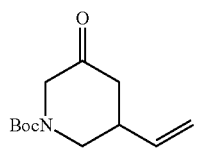 [SMILES: C=CC1CC(=O)CN(C(=O)OC(C)(C)C)C1]

To a flask charged with CuBr×Me$_2$S complex (0.78 g, 3.8 mmol) and dry THF (125 mL) were added HMPA (17.60 mL, 101.40 mmol) and vinylmagnesium bromide 1M solution in THF (88.72 mL, 88.72 mmol) at −78° C. under Ar. The reaction mixture was stirred for 15 min followed by a solution of tert-butyl 3-oxo-3,6-dihydropyridine-1(2H)-carboxylate (5 g, 25.35 mmol) and chlorotrimethylsilane (16.08 mL, 126.75 mmol) in THF (75 mL) was added dropwise for over 30 min. The reaction mixture was stirred for 2 h at −78° C. and subsequently overnight at RT. After the reaction was completed, 60 mL of saturated aqueous NH$_4$Cl solution was added, and then the layers were separated. The organic layer was washed with NH$_4$Cl (3×30 mL). The aqueous layer was diluted with H$_2$O (100 mL) and washed with AcOEt (2×40 mL). The combined organic layers were washed with brine (20 mL), dried over MgSO$_4$ and concentrated in vacuo. The crude product was purified by silica gel column chromatography using hexane/EtOAc (1:0 to 1:4) as an eluent. The desired product was obtained as a colorless oil. Yield: 4.23 g (74%). ESI+MS: m/z=170.15 (M−56+1)$^+$. $^1$H NMR (700 MHz, 300 K, chloroform-d) δ 5.77 (ddd, J=17.0, 10.5, 6.3 Hz, 1H), 5.15-5.10 (m, 2H), 4.09 (d, J=18.0 Hz, 1H), 4.05-3.72 (m, 2H), 3.21 (bs, 1H), 2.78-2.71 (m, 1H), 2.61 (dd, J=16.3, 4.7 Hz, 1H), 2.37 (dd, J=16.2, 10.0 Hz, 1H), 1.46 (s, 9H).

Step C. tert-Butyl 3-hydroxy-3-(trichloromethyl)-5-vinylpiperidine-1-carboxylate

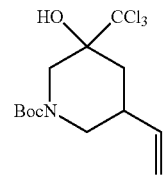

To flask with tert-butyl 3-oxo-5-vinylpiperidine-1-carboxylate (406 mg, 1.80 mol), malonic acid (187 mg, 1.80 mol) were added. Reaction was stirred overnight at RT. Next, reaction mixture was poured with AcOEt (50 mL), H$_2$O (2 mL) and was washed with brine (3×10 mL). Organic solution containing product was dried over MgSO$_4$, filtered and concentrated in vacuo. Product was purified by silica gel column chromatography starting from 100% n-hexane and ending at AcOEt/n-hexane, 1:4. Product was obtained as mixture of four stereoisomers (the mixture of two diastereoisomers and two enantiomers). The correlation between enantiomeric mixture of the two sets of diastereoisomers was determined by LCMS (major 70%, lower retention time C18-column and minor 30%, higher retention time C18-column). The tert-butyl-3-hydroxy-3-(trichloromethyl)-5-vinylpiperidine-1-carboxylate was obtained in (279 mg, 45%) amount as an color less oil. Peak 1 (70%) ESI+MS: m/z=244.05 (M+1-Boc)$^+$ and peak 2 (30%) ESI+MS: m/z=244.00 (M+1-Boc)$^+$.

Step D. 3-Azido-1-(tert-butoxycarbonyl)-5-vinylpiperidine-3-carboxylic acid

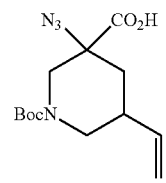 [SMILES: C=CC1CN(C(=O)OC(C)(C)C)CC(N=[N+]=[N-])(C(=O)O)C1]

To flask with tert-butyl-3-hydroxy-3-(trichloromethyl)-5-vinylpiperidine-1-carboxylate (270 mg, 0.78 mol), 1,4-dioxane was poured and next a solution of NaN$_3$ (254 mg, 3.91 mol) and NaOH (157 mg, 3.91 mol) in H$_2$O (5 mL) was added. After reaction was complete, 1,4-dioxane was evaporated and reaction was quenched with saturated NH$_4$Cl and contaminations were extracted with DCM (3×10 mL). The water layer was acidified in flask equipped with septum and next degassed under vacuum through flask with 4M NaOH. Product was extracted with DCM (5×30 mL). Combined organic layer was washed with brine, dried over MgSO$_4$, filtered and concentrated in vacuo. Product 3-azido-1-(tert-butoxycarbonyl)-5-vinylpiperidine-3-carboxylic acid was obtained in (179 mg, 77%) amount as an light yellow oil. ESI-MS: m/z=295.10 (M−1)$^−$.

Step E. 3-Benzyl 1-(tert-butyl) (3R,5S)-3-azido-5-vinylpiperidine-1,3-dicarboxylate and 3-benzyl 1-(tert-butyl) (3S,5R)-3-azido-5-vinylpiperidine-1,3-dicarboxylate

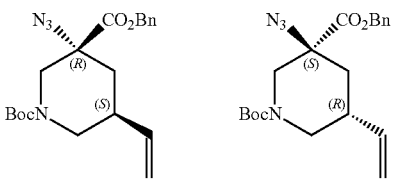

To flask with 3-azido-1-(tert-butoxycarbonyl)-5-vinylpiperidine-3-carboxylic acid (265 mg, 0.89 mmol), CH$_3$CN (4 mL), Cs$_2$CO$_3$ (157 mg, 1.79 mmol) and benzyl bromide (117 µL, 0.98 mmol) were added. Reaction was stirred overnight at RT. Product was purified by silica gel column chromatography starting from 100% n-hexane and ending at EtOAc/n-hexane, 1:4. At these level the enantiomeric mixture of two sets of diastereoisomers was separated by silica gel column chromatography. The major diastereoisomer (140 mg) was separated into its enantiomer using a chiral preparative HPLC method (LumiSep Chiralcel AD column) with propan-2-ol and n-hexane (isocratic, 1%) as an eluent and ELSD detection. Retention time of 3-benzyl 1-(tert-butyl) (3R,5S)-3-azido-5-vinylpiperidine-1,3-dicarboxylate in preparative HPLC was in the range from 17.3 to 20.1 min. Retention time of 3-benzyl 1-(tert-butyl) (3S,5R)-3-azido-5-vinylpiperidine-1,3-dicarboxylate in preparative HPLC was in the range from 22.5 to 28.3 min. The enantiomeric excess for both enantiomers was determined with the use of chiral analytical HPLC method with ELSD detection with RegisPack (5 µm, 4.6×250 mm) column using 2% propan-2-ol in n-hexane as eluent for 15 min. The first enantiomer 3-benzyl 1-(tert-butyl) (3R,5S)-3-azido-5-vinylpiperidine-1,3-dicarboxylate (26 mg, 19%, colorless oil) with the retention time of 8.1 min and the second desired enantiomer 3-benzyl 1-(tert-butyl) (3S,5R)-3-azido-5-vinylpiperidine-1,3-dicarboxylate (31 mg, 22%, colorless oil) at 9.2 min, each with an enantiomeric excess of approximately 98%. ESI+MS: m/z=409.20 (M+23)$^+$. $^1$H NMR (700 MHz, 300 K, Chloroform-d) δ 7.41-7.32 (m, 5H), 5.64 (ddd, J=17.1, 10.5, 6.3 Hz, 1H), 5.13-5.03 (s, 2H), 5.09 (dd, J=22.1, 13.9 Hz, 2H), 4.45-4.23 (m, 2H), 3.12-2.91 (m, 1H), 2.55-2.32 (m, 2H), 2.09-2.00 (m, 1H), 1.68 (t, J=13.0 Hz, 1H), 1.48 (s, 9H).

Step F. 3-Benzyl 1-(tert-butyl) (3R,5R)-3-azido-5-(2-(4,4,5,5-tetramethyl-1,3,2-dioxaborolan-2-yl)ethyl)piperidine-1,3-dicarboxylate

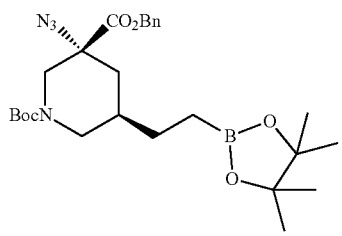 [SMILES: CC(C)(C)OC(=O)N1C[C@H](CCB2OC(C)(C)C(C)(C)O2)C[C@](N=[N+]=[N-])(C(=O)OCc2ccccc2)C1]

A mixture of dppe (1.60 mg, 0.004 mmol) and bis(1,5-cyclooctadiene)diiridium(I) dichloride (1.30 mg, 0.002 mmol) in DCM (0.5 mL) was flushed with argon (bubbling). Subsequently, the separately prepared solution of 4,4,5,5-tetramethyl-1,3,2-dioxaborolane (15 µL, 0.097 mmol) and 3-benzyl 1-(tert-butyl) (3R,5S)-3-azido-5-vinylpiperidine-1,3-dicarboxylate (25 mg, 0.065 mmol) in 0.5 mL of dry DCM was added successively at room temperature. The resulting mixture was stirred at room temperature overnight. After that time the reaction mixture was diluted with DCM (10 mL) and washed with 5% NaHCO$_3$ (1×10 mL) and brine (1×10 mL). The organic layer was dried over MgSO$_4$, filtered and concentrated in vacuo. The crude product was purified by column chromatography on silica gel using Hex/EtOAc (50:1 to 10:1) to give 25 mg (75%) of the corresponding product as a colorless oil. ESI+MS: m/z=415.25 (M−100+1)$^+$; ESI-MS: m/z=559.25 (M+45)$^−$. $^1$H NMR (700 MHz, 300 K, Chloroform-d) δ 7.41-7.30 (m, 5H), 5.23 (br s, 2H), 4.41-4.06 (m, 2H), 2.99 (d, J=81.2 Hz, 1H), 2.17 (br s, 1H), 2.06 (br s, 1H), 1.71 (br s, 1H), 1.47 (s, 9H), 1.27 (br s, 3H), 1.23 (s, 12H), 0.78 (t, J=8.2 Hz, 2H).

Step G. Benzyl (3R,5R)-3-azido-5-(2-(4,4,5,5-tetramethyl-1,3,2-dioxaborolan-2-yl)ethyl)piperidine-3-carboxylate hydrochloride

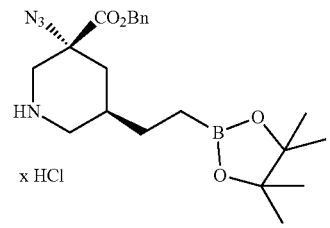 [SMILES: CC1(C)OB(CC[C@H]2CNC[C@@](N=[N+]=[N-])(C(=O)OCc3ccccc3)C2)OC1(C)C]

To a solution of 3-benzyl 1-(tert-butyl) (3R,5R)-3-azido-5-(2-(4,4,5,5-tetramethyl-1,3,2-dioxaborolan-2-yl)ethyl)piperidine-1,3-dicarboxylate (25 mg, 0.047 mmol) in AcOEt (1 mL) 4M HCl in AcOEt (1 mL) was added and the resulting mixture was stirred at room temperature for 1 h. Then the reaction mixture was concentrated under reduced pressure to give 22 mg (99%) of the corresponding product as a colorless oil. ESI+MS: m/z=415.20 (M+1)$^+$. $^1$H NMR (700 MHz, 300 K, Chloroform-d) δ 7.44-7.32 (m, 5H), 7.11 (s, 1H), 5.27-5.21 (m, 2H), 3.54-5.49 (m, 1H), 3.38 (d, J=12.4 Hz, 1H), 3.12 (d, J=12.0 Hz, 1H), 2.44 (br s, 1H), 2.32 (d, J=14.0 Hz, 1H), 2.17 (br s, 1H), 1.40-1.25 (m, 3H), 1.24 (s, 12H), 0.88-0.75 (m, 2H).

Step H. Benzyl (3R,5R)-3-azido-1-((tert-butoxycarbonyl)-L-alanyl)-5-(2-(4,4,5,5-tetramethyl-1,3,2-dioxaborolan-2-yl)ethyl)piperidine-3-carboxylate

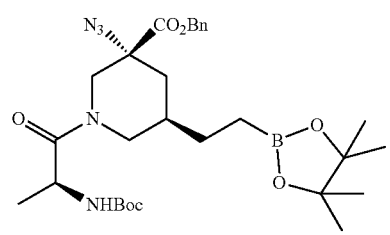 [SMILES: C[C@H](NC(=O)OC(C)(C)C)C(=O)N1C[C@H](CCB2OC(C)(C)C(C)(C)O2)C[C@](N=[N+]=[N-])(C(=O)OCc2ccccc2)C1]

To a solution of benzyl (3R,5R)-3-azido-5-(2-(4,4,5,5-tetramethyl-1,3,2-dioxaborolan-2-yl)ethyl)piperidine-3-carboxylate hydrochloride (22 mg, 0.048 mmol) in DCM (0.8 mL) DIPEA (21 μL, 0.12 mmol) and Boc-L-Ala-OH (9.1 mg, 0.048 mmol) were added. Then to the reaction mixture TBTU (17 mg, 0.053 mmol) was added and stirred at room temperature overnight. The reaction was washed with 1M HCl (1×2 mL), 1M NaOH (1×2 mL) and brine (1×2 mL). The organic layer was dried over MgSO₄, filtered and concentrated in vacuo. The crude product was purified by column chromatography on silica gel using Hex/EtOAc (10:1 to 3:1) to give 10 mg (36%) of the corresponding product as a colorless oil. ESI+MS: m/z=586.35 (M+1)$^+$; 608.35 (M+23)$^+$. (5:2 mixture of rotamers in CDCl₃ solution at room temperature, based on NMR). $^1$H NMR (700 MHz, 300 K, Chloroform-d) δ 7.42-7.32 (m, 5H), 7.11 (s, 1H), 5.58 (dd, J=50.1, 7.8 Hz, 1H), 5.24 (s, 2H), 4.83 (d, J=14.0 Hz, 0.7H), 4.71-4.56 (m, 1.3H), 3.91 (d, J=13.8 Hz, 0.7H), 3.75 (d, J=14.3 Hz, 0.3H), 3.31 (d, J=14.1 Hz, 0.3H), 2.85 (d, J=13.9 Hz, 0.7H), 2.64 (dd, J=13.7, 11.8 Hz, 0.7H), 2.35-2.29 (m, 0.3H), 2.16-2.11 (m, 1H), 1.84-1.68 (m, 1H), 1.43 (s, 9H), 1.35 (d, J=6.9 Hz, 3H), 1.24 (s, 2H), 1.23 (s, 12H), 0.81 (t, J=8.0 Hz, 2H).

Step I. Benzyl (3R,5R)-1-(L-alanyl)-3-azido-5-(2-(4,4,5,5-tetramethyl-1,3,2-dioxaborolan-2-yl)ethyl)piperidine-3-carboxylate hydrochloride

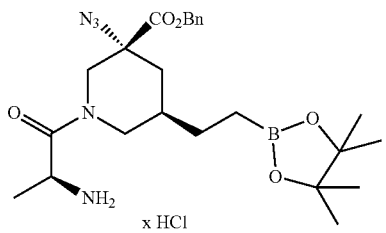 [SMILES: C[C@H](N)C(=O)N1C[C@H](CCB2OC(C)(C)C(C)(C)O2)C[C@](N=[N+]=[N-])(C(=O)OCc2ccccc2)C1]

To a benzyl (3R,5R)-3-azido-1-((tert-butoxycarbonyl)-L-alanyl)-5-(2-(4,4,5,5-tetramethyl-1,3,2-dioxaborolan-2-yl)ethyl)piperidine-3-carboxylate (8 mg, 0.014 mmol) was added 4M HCl in AcOEt (1 mL) and the resulting mixture was stirred at room temperature for 1 h. Then the reaction mixture was concentrated under reduced pressure to give 7.1 mg (99%) of the corresponding product as a colorless film. ESI+MS: m/z=486.30 (M+1)$^+$. $^1$H NMR (700 MHz, 300 K, Chloroform-d) δ 8.53 (br s, 3H), 7.39 (d, J=25.8 Hz, 5H), 5.27 (br s, 2H), 4.75-4.55 (m, 2H), 3.86-3.56 (m, 2H), 2.37-2.07 (m, 2H), 1.88-1.80 (m, 1H), 1.28-1.25 (m, 6H), 1.22 (s, 12H), 0.90-0.72 (m, 2H).

Step J. (2-((3R,5R)-1-(L-Alanyl)-5-azido-5-((benzyloxy)carbonyl)piperidin-3-yl)ethyl)boronic acid hydrochloride

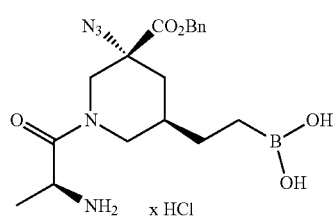

To a suspension of benzyl (3R,5R)-1-(L-alanyl)-3-azido-5-(2-(4,4,5,5-tetramethyl-1,3,2-dioxaborolan-2-yl)ethyl)piperidine-3-carboxylate hydrochloride (6 mg, 0.012 mmol) and phenylboronic acid (1.4 mg, 0.012 mmol) in H₂O (1 mL) was added 2N HCl (0.25 mL) and hexane (1.5 mL) and the mixture was stirred for 30 min at room temperature. The reaction mixture was separated and to the aqueous layer phenylboronic acid (0.3 mg, 0.002 mmol) and hexane were added and the reaction was stirred for additional 30 min. Next, the layers were separated and the aqueous layer was washed with Et₂O (2×3 mL) and concentrated under reduced pressure to give 5 mg (99%) of the corresponding product as a colorless oil. ESI+MS: m/z=404.15 (M+1)$^+$. (3:2 mixture of rotamers in D₂O solution at room temperature, based on NMR). $^1$H NMR (700 MHz, 300 K, Deuterium Oxide) δ 7.54-7.45 (m, 5H), 5.39-5.34 (m, 2H), 4.66-4.55 (m, 1H), 4.55-4.44 (m, 1H), 3.84-3.77 (m, 2H), 3.68 (d, J=14.5 Hz, 0.4H), 3.20 (d, J=13.9 Hz, 0.6H), 2.93 (dd, J=14.0, 11.5 Hz, 0.6H), 2.53-2.46 (m, 0.4H), 2.39 (dd, J=13.9, 2.8 Hz, 0.4H), 2.32-2.26 (m, 0.6H), 1.88-1.73 (m, 2H), 1.56 (d, J=7.0 Hz, 2H), 1.47 (d, J=7.1 Hz, 1H), 1.45-1.31 (m, 1H), 0.90-0.85 (m, 2H).

Step K. (3R,5R)-1-(L-Alanyl)-3-amino-5-(2-boronoethyl)piperidine-3-carboxylic acid dihydrochloride To a solution of (2-((3R,5R)-1(L-alanyl)-5-azido-5-((benzyloxy)carbonyl)piperidin-3-yl)ethyl)boronic acid hydrochloride (4.5 mg, 0.01 mmol), in H₂O/AcOEt (0.5 mL:50 μL) mixture under argon 1 mg 10% Pd/C (wet) was added. The mixture was degassed, charged with H₂, and stirred overnight at room temperature. The mixture was filtered through a pad of Celite, washed with H₂O (2×10 mL) and to the filtrate was added 2 drops of 2M HCl and concentrated in vacuo. The residue was dissolved in H₂O (2 mL), frozen and lyophilized to give 2.3 mg (63%) of the corresponding product as a white foam. ESI+MS: m/z=288.15 (M+1)$^+$; ESI-MS: m/z=286.05 (M-1)$^-$. $^1$H NMR (700 MHz, 300 K, Deuterium Oxide) δ 4.68-4.52 (m, 2H), 3.95-3.78 (m, 1H), 3.39-3.28 (m, 1H), 2.96 (t, J=12.8 Hz, 1H), 2.26-2.15 (m, 1H), 2.00-1.88 (m, 1H), 1.62-1.58 (m, 2H), 1.55-1.47 (m, 3H), 1.37-1.22 (m, 1H), 0.90-0.85 (m, 2H).

Example 33. (3S,5S)-1-(L-Alanyl)-3-amino-5-(2-boronoethyl)piperidine-3-carboxylic acid dihydrochloride

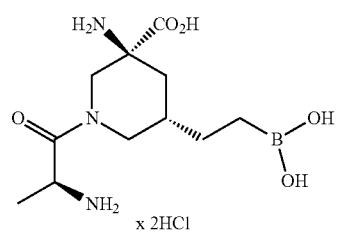 [SMILES: C[C@H](N)C(=O)N1C[C@@H](CCB(O)O)C[C@@](N)(C(=O)O)C1]

Step A. 3-Benzyl 1-(tert-butyl) (3S,5S)-3-azido-5-(2-(4,4,5,5-tetramethyl-1,3,2-dioxaborolan-2-yl)ethyl)piperidine-1,3-dicarboxylate

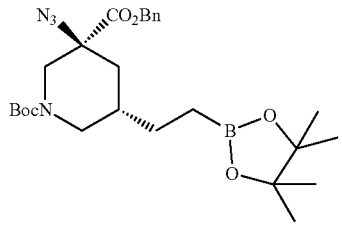 [SMILES: CC(C)(C)OC(=O)N1C[C@@H](CCB2OC(C)(C)C(C)(C)O2)C[C@@](N=[N+]=[N-])(C(=O)OCc2ccccc2)C1]

The title compound was obtained according to step (F) of Example 32, using 3-benzyl 1-(tert-butyl) (3S,5R)-3-azido-5-vinylpiperidine-1,3-dicarboxylate (30 mg, 0.078 mmol), dppe (2 mg, 0.005 mmol), bis(1,5-cyclooctadiene)diiridium (I) dichloride (1.6 mg, 0.0023 mmol), 4,4,5,5-tetramethyl-1,3,2-dioxaborolane (18 µL, 0.116 mmol) and DCM (1 mL). The crude product was purified by column chromatography on silica gel using Hex/EtOAc (50:1 to 10:1) to give 32 mg (80%) of the corresponding product as a colorless oil. ESI+MS: m/z=415.25 (M−100+1)$^+$; ESI-MS: m/z=559.20 (M+45)$^−$. $^1$H NMR (700 MHz, 300 K, Chloroform-d) δ 7.42-7.32 (m, 5H), 5.23 (bs, 2H), 4.45-4.04 (m, 2H), 3.08-2.89 (m, 1H), 2.18 (d, J=19.5 Hz, 1H), 2.06 (d, J=15.7 Hz, 1H), 1.71 (bs, 1H), 1.47 (s, 9H), 1.24 (bs, 3H), 1.23 (s, 12H), 0.79 (t, J=8.2 Hz, 2H).

Step B. Benzyl (3S,5S)-3-azido-5-(2-(4,4,5,5-tetramethyl-1,3,2-dioxaborolan-2-yl)ethyl)piperidine-3-carboxylate hydrochloride

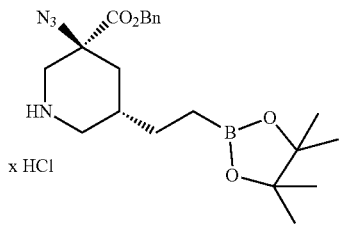 [SMILES: CC1(C)OB(CC[C@@H]2CNC[C@](N=[N+]=[N-])(C(=O)OCc3ccccc3)C2)OC1(C)C]

The title compound was obtained according to step (G) of Example 32, using 3-benzyl 1-(tert-butyl) (3S,5S)-3-azido-5-(2-(4,4,5,5-tetramethyl-1,3,2-dioxaborolan-2-yl)ethyl)piperidine-1,3-dicarboxylate (31 mg, 0.06 mmol), EtOAc (1 mL) and 4M HCl in EtOAc (1 mL). The reaction mixture was concentrated under reduced pressure to give 26 mg (96%) of the corresponding product as white solid. ESI+MS: m/z=415.20 (M+1)$^+$. $^1$H NMR (700 MHz, 300 K, Chloroform-d) δ 7.42-7.33 (m, 5H), 7.11 (s, 1H), 5.28-5.19 (m, 2H), 3.58-5.49 (m, 1H), 3.38 (d, J=13.1 Hz, 1H), 3.12 (d, J=12.9 Hz, 1H), 2.44 (t, J=11.8 Hz, 1H), 2.31 (d, J=14.2 Hz, 1H), 2.16 (bs, 1H), 1.51-1.42 (m, 1H), 1.41-1.32 (m, 1H), 1.30-1.25 (m, 1H), 1.23 (s, 12H), 0.90-0.75 (m, 2H).

Step C. Benzyl (3S,5S)-3-azido-1-((tert-butoxycarbonyl)-L-alanyl)-5-(2-(4,4,5,5-tetramethyl-1,3,2-dioxaborolan-2-yl)ethyl)piperidine-3-carboxylate

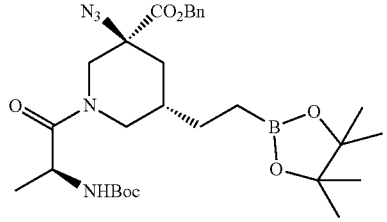 [SMILES: C[C@H](NC(=O)OC(C)(C)C)C(=O)N1C[C@@H](CCB2OC(C)(C)C(C)(C)O2)C[C@@](N=[N+]=[N-])(C(=O)OCc2ccccc2)C1]

The title compound was obtained according to step (H) of Example 32, using benzyl (3S,5S)-3-azido-5-(2-(4,4,5,5-tetramethyl-1,3,2-dioxaborolan-2-yl)ethyl)piperidine-3-carboxylate hydrochloride (25.5 mg, 0.057 mmol), DIPEA (24 µL, 0.14 mmol), Boc-L-Ala-OH (10.7 mg, 0.057 mmol), TBTU (20 mg, 0.062 mmol) and DCM (1 mL). The crude product was purified by column chromatography on silica gel using hexane: AcOEt (10:1 to 2:1) to give 20.5 mg (62%) of the corresponding product as a colorless oil. ESI+MS: m/z=586.35 (M+1)$^+$; 608.35 (M+23)$^+$. (3:2 mixture of rotamers in CDCl$_3$ solution at room temperature, based on NMR). $^1$H NMR (700 MHz, 300 K, Chloroform-d) δ 7.42-7.34 (m, 5H), 7.11 (s, 1H), 5.57 (d, J=7.6 Hz, 0.6H), 5.29 (d, J=8.5 Hz, 0.4H), 5.26-5.20 (m, 2H), 4.80 (d, J=13.8 Hz, 0.6H), 4.72-4.67 (m, 0.4H), 4.65-4.59 (m, 0.6H), 4.58-4.53 (m, 0.4H) 3.89 (dd, J=24.3, 13.8 Hz, 1H), 3.33 (d, J=14.0 Hz, 0.4H), 2.86 (d, J=13.9 Hz, 0.6H), 2.61 (dd, J=13.5, 11.7 Hz, 0.6H), 2.31 (d, J=14.7 Hz, 0.4H), 2.16 (d, J=11.1 Hz, 0.6H), 2.12 (dd, J=13.2, 11.7 Hz, 0.4H), 1.81 (bs, 0.6H), 1.68 (br s, 0.4H), 1.43 (d, J=18.7 Hz, 9H), 1.29 (d, J=6.8 Hz, 3H), 1.26-1.24 (m, 2H), 1.23 (s, 12H), 0.86-0.74 (m, 2H).

Step D. Benzyl (3S,5S)-1-(L-alanyl)-3-azido-5-(2-(4,4,5,5-tetramethyl-1,3,2-dioxaborolan-2-yl)ethyl)piperidine-3-carboxylate hydrochloride

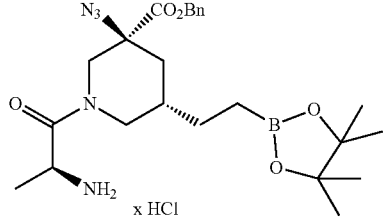 [SMILES: C[C@H](N)C(=O)N1C[C@@H](CCB2OC(C)(C)C(C)(C)O2)C[C@@](N=[N+]=[N-])(C(=O)OCc2ccccc2)C1]

The title compound was obtained according to step (I) of Example 32, using benzyl (3S,5S)-3-azido-1-((tert-butoxycarbonyl)-L-alanyl)-5-(2-(4,4,5,5-tetramethyl-1,3,2-dioxaborolan-2-yl)ethyl)piperidine-3-carboxylate (19 mg, 0.032 mmol), 4M HCl in AcOEt (2 mL). The reaction mixture was concentrated under reduced pressure to give 17 mg (99%) of the corresponding product as a colorless film. ESI+MS: m/z=486.30 (M+1)$^+$. $^1$H NMR (700 MHz, 300 K, Chloroform-d) δ 8.59 (br s, 1H), 8.37 (bs, 2H), 7.42-7.33 (m, 5H), 5.24 (bs, 2H), 4.78-4.38 (m, 2H), 3.82-3.35 (m, 3H), 2.29-2.14 (m, 2H), 1.56-1.42 (m, 1H), 1.35-1.28 (m, 3H) 1.22 (s, 12H), 1.18-1.12 (m, 2H), 0.85-0.77 (m, 2H).

Step E. (2-((3S,5S)-1-(L-Alanyl)-5-azido-5-((benzyloxy)carbonyl)piperidin-3-yl)ethyl)boronic acid hydrochloride

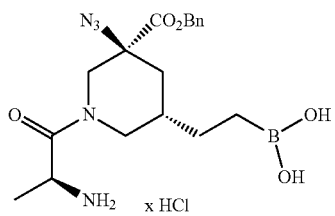 [SMILES: C[C@H](N)C(=O)N1C[C@@H](CCB(O)O)C[C@@](N=[N+]=[N-])(C(=O)OCc2ccccc2)C1]

The title compound was obtained according to step (J) of Example 32, using benzyl (3S,5S)-1-(L-alanyl)-3-azido-5-(2-(4,4,5,5-tetramethyl-1,3,2-dioxaborolan-2-yl)ethyl)piperidine-3-carboxylate hydrochloride (15 mg, 0.029 mmol), phenylboronic acid (4.2 mg, 0.034 mmol), H$_2$O (1.5 mL), 2N HCl (0.25 mL) and hexane (2 mL). The final compound was obtained as a colorless oil (11.6 mg, 92%). ESI+MS: m/z=404.20 (M+1)$^+$. (5:2 mixture of rotamers in D$_2$O solution at room temperature, based on NMR). $^1$H NMR (700 MHz, 300 K, Deuterium Oxide) δ 7.55-7.47 (m, 5H), 5.38-5.32 (m, 2H), 4.60-4.53 (m, 1.3H), 4.50-4.42 (m, 0.7H), 3.83 (dd, J=14.3, 5.1 Hz, 1H), 3.74 (d, J=9.6 Hz, 1H), 3.62 (d, J=14.2 Hz, 0.3H), 3.22 (d, J=13.9 Hz, 0.7H), 2.98 (dd, J=13.8, 11.6 Hz, 0.7H), 2.55-2.50 (m, 0.3H), 2.42 (d, J=14.1 Hz, 0.3H), 2.26 (d, J=13.8 Hz, 0.7H), 1.87-1.71 (m, 2H), 1.63 (d, J=6.9 Hz, 1H), 1.53 (d, J=7.0 Hz, 2H), 1.44-1.36 (m, 1H), 0.92-0.80 (m, 2H).

Step F. (3S,5S)-1-(L-Alanyl)-3-amino-5-(2-boronoethyl)piperidine-3-carboxylic acid dihydrochloride The title compound was obtained according to step (K) of Example 32, using (2-((3S,5S)-1-(L-alanyl)-5-azido-5-((benzyloxy)carbonyl)piperidin-3-yl)ethyl)boronic acid hydrochloride (11 mg, 0.025 mmol), Pd/C (2 mg), H$_2$O (1 mL) and AcOEt (0.1 mL). To the filtrate was added 2 drops of 2M HCl and concentrated in vacuo. The residue was dissolved in H$_2$O (2 mL), frozen and lyophilized to give 6.8 mg (76%) of the corresponding product as a white foam. ESI+MS: m/z=288.15 (M+1)$^+$; 270.20 (M−18+1)$^+$; ESI-MS: m/z=286.05 (M−1)$^-$. $^1$H NMR (700 MHz, 300 K, Deuterium Oxide) δ 4.74-4.70 (m, 1H), 4.61 (q, J=7.1 Hz, 1H), 3.94-3.86 (m, 1H), 3.36 (d, J=14.5 Hz, 1H), 3.10-3.03 (m, 1H), 2.32-2.23 (m, 1H), 2.03-1.92 (m, 1H), 1.85-1.77 (m, 1H), 1.61-1.46 (m, 4H), 1.47-1.40 (m, 1H), 0.91-0.78 (m, 2H).

Human Arginase Inhibition Assay

The inhibitory activities of the compounds of the invention were assessed using recombinant human arginase 1 and 2. Both enzymes were biosynthesized using a prokaryotic expression system (*E. coli*) and purified by fast protein liquid chromatography (FPLC). The compounds were screened in 96-well plates at the total reaction volume of 100 μL. Briefly, recombinant enzymes were incubated with the tested compounds for 1 h at 37° C. in the reaction buffer (100 mM sodium phosphate buffer, 130 mM NaCl, 1 mg/mL BSA, pH 7.4) containing substrate (10 mM L-arginine hydrochloride) and cofactor (200 μM MnCl$_2$). The assay is based on the detection of urea, which is generated during the conversion of L-arginine into L-ornithine catalyzed by ARG1 or ARG2. The colorimetrically detectable product was developed by adding a mixture of reagent A (4 mM oPA, 50 mM boric acid, 1 M sulfuric acid, 0.03% Brij-35) and reagent B (4 mM NED, 50 mM boric acid, 1 M sulfuric acid, 0.03% Brij-35) in equal proportions. The absorbance for each well was measured at 515 nm and the enzyme inhibition was calculated. The urea production in the absence of any tested compound was considered as maximal enzyme activity. The absorbance at the absence of arginase (background) was subtracted from all the values. Normalized values were analyzed using GraphPad Prism 7.0 software by plotting inhibition curves and determining the IC$_{50}$ values.

The IC$_{50}$ values were calculated using GraphPad Prism and divided into the following classes: A=1-249 nM; B=250-499 nM; C=500-999 nM; D=1-10 μM; E>10 μM. The inhibitory activity toward humane arginase 1 of the hydrochloride salts of the exemplary compounds according to the invention is presented in Table 5.

TABLE 5

| Example No. | Arginase 1 Inhibitory Activity Compound Structure | Activity Class (ARG I) |
|---|---|---|
| 1 | (structure) | B |
| 2 | (structure) | E |

TABLE 5-continued

Arginase 1 Inhibitory Activity

| Example No. | Compound Structure | Activity Class (ARG I) |
|---|---|---|
| 3 | (structure: 3-amino-3-carboxy-5-(2-boronoethyl)piperidine N-acylated with glycine) × 2HCl | A |
| 4 | (structure: 3-amino-3-carboxy-5-(2-boronoethyl)piperidine N-acylated with prolyl) × 2HCl | B |
| 5 | (structure: 3-amino-3-carboxy-5-(2-boronoethyl)piperidine N-acylated with valyl) × 2HCl | B |
| 6 | (structure: 3-amino-3-carboxy-5-(2-boronoethyl)piperidine N-acylated with seryl) × 2HCl | A |
| 7 | (structure: 3-amino-3-carboxy-5-(2-boronoethyl)piperidine N-acylated with lysyl) × 3HCl | A |
| 8 | (structure: 3-amino-3-carboxy-5-(2-boronoethyl)piperidine N-acylated with leucyl) × 2HCl | C |

TABLE 5-continued

Arginase 1 Inhibitory Activity

| Example No. | Compound Structure | Activity Class (ARG I) |
|---|---|---|
| 9 | (structure) x 2HCl | C |
| 10 | (structure) x2HCl | B |
| 11 | (structure) x 2 HCl | A |
| 12 | (structure) x 2HCl | B |
| 13 | (structure) x 3 HCl | A |
| 14 | (structure) x2HCl | C |

TABLE 5-continued
Arginase 1 Inhibitory Activity
| Example No. | Compound Structure | Activity Class (ARG I) |
|---|---|---|
| 15 | 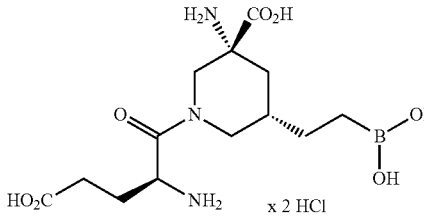 x 2 HCl | C |
| 16 | 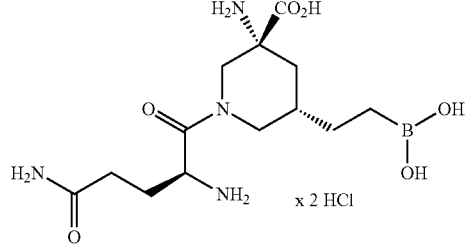 [SMILES: NC(=O)CC[C@H](N)C(=O)N1C[C@@H](CCB(O)O)C[C@](N)(C(=O)O)C1] x 2 HCl | B |
| 17 | 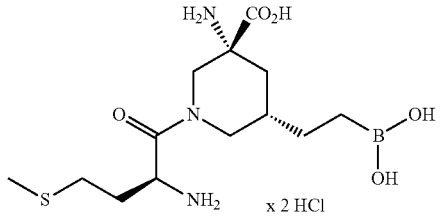 [SMILES: CSCC[C@H](N)C(=O)N1C[C@@H](CCB(O)O)C[C@](N)(C(=O)O)C1] x 2 HCl | B |
| 18 | 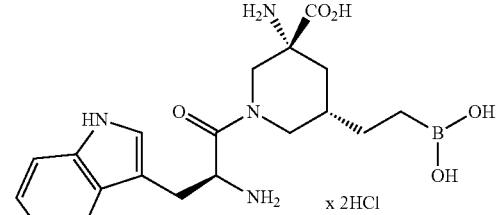 x 2HCl | B |
| 19 | 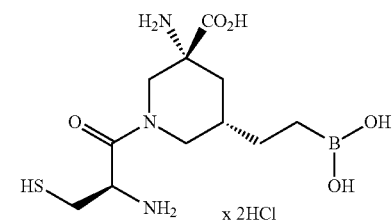 [SMILES: N[C@@H](CS)C(=O)N1C[C@@H](CCB(O)O)C[C@](N)(C(=O)O)C1] x 2HCl | C |
| 20 | 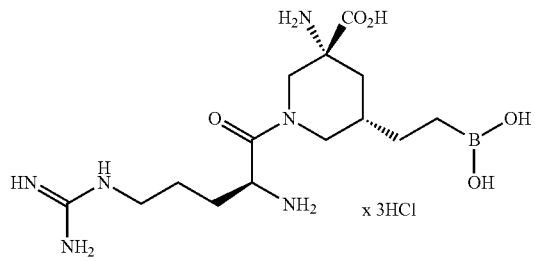 [SMILES: N=C(N)NCCC[C@H](N)C(=O)N1C[C@@H](CCB(O)O)C[C@](N)(C(=O)O)C1] x 3HCl | A |

TABLE 5-continued

Arginase 1 Inhibitory Activity

| Example No. | Compound Structure | Activity Class (ARG I) |
|---|---|---|
| 21 | (structure) x 2HCl | B |
| 22 | (structure) x 3HCl | B |
| 23 | (structure) x 2HCl | D |
| 24 | (structure) x 2HCl | C |
| 25 | (structure) x 2HCl | B |
| 26 | (structure) x 2HCl | B |

TABLE 5-continued
Arginase 1 Inhibitory Activity
| Example No. | Compound Structure | Activity Class (ARG I) |
|---|---|---|
| 27 | 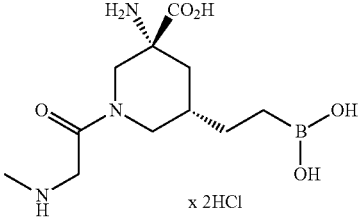 [SMILES: CNCC(=O)N1C[C@@H](CCB(O)O)C[C@](N)(C(=O)O)C1] x 2HCl | B |
| 28 | 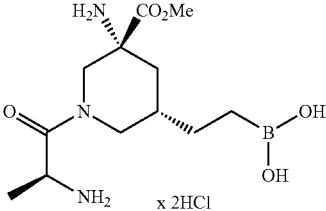 [SMILES: COC(=O)[C@@]1(N)C[C@H](CCB(O)O)CN(C(=O)[C@H](C)N)C1] x 2HCl | E |
| 29 | 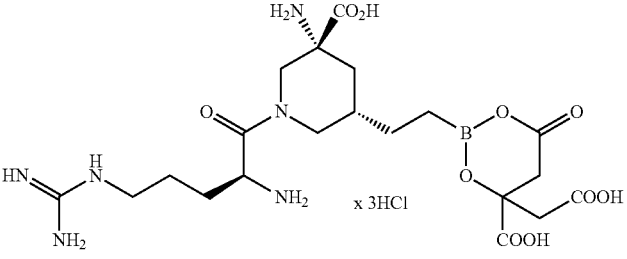 [SMILES: N=C(N)NCCC[C@H](N)C(=O)N1C[C@@H](CCB2OC(=O)CC(CC(=O)O)(C(=O)O)O2)C[C@](N)(C(=O)O)C1] x 3HCl | A |
| 30 | 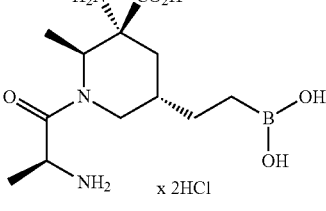 x 2HCl | A |
| 31 | 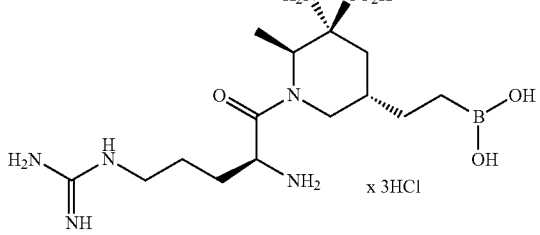 x 3HCl | B |
| 32 | 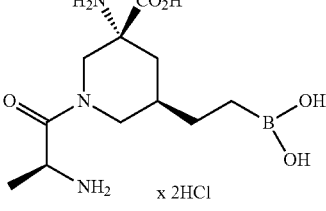 x 2HCl | E |

TABLE 5-continued
Arginase 1 Inhibitory Activity
| Example No. | Compound Structure | Activity Class (ARG I) |
|---|---|---|
| 33 | 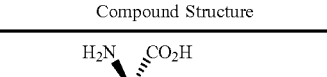 | E |
The inhibitory activity toward humane arginase 2 of the hydrochloride salts of the selected exemplary compounds according to the invention is presented in Table 6.
TABLE 6
Arginase 2 Inhibitory Activity
| Example No. | Compound Structure | Activity Class (ARG II) |
|---|---|---|
| 1 | 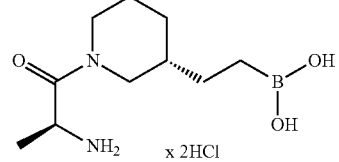 | C |
| 3 | 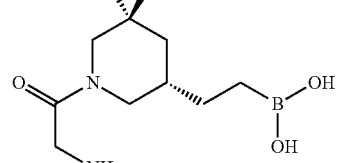 | C |
| 6 | 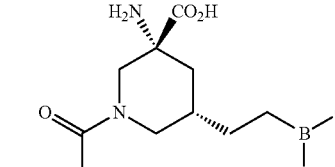 | C |
| 7 | 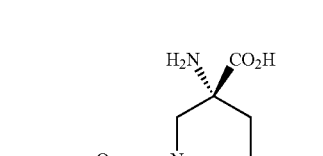 | C |

TABLE 6-continued

Arginase 2 Inhibitory Activity

| Example No. | Compound Structure | Activity Class (ARG II) |
|---|---|---|
| 11 | (structure with H$_2$N, CO$_2$H, piperidine, benzyl, NH$_2$, boronic acid; × 2 HCl) | D |
| 13 | (structure with H$_2$N, CO$_2$H, piperidine, imidazole, NH$_2$, boronic acid; × 3 HCl) | C |
| 20 | (structure with H$_2$N, CO$_2$H, piperidine, guanidino sidechain, NH$_2$, boronic acid; × 3HCl) | B |
| 30 | (structure with H$_2$N, CO$_2$H, methyl-piperidine, NH$_2$, boronic acid; × 2HCl) | C |

Evaluation of Pharmacokinetic (PK) and Pharmacodynamic (PD) Properties

Example 34. Pharmacokinetic and Pharmacodynamic Studies

PK/PD studies were performed using BALB/c mice or Sprague-Dawley rats. The compounds were tested after intravenous and oral (intragastric) administration at doses of 3 mg/kg or 10 mg/kg, respectively. Saline solution (suitable for infusions) was used as vehicle. Blood samples were collected from the animals to EDTA tubes in relevant time-points (3 samples per time-point), usually up to 24 h following the administration. The concentrations of the tested compounds and L-arginine were determined in blood plasma by LC-MS method. The pharmacokinetic parameters ($C_{max}$, $t_{max}$, AUC, CL, $V_{ss}$, $t_{1/2}$, F) were determined by a non-compartmental method using standard equations in MS Excel software. Results are shown in FIGS. 3-6.

What is claimed is:

1. A compound of the Formula (I):

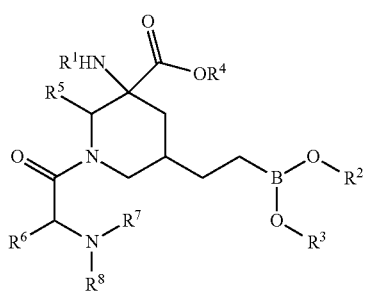

(I)

wherein:

R$^1$ is selected from the group consisting of H, straight-chain or branched (C$_1$-C$_6$)alkyl, HC(O)—, and (C$_1$-C$_6$)alkyl-C(O)—;

R² and R³ are each independently selected from hydrogen, straight-chain or branched $(C_1-C_6)$alkyl or $(C_1-C_6)$alkyl-C(O)—, or R² and R³ taken together with the boron atom and oxygen atoms to which they are bound form a 4-, 5-, 6- or 7-membered ring that is fully saturated, or partially saturated, or R² and R³ taken together with the boron atom and oxygen atoms to which they are bound form a diester of the boronic acid and polyalcohols selected from: pinanediol, mannitol, glycerol, xylitol, sorbitol, or erythritol, or R² and R³ taken together with the boron atom and oxygen atoms to which they are bound form an anhydride or mixed ester-anhydride of the boronic acid and hydroxy acids or di-carboxylic acids selected from: iminodiacetic acid or N-methyliminodiacetic acid or oxalic acid or tartaric acid or citric acid or malic acid or malonic acid or mandelic acid or glycolic acid or lactic acid or 3-hydroxypropionic acid;

R⁴ is selected from the group consisting of H, straight-chain and branched $(C_1-C_6)$alkyl;

R⁵ is selected from the group consisting of H, F, methyl, ethyl, propyl, isopropyl, —CH₂NH₂, —CH₂NHCH₃, —CH₂NHCH₂CH₃, —CH₂NHCH(CH₃)₂, —CH₂N(CH₃)₂, —CH₂N(CH₃)CH₂CH₃, —CH₂N(CH₂CH₃)₂, —CH₂N(CH₃)CH(CH₃)₂, —CH₂-azetidinyl, —CH₂-pyrrolidinyl, and —CH₂-piperidinyl;

R⁶ is selected from the amino acid side chains of Gly, Ala, Val, Ser, Phe, Lys, Thr, Met, Tyr, His, Asp, Glu, Asn, Gln, Cys, Sec, Ile, Leu, Arg, Orn, Cit, Trp, 1-Me-Trp and Nva; and R⁷ and R⁸ are each independently selected from hydrogen and methyl, or, when R⁷ is H, R⁶ and R⁸ together with the nitrogen atom carrying R⁸ form a pyrrolidine ring (proline side chain);

or a pharmaceutically acceptable salt thereof.

2. A compound according to claim 1, having the Formula (Ia):

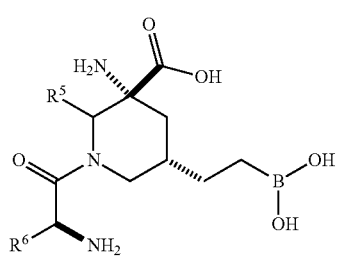

(Ia)

wherein:
R⁵ is selected from the group consisting of H, —CH₃, —CH₂NH₂, —CH₂NHCH₃, —CH₂N(CH₃)₂, and —CH₂-pyrrolidinyl; and R⁶ is selected from the amino acid side chain of Gly, Ala, Val, Ser, Phe, Lys, Thr, Met, Tyr, His, Asp, Glu, Asn, Gln, Cys, Sec, Ile, Leu, Arg, Orn, Cit, Trp, 1-Me-Trp and Nva;

or a pharmaceutically acceptable salt thereof.

3. A compound according to claim 1, having the Formula (Ib):

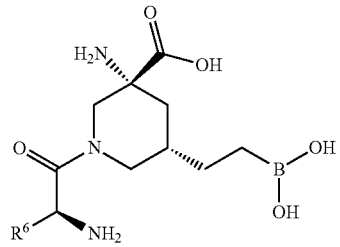

(Ib)

wherein:
R⁶ is selected from the amino acid side chain of Gly, Ala, Val, Ser, Phe, Lys, Thr, Met, Tyr, His, Asp, Glu, Asn, Gln, Cys, Sec, Ile, Leu, Arg, Orn, Cit, Trp, 1-Me-Trp or Nva or a pharmaceutically acceptable salt thereof.

4. A compound according to claim 1, wherein:
R⁵ is —CH₂NH₂ or —CH₂N(CH₃)₂ or —CH₂NHCH₃ or —CH₂N(CH₃)₂ or —CH₂N(CH₃)CH₂CH₃ or —CH₂-pyrrolidinyl or —CH₂-azetidinyl or CH₂-piperidinyl.

5. A compound according to claim 1, wherein:
R⁶ is selected from the amino acid side chains of Gly, Ala, Val, Ser, Phe, Lys, Thr, Met, Tyr, His, Asp, Glu, Asn, Gln, Cys, Sec, Ile, Leu, Arg, Orn, Cit, Trp, 1-Me-Trp, and Nva.

6. A compound according to claim 1, wherein:
R⁶ is selected from the amino acid side chains of Gly, Ala, Val, Ser, Phe, Lys, Thr, Met, Tyr, His, Asp, Glu, Asn, Gln, Cys, Sec, Ile, Leu, Arg, Orn, Cit, Trp, and 1-Me-Trp.

7. A compound according to claim 1, wherein:
R¹ is H; R² is H; R³ is H; R⁴ is H; R⁷ is H; and R⁸ is H.

8. A compound according to claim 1, selected from the following compounds:
(3R,5S)-1-(L-alanyl)-3-amino-5-(2-boronoethyl)piperidine-3-carboxylic acid;
(3S,5R)-1-(L-alanyl)-3-amino-5-(2-boronoethyl)piperidine-3-carboxylic acid;
(3R,5S)-3-amino-5-(2-boronoethyl)-1-glycylpiperidine-3-carboxylic acid;
(3R,5S)-1-(L-prolyl)-3-amino-5-(2-boronoethyl)piperidine-3-carboxylic acid;
(3R,5S)-1-(L-valyl)-3-amino-5-(2-boronoethyl)piperidine-3-carboxylic acid;
(3R,5S)-1-(L-seryl)-3-amino-5-(2-boronoethyl)piperidine-3-carboxylic acid;
(3R,5S)-1-(L-lysyl)-3-amino-5-(2-boronoethyl)piperidine-3-carboxylic acid;
(3R,5S)-1-(L-leucyl)-3-amino-5-(2-boronoethyl)piperidine-3-carboxylic acid;
(3R,5S)-1-(L-isoleucyl)-3-amino-5-(2-boronoethyl)piperidine-3-carboxylic acid; and
(3R,5S)-1-(L-tyrosyl)-3-amino-5-(2-boronoethyl)piperidine-3-carboxylic acid
(3R,5S)-1-(L-phenylalanyl)-3-amino-5-(2-boronoethyl)piperidine-3-carboxylic acid
(3R,5S)-1-(L-threonyl)-3-amino-5-(2-boronoethyl)piperidine-3-carboxylic acid
(3R,5S)-1-(L-histidyl)-3-amino-5-(2-boronoethyl)piperidine-3-carboxylic acid
(3R,5S)-1-(L-aspartyl)-3-amino-5-(2-boronoethyl)piperidine-3-carboxylic acid
(3R,5S)-1-(L-glutamyl)-3-amino-5-(2-boronoethyl)piperidine-3-carboxylic acid (3R,5S)-1-(L-glutaminyl)-3-amino-5-(2-boronoethyl)piperidine-3-carboxylic acid
(3R,5S)-1-(L-methionyl)-3-amino-5-(2-boronoethyl)piperidine-3-carboxylic acid
(3R,5S)-1-(L-tryptophyl)-3-amino-5-(2-boronoethyl)piperidine-3-carboxylic acid
(3R,5S)-1-(L-cysteinyl)-3-amino-5-(2-boronoethyl)piperidine-3-carboxylic acid
(3R,5S)-1-(L-arginyl)-3-amino-5-(2-boronoethyl)piperidine-3-carboxylic acid
(3R,5S)-3-amino-1-((S)-2-amino-5-ureidopentanoyl)-5-(2-boronoethyl) piperidine-3-carboxylic acid
(3R,5S)-3-amino-5-(2-boronoethyl)-1-((S)-2,5-diaminopentanoyl)piperidine-3-carboxylic
(3R,5S)-1-(D-alanyl)-3-amino-5-(2-boronoethyl)piperidine-3-carboxylic acid
(3R,5S)-3-amino-5-(2-boronoethyl)-1-(1-methyl-D-tryptophyl)piperidine-3-carboxylic acid
(3R,5S)-3-amino-1-((S)-2-aminopentanoyl)-5-(2-boronoethyl)piperidine-3-carboxylic acid
(3R,5S)-1-(L-asparaginyl)-3-amino-5-(2-boronoethyl)piperidine-3-carboxylic acid
(3R,5S)-3-amino-5-(2-boronoethyl)-1-(methylglycyl)piperidine-3-carboxylic acid
(2-((3S,5R)-1-(L-alanyl)-5-amino-5-(methoxycarbonyl)piperidin-3-yl)ethyl)boronic acid
(3R,5S)-1-(L-arginyl)-3-amino-5-(2-(4-carboxy-4-(carboxymethyl)-6-oxo-1,3,2-dioxaborinan-2-yl)ethyl)piperidine-3-carboxylic acid
(2S,3R,5S)-1-(L-alanyl)-3-amino-5-(2-boronoethyl)-2-methylpiperidine-3-carboxylic acid
(2S,3R,5S)-1-(L-Arginyl)-3-amino-5-(2-boronoethyl)-2-methylpiperidine-3-carboxylic acid
(3R,5R)-1-(L-alanyl)-3-amino-5-(2-boronoethyl)piperidine-3-carboxylic acid
(3S,5S)-1-(L-alanyl)-3-amino-5-(2-boronoethyl)piperidine-3-carboxylic acid
or a pharmaceutically acceptable salt thereof.

9. A pharmaceutical composition comprising (i) a therapeutically active amount of at least one compound as claimed in claim 1, or a pharmaceutically acceptable salt thereof; and (ii) a pharmaceutically acceptable carrier, vehicle or excipient therefor.

10. A method for the treatment of a cancer in a subject, comprising administering to the subject a therapeutically effective amount of at least one compound as claimed in claim 1, or a pharmaceutically acceptable salt thereof.

11. A method according to claim 10, wherein the cancer is a gastric cancer.

12. A method according to claim 10, wherein the at least one compound is administered simultaneously or sequentially with one or more chemotherapeutic agents.

13. A method according to claim 12, wherein the one or more additional chemotherapeutic agents are selected from the group consisting of AB122, AB154, AB680, AB928, BMS-202, BMS-813160, BMS-986016, BMS-986205, BMS-986207, CA-170, CA-327, EOS200271, epacadostat, GDC-0919, LY3321367, 1-methyl-D-tryptophan, MGA012, MK-7684, OMP-313M32, PF-06840003, REGN2810, SHR-1210, and TSR-022.

14. A method according to claim 12, wherein the one or more additional chemotherapeutic agents are selected from the group consisting of atezolizumab, avelumab, durvalumab, ipilimumab, nivolumab, pembrolizumab, and pidilizumab.

15. A process for preparing a compound of Formula Ib:

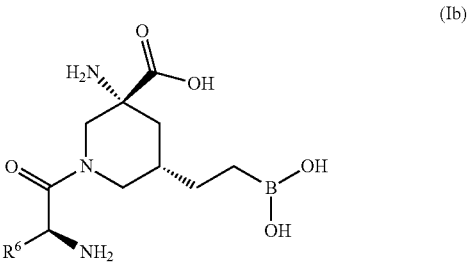

(Ib)

or a precursor thereof, wherein:
$R^6$ is selected from the amino acid side chain of Gly, Ala, Val, Ser, Phe, Lys, Thr, Met, Tyr, His, Asp, Glu, Asn, Gln, Cys, Sec, Ile, Leu, Arg, Orn, Cit, Trp; 1-Me-Trp and Nva;
or a pharmaceutically acceptable salt thereof;
comprising:
(a) reducing an ester of the formula

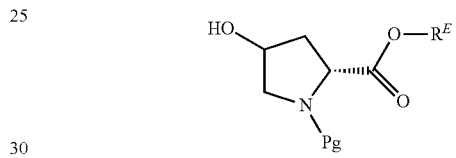

where
$P_g$ is methyl substituted with 1, 2, or 3 phenyl groups, where each phenyl group is optionally substituted with 1, 2 or 3 groups independently selected from halogen, nitro, $C_1$-$C_6$ alkoxy, or $C_1$-$C_6$ alkyl;
$R^E$ is $C_1$-$C_6$ alkyl, $C_3$-$C_6$ cycloalkyl, $C_3$-$C_6$ cycloalkyl($C_1$-$C_6$)alkyl, or methyl substituted with 1, 2, or 3 phenyl groups, where each phenyl group is optionally substituted with 1, 2 or 3 groups independently selected from halogen, nitro, $C_1$-$C_6$ alkoxy, or $C_1$-$C_6$ alkyl to yield a protected hydroxymethylpyrrolidine of the formula:

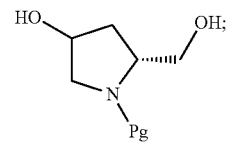

(b) subjecting the protected hydroxymethylpyrrolidine to ring expansion conditions to produce a protected piperidine of the formula:

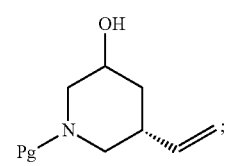

(c) oxidizing the protected piperidine to form an enantiomerically enriched product comprising a ketone of the formula:

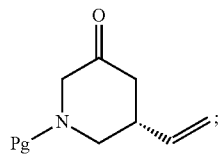

(d) reacting the ketone with cyanide and an amine source to yield an α-cyanoamine of the formula:

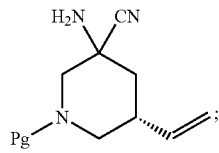

(e) acylating the amino group of the α-cyanoamine to produce an acylated α-cyanoamine of the formula:

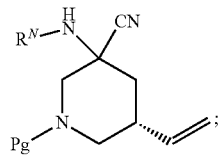

wherein $R^N$ is $C_2$-$C_6$ alkanoyl.

16. A process according to claim 15, further comprising
(f) subjecting the acylated α-cyanoamine to hydroboration conditions; and
(g) deprotecting the resulting cyclic boronate ester to produce a boronic acid of the formula:

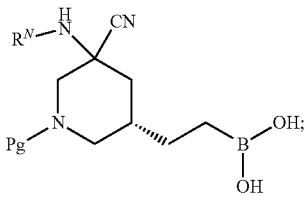

17. A process according to claim 16, further comprising
(h) hydrolyzing the acyl group to yield an α-amino acid with an unprotected amino group; and
(i) protecting the amino group of the α-amino acid to generate a boronic acid of Formula B-1:

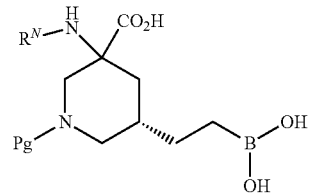

wherein $R^N$ represents a nitrogen protecting group.

18. A process according to claim 17, further comprising removing protecting group Pg from the piperidine of formula B-1; and
reacting the resulting deprotected piperidine compound with a compound of the formula:

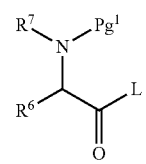

wherein
L is a leaving group;
$Pg^1$ is a nitrogen protecting group;
$R^6$ represents a side chain of an amino acid selected from the group consisting of Gly, Ala, Val, Ser, Phe, Lys, Thr, Met, Tyr, His, Asp, Glu, Asn, Gln, Cys, Sec, Ile, Leu, Arg, Orn, Cit, Trp; 1-Me-Trp and Nva; and
$R^7$ is hydrogen or methyl.

19. A method according to claim 10 wherein the cancer is selected from the group consisting of colon cancer, ovarian cancer, breast cancer, pancreatic cancer, lung cancer, melanoma, leukemia, colorectal cancer, pancreatic cancer, gastrointestinal carcinoid tumor, gastrointestinal stromal tumors, and small intestine cancer.

20. A method according to claim 12, wherein the one or more chemotherapeutic agents is selected from the group consisting of alkylating antineoplastic agents, antimetabolites, anti-microtubule agents, topoisomerase inhibitors, cytotoxic antibiotics or targeted therapies.

21. A method according to claim 20, wherein the targeted therapies are selected from the group consisting of antibodies, antibodies drug conjugates, cell-based immunotherapies, nanoparticles, anti-cancer vaccines, and radiotherapy.

22. A process according to claim 18, further comprising removing protecting groups $R^N$ and $Pg^1$.

* * * * *